US012616681B2

(12) United States Patent
Markowitz et al.

(10) Patent No.: US 12,616,681 B2
(45) Date of Patent: May 5, 2026

(54) COMPOSITIONS AND METHODS FOR TREATING RENAL INJURY

(71) Applicants: CASE WESTERN RESERVE UNIVERSITY, Cleveland, OH (US); INJE INDUSTRY ACADEMIC COOPERATION FOUNDATION, Gyeongsangnam-do (KR)

(72) Inventors: Sanford Markowitz, Pepper Pike, OH (US); Sun-Hee Kim, Gyeongsangnam-do (KP); Hye Jung Kim, Gyeongsangnam-do (KP); Ki Beom Bae, Gyeongsangnam-do (KP)

(73) Assignees: CASE WESTERN RESERVE UNIVERSITY, Cleveland, OH (US); INJE INDUSTRY ACADEMIC COOPERATION FOUNDATION, Gyeongsangnam-Do (KR)

( * ) Notice: Subject to any disclaimer, the term of this patent is extended or adjusted under 35 U.S.C. 154(b) by 687 days.

(21) Appl. No.: 17/892,585

(22) Filed: Aug. 22, 2022

(65) Prior Publication Data

US 2023/0052363 A1 Feb. 16, 2023

Related U.S. Application Data

(63) Continuation-in-part of application No. PCT/US2021/019084, filed on Feb. 22, 2021, and a continuation-in-part of application No. PCT/US2019/025812, filed on Apr. 4, 2019.

(60) Provisional application No. 62/979,813, filed on Feb. 21, 2020.

(51) Int. Cl.

| | |
|---|---|
| *A61K 31/4365* | (2006.01) |
| *A61K 49/04* | (2006.01) |
| *A61P 13/12* | (2006.01) |

(52) U.S. Cl.

CPC ...... *A61K 31/4365* (2013.01); *A61K 49/0438* (2013.01); *A61P 13/12* (2018.01)

(58) Field of Classification Search

CPC ........................ A61K 31/4365; A61K 49/0438

See application file for complete search history.

(56) References Cited

U.S. PATENT DOCUMENTS

| | | | |
|---|---|---|---|
| 3,382,247 | A | 5/1968 | Anthony et al. |
| 4,725,676 | A | 2/1988 | Agback et al. |
| 4,889,846 | A | 12/1989 | Crossley |

(Continued)

FOREIGN PATENT DOCUMENTS

| | | | |
|---|---|---|---|
| AR | 060498 A1 | 6/2008 | |
| AU | 2013/249434 B2 | 10/2017 | |

(Continued)

OTHER PUBLICATIONS

"Compositions and Methods of Modulating Short-Chain Dehydrogenase Activity"; Saudia Arabia Patent Application No. 621422063; First Examination Report; Aug. 18, 2022; 6 pgs.

(Continued)

*Primary Examiner* — Savitha M Rao

(74) *Attorney, Agent, or Firm* — Tarolli, Sundheim, Covell & Tummino LLP

(57) ABSTRACT

A method for preventing or treating renal disorder, disease, and/or injury includes administering to the subject and/or kidney a therapeutically effective amount of a 15-PGDH inhibitor.

12 Claims, 36 Drawing Sheets

A

B

(56) References Cited

U.S. PATENT DOCUMENTS 4,910,226 A 3/1990 Holt et al.
4,966,974 A 10/1990 Klausener et al.
4,973,474 A 11/1990 Hocquaux et al.
5,006,532 A 4/1991 Baker et al.
5,015,629 A 5/1991 diZerega
5,041,157 A 8/1991 Seiler et al.
5,217,521 A 6/1993 Durr
5,405,842 A 4/1995 Silverman
5,411,981 A 5/1995 Gaillard-Kelly et al.
5,438,058 A 8/1995 Dufetel et al.
5,445,164 A 8/1995 Worthen et al.
5,460,964 A 10/1995 McGlave et al.
5,466,694 A 11/1995 Terranova et al.
5,468,888 A 11/1995 Bouboutou et al.
5,480,913 A 1/1996 Liao et al.
5,516,779 A 5/1996 Von Langen et al.
5,529,769 A 6/1996 Cho et al.
5,565,467 A 10/1996 Batchelor et al.
5,631,282 A 5/1997 Goetz
5,635,387 A 6/1997 Fei et al.
5,650,145 A 7/1997 Saint-Leger
5,677,136 A 10/1997 Simmons et al.
5,681,559 A 10/1997 DiGuisto et al.
5,716,827 A 2/1998 Tsukamoto et al.
5,750,397 A 5/1998 Tsukamoto et al.
5,756,092 A 5/1998 Michelet et al.
5,759,793 A 6/1998 Schwartz et al.
5,760,043 A 6/1998 Dufetel et al.
5,772,990 A 6/1998 Hocquaux et al.
5,807,895 A 9/1998 Stratton et al.
6,027,896 A 2/2000 Roses et al.
6,121,254 A 9/2000 Saint-Leger
6,214,533 B1 4/2001 Ho et al.
6,281,227 B1 8/2001 Choi-Sledeski et al.
6,414,027 B1 7/2002 Neal
6,465,421 B1 10/2002 Duranton et al.
6,468,972 B1 10/2002 Pruche et al.
7,004,913 B1 2/2006 Rutenberg et al.
7,022,675 B2 4/2006 Rodgers et al.
7,091,216 B2 8/2006 Toupence et al.
7,131,958 B2 11/2006 Deverre
7,147,626 B2 12/2006 Goodman et al.
7,189,724 B2 3/2007 An et al.
7,294,641 B2 11/2007 Boulle et al.
7,320,967 B2 1/2008 Michelet et al.
7,396,525 B2 7/2008 Rozot et al.
7,629,112 B1 12/2009 Zengerle et al.
7,705,041 B2 4/2010 Michelet et al.
8,068,897 B1 11/2011 Gazdzinski
8,202,882 B2 6/2012 Hoelzemann et al.
8,637,558 B2 1/2014 Cho et al.
8,642,660 B2 2/2014 Goldfarb
9,649,350 B2 5/2017 Choi et al.
9,789,116 B2 10/2017 Markowitz et al.
9,790,233 B2 10/2017 Markowitz et al.
9,801,863 B2 10/2017 Markowitz et al.
10,301,320 B2 5/2019 Markowitz et al.
10,420,752 B2 9/2019 Markowitz et al.
10,869,871 B2 12/2020 Markowitz et al.
10,945,998 B2 3/2021 Markowitz et al.
11,426,420 B2 8/2022 Markowitz et al.
2002/0044953 A1 4/2002 Michelet et al.
2002/0045659 A1 4/2002 Michelet et al.
2003/0083381 A1 5/2003 Kumagai et al.
2003/0096823 A1 5/2003 Asp et al.
2004/0052760 A1 3/2004 Michelet et al.
2004/0087593 A1 5/2004 Clark et al.
2004/0241726 A1 12/2004 Liew
2004/0241727 A1 12/2004 Liew
2004/0241729 A1 12/2004 Liew
2005/0026923 A1 2/2005 An et al.
2005/0187221 A1 8/2005 Matsuda et al.
2006/0019976 A1 1/2006 Karp et al.
2006/0034786 A1 2/2006 Michelet et al.
2006/0051540 A1 3/2006 Kagawa
2006/0089349 A1 4/2006 Gundertofte et al.
2006/0233797 A1 10/2006 Gujrathi
2006/0287284 A1 12/2006 Schutze et al.
2007/0049603 A1 3/2007 Miknis et al.
2007/0059265 A1 3/2007 Boulle
2007/0071699 A1 3/2007 Boulle
2007/0078175 A1 4/2007 Boulle et al.
2007/0155884 A1 7/2007 Pellegatti et al.
2007/0219234 A1 9/2007 Oizumi et al.
2008/0039459 A1 2/2008 Folkes et al.
2008/0206320 A1 8/2008 Michelet et al.
2008/0249117 A1 10/2008 Michelet et al.
2009/0105210 A1 4/2009 Ashton et al.
2009/0118337 A1 5/2009 Davis
2009/0163545 A1 6/2009 Goldfarb
2010/0022521 A1 1/2010 Nogradi et al.
2010/0076041 A1 3/2010 Kilburn et al.
2010/0099672 A1 4/2010 Karp et al.
2010/0120732 A1 5/2010 Tabunoki
2010/0190853 A1 7/2010 Rethore et al.
2010/0234369 A1 9/2010 Hoelzemann et al.
2011/0009374 A1 1/2011 Keller
2011/0014250 A1 1/2011 Michelet et al.
2011/0034564 A1 2/2011 Parkkinen
2011/0142816 A1 6/2011 Landry et al.
2011/0195031 A1 8/2011 Du
2011/0269954 A1 11/2011 Cho et al.
2012/0302586 A1 11/2012 Rathod et al.
2013/0078632 A1 3/2013 Krishnadath
2013/0190297 A1 7/2013 DeJonghe et al.
2013/0316942 A1* 11/2013 Mograbi ................. A61P 11/04
514/17.7
2015/0072998 A1 3/2015 Markowitz et al.
2015/0118744 A1 4/2015 Tanaka et al.
2015/0202241 A1 7/2015 Choi et al.
2016/0136185 A1 5/2016 Shin et al.
2016/0311825 A1 10/2016 Farmer et al.
2016/0376430 A1 12/2016 Kusumoto et al.
2017/0165241 A1 6/2017 Markowitz et al.
2017/0173028 A1 6/2017 Markowitz et al.
2017/0174704 A1 6/2017 Gigstad et al.
2017/0216265 A1 8/2017 Markowitz et al.
2017/0266141 A1 9/2017 Nagy et al.
2018/0064694 A1 3/2018 Markowitz et al.
2018/0118756 A1 5/2018 Markowitz et al.
2018/0125829 A1 5/2018 Markowitz et al.
2019/0126044 A1 5/2019 Lozano
2019/0275014 A1 9/2019 Markowitz et al.
2019/0365769 A1 12/2019 Markowitz et al.
2020/0030348 A1 1/2020 Markowitz et al.
2020/0061073 A1 2/2020 Markowitz et al.
2020/0095206 A1 3/2020 Markowitz et al.
2020/0140453 A1 5/2020 Markowitz et al.
2020/0147063 A1 5/2020 Markowitz et al.
2020/0165249 A1 5/2020 Panarese et al.
2021/0032265 A1 2/2021 Markowitz et al.
2021/0094968 A1 4/2021 Markowitz et al.
2021/0100778 A1 4/2021 Markowitz et al.
2021/0100779 A1 4/2021 Markowitz et al.
2021/0106587 A1 4/2021 Markowitz et al.
2021/0108177 A1 4/2021 Di Santo et al.
2021/0283113 A1 9/2021 Markowitz et al.
2021/0317132 A1 10/2021 Markowitz et al.
2021/0386070 A1 12/2021 Arlt et al.
2023/0039604 A1 2/2023 Markowitz et al.
2023/0052363 A1 2/2023 Markowitz et al.
2023/0116062 A1 4/2023 Markowitz et al.

FOREIGN PATENT DOCUMENTS

AU 2016/248080 A1 11/2017
AU 2014/342811 B2 1/2019
AU 2018/200368 B2 7/2019
AU 2018/215678 A1 8/2019
AU 2018/249956 A1 11/2019
AU 2019/250163 A1 11/2019
AU 2016/229918 B2 10/2020
AU 2019/247838 A1 10/2020
AU 2019/202208 B2 12/2020

(56) References Cited

FOREIGN PATENT DOCUMENTS

| | | | |
|---|---|---|---|
| AU | 2021/201332 | A1 | 3/2021 |
| AU | 2019/384821 | A1 | 6/2021 |
| AU | 2021/204985 | A1 | 8/2021 |
| AU | 2017/300377 | B2 | 4/2022 |
| AU | 2022/201982 | A1 | 4/2022 |
| AU | 2022/205248 | A1 | 8/2022 |
| AU | 2018/272108 | B2 | 9/2022 |
| AU | 2021/200610 | B2 | 9/2022 |
| AU | 2021/224268 | A1 | 9/2022 |
| AU | 2021/201332 | B2 | 11/2022 |
| AU | 2021/275122 | A1 | 12/2022 |
| CA | 2007351 | A1 | 7/1990 |
| CA | 2870666 | A1 | 10/2013 |
| CA | 2927730 | A1 | 4/2016 |
| CA | 2979203 | A1 | 9/2016 |
| CA | 2974266 | A1 | 7/2017 |
| CA | 2984594 | A1 | 10/2017 |
| CA | 3031091 | A1 | 1/2018 |
| CA | 3052466 | A1 | 8/2018 |
| CA | 3059255 | A1 | 10/2018 |
| CA | 3068445 | A1 | 11/2018 |
| CA | 2984588 | C | 10/2019 |
| CA | 3095308 | A1 | 10/2019 |
| CA | 3120858 | A1 | 5/2020 |
| CA | 3168728 | A1 | 8/2021 |
| CA | 3183262 | A1 | 11/2021 |
| CL | 2020002741 | A1 | 1/2021 |
| CL | 2021001288 | A1 | 1/2022 |
| CL | 2021003378 | A1 | 8/2022 |
| CN | 1589793 | A | 3/2005 |
| CN | 102888208 | B | 2/2015 |
| CN | 107921025 | A | 4/2018 |
| CN | 108012528 | A | 5/2018 |
| CN | 110573154 | A | 12/2019 |
| CN | 110582277 | A | 12/2019 |
| CN | 110891568 | A | 3/2020 |
| CN | 111132982 | A | 5/2020 |
| CN | 11273944 | A | 4/2021 |
| CN | 113507931 | A | 10/2021 |
| EP | 0142811 | A2 | 5/1985 |
| EP | 0271273 | A2 | 6/1988 |
| EP | 0378508 | A2 | 7/1990 |
| EP | 0434624 | A1 | 6/1991 |
| EP | 0648488 | B1 | 11/2000 |
| EP | 1080728 | A1 | 3/2001 |
| EP | 1175890 | A1 | 1/2002 |
| EP | 1175891 | A1 | 1/2002 |
| EP | 0854700 | B1 | 5/2002 |
| EP | 0680745 | B1 | 11/2002 |
| EP | 2564841 | B1 | 5/2015 |
| EP | 2838533 | B1 | 10/2017 |
| EP | 3267995 | A1 | 1/2018 |
| EP | 3280398 | A1 | 2/2018 |
| EP | 3283074 | A1 | 2/2018 |
| EP | 3295940 | A1 | 3/2018 |
| EP | 3484473 | A1 | 5/2019 |
| EP | 3057973 | B1 | 9/2019 |
| EP | 3548035 | A1 | 10/2019 |
| EP | 3576737 | A1 | 12/2019 |
| EP | 3606520 | A1 | 2/2020 |
| EP | 3630773 | A1 | 4/2020 |
| EP | 3781154 | A1 | 2/2021 |
| EP | 3883577 | A1 | 9/2021 |
| EP | 4106748 | | 12/2022 |
| EP | 4153299 | | 3/2023 |
| FR | 2838641 | A1 | 10/2003 |
| FR | 2860431 | A1 | 4/2005 |
| JP | S5130286 | | 3/1976 |
| JP | S60-172984 | A | 9/1985 |
| JP | H02-288810 | A | 11/1990 |
| JP | H04-234888 | A | 8/1992 |
| JP | H09-295921 | A | 11/1997 |
| JP | H10-287532 | A | 10/1998 |
| JP | 2003/286171 | A | 10/2003 |
| JP | 2004-067629 | A | 3/2004 |
| JP | 2004/528319 | A | 9/2004 |
| JP | 2005/515182 | A | 5/2005 |
| JP | 2005/325099 | A | 11/2005 |
| JP | 2004/528319 | A5 | 1/2006 |
| JP | 2006-522746 | A | 10/2006 |
| JP | 2006/522750 | A | 10/2006 |
| JP | 2006/522750 | A5 | 5/2007 |
| JP | 2007/527850 | A | 10/2007 |
| JP | 2008/507518 | A | 3/2008 |
| JP | 2008527011 | A | 7/2008 |
| JP | 2008/536855 | A | 9/2008 |
| JP | 2008/536855 | A5 | 5/2009 |
| JP | 2009/520016 | A | 5/2009 |
| JP | 2009/535335 | A | 10/2009 |
| JP | 2009/535335 | A5 | 1/2010 |
| JP | 2010/053332 | A | 3/2010 |
| JP | 2010/520864 | A | 6/2010 |
| JP | 2007/527850 | A5 | 7/2010 |
| JP | 2011/500610 | A | 1/2011 |
| JP | 2013/506004 | A | 2/2013 |
| JP | 2013/506004 | A5 | 10/2013 |
| JP | 2015-514770 | A | 5/2015 |
| JP | 2016/531864 | A | 10/2016 |
| JP | 2016-537328 | A | 12/2016 |
| JP | 2017/514809 | A | 6/2017 |
| JP | 6203820 | B2 | 9/2017 |
| JP | 2018/511581 | A | 4/2018 |
| JP | 2018/511616 | A | 4/2018 |
| JP | 2018/511616 | A5 | 5/2019 |
| JP | 6517197 | B2 | 5/2019 |
| JP | 2019/135253 | A | 8/2019 |
| JP | 2020/502070 | A | 1/2020 |
| JP | 2020/503851 | A | 2/2020 |
| JP | 2020/514323 | A | 5/2020 |
| JP | 2020/516617 | A | 6/2020 |
| JP | 2020/516617 | A5 | 7/2020 |
| JP | 6789542 | B2 | 11/2020 |
| JP | 2020/502070 | A5 | 1/2021 |
| JP | 2021/020942 | A | 2/2021 |
| JP | 2020/514323 | A5 | 3/2021 |
| JP | 2021/038247 | A | 3/2021 |
| JP | 2021/519797 | A | 8/2021 |
| JP | 2022/507888 | A | 1/2022 |
| JP | 2021/519797 | A5 | 4/2022 |
| JP | 2022/141930 | A | 9/2022 |
| JP | 7139308 | B2 | 9/2022 |
| JP | 2022/163172 | A | 10/2022 |
| JP | 2022/174196 | A | 11/2022 |
| JP | 2022/191415 | A | 12/2022 |
| KR | 2008/0112764 | A | 12/2008 |
| KR | 2010/0137090 | A | 12/2010 |
| KR | 10-2012-0025903 | A | 3/2012 |
| KR | 2013/0103945 | A | 9/2013 |
| RU | 2006/127472 | A | 2/2008 |
| SA | 14404 | B1 | 12/2023 |
| WO | WO 1990/006100 | A1 | 6/1990 |
| WO | WO 1993/013664 | A2 | 7/1993 |
| WO | WO 1995/011003 | A1 | 4/1995 |
| WO | 1997/039750 | A1 | 10/1997 |
| WO | WO 1998/027092 | A1 | 6/1998 |
| WO | WO 1998/033497 | A1 | 8/1998 |
| WO | WO 2001/017480 | A2 | 3/2001 |
| WO | WO 2001/072268 | A1 | 10/2001 |
| WO | WO 2001/074307 | A2 | 10/2001 |
| WO | WO 2001/074313 | A2 | 10/2001 |
| WO | WO 2001/074314 | A2 | 10/2001 |
| WO | WO 2001/074315 | A2 | 10/2001 |
| WO | WO 2004/012671 | A2 | 2/2004 |
| WO | WO 2004/089415 | A2 | 10/2004 |
| WO | WO 2004/089416 | A2 | 10/2004 |
| WO | WO 2004/089471 | A2 | 10/2004 |
| WO | WO 2004/099204 | A1 | 11/2004 |
| WO | 2005/002503 | A1 | 1/2005 |
| WO | WO 2005/021552 | A1 | 3/2005 |
| WO | WO 2005/028676 | A2 | 3/2005 |
| WO | WO 2005/030773 | A1 | 4/2005 |
| WO | WO 2005/046434 | A2 | 5/2005 |
| WO | WO 2005/062735 | A2 | 7/2005 |
| WO | WO 2005/090333 | A1 | 9/2005 |

(56) References Cited

FOREIGN PATENT DOCUMENTS

| | | | |
|---|---|---|---|
| WO | WO 2006/019832 | A1 | 2/2006 |
| WO | WO 2006/048264 | A2 | 5/2006 |
| WO | WO 2006/048266 | A2 | 5/2006 |
| WO | WO 2006/074226 | A2 | 7/2006 |
| WO | WO 2006/078676 | A2 | 7/2006 |
| WO | WO 2006/096649 | A2 | 9/2006 |
| WO | WO 2006/098961 | A2 | 9/2006 |
| WO | WO 2006/138275 | A2 | 12/2006 |
| WO | WO 2007/013665 | A2 | 2/2007 |
| WO | WO 2007/019180 | A2 | 2/2007 |
| WO | WO 2007/027855 | A2 | 3/2007 |
| WO | WO 2007/038519 | A1 | 4/2007 |
| WO | WO 2007/072095 | A1 | 6/2007 |
| WO | WO 2007/100775 | A2 | 9/2007 |
| WO | WO 2007/101224 | A2 | 9/2007 |
| WO | WO 2007/127183 | A1 | 11/2007 |
| WO | WO 2008/063671 | A2 | 5/2008 |
| WO | 2008/157500 | A1 | 12/2008 |
| WO | WO 2008/156614 | A2 | 12/2008 |
| WO | WO 2009/029669 | A1 | 3/2009 |
| WO | WO 2009/073460 | A2 | 6/2009 |
| WO | WO 2009/082691 | A1 | 7/2009 |
| WO | WO 2009/111648 | A1 | 9/2009 |
| WO | WO 2009/120877 | A2 | 10/2009 |
| WO | WO 2010/023181 | A1 | 3/2010 |
| WO | WO 2010/045017 | A1 | 4/2010 |
| WO | WO 2010/052569 | A2 | 5/2010 |
| WO | WO 2010/077101 | A2 | 7/2010 |
| WO | WO 2010/080996 | A1 | 7/2010 |
| WO | WO 2010/091808 | A1 | 8/2010 |
| WO | WO 2010/111711 | A2 | 9/2010 |
| WO | WO 2011/041304 | A2 | 4/2011 |
| WO | WO 2011/042860 | A2 | 4/2011 |
| WO | WO 2011/094847 | A1 | 8/2011 |
| WO | WO 2011/147753 | A1 | 12/2011 |
| WO | 2012/058671 | A1 | 5/2012 |
| WO | WO 2012/146933 | A1 | 11/2012 |
| WO | WO 2013/034927 | A1 | 3/2013 |
| WO | WO 2013/082243 | A1 | 6/2013 |
| WO | WO 2013/083991 | A1 | 6/2013 |
| WO | WO 2013/112699 | A2 | 8/2013 |
| WO | WO 2013/158649 | A1 | 10/2013 |
| WO | WO 2013/180336 | A1 | 12/2013 |
| WO | WO 2014/081617 | A1 | 5/2014 |
| WO | WO 2014/081878 | A2 | 5/2014 |
| WO | WO 2014/160183 | A1 | 10/2014 |
| WO | WO 2014/160947 | A1 | 10/2014 |
| WO | WO 2015/005239 | A1 | 1/2015 |
| WO | WO 2015/065716 | A1 | 5/2015 |
| WO | WO 2015/077382 | A2 | 5/2015 |
| WO | 2015/161142 | A1 | 10/2015 |
| WO | WO 2016/106340 | A2 | 6/2016 |
| WO | WO 2016/124939 | A1 | 8/2016 |
| WO | 2016144958 | A1 | 9/2016 |
| WO | 2016/168472 | A1 | 10/2016 |
| WO | WO 2017/152044 | A1 | 9/2017 |
| WO | WO 2018/017582 | A1 | 1/2018 |
| WO | WO 2018/102552 | A1 | 6/2018 |
| WO | WO 2018/145080 | A1 | 8/2018 |
| WO | WO 2018/187810 | A1 | 10/2018 |
| WO | WO 2018/196870 | A1 | 11/2018 |
| WO | WO 2018/218251 | A1 | 11/2018 |
| WO | WO 2018/227134 | A1 | 12/2018 |
| WO | WO 2019/010482 | A1 | 1/2019 |
| WO | WO2019195565 | A1 | 10/2019 |
| WO | WO 2020/051207 | A2 | 3/2020 |
| WO | WO 2020/106998 | A1 | 5/2020 |
| WO | WO 2020/160151 | | 8/2020 |
| WO | WO 2020/252146 | A1 | 12/2020 |
| WO | WO 2021/151014 | A1 | 7/2021 |
| WO | WO 2021/168430 | A1 | 8/2021 |
| WO | WO 2021/236779 | A1 | 11/2021 |
| WO | WO 2021/252936 | A1 | 12/2021 |
| WO | WO 2021/236779 | A9 | 1/2022 |
| WO | WO 2022/032230 | A1 | 2/2022 |
| WO | WO 2022/087631 | A1 | 4/2022 |
| WO | WO 2022/126125 | A1 | 6/2022 |

OTHER PUBLICATIONS

Panama Application No. 93501-01, Office Action dated Feb. 16, 2024.

Iran-Nejad Akram et al: "Preventive role of estradiol on kidney injury induced by renal Ischemia-Reperfusion in male and female rats", International Journal of Preventive Medicine, vol. 6, No. 1, Jan. 1, 2015 (Jan. 1, 2015), p. 22.

Chang W-C et al: "Induction of a decrease in renal NADA+-dependent 15-hydroxyprostaglandin dehydrogenase activity by estradiol in rats", Biochemical Pharmacology, Elsevier, US, vol. 34, No. 12, Jun. 15, 1985 (Jun. 15, 1985), pp. 2073-2076.

European Application No. 19780850.4, Office Action dated Nov. 22, 2024.

Chinese Application No. 201980024926.5 Office Action dated Mar. 1, 2023.

Chinese Application No. 2019800249265 Search Report dated Feb. 27, 2023.

Japanese Application No. 2020-553610 Office Action dated Apr. 4, 2023.

Japanese Application No. 2022-128740, Office Action dated Jun. 25, 2024.

Registry (STN) [online], Jul. 9, 2015, pp. 1 to 10, date of search: Sep. 1, 2023, components of CAS Registration Nos. 296242-98-3, 311777-19-2, 331431-80-2, 331431-88-0, 332404-52-1, 332404-53-2, 332404-54-3, 332404-55-4, 622806-06-8, 622806-14-8, 622806-22-8, 622806-54-6, 913494-73-2, 1052069-68-7, and 1798165-36-2.

Sawicki, E. et al., and Ultraviolet-visible absorption spectra of quinoxaline derivatives, Journal of Organic Chemistry, 1957, and vol. 22 and pp. 625 to 629.

Zhao, Z. et al., Development of potent, allosteric dual Akt1 and Akt2 inhibitors with improved physical properties and cell activity, Bioorganic & Medicinal Chemistry Letters, 2008, and vol. 18, No. 1, and pp. 49 to 53.

Australian Application No. 2019247838, Examination Report dated Feb. 28, 2024.

Chinese Application No. 201880023858.6, Office Action dated Jul. 19, 2023.

Chinese Application No. 2018800238586, Search Report.

Eurasian Application No. 202191422, Office Action dated Jul. 5, 2023.

Indonesian Application No. P00202104544, Office Action dated Apr. 14, 2023.

Chinese Application No. 201880044387.7; Chinese Office Action dated Aug. 10, 2022; 5 pgs.

Chinese Application No. 201980024926.5, Office Actin dated Oct. 26, 2023.

European Application No. 17831696.4, Office Action dated Nov. 17, 2023.

Colombian Application No. NC2021/0008018, Office Action dated Dec. 28, 2023.

Japanese Application No. 2021-528862, Office Action dated Jan. 9, 2024.

Chinese Application No. 201880023858.6; Chinese Office Action dated Sep. 5, 2022; 6 pgs.

Chinese Application No. 2018800238586; Chinese Search Report; dated Aug. 30, 2022; 3 pgs.

International Search Report, Written Opinion, and International Preliminary Report on Patentability issued in PCT International Application No. PCT/US2013/036790, ISA/KR Korean Intellectual Property Office, Daejeon Metropolitan City, Republic of Korea. 13 pages.

International Search Report, Written Opinion, and International Preliminary Report on Patentability issued in PCT/US2014/060761, ISA/US United States Patent and Trademark Office, Alexandria, VA. 14 pages.

(56) References Cited

OTHER PUBLICATIONS

International Search Report and Written Opinion and International Preliminary Report on Patentability issued in PCT International Application No. PCT/US2016/021374, ISA/US United States Patent and Trademark Office, Alexandria, VA. 15 pages.
International Search Report, Written Opinion, and International Preliminary Report on Patentability issued in PCT/US2016/027549, ISA/US United States Patent and Trademark Office, Alexandria, VA. 16 pages.
International Search Report, Written Opinion, and International Preliminary Report on Patentability issued in PCT/US2017/042620, ISA/US United States Patent and Trademark Office, Alexandria, VA. 24 pages.
International Search Report, Written Opinion, and International Preliminary Report on Patentability issued in PCT/US2017/063959, ISA/US United States Patent and Trademark Office, Alexandria, VA. 31 pages.
International Search Report, Written Opinion, and International Preliminary Report on Patentability issued in PCT/US2018/017044, ISA/US United States Patent and Trademark Office, Alexandria, VA. 15 pages.
International Search Report and Written Opinion and International Preliminary Report on Patentability issued in PCT International Application No. PCT/US2018/026739, ISA/US United States Patent and Trademark Office, Alexandria, VA. 17 pages.
International Search Report, Written Opinion, and International Preliminary Report on Patentability issued in PCT/US2018/034944, ISA/US United States Patent and Trademark Office, Alexandria, VA. 15 pages.
International Search Report, Written Opinion, and International Preliminary Report on Patentability issued in PCT/US2019/025812, ISA/US United States Patent and Trademark Office, Alexandria, VA. 16 pages.
International Search Report and Written Opinion and International Preliminary Report on Patentability issued in PCT/US2019/062686, ISA/RU Federal Institute of Industrial Property, Moscow, RU. 15 pages.
International Search Report, Written Opinion, and International Preliminary Report on Patentability issued in PCT/US2021/019084, ISA/US United States Patent and Trademark Office, Alexandria, VA. 13 pages.
International Search Report, Written Opinion, and International Preliminary Report on Patentability issued in PCT/US2021/033170, ISA/EP European Patent Office, NL. 28 pages.
International Search Report and Written Opinion issued in PCT/US2021/045231, ISA/US United States Patent and Trademark Office, Alexandria, VA. 9 pages.
International Search Report and Written Opinion issued in PCT/US2022/12423, ISA/US United States Patent and Trademark Office, Alexandria, VA. 12 pages.
Abulwerdi, F.A., et al., "Development of Small Molecules with a Non-Canonical Binding Mode to HIV-1 Trans Activation Response (TAR) RNA," *Journal of Medicinal Chemistry*, Dec. 22, 2016, pp. 11148-11160, 59(24), American Chemical Society, Washington, DC, US.
Ahmad, Muzamil, et al., "The $PGE_2EP2$ receptor and its selective actibvation are beneficial against ischemic stroke," *Experimental & Translational Stroke Medicine*, 2010, 8 pages, vol. 2, No. 12, BioMed Central, UK.
"AKos Screening Samples ca. 3.5 million compounds Version Dec. 2007," Web page <www.akosgmbh.de/AKosSamples/index.html>, 3 pages, Dec. 19, 2007, retrieved from the Internet Archive Wayback Machine via Page Vault <http://web.archive.org/web/20071219115313/http://www.akosgmbh.de/AKosSamples/index.html> on Sep. 29, 2022.
Almeida, Camila Bononi, et al., "High Expression of the cGMP-specific Phosphodiesterase, PDE9A, in Sickle Cell Disease (SCD) and the Effects of its Inhibition in Erythroid Cells and SCD Neutrophils," *British Journal of Haematology*, Sep. 2008, pp. 836-844, 142(5), Blackwell Publishing Ltd, Oxford, UK.
Almeida, Camila Bononi, et al., "Hydroxyurea and a cGMP-amplifying Agent Have Immediate Benefits on Acute Vaso-Occlusive Events in Sickle Cell Disease Mice," Blood, Oct. 4, 2012, 23 pages, 120(14), American Society of Hematology, Washington, DC, US.
Al-Najjar, Belal O., et al., "Pharmacophore Modeling and 3D-QSAR Studies of 15-Hydroxyprostaglandin Dehydrogenase (15-PGDH) Inhibitors," *Indian Journal of Chemistry*, Nov. 2017, pp. 1200-1207, vol. 563, Scientific Publishers of India, IN.
Alvarez, F.J., and Slade, R.T., "Kinetics and Mechanism of Degradation of Zileuton, a Potent 5-Lipoxygenase Inhibitor," *Pharmaceutical Research*, 1992, pp. 1465-1473, vol. 9, No. 11, Plenum Publishing Corporation—Springer Science and Business Media, DE.
Antczak, M.I., et al., "nhibitors of 15-Prostaglandin Dehydrogenase To Potentiate Tissue Repair", *Journal of Medicinal Chemistry*, 2017, pp. 3979-4001, vol. 60, No. 9, American Chemical Society, Washington, DC, US.
Archelas, A., et al., "Absolute Configuration of α-Methylstyrene Oxide: The Correct Absolute Configuration/ Optical Rotation Correlation", *The Journal of Organic Chemistry*, Aug. 1, 1999, pp. 6112-6114, vol. 64, No. 16, American Chemical Society, Washington, DC, US.
Asati, V., et al., "Molecular Modeling Studies of Some Thiazolidine-2,4-Dione Derivatives as 15-PGDH Inhibitors," *Medicinal Chemistry Research*, Aug. 29, 2015, pp. 94-108, vol. 25, Springer Science + Business Media, DE.
Astatech, "AstaTech Inc. Catalog Product Search Result," Compound: 6-BROMO-3-methylpyrimidin-4(3H)-one, 2 pages, Oct. 18, 2022, retrieved via Page Vault https://astatechnic.com/CPSResult.php?CRNO=183100 on Oct. 18, 2022.
Bagshaw, S. M., et al., "A comparison of the RIFLE and AKIN criteria for acute kidney injury in critically ill patients," *Nephrology Dialysis Transplantation*, May 2008, pp 1569-1574, vol. 23, Issue 5, Oxford University Press, Oxford, UK, retrieved from https://academic.oup.com/ndt/article/23/5/1569/1809429, on Oct. 18, 2022.
Baker, Michael E. "Licorice and Enzymes Other Than IIβ-Hydroxysteroid Dehydrogenase: An Evolutionary Perspective," *Steroids*, Feb. 1994, pp. 136-141, vol. 59, Issue 2, Butterworth-Heinemann, Elsevier, Ltd, Oxford, UK.
Bakhle, Y.S., "Action of Prostaglandin Dehydrogenase Inhibitors on Prostaglandin Uptake in Rat Isolated Lung," *British Journal of Pharmacology*, Apr. 1979, pp. 635-639, 65(4), British Pharmacological Society, Macmillan Journals Ltd, UK.
Baliga, B.S, et al., "Combined Effects of Arginine and Hydroxyurea on BFU-E Derived Colony Growth and HbF Synthesis in Erythroid Progenitors Isolated from Sickle Cell Blood," *Cellular and Molecular Biology*, 2010, pp. OL1290-OL1298, vol. 56, No. 3, Cellular and Molecular Biology Association, Paris, FR.
Bärnthaler, Thomas, et al., "Inhibiting Eicosanoid Degradation Exerts Antifibrotic Effects in a Pulmonary Fibrosis Mouse Model and Human Tissue," *Journal of Allergy and Clinical Immunology*, Mar. 2020, pp. 818-833, vol. 145, No. 3, Elsevier Inc, Amsterdam, NL.
Battistini, Bruno, et al., "COX-1 and COX-2: Toward the Development of More Selective NSAIDS," Advances in prostaglandin research were presented at the 9th International Conference on Prostaglandins and Related Compounds in Florence, Italy, Jun. 6-10, 1994, and the 12th International Congress of Pharmacology in Montreal, Canada, Jul. 24-29, 1994, *Drug News & Perspectives Meeting Report,*Oct. 1994, pp. 501-512, 7(8).
Becker, C., et al., "In Vivo Imaging of Colitis and Colon Cancer Development in Mice Using High-Resolution Chromoendoscopy," *Gut*, 2005, pp. 950-954, vol. 54, BMJ, UK.
Berg, Daniel J., et al. "Rapid Development of Colitis in NSAID-Treated IL-10-Deficient Mice", *Gastroenterology*, 2002, pp. 1527-1542, vol. 123, No. 5, American Gastroenterological Association, W.B. Saunders, Philadelphia, PA.
Berk, L.B., et al., "16,16-Dimethyl Prostaglandin E2 and/or Syngeneic Bone Marrow Transplantation Increase Mouse Survival After Supra-Lethal Total Body Irradiation," *International Journal of Radiation Oncology Biology Physics*, Jun. 1990, pp. 1387-1392, vol. 18, No. 6, Pergamon Press plc, Oxford, UK.

(56) References Cited

OTHER PUBLICATIONS

Berry, C.N., et al., "Inhibition of Prostaglandin 15-Hydroxydehydrogenase by Sulphasalazine and a Novel Series of Potent Analogues," *Biochemical Pharmacology*, Oct. 1, 1983, pp. 2863-2871, vol. 32, No. 19, Pergamon Press Ltd., GB.

Bertram, Lars, et al., "Systematic meta-analyses of Alzheimer disease genetic association studies: the AlzGene database," *Nature Genetics*, Jan. 2007, pp. 17-23, vol. 39, No. 1, Nature Publishing Group, UK.

Bertram, Lars, et al., "Is $\alpha$-T catenin (VR22) an Alzheimer's disease risk gene?", *Journal of Medical Genetics: Electronic Letters*, Jan. 2007, pp 1-4, vol. 44, No. 1, BMJ Group, UK.

Blackwell, G.J., and Flower, R.J., "A Rapid Method for the Estimation of Prostaglandin 15-Hydroxydehydrogenase Activity and its Application to Pharmacology," *British Journal of Pharmacology*, 1976, pp. 589-597, vol. 57, Issue 4, British Pharmacological Society, UK.

Blake, Martin I., et al., "Studies with Deuterated Drugs", *Journal of Pharmaceutical Sciences*, Mar. 1975, pp. 367-391, vol. 64, No. 3, Elsevier, Amsterdam, NL.

Borm, Michelle E.A., and Bouma, Gerd, "Animal Models of Inflammatory Bowel Disease," *Drug Discovery Today: Disease Models*, Dec, 2004, pp. 437-443, vol. 1, Issue 4, Elsevier, Amsterdam, NL.

Bray, James E., et al., "The Human Short-Chain Dehydrogenase/Reductase (SPR) Superfamily: A Bioinformatics Summary," *Chemico-Biological Interactions*, Mar. 16, 2009, pp. 99-109, vol. 178, Issues 1-3, Elsevier, Amsterdam, NL.

Breyer, Richard M., et al., "Prostanoid Receptors: Subtypes and Signaling," *Annual Review of Pharmacology and Toxicology*, 2001, 32 pages including pp. 661-690, vol. 41, Annual Reviews, San Mateo, CA, US.

Brown, J.R., et al., "COX-2: A Molecular Target for Colorectal Cancer Prevention," *Journal of Clinical Oncology*, Apr. 20, 2005, pp. 2840-2855, vol. 23, No. 12, American Society of Clinical Oncology, Lippincott Williams and Wilkins, Philadelphia, PA, US.

Cahn, R.S., and Ingold, C.K., "Specification of Configuration about Quadricovalent Asymmetric Atoms," *Journal of the Chemical Society*, 1951, pp. 612-622, Chemical Society, UK.

Cahn, R.S., et al., "The Specification of Asymmetric Configuration in Organic Chemistry," *Experientia*, 1956, pp. 81-94, vol. 12, No. 3, Springer Science + Business Media, Berlin, DE.

Cahn, R.S., "An Introduction to the Sequence Rule: A System for the Specification of Absolute Configuration," *Journal of Chemical Education*, Mar. 1964, pp. 116-125, vol. 41, No. 3, American Chemical Society, Washington, DC.

Cahn, R.S., et al., "Specification of Molecular Chirality," *Angew. Chem. Inter. Edit.*, 1966, pp. 385-415, vol. 5, No. 4, Wiley-VCH, Weinheim, DE.

Cahn, R.S., et al., Errata "Specification of Molecular Chirality," ,*Angew. Chem. Inter. Edit.*, 1966, p. 511, vol. 5, No. 5, Wiley-VCH, Weinheim, DE.

Cancer Genome Atlas Network, "Comprehensive molecular characterization of human colon and rectal cancer," *Nature*, Jul. 19, 2012, pp. 330-337, vol. 487, Macmillan Publishers Limited, UK.

Cancer Genome Atlas Network, "Comprehensive molecular portraits of human breast tumours," Nature: Oct. 4, 2012, pp. 61-70, vol. 490, Macmillan Publishers Limited, UK.

Cancer Genome Atlas Network, "Integrated genomic analyses of ovarian carcinoma," *Nature*, Jun. 30, 2011, pp. 609-615, vol. 474, and Erratum, *Nature*, Oct. 11, 2012, p. 292, vol. 490, Macmillan Publishers Limited, UK.

Castellone, M.D., et al., "Prostaglandin $E_2$ Promotes Colon Cancer Cell Growth Through a $G_s$-Axin-β-Catenin Signaling Axis," *Science*, Dec. 2, 2005, pp. 1504-1510, vol. 310, Issue 5753, American Association for the Advancement of Science, Washington, DC, US.

Chang, Kyung Hee., et al., "Vasculopathy-Associated Hyperangiotensinemia Mobilizes Haematopoietic Stem Cells/Progenitors Through Endothelial $AT_2R$ and Cytoskeletal Dysregulation," *Nature Communications*, Jan. 9, 2015, 11 pages, 6, Article 5914, Macmillan Publishers Limited, Nature Research, London, UK.

Chassaing, B. et al., "Dextran Sulfate Sodium (DSS)-Induced Colitis in Mice." Current Protocals in Immunology; (Feb. 4, 2015), 16 pages, vol. 104:Unit—15.25, John Wiley & Sons, Inc, US. NIH-PA Author Manuscript Submitted.

"ChemBridge | Screening Libraries: Key Facts," Web page <www.chembridge.com/screening_libraries/>, 2 pages, Jan. 22, 2013, retrieved from the Internet Archive Wayback Machine via Page Vault <http://web.archive.org/web/20130122020518/https://www.chembridge.com/screening_libraries/>on Sep. 29, 2022.

Chemtob, Sylvain, et al., "Deficiency in Prostaglandin $E_2$ ($PGE_2$) Receptors, Mainly $EP_2$ Subtype, on Brain Synaptosomes in Early Development: Implications on Cerebral Metabolism," *Seminars in Perinatology*, Feb. 1994, pp. 23-29, vol. 18, No. 1, W.B. Saunders Company, Philadelphia, PA, US.

Chen, H., et al., "Prostaglandin E2 Mediates Sensory Nerve Regulation of Bone Homeostasis," *Nature Communications*, Jan. 14, 2019, pp. 1-13, vol. 10, Issue 1, Article No. 181, Nature Research, London, UK.

Chi, Xiuling, et al., "15-Hydroxyprostaglandin Dehydrogenase(15-PGDH) is Up-Regulated by Flurbiprofen and Other Non-Steroidal Anti-Inflammatory Drugs in Human Colon Cancer HT29 Cells," *Archives of Biochemistry and Biophysics*, Jul. 15, 2009, pp. 139-145, vol. 487, No. 2, Elsevier, Amsterdam, NL.

Childs, April C., et al., "Doxorubicin Treatment in Vivo Causes Cytochrome c Release and Cardiomyocyte Apoptosis, As Well As Increased Mitochondrial Efficiency, Superoxide Dismutase Activity, and Bcl-2:Bax Ratio," *Cancer Research*, Aug. 15, 2002, pp. 4592-4598, vol. 62, American Association for Cancer Research, Philadelphia, PA, US.

Cho, H., Tai, H.-H., "Inhibition of $NAD^+$-dependent 15-hydroxyprostaglandin dehydrogenase(15-PGDH) by cyclooxygenase inhibitors and chemopreventive agents," *Prostaglandinsz Leukotrienesz and Essential Fatty Acids*, 2002, p. 461-465, vol. 67(6), Elsevier Science Ltd, Amsterdam, NL.

Cho, Hoon, and Tai, Hsin-Hsiung, "Thiazolidinediones as a Novel Class of NAD+-Dependent 15-Hydroxyprostaglandin Dehydrogenase Inhibitors," *Archives of Biochemistry and Biophysics*, 2002, pp. 247-251, vol. 405, Academic Press, Elsevier Science (USA).

Cho, Hoon, et al., "Role of glutamine 148 of human 15-hydroxyprostaglandin dehydrogenase in catalytic oxidation of prostaglandin E2", *Bioorganic & Medicinal Chemistry*, 2006, pp. 6486-6491, vol. 14, Elsevier Ltd, Amsterdam, NL.

Choi, Dubok, et al., "Control of the Intracellular Levels of Prostaglandin $E_2$ Through Inhibition of the 15-Hydroxyprostaglandin Dehydrogenase for Wound Healing," *Bioorganic and Medicinal Chemistry*, 2013, 8 pages, Elsevier, Amsterdam, NL.

Clifford, P.C., et al., "Treatment of Vasospastic Disease with Prostaglandin $E_1$," *British Medical Journal*, Oct. 18, 1980, pp. 1031-1034, vol. 281, British Medical Association, UK.

Colombe, L., "Prostaglandin Metabolism in Human Hair Follicle," *Experimental Dermatology*, 2007, pp. 762-769, vol. 16, No. 9, Blackwell Munksgaard, Copenhagen, DK.

Combrinck, M., et al. "Levels of CSF Prostaglandin $E_2$, Cognitive Decline, and Survival in Alzheimer's disease," *Journal of Neurology, Neurosurgery, and Psychiatry*, Jun. 8, 2005, pp. 85-88, vol. 77, pp. 85-88, BMJ Group, London, UK.

Cooper, H. S. et al., "Clinicopathologic Study of Dextran Sulfate Sodium Experimemal Murine Coiitis," *Laboratory Investigation*, (1993), pp. 238-249, vol. 69, No. 2, The United States and Canadian Academy of Pathology, Inc., USA.

Coteron, J.M., et al., "Structure-Guided Lead Optimization of Triazolopyrimidine-Ring Substituents Identifies Potent *Plasmodium falciparum* Dihydroorotate Dehydrogenase Inhibitors with Clinical Candidate Potential", *Journal of Medicinal Chemistry*, Aug. 11, 2011, pp. 5540-5561, vol. 54, No. 15, American Chemical Society, Washington, DC, US.

Croft, D., et al., "The Reactome pathway knowledgebase," *Nucleic acids research*, 2014, pp. D472-D477, vol. 42, Oxford University Press, UK.

(56) References Cited

OTHER PUBLICATIONS

Cudaback, Eiron, et al., "Therapeutic Implications of the Prostaglandin Pathway in Alzheimer's Disease," *Biochemical Pharmacology*, Apr. 15, 2014, pp. 565-572, vol. 88, Issue 4, Elsevier Inc., Amsterdam, NL.
Cutler, Corey, et al., "Prostaglandin-Modulated Umbilical Cord Blood Hematopoietic Stem Cell Transplantation," Blood, 2013, 30 pages, American Society of Hematology, Washington, DC, US.
Dai, Liying, et al., "Inverse Expression of Prostaglandin $E_2$-Related Enzymes Highlights Differences Between Diverticulitis and Inflammatory Bowel Disease," *Digestive Diseases and Sciences*, 2015, pp. 1236-1246, vol. 60, Springer Science + Business Media, Berlin, DE.
Dalvi, Siddhartha, et al., "Exogenous Arachidonic Acid Mediates Permeability of Human Brain Microvessel Endothelial Cells through Prostaglandin $E_2$ Activation of $EP_3$ and $EP_4$ Receptors," *Journal of Neurochemistry*, Apr. 27, 2015, pp. 867-879, vol. 135, International Society for Neurochemistry, Wiley-Blackwell, Hoboken, NJ, US.
Deng, Yang, et al., "Lipopolysaccharide Stimulates Bovine Endometrium Explants through Toll-Like Receptor 4 Signaling and $PGE_2$ Synthesis," *Prostaglandins, Leukotrienes, and Essential Fatty Acids*, May 2021, Abstract only—2pages, vol. 168, Elsevier Ltd., Amsterdam, NL.
Desai, A., et al., "A Second-Generation 15-PGDH Inhibitor Promotes Bone Marrow Transplant Recovery Independently of Age, Transplant Dose, and Granulocyte Colony-Stimulating Factor Support," *Haematologica*, 2018, pp. 1054-1064, 103(6), Ferrata Storti Foundation, IT.
Dong, Yuanqiang, et al., "Effects of SW033291 on the Myogenesis of Muscle-Derived Stem Cells and Muscle Regeneration," *Stem Cell Research and Therapy*, 2020, 17 pages, vol. 11, Issue 76, BioMedCentral, London, UK.
Douville, Christopher, et al., "Assessing Aneuploidy with Repetitive Element Sequencing," *Proceedings of the National Academy of Sciences*, Mar. 3, 2020, pp. 4858-4863, vol. 117, No. 9, United States National Academy of Sciences, Washington, DC, US.
Dowd, Noreen P., et al., "Inhibition of Cyclooxygenase-2 Aggravates Doxorubicin-Mediated Cardiac Injury in Vivo," *The Journal of Clinical Investigation*, Aug. 15, 2001, pp. 585-590, vol. 108, No. 4, American Society for Clinical Investigation, US.
Doxorubicin Hydrochloride Package Insert and Package Label Display Panel, Revised: Jan. 2021, 16 pages, Teva Pharmaceuticals USA, Inc., Labeler: Actavis Pharma, Inc.
Duveau, Damien Y., et al., "Discovery of two small molecule inhibitors, ML387 and ML388, of human $NAD^+$-dependent 15-hydroxyprostaglandin dehydrogenase," *Probe Reports from the NIH Molecular Libraries Program*, 2013, 26 pages, National Center for Biotechnology Information, US.
Duveau, Damien Y., et al., "Structure-activity relationship studies and biological characterization of human $NAD^+$-dependent 15 hydroxyprostaglandin dehydrogenase inhibitors", *Bioorganic and Medicinal Chemistry Letters*, Jan. 15, 2014, pp. 630-635, vol. 24, Elsevier, Amsterdam, NL.
Echeverria, Valentina, et al., "Stimulation of $PGE_2$ Receptors $EP_2$ and $EP_4$ Protects Cultured Neurons Against Oxidative Stress and Cell Death Following β-Amyloid Exposure," *European Journal of Neuroscience*, 2005, pp. 2199-2206, vol. 22, Federation of European Neuroscience Societies, Wiley-Blackwell, Hoboken, NJ.
"Enamine—Screening Compounds," Web page <http://www.enamine.net/index.php?option=com_content&task=view&id=22&menuid=51&PHPSESSID=64a4f248f69d671a413f487bb62c4d90>, 2 pages, Jun. 30, 2007, retrieved from the Internet Archive Wayback Machine via Page Vault <http://web.archive.org/web/20070630171813/http://www.enamine.net/index.php?option=com_content&task=view&id=22&menuid=51&PHPSESSID=64a4f248f69d671a413f487bb62c4d90> on Sep. 29, 2022.
Ensor, C.M, et al., "Site-Directed Mutagenesis of the Conserved Tyrosine 151 of Human Placental $NAD^+$-dependent 15-Hydroxyprostaglandin Dehydrogenase Yields a Catalytically Inactive Enzyme", *Biochemical and Biophysical Research Communications*, Apr. 30, 1991, pp. 840-845, vol. 176, No. 2, Academic Press, Inc., Elsevier, Amsterdam, NL.
Ensor, Charles Mark, et al., "Bacterial expression and site-directed mutagenesis of two critical residues (tyrosine-151 and lysine-155) of human placental $NAD^{+}$*-dependent 15-hydroxyprostaglandin dehydrogenase*", *Biochimica et Biophysica Acta*, 1994, pp. 151-156, vol. 1208, Elsevier Science B.B., Amsterdam, NL.
Eridani, S., and Mosca, A., "Fetal hemoglobin reactivation and cell engineering in the treatment of sickle dell anemia," *Journal of Blood Medicine*, Feb. 28, 2011, pp. 23-30, vol. 2, Dove Medical Press, UK.
Esrick, Erica B., et al., "Inactivation of HDAC1 or HDAC2 induces gamma globulin expression without altering cell cycle or proliferation," *American Journal of Hematology*, Jul. 2015, pp. 624-628, vol. 90, No. 7, Wiley Pharmaceuticals, Inc., Hoboken, NJ, US.
European Directorate for the Quality of Medicines & Healthcare, Structure/ Nomenclature Guide, "A Guide to the Graphic Representation and Nomenclature of Chemical Formulae in the European Pharmacopoeia," *European Pharmacopoeia*, 2011, 40 pages, $2^{nd}$ Edition, Council of Europe, Strasbourg, FR.
Fauchier, L., et al., "Use of Anticoagulants and Antiplatelet Agents in Stable Outpatients with Coronary Artery Disease and Atrial Fibrillation. International Clarify Registry," *PLOS One*, Apr. 27, 2015, 23 pages, 10(4), Public Library of Science, San Francisco, CA, US.
Filippini, A., et al., "Covid-19 Acute Respiratory Distress Syndrome: Can Iloprost Have a Role for This Treatment?" *Respiratory Medicine Case Reports*, 2021, 101358, 4 pages, vol. 32, Elsevier, NL.
Fitzpatrick, F.A., et al., "The Stability of 13,14-Dihydro-15 Keto-$PGE_2$," *Prostaglandins*, Jun. 1980, pp. 917-931, vol. 19, No. 6., Elsevier Inc., NL.
Frias, M.A., et al., "The $PGE_2$-Stat3 Interaction in Doxorubicin-Induced Myocardial Apoptosis," *Cardiovascular Research*, 2008, pp. 69-77, vol. 80, Published on behalf of the European Society of Cardiology, Oxford University Press, Oxford, UK.
Frisch, Benjamin, et al., "In Vivo Prostaglandin $E_2$ Treatment Alters the Bone Marrow Microenvironment and Preferentially Expands Short-Term Hematopoietic Stem Cells," *Blood*, Nov. 5, 2009, 12 pages including pp. 4054-4063, vol. 114, No. 19, American Society of Hematology, Washington, DC, US.
Galiè, Nazzareno, et al., "Guidelines for the diagnosis and treatment of pulmonary hypertension," *European Heart Journal*, 2009, pp. 2493-2537, vol. 30, European Society of Cardiology, Oxford University Press, Oxford, UK.
Gentile, P., et al., "In Vivo Modulation of Murine Myelopoiesis Following Intravenous Administration of Prostaglandin E2", *Blood*, 1983, 8 pages including pp. 1100-1107, vol. 62, No. 5, American Society of Hematology, Washington, DC, US.
Ghiso, Jorge, et al., "Cerebral amyloidosis, amyloid angiopathy, and their relationship to stroke and dementia," Journal of Alzheimer's Disease, 2001, pp. 65-73, vol. 3, No. 1, IOS Press, Amsterdam, NL.
Girgis, Adel S., et al., "Synthesis of new 3-pyridinecarboxylates of potential vasodilation properties," *European Journal of Medicinal Chemistry*, 2008, vol. 43, pp 1818-1827, Elsevier, NL.
Giugliano, Robert P., et al., "Edoxaban versus Warfarin in Patients with Atrial Fibrillation," *The New England Journal of Medicine*, Nov. 28, 2013, pp. 2093-2104, vol. 369, No. 22, Massachusetts Medical Society, Waltham, MA, US.
Goessling, Wolfram, et al., "Genetic Interaction of PGE2 and Wnt Signaling Regulates Developmental Specification of Stem Cells and Regeneration," *Cell*, Mar. 20, 2009, pp. 1136-1147, vol. 136, Issue 6, Cell Press, Elsevier Inc., Cambridge, MA, US.
Goessling, Wolfram, et al., "Prostaglandin E2 Enhances Human Cord Blood Stem Cell Xenotransplants and Shows Long-Term Safety in Preclinical Nonhuman Primate Transplant Models," *Cell Stem Cell*, Apr. 8, 2011, pp. 445-458, vol. 8, Cell Press, Elsevier Inc., Cambridge, MA, US.
Gu, Xiaosong, et al., "Prostaglandin E2 Reduces Cardiac Contractility via EP3 Receptor," *Circulation: Heart Failure*, Aug. 2016, 8 pages, e003291, vol. 9, Issue 8, American Heart Association, Lippincott Williams & Wilkins, Philadelphia, PA, US.

(56) References Cited

OTHER PUBLICATIONS

Guo, Jian-You, et al., "Chronic unpredictable mild stress induces parallel reductions of 15-PGDH in the hypothalamus and lungs in rats," *Behavioural Brain Research*, 2015, pp. 278-284, vol. 286, Elsevier B.V., NL.
Hagedorn, E. J., et al., "Getting More for Your Marrow: Boosting Hematopoietic Stem Cell Numbers with PGE2", *Experimental Cell Research*, 2014, 7 pages, Elsevier Inc., Amsterdam, NL.
Hall, P. R. et al., "Small Molecule Inhibitors of Hantavirus Infection", *Bioorganic & Medicinal Chemistry Letters*, Dec. 1, 2010, pp. 7085-7091, vol. 20, No. 23, Elsevier, Amsterdam, NL.
Hamed, S., et al., "Erythropoietin Improves Myocardial Performance in Doxorubicin-Induced Cardiomyopathy," *European Heart Journal*, 2006, pp. 1876-1883, vol. 27, Oxford University Press, Oxford, UK.
Hamid, N., et al., "A Neural System Dynamics Modeling Platform And Its Applications In Randomized Controlled Trial Data Analysis," *Informatics in Medicine Unlocked*, 2021, 13 pages, 100612, vol. 24, Elsevier Ltd., Amsterdam, NL.
Hamza, Adel, et al., "Understanding human 15-hydroxyprostaglandin dehydrogenase binding with $NAO^+$ and $PGE_2$ by homology modeling, docking and molecular dynamics simulation," *Bioorganic & Medicinal Chemistry*, pp. 4544-4551, vol. 13, Elsevier Ltd., Amsterdam, NL.
Hanai, H., et al., "Curcumin Maintenance Therapy for Ulcerative Colitis: Randomized, Multicenter, Double-Blind, Placebo-Controlled Trial," *Clinical Gastroenterology and Hepatology*, Dec. 2006, pp. 11502-1506, vol. 4, Issue 5, Elsevier, Amsterdam, NL.
Hao, C.M., "Physiological Regulation of Prostaglandins in the Kidney," *Annual Review of Physiology*, 2008, 25 pages including pp. 357-377, vol. 70, Annual Reviews, San Mateo, CA, US.
Hao, G., et al., "Protective Effects of Berberine Against Doxorubicin-Induced Cardiotoxcity in Rats by Inhibiting Metabolism of Doxorubicin," *Xenobiotica*, 2015, pp. 1024-1029, vol. 45, Issue 11, Informa, London, UK.
Harrowven, D. C. "'Cascade' Radical Reactions in Synthesis: Condensed Thiophenes from Ketenethioacetals," *Tetrahedron Letters*, 1993, pp. 5653-5656, vol. 34, No. 35, Elsevier, Amsterdam, NL.
Hassan, M., et al., "Modulatory Effects of Meloxicam on Cardiotoxicity and Antitumor Activity of Doxorubicin in Mice," *Cancer Chemotherapy and Pharmacology*, Jul. 23, 2014, pp. 559-569, vol. 74, Springer Science + Business Media, Berlin, DE.
Heyman, Samuel N., et al., "Animal models of renal dysfunction: acute kidney injury," *Expert Opinon on Drug Discovery*, 2009, pp. 629-641, 4(6), Taylor & Francis, UK.
Heyman, Samuel N. , et al., "Acute Kidney Injury: Lessons from Experimental Models," *Experimental Models for Renal Diseases: Pathogenesis and Diagnosis*, 2011, pp. 286-296, vol. 169, Karger, Basel, CH.
Hoffman, Corey M., et al., "Minireview: Complexity of Hematopoietic Stem Cell Regulation in the Bone Marrow Microenvironment", *Molecular Endocrinology*, 2014, pp. 1-11, vol. 28, The Endocrine Society, Washington, DC, US.
Hoggatt, J., et al., "Prostaglandin $E_2$ Enhances Hematopoietic Stem Cell Homing, Survival, and Proliferation," *Blood*, May 28, 2009, cover page, pp. 5444-5455, vol. 113, No. 22, American Society for Hematology, Washington, DC, US.
Hoggatt, J., et al., "Differential Stem- and Progenitor-Cell Trafficking by Prostaglandin E2", *Nature*, 00 Month 2013, 7 pages, vol. 000, Nature Portfolio, London, UK.
Hoggatt, J., et al., "Prostaglandin $E_2$ Enhances Long-Term Repopulation but Does not Permanently Alter Inherent Stem Cell Competitiveness", *Blood*, Oct. 24, 2013, pp. 2997-3000, vol. 122, No. 17, American Society of Hematology, Washington, DC, US.
Hoggatt, Jonathan, et al., "Recovery from Hematopoietic Injury by Modulating Prostaglandin $E_2$ Signaling Post-Irradiation", *Blood Cells, Molecules and Diseases*, 2013, pp. 147-153, vol. 50, Elsevier Inc., Amsterdam, NL.
Hong, Yu Ah, et al., Paricalcitol Pretreatment Attenuates Renal lschemia-Reperfusion Injury via Prostaglandin $E_2$ Receptor E4 Pathway, *Oxidative Medicine and Cellular Longevity*, 2017, 17 pages, vol. 2017, Hindawi Publishing Corporation, London, UK.
Hoult, J.R.S., and Moore, P.K., "Sulphasalazine is a Potent Inhibitor of Prostaglandin 15-Hydroxydehydrogenase: Possible Basis for Therapeutic Action in Ulcerative Colitis," *British Journal of Pharmacology*, 1978, pp. 6-8, vol. 64, Macmillan Journals Ltd, UK.
Hoyt, A.L., et al., "On the nature of the chain-extending species in organolithium initiated stereospecific reagent-controlled homologation reactions using α-chloroalkyl aryl sulfoxides," *Tetrahedron Letters*, 2015, vol. I 56, pp. 2980-2982, Elsevier Ltd., NL.
Hu, B., et al., "Orally Bioavailable Quinoxaline Inhibitors of 15-Prostaglandin Dehydrogenase(15-PGDH) Promote Tissue Repair and Regeneration." Journal of Medicinal Chemistry, (Nov. 2022), pp. 15327-15343, 65, ACS Publications, Washington, DC.
Huang, X., et al., "Safety and Efficacy of Bivalirudin Monotherapy in Patients with Non-ST-Segment Elevation Acute Coronary Syndromes with Positive Biomarkers Undergoing Percutaneous Coronary Intervention: A Report From The Acute Catheterization and Urgent Intervention Triage Strategy Trial," *Coronary Artery Disease*, Jan. 1, 2020, pp. 59-65, vol. 31, Issue 1, Wolters Kluwer Health, Inc., Lippincott Williams & Wilkins, Philadelphia, PA, US.
Huang, W.J., and Tang, X.X., "Virus Infection Induced Pulmonary Fibrosis," *Journal of Translational Medicine*, 2021, 15 pages, vol. 19, Issue 496, BioMedCentral, UK.
Hughes, P.A., et al., "Experimental Colitis Models," *TRP Channels in Drug Discovery*: vol. II, Chapter 23, Jan. 1, 2012, pp 379-390, Humana Press, Springer, Munich, DE.
Hunt, T. K., et al., "Coagulation and Macrophage Stimulation of Angiogenesis and Wound Healing," *The Surgical Wound*, ed. F. Dineen & G. Hildrick-Smith, 1981, 21 pages including pp. 1-18, Lea & Febiger, Philadelphia, PA.
"Inflammatory Bowel Disease," Web page <https://www.healthline.com/health/inflammatory-bowel-disease>, 6 pages, Jan. 7, 2015, retrieved from the Internet Archive Wayback Machine via Page Vault <http://web.archive.org/web/20070630171813/http://www.enamine.net/index.php?option=com_content&task=view&id=22&menuid=51&PHPSESSID=64a4f248f69d671a413f487bb62c4d90> on Oct. 25, 2022.
Iqubal, A., et al., "Clinical Updates on Drug-Induced Cardiotoxicity," *International Journal of Pharmaceutical Sciences and Research*, 2018, pp. 16-26, vol. 9, Issue 1, Society of Pharmaceutical Sciences and Research, Panchkula, Haryana, IN.
Jadapalli, J.K., et al., "Doxorubicin Triggers Splenic Contraction and Irreversible Dysregulation of COX and LOX That Alters the Inflammation-Resolution Program in the Myocardium," *American Journal of Physiology—Heart and Circulatory Physiology*, 2018, pp. H1091-H1100, vol. 315, American Physiological Society, Rockville, MD, US.
Jadhav, A., et al., "Potent and Selective Inhibitors of $NAD^+$-Dependent 15-Hydroxyprostaglandin Dehydrogenase (HPGD)", *Molecular Libraries, Pathways to Discovery*, Jul. 8, 2011, 36 pages, NIH.
Jain, D., et al., "Cardiac Complications of Cancer Therapy: Pathophysiology, Identification, Prevention, Treatment, and Future Directions," *Current Cardiology Reports*, 2017, 12 pages, vol. 19, Issue 36, Springer Science + Business Media, Berlin, DE.
Johansson, J.U., et al., "Prostaglandin signaling suppresses beneficial microglial function in Alzheimer's disease models." *The Journal of Clinical Investigation*, (Jan. 2015), pp. 350-364, vol. 125, No. 1, American Society for Clinical Investigation, US.
Johnston, Dudley E., "Wound Healing in Skin," *Plastic and Reconstructive Surgery, Veterinary Clinics of North American: Small Animal Practice*, Jan. 1990, pp. 1-25, vol. 20, No. 1, W.B. Saunders Ltd., US.
Jolly, L., et al. "Influenza Promotes Collagen Deposition via αvβ6 Integrin-Mediated Transforming Growth Factor β activation," *The Journal of Biological Chemistry*, Dec. 19, 2014, pp. 35246-35263, vol. 289, No. 51, pp. 35246-35263, American Society for Biochemistry and Molecular Biology, Rockville, MD, US.

(56) References Cited

OTHER PUBLICATIONS

Julkunen, I., et al., "Inflammatory Response to Influenza A Virus Infection," *Vaccine*, 2001, pp. 532-537, vol. 19, Elsevier Science Ltd., Amsterdam, NL.
Jung, P., et al., "Isolation and in vitro Expansion of Human Colonic Stem Cells," *Nature Medicine*, Oct. 2011, pp. 1225-1227, vol. 17, No. 10, Nature Publishing Group, London, UK.
Kabashima, K., et al., "The Prostaglandin Receptor EP4 Suppresses Colitis, Mucosal Damage and CD4 Cell Activation in the Gut", *The Journal of Clinical Investigation*, Apr. 2002, pp. 883-893, vol. 109, No. 7, American Society for Clinical Investigation, US.
Kalugin, V.E. et al. "Functionalized Sulfur-Containing Compounds. 13. *Synthesis of Substituted 3-amino-2-(organylsulfinyl)-and-(organylsulfonyl)thieno[2,3-b]pyridines," *Russian Chemical Bulletinz International Edition*, Mar. 2006, pp. 529-534, vol. 55, No. 3, Springer Science + Business Media, Berlin, DE.
Kalugin, V.E., et al., "Utilization of Potassium Carbonate for the Synthesis of 2-(organylsulfonyl)thieno[2,3-b]pyridine Derivatives," *Russian Chemical Bulletin, International Edition*, Feb. 2019, pp. 357-364, vol. 68, No.2, Springer Science + Business Media, Berlin, DE.
Kang, G.-J., et al., "High-Mobility Group Box 1 Suppresses Resolvin D1-Induced Phagocytosis via Induction of Resolvin D1-Inactivating Enzyme, 15-Hydroxyprostaglandin Dehydrogenase," *Biochimica et Biophysica Acta*, 2015, pp. 1981-1988, vol. 1852, No. 9, Elsevier B.V., Amsterdam, NL.
Karna, Sandeep, et al., "Novel Potent 15-Hydroxyprostaglandin Dehydrogenase Inhibitors," *Journal of Advanced Engineering and Technology*, 2010, pp. 301-304, vol. 3, No. 3.
Karna, Sandeep, "In-vitro Wound Healing Effect of 15-Hydroxyprostaglandin Dehydrogenase Inhibitor from Plant," *Pharmacognosy Magazine*, Apr. 7, 2017, pp. S122-S126, vol. 13, Issue 49, Supplement 1, Wolters Kluwer—Medkenow Publications, Mumbai, IN.
Katz, J.A., "The Practical Use of Corticosteroids in the Treatment of Inflammatory Bowel Disease," *Practical Gastroenterology*, Jan. 2005, pp. 14, 16, 18, 21, 22, 25, Shugar Publishing, Westhampton Beach, NY, US.
Kawaguchi, H., et al., "The Role of Prostaglandins in the Regulation of Bone Metabolism," *Clinical Orthopaedics and Related Research*, 1995, pp. 36-46, No. 313, J.B. Lippincott and Company, Philadelphia, PA.
Keller, M.D., J., et al., "Short-term Effect of Local Application of $PGE_2$ on Callus in Rabbit Osteotomy," *EurJ Exp Musculoskel Res*, 1992, vol. 1, pp. 86-92.
Kim, M. et al., "Decreased Catalytic Activity of the Insulin-degrading Enzyme in Chromosome 10-Linked Alzheimer Disease Families," *The Journal of Biological Chemistry*, Mar. 16, 2007, pp. 7825-7832, vol. 282, No. 11, The American Society for Biochemistry and Molecular Biology, Inc., USA.
Kim, H.J., et al., "Inhibition of 15-PGDH Prevents Ischemic Renal Injury by the $PGE_2/EP_4$ Signaling Pathway Mediating Vasodilation, Increased Renal Blood Flow, and Increased Adenosine/$A_{2A}$ Receptors," *American Journal of Physiology—Renal Physiology*, 2020, F1054-F1066, vol. 319, American Physiological Society, Rockville, MD.
Kimball, Frances A., et al., "Plasma Concentrations of 9-Deoxo-16,16-Dimethyl-9-methylene-$PGE_2$ In Rhesus Monkeys after Administration by Various Routes," *Prostaglandins*, Sep. 1980, pp. 559-569, vol. 20, No. 3, Elsevier, Amsterdam, NL.
Kishore, A.H., et al., "Prostaglandin Dehydrogenase is a Target for Successful Induction of Cervical Ripening," *Proceedings of the National Academy of Sciences*, Jul. 17, 2017, pp. E6427-E6436, vol. 114, No. 29, United States National Academy of Sciences, Washington, DC, US.
Kishore, B.K, et al., "Ticagrelor Reduces Urinary Concentration and Arginine Vasopressin (AVP) Levels: Potential Use in AVP Excess States," *Kidney Week*, Oct. 23, 2018, Poster SA-P01018, San Diego, CA, in the Journal of the American Society of Nephrology, 2018, p. 1002, vol. 29, American Society of Nephrology, Washington, DC, US.
Konturek, P.C., et al., "Prostaglandins as Mediators of Cox-2 Derived Carcinogenesis in Gastrointestinal Tract," Journal of Physiology and Pharmacology, Sep. 1, 2005, 12 pages, vol. 56, Suppl. 5.
Konturek, S.J., et al., "Prostaglandins and Ulcer Healing," Journal of Physiology and Pharmacology, 2005, 22 pages, vol. 56, No. 5.
Kurland, J.I., et al., "Role for Monocyte-Macrophage-Derived Colony-Stimulating Factor and Prostaglandin E in the Positive and Negative Feedback Control of Myeloid Stem Cell Proliferation," *Blood*, 1978, 21 pages including pp. 388-407, vol. 52, American Society of Hematology, Washington, DC, US.
Lakatos et al., "The Role of PPARs in Lung Fibrosis," *PPAR Research*, Jul. 2, 2007, pp. 1-10, Hindawi Publishing Corporation, London, UK.
Lam, P.-Y., et al., "Cyp1 Inhibition Prevents Doxorubicin-Induced Cardiomyopathy in a Zebrafish Heart Failure Model," *ChemBioChem*, Jul. 1, 2020, pp. 1905-1910, vol. 21, Issue 13, Wiley-VCH, Weinheim, DE.
Lewis, J.D., et al., "An Open-Label Trial of the PPARγ Ligand Rosiglitazone for Active Ulcerative Colitis," *The American Journal of Gastroenterology*, 2001, pp. 3323-3328, vol. 96, No. 12, Elsevier Science Inc., NL.
Li, J., et al., "Neutrophil AKT2 Regulates Heterotypic Cell-Cell Interactions During Vascular Inflammation," *Journal of Clinical Investigation*, Apr. 2014, 15 pages including pp. 1483-1496, vol. 124, Issue 4, American Society for Clinical Investigation, US.
Li, T., et al., "$PGE_2$ Increases Inflammatory Damage in *Escherichia coli*-infected Bovine Endometrial Tissue in vitro Via the EP4-PKA Signaling Pathway," *Biology of Reproduction*, 2019, pp. 175-186, vol. 100, Issue 1, Oxford University Press, Oxford, UK.
Li, T., et al., "Prostaglandin $E_2$ Promotes Nitric Oxide Synthase 2, Platelet-Activating Factor Receptor, and Matrix Metalloproteinase-2 Expression in *Escherichia coli*-challenged ex vivo Endometrial Explants via the Prostaglandin $E_2$ Receptor 4/Protein Kinase A Signaling Pathway," *Theriogenology*, Aug. 2019, pp. 65-73, vol. 134, Elsevier, Amsterdam, NL.
Li, N., et al., "Ferritinophagy-Mediated Ferroptosis is Involved in Sepsis-Induced Cardiac Injury," *Free Radical Biology and Medicine*, 2020, pp. 303-318, vol. 160, Elsevier, Amsterdam, NL. Submitted in 2 parts.
Lian, W.-S., et al., "The Prostaglandin Agonist Beraprost Aggravates Doxorubicin-Mediated Apoptosis by Increasing iNOS Expression in Cardiomyocytes," *Current Vascular Pharmacology*, Jan. 1, 2015, pp. 54-63, vol. 13, No. 1, Bentham Science Publishers, UK.
Liu, Y.-C. et al., "Triazolopyrimidines as a New Herbicidal Lead for Combating Weed Resistance Associated with Acetohydroxyacid Synthase Mutation", *Journal of Agricultural and Food Chemistry*, 2016, pp. 4845-4857, vol. 64, No. 24, American Chemical Society, Washington, DC, US.
Liu, C., et al., "Development and Stimulation of a Sensitive and Rapid UHPLC-MS/MS Method for the Simultaneous Quantification of the Common Active and Inactive Metabolites of Vicagrel and Clopidogrel in Human Plasma," *Journal of Pharmaceutical and Biomedical Analysis*, Feb. 5, 2018, pp. 394-402, vol. 149, Elsevier, Amsterdam, NL.
Liu, C., et al., "Pharmacokinetics and Pharmacokinetic/Pharmacodynamic Relationship of Vicagrel, a Novel Thineopyridine $P2Y_{12}$ Inhibitor, Compared with Clopidogrel in Healthy Chinese Subjects Following Single Oral Dosing," *European Journal of Pharmaceutical Sciences*, Jan. 15, 2019, pp. 151-160, vol. 127, Elsevier, Amsterdam, NL.
Lopes, J.A., et al., "The Rifle and Akin Classifications for Acute Kidney Injury: A Critical and Comprehensive Review," *Clinical Kidney Journal*, 2013, pp. 8-14, vol. 6, Oxford University Press, Oxford, UK.
Lorente, A., et al., "Synthesis of Heterocyclic Compounds. XXXIX [1]. Synthesis of 5-Cyano-Z-Phenyl-4-Thioxo-3,4-Dihydropyrimidines," *Journal of Heterocyclic Chemistry*, 1985, pp. 49-51, vol. 22, Wiley-Blackwell, Hoboken, NJ, US.
Lovgren, A.K., et al., "COX-2-Derived Prostacyclin Protects Against Bleomycin-Induced Pulmonary Fibrosis," *American Journal of*

(56) References Cited

OTHER PUBLICATIONS

*Physiology—Lung Cellular and Molecular Physiology*, pp. L144-L156, Feb. 10, 2006, vol. 291, The American Physiological Society, Rockville, MD, US.
Lu, L., et al., "Animal Models of Gastrointestinal Inflammation and Cancer," *Life Sciences*, 2014, pp. 1-6, vol. 108, Issue 1, Elsevier, Amsterdam, NL.
Luca, G., "The Future of Targeted Therapy: Combining Novel Agents," *Oncology*, 2002, pp. 47-56, vol. 63 (Supplement 1), Karger Publishers, Basel, CH.
Luu, A.Z., "Role of Endothelium in Doxorubicin-Induced Cardiomyopathy," *JACC: Basic to Translational Science*, Dec. 2018, pp. 861-870, vol. 3, No. 6, Elsevier on behalf of American College of Cardiology, Amsterdam, NL.
Ma, F., et al., "Discovery and Structure-Activity Relationships Study of Thieno[2,3-b]pyridine Analogues as Hepatic Gluconeogenesis Inhibitors," *European Journal of Medicinal Chemistry*, May 25, 2018, Abstract, vol. 152, Elsevier, Amsterdam, NL.
Makala, L., et al., "FK228 Analogues Induce Fetal Hemoglobin in Human Erythroid Progenitors," *Anemia*, 2012, Article ID 428137, 13 pages, vol. 2012, Hindawi Publishing Corporation, London, UK.
Mallipeddi, P.L., et al., "Structural Insights into Novel 15-Prostaglandin Dehydrogenase Inhibitors," *Molecules*, 2021, 17 pages, 5903, Multidisciplinary Digital Publishing Institute, Basel, CH.
Markowitz, S., et al., "Aspirin and Colon Cancer—Targeting Prevention", The New England Journal of Medicine, May 24, 2007, pp. 2195-2198, vol. 356, No. 21, Massachusetts Medical Society, MA, US.
Markowitz, S., et al., "Molecular Origins of Cancer—Molecular Basis of Colorectal Cancer," *The New England Journal of Medicine*, Dec. 17, 2009, pp. 2449-2460, vol. 361, No. 25, Massachusetts Medical Society, MA, US.
Mayo Clinic, "Diseases and Conditions—Chronic Kidney Disease," Web page <www.mayoclinic.org/diseases-conditions/kidney-disease/basics/causes/con20026778>, Jan. 7, 2015, retrieved from the Internet Archive Wayback Machine via Page Vault <http://web.archive.org/web/20150107203836/www.mayoclinic.org/diseases-conditions/kidney-disease/basics/causes/con-20026778> on Oct. 25, 2022.
Mayo Clinic, "Diseases and Conditions—Chronic kidney disease", Jan. 30, 2015, http://www.mayoclinic.org/diseases-conditions/kidney-disease/basics/causes/con-20026778, accessed Dec. 11, 2015.
Mayo Clinic, "Chronic kidney disease—Care at Mayo Clinic," Oct. 25, 2022, retrieved from Page Vault https://www.mayoclinic.org/diseases-conditions/chronic-kidney-disease/care-at-mayo-clinic/mac-20354531 on Oct. 25, 2022.
Mayo Clinic, "Chronic kidney disease—Diagnosis and treatment," Oct. 25, 2022, retrieved from Page Vault https://www.mayoclinic.org/diseases-conditions/chronic-kidney-disease/diagnosis-treatment/drc-20354527 on Oct. 25, 2022.
Mayo Clinic, "Chronic kidney disease—Doctors and departments," Oct. 25, 2022, retrieved from Page Vault https://www.mayoclinic.org/diseases-conditions/chronic-kidney-disease/doctors-departments/ddc-20354530 on Oct. 25, 2022.
Mayo Clinic, "Chronic kidney disease—Symptoms and causes," Oct. 25, 2022, retrieved from Page Vault https://www.mayoclinic.org/diseases-conditions/chronic-kidney-disease/symptoms-causes/syc-20354521 on Oct. 25, 2022.
McCaffrey, T.A., et al., "Genomic Profiling Reveals the Potential Role of TCLIA and MDRI Deficiency in Chemotherapy-Induced Cardiotoxicity," *International Journal of Biological Sciences*, 2013, pp. 350-360, vol. 9, Issue 4, Ivyspring International Publisher Pty Ltd, AU.
McCullough, Louise, et al., "Neuroprotecive Function of the $PGE_2$ EP2 Receptor in Cerebral Ischemia," *The Journal of Neuroscience*, Jan. 7, 2004, pp. 257-268, vol. 24, No. 1, Society for Neuroscience, Washington, DC, US.
Michelet, J.F., et al., "Expression of $NAD^+$ Dependent 15-Hydroxyprostaglandin Dehydrogenase and Protection of Prostaglandins in Human Hair Follicle," *Experimental Dermatology*, 2008, pp. 821-828, vol. 17, No. 10, Wiley, Hoboken, NJ, US.
Mitchell, C., and Willenbring, H., "A Reproducible and Well-Tolerated Method for ⅔ Partial Hepatectomy in Mice," *Nature Protocols*, 2008, pp. 1167-1170, vol. 3, No. 7, Nature Publishing Group, London, UK.
Montrose, D.C., et al., "The Role of $PGE_2$ in Intestinal Inflammation and Tumorigenesis," *Prostaglandins and Other Lipid Mediators*, 2015, 23 pages, Elsevier, Amsterdam, NL.
Mordente, A., et al., "Human Heart Cytosolic Reductases and Anthracycline Cardiotoxicity", *IUBMB Life*, 2001, pp. 83-88, vol. 52, John Wiley and Sons, Hoboken, NJ, US.
Morishita, Yoshiyuki, et al., "Establishment of Acute Kidney Injury Mouse Model by 0.75% Adenine Ingestion," *Renal Failure*, 2011, pp. 1013-1018, vol. 33, No. 10, Informa Healthcare USA, Inc., US.
Moustafa, Y.M., et al., "15-PGDH Inhibitors: The Antiulcer Effects of Carbenoxolone, Pioglitazone and Verapamil in Indomethacin Induced Peptic Ulcer Rats," *European Review for Medical and Pharmacological Sciences*, 2013, pp. 2000-2009, vol. 17, Verduci Editore, Rome, IT.
Myung, Seung-Jae, et al., "15-Hydroxyprostaglandin dehydrogenase is an in vivo suppressor of colon tumorigenesis," *Proceedings of the National Academy of Sciences*, Aug. 8, 2006, pp. 12098-12102, vol. 103, No. 32, United States National Academy of Sciences, Washington, DC, US.
Na, H.-K., et al., "15-Hydroxyprostaglandin Dehydrogenase as a Novel Molecular Target for Cancer Chemoprevention and Therapy," *Biochemical Pharmacology*, 2011, pp. 1352-1360, vol. 82, Elsevier, Amsterdam, NL.
Nakanishi, M., and Rosenberg, D.W., "Multifaceted Roles of $PGE_2$ in Inflammation and Cancer," *Seminars in Immunopathology*, 2013, pp. 123-137, vol. 35, Springer, Berlin, DE.
Nasrallah, Rania, et al., "$PGE_2$, Kidney Disease, and Cardiovascular Risk: Beyond Hypertension and Diabetes," *Journal of the American Society of Nephrology*, 2016, pp 666-676, vol. 27, American Society of Nephrology, US.
Neilan, T.G., et al., "Disruption of COX-2 Modulates Gene Expression and the Cardiac Injury Response to Doxorubicin," *American Journal of Physiology—Heart and Circulatory Physiology*, Apr. 14, 2006, pp. H532-H536, vol. 291, American Physiological Society, Rockville, MD, US.
Niesen., F.H., et al., "High-Affinity Inhibitors of Human $NAD^+$-Dependent 15-Hydroxyprostaglandin Dehydrogenase: Mechanisms of Inhibition and Structure-Activity Relationships", *PLoS One*, Nov. 2010, e13719, 12 pages, vol. 5, issue 11, Public Library of Science, San Francisco, CA, US.
Noe, A., et al., "High Incidence of Severe Cyclosporine Neurotoxicity in Children Affected by Haemoglobinopaties Undergoing Myeloablative Haematopoietic Stem Cell Transplantation: Early Diagnosis and Prompt Intervention Ameliorates Neurological Outcome," *Italian Journal of Pediatrics*, Feb. 6, 2010, Article No. 14, pp. 1-6, vol. 36, BioMedCentral, London, UK.
Nogradi, K., et al., "Thieno[2,3-b]pyridines as Negative Allosteric Modulators of Metabotropic GluR5 Receptors: Hit-To-Lead Optimization," *Bioorganic and Medicinal Chemistry Letters*, 2014, pp. 3845-3849, vol. 24, Elsevier, Amsterdam, NL.
North, T.E., et al., "Prostaglandin E2 Regulates Vertebrate Haematopoietic Stem Cell Homeostasis," *Nature*, Jun. 21, 2007, pp. 1007-1011, vol. 447, Nature Research, London, UK.
North, Trista E., "PGE2-Regulated wnt Signaling and N-Acetylcysteine Are Synergistically Hepatoprotective in Zebrafish Acetaminophen Injury", *Proceedings of the National Academy of Sciences*, Oct. 5, 2010, pp. 17315-17320, vol. 107, No. 40, United States National Academy of Sciences, Washington, DC, US.
Obeid, J., et al., "TYR-179 and LYS-183 are Essential for Enzymatic Activity of 11 β-Hydroxysteroid Dehydroxysteroid Dehydrogenase," *Biochemical and Biophysical Research Communications*, Oct. 15, 1992, Abstract, vol. 188, Issue 1, Academic Press, Elsevier, Amsterdam, NL.
Oh, S.Y., et al., "Comparison of Experimental Mouse Models of Inflammatory Bowel Disease," *International Journal of Molecular Medicine*, 2014, pp. 333-340, vol. 33, Issue 2, Spandidos Publications, UK.
Olson, L.E., et al., "Protection from Doxorubicin-Induced Cardiac Toxicity in Mice with a Null Allele of Carbonyl Reductase 1",

(56) References Cited

OTHER PUBLICATIONS

*Cancer Research*, Oct. 15, 2003, six pages including pp. 6602-6606, vol. 63, American Association for Cancer Research, Philadelphia, PA, US.

Otani, T., et al., "Levels of $NAD^+$-dependent 15-Hydroxyprostaglandin Dehydrogenase are Reduced in Inflammatory Bowel Disease: Evidence for Involvement of TNF-α", *American Journal of Physiology—Gastrointestinal and Liver Physiology*, 2006, G361-G368, vol. 290, American Physiological Society, Rockville, MD, US.

Packer, Milton, et al., "Consensus recommendations for the management of chronic heart failure. On behalf of the membership of the advisory council to improve outcomes nationwide in heart failure," *The American Journal of Cardiology*, Jan. 21, 1999, pp. 1a-38a, vol. 83 (2a), Elsevier Inc., NL.

Park, S.H., et al., "Effect of Thiazolidinedione Phenylacetate Derivatives on Wound-Healing Activity," *Archives of Pharmacal Research*, 2019, pp. 790-814, vol. 42, Springer Science + Business Media, Berlin, DE.

Parveen, H., et al., "Synthesis and Characterization of a New Series of Hydroxy Pyrazolines," Synthetic Communications, 2008, pp. 3973-3983, vol. 38, Taylor and Francis, London, UK.

Patani, L., et al., "Bioisosterism: A Rational Approach in Drug Design," *Chemical Reviews*, 1996, pp. 3147-3176, vol. 96, No. 8, American Chemical Society, Washington, DC, US.

Pelus, L.M., et al., "Pleiotropic Effects of Prostaglandin $E_2$ in Hematopoiesis; Prostaglandin $E_2$ and Other Eicosanoids Regulate Hematopoietic Stern and Progenitor Cell Function," *Prostaglandins and Other Lipid Mediators*, 2011, pp. 3-9, vol. 96, Elsevier, Amsterdam, NL.

Pelus, L.M., et al., "Pulse Exposure of Haematopoietic Grafts to Prostaglandin $E_2$ in vitro Facilitates Engraftment and Recovery," *Cell Proliferation*, 2011, pp. 22-29, vol. 44, Suppl. 1, Wiley, Hoboken, NJ, US.

Perse, M., and Cerar, A., "Dextran Sodium Sulphate Colitis Mouse Model: Traps and Tricks," *Journal of Biomedicine and Biotechnology*, 2012, Article ID 718617, 13 pages, vol. 2012, Hindawi Publishing Corporation, London, UK.

Piao, Y.L., et al., "Wound Healing Effects of New 15-Hydroxyprostaglandin Dehydrogenase Inhibitors," *Prostaglandins, Leukotrienes and Essential Fatty Acids*, 2014, pp. 325-332, vol. 91, Elsevier, Amsterdam, NL.

Piao, Y.L., et al., "Cell-based Biological Evaluations of 5-(3-bromo-4-phenethoxybenzylidene)thiazolidine-2,4-dione As Promising Wound Healing Agent," *Bioorganic and Medicinal Chemistry*, May 1, 2015, pp. 2098-2103, vol. 23, Issue 9, Elsevier, Amsterdam, NL.

Piska, K., et al., "Metabolic Carbonyl Reduction of Anthracyclines—Role in Cardiotoxicity and Cancer Resistance: Reducing Enzymes as Putative Targets for Novel Cardioprotective and Chemosensitizing Agents", *Investigational New Drugs*, 2017, pp. 375-385, vol. 35, Springer, Berlin, DE.

Porter, G.A., "Contrast-Associated Nephropathy," *The American Journal of Cardiology*, Sep. 5, 1989, pp. 22E-26E, vol. 64, Issue 9, Elsevier, Amsterdam, NL.

Porter, R.L., et al., "Prostaglandin E2 Increases Hematopoietic Stem Cell Survival and Accelerates Hematopoietic Recovery After Radiation Injury," *Stem Cells*, 2013, pp. 372-383, vol. 31, AlphaMed Press, Hoboken, NJ, US.

Randhawa, P.K., et al., "A Review on Chemical-Induced Inflammatory Bowel Disease Models in Rodents," *Korean Journal of Physiology and Pharmacology*, Aug. 2014, pp. 279-288, vol. 18, Issue 4, The Korean Journal of Physiology and Pharmacology, KR.

Renneville, A., et al., "EHMT1 and EHMT2 Inhibition Induces Fetal Hemoglobin Expression," *Blood*, Oct. 15, 2015, pp. 1930-1939, vol. 126, No. 16, American Society of Hematology, Washington, DC, US.

Rieder, F., et al., "Animal Models of Intestinal Fibrosis: New Tools for the Understandig of Pathogenesis and Therapy of Human Disease," *American Journal of Physiology—Gastrointestinal and Liver Physiology*, Aug. 9, 2012, 6786-6801, 303(4, Pt. 1), American Physiological Society, Rockville, MD, US.

Roberts, C.R., "Is Asthma a Fibrotic Disease," *Chest*, Mar. 1995, vol. 107, pp. 111S-117S, American College of Chest Physicians, Glenview, IL, US.

Robison, T.W., and Giri, S.N., "Effects of Chronic Administration of Doxorubicin on Plasma Levels of Prostaglandins, Thromboxane $B_2$, and Fatty Acids in Rats," *Cancer Chemotherapy and Pharmacology*, May 1987, pp. 213-220, vol. 19, Springer Science + Business Media, Berlin, DE.

Rocchiccioli, F., et al., "Quantitative Gas Chromatography-Chemical Ionization Mass Spectrometry of 2-Ketoglutarate from Urine as its O-trimethylsilyl-quinoxalinol Derivative", *Journal of Chromatography*, Dec. 11, 1981, pp. 325-332, vol. 226, No. 2, Elsevier, Amsterdam, NL.

Rogaeva, Ekaterina, et al., "The neuronal sortilin-related receptor SORL1 is genetically associated with Alzheimer disease," *Nature Genetics*, Feb. 2007, pp. 168-177, vol. 39, No. 2, Nature Publishing Group, UK.

Ronzoni, L., et al., "Modulation of Gamma Globulin Genes Expression by Histone Deacetylase Inhibitors: An in vitro Study," Mar. 7, 2014, pp. 714-721, vol. 165, British Journal of Hematology, John Wiley & Sons, UK.

Rossi, F., et al., "Cardiotoxicity of Doxorubicin: Effects of Drugs Inhibiting the Release of Vasoactive Substances," *Pharmacology & Toxicology*, Aug. 1994, Abstract, vol. 75, Issue 2, Pharmacology & Toxicology, DK.

Sasaki, S., et al., "Prostaglandin $E_2$ Inhibits Lesion Formation in Dextran Sodium Sulphate-Induced Colitis in Rats and Reduces the Levels of Mucosal Inflammatory Cytokines", *Scandinavian Journal of Immunology*, 2000, pp. 23-28, vol. 51, Wiley, UK.

Schaefer, C.F., et al., "PID: The Pathway Interaction Database," *Nucleic Acids Research*, 2009, pp. D674-D679, vol. 37, Oxford University Press, Oxford, UK.

Seo, S.Y., et al., "Effect of 15-Hydroxyprostaglandin Dehydrogenase Inhibitor on Wound Healing," *Prostaglandinsz Leukotrienesz and Essential Fatty Acids*, 2015, pp. 35-41, vol. 97, Elsevier, Amsterdam, NL.

Seto, M., et al., "Orally Active CCR5 Antagonists as Anti-HIV-1 Agents. Part 3: Synthesis and Biological Activities of 1-Benzazepine Derivatives Containing a Sulfoxide Moiety," *Bioorganic and Medicinal Chemistry*, 2005, pp. 363-386, vol. 13, Elsevier, Amsterdam, NL.

Shannon, P., et al., "Cytoscape: A Software Environment for Integrated Models of Biomolecular Interaction Networks," *Genome Research*, 2003, 8 pages including pp. 2498-2504, vol. 13, Cold Spring Harbor Laboratory Press, Cold Spring Harbor, NY, US.

Sharkey, L.C., et al., "Differential Cardiotoxicity in Response to Chronic Doxorubicin Treatment in Male Spontaneous Hypertension-Heart Failure (SHHF), Spontaneously Hypertensive (SHR), and Wistar Kyoto (WKY) Rats," *Toxicology and Applied Pharmacology*, 2013, pp. 47-57, vol. 273, Issue 1, Elsevier, Amsterdam, NL.

Shi, J., et al., "Inflammatory Prostaglandin E2 Signaling in a Mouse Model of Alzheimer Disease," *Annals of Neurology*, (Nov. 2012), pp. 1-11, vol. 72, Iss. 5, John Wiley and Sons, Hoboken, NJ, US.

Smith, J.N.P., et al., "Inhibition of 15-PGDH Protects Mice from Immune-Mediated Bone Marrow Failure," *Biology of Blood and Marrow Transplantation*, 2020, pp. 1552-1556, vol. 26, Elsevier, Amsterdam, NL.

Smith, J.N.P., "Therapeutic Targeting of 15-PGDH in Murine Pulmonary Fibrosis," *Scientific Reports*, 2020, 11657, 10 pages, vol. 10, Nature Research, London, UK.

Smusz, S., et al., "Fingerprint-based Consensus Virtual Screening Towards Structurally New 5-$HT_6$R Ligands," *Bioorganic and Medicinal Chemistry Letters*, 2015, pp. 1827-1830, vol. 25, Issue 9, Elsevier, Amsterdam, NL.

Solomon, L., et al., "The Dextran Sulphate Sodium (DSS) Model of Colitis: An Overview," *Comparative Clinical Pathology*, Mar. 4, 2010, pp. 235-239, vol. 19, Springer, Munich, DE.

Somasundaram, S., et al., "The DNMT1-Associated lincRNA DACOR1 Reprograms Genome-Wide DNA Methylation in Colon Cancer," *Clinical Egigenetics*, 2018, 15 pages, 10:127, BioMedCentral, London, UK.

Sood, A., et al., "A Prospective, Open-Label Trial Assessing Dexamethasone Pulse Therapy in Moderate to Sever Ulcerative

(56) References Cited

OTHER PUBLICATIONS

Colitis," *Journal of Clinical Gastroenterology*, Oct. 2002, pp. 328-331, vol. 35, Issue 4, Lippincott Williams & Wilkins, Philadelphia, PA, US.
"Specs," Web page <www.specs.net/>, 2 pages, Dec. 25, 2003, retrieved from the Internet Archive Wayback Machine without Page Vault <http://web.archive.org/web/20031225052253/http://www.specs.net/> on Oct. 26, 2022.
"Specs," Web page <www.specs.net/>, 2 pages, Dec. 25, 2003, retrieved from the Internet Archive Wayback Machine via Page Vault <http://web.archive.org/web/20031225052253/http://www.specs.net/> on Sep. 29, 2022.
Speth, J. M., et al., "Pharmacologic Increase in HIF1α Enhances Hematopoietic Stem and Progenitor Homing and Engraftment," *Blood*, Jan. 9, 2014, six pages including pp. 203-207, vol. 123, No. 2, American Society of Hematology, Washington, DC, US.
St George-Hyslop, P.H., et al., "The Genetic Defect Causing Familial Alzheimer's Disease Maps on Chromosome 21," *Science*, Feb. 20, 1987, pp. 885-890, vol. 235, Issue 4791, American Association for the Advancement of Science, Washington, DC, US.
Tai, H.-H., et al., "Prostaglandin Catabolizing Enzymes", *Prostaglandins and Other Lipid Mediators*, 2002, pp. 483-493, Elsevier Science Inc., Amsterdam, NL.
Tanaka, N., et al., "Crystal Structures of the Binary and Ternary Complexes of 7α-Hydroxysteroid Dehydrogenase from *Escherichia coli*," *Biochemistry*, Jun. 18, 1996, pp. 7715-7730, vol. 35, Issue 24, American Chemical Society, Washington, DC, US.
Tanaka, Y., et al., "Systems Analysis of ATF3 in Stress Response and Cancer Reveals Opposing Effects on Pro-Apoptotic Genes in p53 Pathway," *PLoS One*, Oct. 2011, e26848, 12 pages, vol. 6, Issue 10, Public Library of Science, San Francisco, CA, US.
Tatsuwaki, H., et al., "Reduction of 15-Hydroxyprostaglandin Dehydrogenase Expression Is An Independent Predictor of Poor Survival Associated with Enhanced Cell Proliferation in Gastric Adenocarcinoma," *Cancer Science*, Feb. 2010, pp. 550-558, vol. 101, No.2, Wiley-Blackwell, Hoboken, NJ, US.
Tessner, T.G., et al., "Prostaglandins Prevent Decreased Epithelial Cell Proliferation Associated With Dextran Sodium Sulfate Injury in Mice", *Gastroenterology*, Oct. 1998, pp. 874-882, vol. 115, No. 4, Elsevier, Amsterdam, NL.
Tong, M ., et al., "15-Hydroxyprostaglandin Dehydrogenase Can Be Induced by Dexamethasone and Other Glucocorticoids at the Therapeutic Level in A549 Human Lung Adenocarcinoma Cells," *Archives of Biochemistry and Biophysics*, Mar. 1, 2005, pp. 50-55, vol. 435, issue 1, Elsevier, Amsterdam, NL.
Valatas, V., et al., "Experimental Colitis Models: Insights into the Pathogenesis of Inflammatory Bowel Disease and Translational Issues," *European Journal of Pharmacology*, 2015, pp. 253-264, vol. 759, Elsevier, Amsterdam, NL.
Varadan, V., et al., "The Integration of Biological Pathway Knowledge in Cancer Genomics," *IEEE Signal Processing Magazine*, Jan. 2012, 20 pages, vol. 29, Issue 1, IEEE Signal Processing Society, Piscataway, NJ, US.
Vaske, C.J., et al, "Inference of patient-specific pathway activities from multi-dimensional cancer genomics data using Paradigm," *Bioinformatics*, 2010, pp i237-i245, vol. 26, Oxford University Press, Oxford, UK.
Vukicevic, S., et al., "Role of EP2 and EP4 Receptor-Selective Agonists of Prostaglandin $E_2$ in Acute and Chronic Kidney Failure," *Kidney International*, 2006, pp. 1099-1106, vol. 70, Elsevier on behalf of the International Society of Nephrology, Amsterdam, NL.
Wallace, J.L., "Prostaglandins, NSAIDs, and Gastric Mucosal Protection: Why Doesn't the Stomach Digest Itself?" *Physiol Reviews*, 2008, pp. 1547-1565, vol. 88, No. 4, The American Physiological Society, Rockville, MD, US.
Wang, J., et al., "Design, Synthesis, and Pharmacological Evaluation of Novel Piperlongumine Derivatives as Potential Antiplatelet Aggregation Candidate," *Chemical Biology and Drug Design*, 2016, pp. 883-840, vol. 87, Issue 6, John Wiley & Sonse A/S, Hoboken, NJ.
Wang, J., et al., "Chemopreventive Efficacy of the Cyclooxygenase-2 (Cox-2) Inhibitor, Celecoxib, is Predicted By Adenoma Expression of Cox-2 and 15-PGDH," *Cancer Epidemiology, Biomarkers, and Prevention*, Jul. 2018, 20 pages, vol. 27, Issue 7, American Association for Cancer Research, Philadelphia, PA, US.
Wang, Q., et al., "Discovery of Novel Allosteric Effectors Based on the Predicted Allosteric Sites for *Escherichia coli* D-3-Phosphoglycerate Dehydrogenase", PLOS One, Apr. 14, 2014, p. e94829, vol. 9, issue 4, Public Library of Science, San Francisco, CA, US.
Wang, Y.F., et al., "Meta-Analysis of Drug-Eluting Versus Bare Mtal Stents in Patients with Indications for Oral Anticoagulation Undergoing Coronary Stenting," Acta Cardiologica, 2014, pp. 237-244, vol. 69, Issue 3, Belgian Society of Cardiology, BE, Springer.
Wei, Q., and Dong, Z., "Mouse Model of Ischemic Acute Kidney Injury: Technical Notes and Tricks," *American Journal of Physiology—Renal Physiology*, Sep. 19, 2012, F1487-F1494, vol. 303, American Physiological Society, Rockville, MD, US.
Westbrook, A.M., et al., "Mouse Models of Intestinal Inflammation and Cancer," *Archives of Toxicology*, 2016, 22 pages, vol. 90, Issue 9, Springer-Verlag, DE.
Wirtz, S., and Neurath, M.F., "Mouse Models of Inflammatory Bowel Disease," *Advanced Drug Delivery Reviews*, 2007, pp. 1073-1083, vol. 59, Issue 11, Elsevier B.V., Amsterdam, NL.
Wu, Y., et al., "Synthesis and SAR of Thiazolidinedione Derivatives as 15-PGDH Inhibitors," *Bioorganic and Medicinal Chemistry*, Feb. 15, 2010, Abstract, vol. 18, Issue 4, Elsevier Ltd., Amsterdam, NL.
Wu, Y., et al. "Synthesis and Biological Evaluation of Novel Thiazolidinedione Analogues as 15-Hydroxyprostaglandin Dehydrogenase Inhibitors," *Journal of Medicinal Chemistry*, 2011, pp. 5260-5264, vol. 54, American Chemical Society, Washington, DC, US.
Xie, M., et al., "Effects of small molecule inhibitor SW033291 on hepatic ischemia-reperfusion injury in mice." *Biochemical and Biophysical Research Communications*, (Jul. 2022), pp. 70-74, vol. 615, Elsevier, Amsterdam, NL.
Yan, M., et al., "15-Hydroxyprostaglandin dehydrogenase, a COX-2 oncogene antagonist, is a TGF-β-induced suppressor of human gastrointestinal cancers", *Proceedings of the National Academy of Sciences*, Dec. 14, 2004, pp. 17468-17473, vol. 101, No. 50, United States National Academy of Sciences, Washington, DC, US.
Yan, C., et al., "Cyclooxygenases, Microsomal Prostaglandin E Synthase-1, and Cardiovascular Function," *The Journal of Clinical Investigation*, 2006, pp. 1391-1399, vol. 116, Issue 5, American Society for Clinical Investigation, US.
Yan, Min, et al, "15-Hydroxyprostaglandin dehydrogenase inactivation as a mechanism of resistance to celecoxib chemoprevention of colon tumors", *Proceedings of the National Academy of Sciences*, Jun. 9, 2009, pp. 9409-9413, vol. 106, No. 23, United States National Academy of Sciences, Washington, DC, US.
Yang, H., et al., "Altered Hippocampal Long-Term Synaptic Plasticity in Mice Deficient in the PGE2 EP2 Receptor," *Journal of Neurochemistry*, 2009, pp. 295-304, vol. 108, Wiley-Blackwell, Hoboken, NJ, US.
Yao, R., et al., "Comparison of Clinical Efficacy of Different Statins on Cardiovascular Events Following Percutaneous Coronary Intervention," *International Journal of Clinical and Experimental Medicine*, 2017, 11286, vol. 10, Issue 7, e-Century Publishing Corporation, Madison, WI, US, Article Retracted.
Yeh, F.-L., et al., "Keloid-Derived Fibroblasts Have a Diminished Capacity to Produce Prostaglandin $E_2$," *Burns*, 2006, pp. 299-304, vol. 32, Elsevier Ltd., Amsterdam, NL.
Zhan, C., et al., "A dopamine-precursor-based nanoprodrug for in-situ drug release and treatment of acute liver failure by inhibiting NLRP3 inflammasome and facilitating liver regeneration." *Biomaterials*, (Jan. 2021), pp. 1-13, vol. 268, Elsevier, Amsterdam, NL.
Zhang, Y., "Inhibition of the Prostaglandin Degrading Enzyme 15-PGDH Potentiates Tissue Regeneration," *Science*, Jun. 12, 2015, p. 1223, pp. aaa2340-1 to aaa2340-8, vol. 348, Issue 6240, American Association for the Advancement of Science, Washington, DC, US.

(56) References Cited

OTHER PUBLICATIONS

Zhang, Y., et al., "Prasugrel Suppresses Development of Lithium-Induced Nephrogenic Diabetes Insipidus in Mice," *Purinergic Signalling*, 2017, pp. 239-248, vol. 13, Springer Science + Business Media, Berlin, DE.
Zhang, Y., et al., "Impacts of CYP2C19 Genetic Polymorphisms on Bioavailability and Effect on Platelet Adhesion of Vicagrel, a Novel Thienopyridine $P2Y_{12}$ Inhibitor," *British Journal of Clinical Pharmacology*, 2020, pp. 1860-1874, vol. 86, The British Pharmacological Society, Wiley-Blackwell, Hoboken, NJ, US.
Zhao, L., et al., "Design, Synthesis and SAR of Thienopyridines as Potent CHK1 Inhibitors," *Bioorganic and Medicinal Chemistry Letters*, Dec. 15, 2010, pp. 7216-7221, vol. 20, Issue 24, Elsevier Ltd., Amsterdam, NL.
Zhou, Y., and Gong, Y., "Asymmetric Copper(II)-Catalysed Nitroaldol (Henry) Reactions Utilizing a Chiral $C_1$-Symmetric Dinitrogen Ligand," *European Journal of Organic Chemistry*, 2011, pp. 6092-6099, vol. 2011, Issue 30, Wiley-VCH Verlag GmbH & Co. KGaA, Weinheim, DE.
CAS Registry No. 296798-64-6 [online database], STN Entry Date Oct. 18, 2000 [retrieved on Oct. 21, 2022], Retrieved from SciFinder <https://scifinder-n.cas.org/>, substance detail downloaded to PDF.
CAS Registry No. 299406-22-7 [online database], STN Entry Date Oct. 26, 2000 [retrieved on Oct. 24, 2022], Retrieved from SciFinder <https://scifinder-n.cas.org/>, substance detail downloaded to pdf.
CAS Registry No. 299920-58-4 [online database], STN Entry Date Oct. 27, 2000 [retrieved on Sep. 21, 2022], Retrieved from SciFinder <https://scifinder-n.cas.org/>, substance detail downloaded to PDF.
CAS Registry No. 299920-59-5 [online database], STN Entry Date Oct. 27, 2000 [retrieved on Sep. 21, 2022], Retrieved from SciFinder <https://scifinder-n.cas.org/>, substance detail downloaded to PDF.
CAS Registry No. 299920-60-8 [online database], STN Entry Date Oct. 27, 2000 [retrieved on Feb. 8, 2023], Retrieved from SciFinder <https://scifinder-n.cas.org/>, substance detail downloaded to PDF.
CAS Registry No. 299920-61-9 [online database], STN Entry Date Oct. 27, 2000 [retrieved on Sep. 16, 2022], Retrieved from SciFinder <https://scifinder-n.cas.org/>, substance detail downloaded to PDF.
CAS Registry No. 299920-78-8 [online database], STN Entry Date Oct. 27, 2000 [retrieved on Sep. 21, 2022], Retrieved from SciFinder <https://scifinder-n.cas.org/>, substance detail downloaded to PDF.
CAS Registry No. 306766-39-2 [online database], STN Entry Date Dec. 5, 2000 [retrieved on Oct. 24, 2022], Retrieved from SciFinder <https://scifinder-n.cas.org/>, substance detail downloaded to pdf.
CAS Registry No. 313245-69-1 [online database], STN Entry Date Jan. 9, 2001 [retrieved on Oct. 24, 2022], Retrieved from SciFinder <https://scifinder-n.cas.org/>, substance detail downloaded to pdf.
CAS Registry No. 313245-70-4 [online database], STN Entry Date Jan. 9, 2001 [retrieved on Sep. 16, 2022], Retrieved from SciFinder <https://scifinder-n.cas.org/>, substance detail downloaded to PDF.
CAS Registry No. 331447-76-8 [online database], STN Entry Date Apr. 16, 2001 [retrieved on Sep. 16, 2022], Retrieved from SciFinder <https://scifinder-n.cas.org/>, substance detail downloaded to PDF.
CAS Registry No. 331655-85-7 [online database], STN Entry Date Apr. 17, 2001 [retrieved on Sep. 16, 2022], Retrieved from SciFinder <https://scifinder-n.cas.org/>, substance detail downloaded to PDF.
CAS Registry No. 331655-86-8 [online database], STN Entry Date Apr. 17, 2001 [retrieved on Sep. 16, 2022], Retrieved from SciFinder <https://scifinder-n.cas.org/>, substance detail downloaded to PDF.
CAS Registry No. 332945-05-8 [online database], STN Entry Date Apr. 26, 2001 [retrieved on Oct. 24, 2022], Retrieved from SciFinder <https://scifinder-n.cas.org/>, substance detail downloaded to pdf.
CAS Registry No. 348151-19-9 [online database], STN Entry Date Jul. 25, 2001 [retrieved on Sep. 21, 2022], Retrieved from SciFinder <https://scifinder-n.cas.org/>, substance detail downloaded to PDF.
CAS Registry No. 350511-89-6 [online database], STN Entry Date Aug. 6, 2001 [retrieved on Sep. 16, 2022], Retrieved from SciFinder <https://scifinder-n.cas.org/>, substance detail downloaded to PDF.
CAS Registry No. 369400-43-1 [online database], STN Entry Date Nov. 13, 2001 [retrieved on Sep. 16, 2022], Retrieved from SciFinder <https://scifinder-n.cas.org/>, substance detail downloaded to PDF.
CAS Registry No. 369402-41-5 [online database], STN Entry Date Nov. 13, 2001 [retrieved on Sep. 16, 2022], Retrieved from SciFinder <https://scifinder-n.cas.org/>, substance detail downloaded to PDF.
CAS Registry No. 370572-70-6 [online database], STN Entry Date Nov. 16, 2001 [retrieved on Sep. 21, 2022], Retrieved from SciFinder <https://scifinder-n.cas.org/>, substance detail downloaded to PDF.
CAS Registry No. 370870-44-3 [online database], STN Entry Date Nov. 19, 2001 [retrieved on Sep. 21, 2022], Retrieved from SciFinder <https://scifinder-n.cas.org/>, substance detail downloaded to PDF.
CAS Registry No. 371116-23-3 [online database], STN Entry Date Nov. 20, 2001 [retrieved on Sep. 16, 2022], Retrieved from SciFinder <https://scifinder-n.cas.org/>, substance detail downloaded to PDF.
CAS Registry No. 371117-75-8 [online database], STN Entry Date Nov. 20, 2001 [retrieved on Sep. 21, 2022], Retrieved from SciFinder <https://scifinder-n.cas.org/>, substance detail downloaded to PDF.
CAS Registry No. 371118-22-8 [online database], STN Entry Date Nov. 20, 2001 [retrieved on Sep. 21, 2022], Retrieved from SciFinder <https://scifinder-n.cas.org/>, substance detail downloaded to PDF.
CAS Registry No. 371144-00-2 [online database], STN Entry Date Nov. 20, 2001 [retrieved on Sep. 16, 2022], Retrieved from SciFinder <https://scifinder-n.cas.org/>, substance detail downloaded to PDF.
CAS Registry No. 371208-33-2 [online database], STN Entry Date Nov. 21, 2001 [retrieved on Sep. 16, 2022], Retrieved from SciFinder <https://scifinder-n.cas.org/>, substance detail downloaded to PDF.
CAS Registry No. 371213-13-7 [online database], STN Entry Date Nov. 21, 2001 [retrieved on Sep. 21, 2022], Retrieved from SciFinder <https://scifinder-n.cas.org/>, substance detail downloaded to PDF.
CAS Registry No. 371222-38-7 [online database], STN Entry Date Nov. 21, 2001 [retrieved on Sep. 21, 2022], Retrieved from SciFinder <https://scifinder-n.cas.org/>, substance detail downloaded to PDF.
CAS Registry No. 371232-15-4 [online database], STN Entry Date Nov. 21, 2001 [retrieved on Sep. 21, 2022], Retrieved from SciFinder <https://scifinder-n.cas.org/>, substance detail downloaded to PDF.
CAS Registry No. 371926-65-7 [online database], STN Entry Date Nov. 27, 2001 [retrieved on Sep. 16, 2022], Retrieved from SciFinder <https://scifinder-n.cas.org/>, substance detail downloaded to PDF.
CAS Registry No. 384861-16-9 [online database], STN Entry Date Jan. 20, 2002 [retrieved on Sep. 21, 2022], Retrieved from SciFinder <https://scifinder-n.cas.org/>, substance detail downloaded to PDF.
CAS Registry No. 420824-06-2 [online database], STN Entry Date May 23, 2002 [retrieved on Sep. 16, 2022], Retrieved from SciFinder <https://scifinder-n.cas.org/>, substance detail downloaded to PDF.
CAS Registry No. 420825-11-2 [online database], STN Entry Date May 23, 2002 [retrieved on Sep. 21, 2022], Retrieved from SciFinder <https://scifinder-n.cas.org/>, substance detail downloaded to PDF.
CAS Registry No. 420825-38-3 [online database], STN Entry Date May 23, 2002 [retrieved on Sep. 21, 2022], Retrieved from SciFinder <https://scifinder-n.cas.org/>, substance detail downloaded to PDF.
CAS Registry No. 442152-75-2 [online database], STN Entry Date Aug. 2, 2002 [retrieved on Sep. 21, 2022], Retrieved from SciFinder <https://scifinder-n.cas.org/>, substance detail downloaded to PDF.
CAS Registry No. 442152-82-1 [online database], STN Entry Date Aug. 2, 2002 [retrieved on Sep. 16, 2022], Retrieved from SciFinder <https://scifinder-n.cas.org/>, substance detail downloaded to PDF.
CAS Registry No. 442152-88-7 [online database], STN Entry Date Aug. 2, 2002 [retrieved on Sep. 16, 2022], Retrieved from SciFinder <https://scifinder-n.cas.org/>, substance detail downloaded to PDF.
CAS Registry No. 442152-94-5 [online database], STN Entry Date Aug. 2, 2002 [retrieved on Sep. 16, 2022], Retrieved from SciFinder <https://scifinder-n.cas.org/>, substance detail downloaded to PDF.
CAS Registry No. 442153-01-7 [online database], STN Entry Date Aug. 2, 2002 [retrieved on Sep. 16, 2022], Retrieved from SciFinder <https://scifinder-n.cas.org/>, substance detail downloaded to PDF.
CAS Registry No. 442153-03-9 [online database], STN Entry Date Aug. 2, 2002 [retrieved on Sep. 21, 2022], Retrieved from SciFinder <https://scifinder-n.cas.org/>, substance detail downloaded to PDF.
CAS Registry No. 448191-85-3 [online database], STN Entry Date Sep. 9, 2002 [retrieved on Sep. 21, 2022], Retrieved from SciFinder <https://scifinder-n.cas.org/>, substance detail downloaded to PDF.
CAS Registry No. 448191-89-7 [online database], STN Entry Date Sep. 9, 2002 [retrieved on Sep. 21, 2022], Retrieved from SciFinder <https://scifinder-n.cas.org/>, substance detail downloaded to PDF.

(56) References Cited

OTHER PUBLICATIONS

CAS Registry No. 452922-28-0 [online database], STN Entry Date Sep. 19, 2002 [retrieved on Sep. 16, 2022], Retrieved from SciFinder <https://scifinder-n.cas.org/>, substance detail downloaded to PDF.

CAS Registry No. 457958-02-0 [online database], STN Entry Date Oct. 2, 2002 [retrieved on Sep. 16, 2022], Retrieved from SciFinder <https://scifinder-n.cas.org/>, substance detail downloaded to PDF.

CAS Registry No. 457958-03-1 [online database], STN Entry Date Oct. 2, 2002 [retrieved on Sep. 16, 2022], Retrieved from SciFinder <https://scifinder-n.cas.org/>, substance detail downloaded to PDF.

CAS Registry No. 457958-04-2 [online database], STN Entry Date Oct. 2, 2002 [retrieved on Sep. 16, 2022], Retrieved from SciFinder <https://scifinder-n.cas.org/>, substance detail downloaded to PDF.

CAS Registry No. 457958-05-3 [online database], STN Entry Date Oct. 2, 2002 [retrieved on Sep. 16, 2022], Retrieved from SciFinder <https://scifinder-n.cas.org/>, substance detail downloaded to PDF.

CAS Registry No. 457958-06-4 [online database], STN Entry Date Oct. 2, 2002 [retrieved on Sep. 21, 2022], Retrieved from SciFinder <https://scifinder-n.cas.org/>, substance detail downloaded to PDF.

CAS Registry No. 457958-16-6 [online database], STN Entry Date Oct. 2, 2002 [retrieved on Sep. 16, 2022], Retrieved from SciFinder <https://scifinder-n.cas.org/>, substance detail downloaded to PDF.

CAS Registry No. 457958-17-7 [online database], STN Entry Date Oct. 2, 2002 [retrieved on Sep. 16, 2022], Retrieved from SciFinder <https://scifinder-n.cas.org/>, substance detail downloaded to PDF.

CAS Registry No. 457958-18-8 [online database], STN Entry Date Oct. 2, 2002 [retrieved on Sep. 21, 2022], Retrieved from SciFinder <https://scifinder-n.cas.org/>, substance detail downloaded to PDF.

CAS Registry No. 457958-30-4 [online database], STN Entry Date Oct. 2, 2002 [retrieved on Sep. 16, 2022], Retrieved from SciFinder <https://scifinder-n.cas.org/>, substance detail downloaded to PDF.

CAS Registry No. 457958-31-5 [online database], STN Entry Date Oct. 2, 2002 [retrieved on Sep. 21, 2022], Retrieved from SciFinder <https://scifinder-n.cas.org/>, substance detail downloaded to PDF.

CAS Registry No. 457958-32-6 [online database], STN Entry Date Oct. 2, 2002 [retrieved on Sep. 16, 2022], Retrieved from SciFinder <https://scifinder-n.cas.org/>, substance detail downloaded to PDF.

CAS Registry No. 457958-38-2 [online database], STN Entry Date Oct. 2, 2002 [retrieved on Sep. 16, 2022], Retrieved from SciFinder <https://scifinder-n.cas.org/>, substance detail downloaded to PDF.

CAS Registry No. 457958-39-3 [online database], STN Entry Date Oct. 2, 2002 [retrieved on Sep. 16, 2022], Retrieved from SciFinder <https://scifinder-n.cas.org/>, substance detail downloaded to PDF.

CAS Registry No. 457958-40-6 [online database], STN Entry Date Oct. 2, 2002 [retrieved on Sep. 21, 2022], Retrieved from SciFinder <https://scifinder-n.cas.org/>, substance detail downloaded to PDF.

CAS Registry No. 457958-41-7 [online database], STN Entry Date Oct. 2, 2002 [retrieved on Sep. 16, 2022], Retrieved from SciFinder <https://scifinder-n.cas.org/>, substance detail downloaded to PDF.

CAS Registry No. 457958-49-5 [online database], STN Entry Date Oct. 2, 2002 [retrieved on Sep. 16, 2022], Retrieved from SciFinder <https://scifinder-n.cas.org/>, substance detail downloaded to PDF.

CAS Registry No. 457958-50-8 [online database], STN Entry Date Oct. 2, 2002 [retrieved on Sep. 21, 2022], Retrieved from SciFinder <https://scifinder-n.cas.org/>, substance detail downloaded to PDF.

CAS Registry No. 459147-27-4 [online database], STN Entry Date Oct. 4, 2002 [retrieved on 2022-09-16], Retrieved from SciFinder <https://scifinder-n.cas.org/>, substance detail downloaded to PDF.

CAS Registry No. 459147-39-8 [online database], STN Entry Date Oct. 4, 2002 [retrieved on Sep. 16, 2022], Retrieved from SciFinder <https://scifinder-n.cas.org/>, substance detail downloaded to PDF.

CAS Registry No. 459147-74-1 [online database], STN Entry Date Oct. 4, 2002 [retrieved on Sep. 21, 2022], Retrieved from SciFinder <https://scifinder-n.cas.org/>, substance detail downloaded to PDF.

CAS Registry No. 459150-70-0 [online database], STN Entry Date Oct. 4, 2002 [retrieved on Sep. 21, 2022], Retrieved from SciFinder <https://scifinder-n.cas.org/>, substance detail downloaded to PDF.

CAS Registry No. 459150-74-4 [online database], STN Entry Date Oct. 4, 2002 [retrieved on Sep. 16, 2022], Retrieved from SciFinder <https://scifinder-n.cas.org/>, substance detail downloaded to PDF.

CAS Registry No. 459150-94-8 [online database], STN Entry Date Oct. 4, 2002 [retrieved on Sep. 16, 2022], Retrieved from SciFinder <https://scifinder-n.cas.org/>, substance detail downloaded to PDF.

CAS Registry No. 459151-05-4 [online database], STN Entry Date Oct. 4, 2002 [retrieved on Sep. 21, 2022], Retrieved from SciFinder <https://scifinder-n.cas.org/>, substance detail downloaded to PDF.

CAS Registry No. 459152-84-2 [online database], STN Entry Date Oct. 4, 2002 [retrieved on Sep. 16, 2022], Retrieved from SciFinder <https://scifinder-n.cas.org/>, substance detail downloaded to PDF.

CAS Registry No. 459153-20-9 [online database], STN Entry Date Oct. 4, 2002 [retrieved on Sep. 16, 2022], Retrieved from SciFinder <https://scifinder-n.cas.org/>, substance detail downloaded to PDF.

CAS Registry No. 459153-24-3 [online database], STN Entry Date Oct. 4, 2002 [retrieved on Sep. 21, 2022], Retrieved from SciFinder <https://scifinder-n.cas.org/>, substance detail downloaded to PDF.

CAS Registry No. 459153-30-1 [online database], STN Entry Date Oct. 4, 2002 [retrieved on Sep. 16, 2022], Retrieved from SciFinder <https://scifinder-n.cas.org/>, substance detail downloaded to PDF.

CAS Registry No. 459153-75-4 [online database], STN Entry Date Oct. 4, 2002 [retrieved on Sep. 21, 2022], Retrieved from SciFinder <https://scifinder-n.cas.org/>, substance detail downloaded to PDF.

CAS Registry No. 459154-25-7 [online database], STN Entry Date Oct. 4, 2002 [retrieved on Sep. 16, 2022], Retrieved from SciFinder <https://scifinder-n.cas.org/>, substance detail downloaded to PDF.

CAS Registry No. 459154-76-8 [online database], STN Entry Date Oct. 4, 2002 [retrieved on Sep. 16, 2022], Retrieved from SciFinder <https://scifinder-n.cas.org/>, substance detail downloaded to PDF.

CAS Registry No. 459154-80-4 [online database], STN Entry Date Oct. 4, 2002 [retrieved on Sep. 16, 2022], Retrieved from SciFinder <https://scifinder-n.cas.org/>, substance detail downloaded to PDF.

CAS Registry No. 459155-72-7 [online database], STN Entry Date Oct. 4, 2002 [retrieved on Sep. 16, 2022], Retrieved from SciFinder <https://scifinder-n.cas.org/>, substance detail downloaded to PDF.

CAS Registry No. 459155-77-2 [online database], STN Entry Date Oct. 4, 2002 [retrieved on Sep. 16, 2022], Retrieved from SciFinder <https://scifinder-n.cas.org/>, substance detail downloaded to PDF.

CAS Registry No. 459155-84-1 [online database], STN Entry Date Oct. 4, 2002 [retrieved on Sep. 21, 2022], Retrieved from SciFinder <https://scifinder-n.cas.org/>, substance detail downloaded to PDF.

CAS Registry No. 693820-48-3 [online database], STN Entry Date Jun. 16, 2004 [retrieved on Sep. 16, 2022], Retrieved from SciFinder <https://scifinder-n.cas.org/>, substance detail downloaded to PDF.

CAS Registry No. 924846-44-6 [online database], STN Entry Date Mar. 5, 2007 [retrieved on Sep. 16, 2022], Retrieved from SciFinder <https://scifinder-n.cas.org/>, substance detail downloaded to PDF.

CAS Registry No. 957625-42-2 [online database], STN Entry Date Dec. 11, 2007 [retrieved on Sep. 21, 2022], Retrieved from SciFinder <https://scifinder-n.cas.org/>, substance detail downloaded to PDF.

CAS Registry No. 957939-31-0 [online database], STN Entry Date Dec. 13, 2007 [retrieved on Sep. 16, 2022], Retrieved from SciFinder <https://scifinder-n.cas.org/>, substance detail downloaded to PDF.

CAS Registry No. 957948-58-2 [online database], STN Entry Date Dec. 13, 2007 [retrieved on Sep. 16, 2022], Retrieved from SciFinder <https://scifinder-n.cas.org/>, substance detail downloaded to PDF.

CAS Registry No. 957957-90-3 [online database], STN Entry Date Dec. 13, 2007 [retrieved on Sep. 21, 2022], Retrieved from SciFinder <https://scifinder-n.cas.org/>, substance detail downloaded to PDF.

CAS Registry No. 1015864-36-4 [online database], STN Entry Date Apr. 20, 2008 [retrieved on Sep. 16, 2022], Retrieved from SciFinder <https://scifinder-n.cas.org/>, substance detail downloaded to PDF.

CAS Registry No. 1015864-38-6 [online database], STN Entry Date Apr. 20, 2008 [retrieved on Sep. 21, 2022], Retrieved from SciFinder <https://scifinder-n.cas.org/>, substance detail downloaded to PDF.

CAS Registry No. 1020685-61-3 [online database], STN Entry Date May 14, 2008 [retrieved on Sep. 16, 2022], Retrieved from SciFinder <https://scifinder-n.cas.org/>, substance detail downloaded to PDF.

CAS Registry No. 1020685-65-7 [online database], STN Entry Date May 14, 2008 [retrieved on Sep. 16, 2022], Retrieved from SciFinder <https://scifinder-n.cas.org/>, substance detail downloaded to PDF.

CAS Registry No. 1020686-01-4 [online database], STN Entry Date May 14, 2008 [retrieved on Sep. 16, 2022], Retrieved from SciFinder <https://scifinder-n.cas.org/>, substance detail downloaded to PDF.

(56) References Cited

OTHER PUBLICATIONS

CAS Registry No. 1020686-06-9 [online database], STN Entry Date May 14, 2008 [retrieved on Sep. 21, 2022], Retrieved from SciFinder <https://scifinder-n.cas.org/>, substance detail downloaded to PDF.

CAS Registry No. 1020686-10-5 [online database], STN Entry Date May 14, 2008 [retrieved on Sep. 21, 2022], Retrieved from SciFinder <https://scifinder-n.cas.org/>, substance detail downloaded to PDF.

CAS Registry No. 1020686-49-0 [online database], STN Entry Date May 14, 2008 [retrieved on Sep. 16, 2022], Retrieved from SciFinder <https://scifinder-n.cas.org/>, substance detail downloaded to PDF.

CAS Registry No. 1020686-53-6 [online database], STN Entry Date May 14, 2008 [retrieved on Sep. 21, 2022], Retrieved from SciFinder <https://scifinder-n.cas.org/>, substance detail downloaded to PDF.

CAS Registry No. 1020686-57-0 [online database], STN Entry Date May 14, 2008 [retrieved on Sep. 16, 2022], Retrieved from SciFinder <https://scifinder-n.cas.org/>, substance detail downloaded to PDF.

CAS Registry No. 1020686-77-4 [online database], STN Entry Date May 14, 2008 [retrieved on Sep. 16, 2022], Retrieved from SciFinder <https://scifinder-n.cas.org/>, substance detail downloaded to PDF.

CAS Registry No. 1020686-81-0 [online database], STN Entry Date May 14, 2008 [retrieved on Sep. 21, 2022], Retrieved from SciFinder <https://scifinder-n.cas.org/>, substance detail downloaded to PDF.

CAS Registry No. 1020687-17-5 [online database], STN Entry Date May 14, 2008 [retrieved on Sep. 16, 2022], Retrieved from SciFinder <https://scifinder-n.cas.org/>, substance detail downloaded to PDF.

CAS Registry No. 1112019-47-2 [online database], STN Entry Date Feb. 26, 2009 [retrieved on Sep. 16, 2022], Retrieved from SciFinder <https://scifinder-n.cas.org/>, substance detail downloaded to PDF.

CAS Registry No. 1115479-64-5 [online database], STN Entry Date Mar. 4, 2009 [retrieved on Sep. 16, 2022], Retrieved from SciFinder <https://scifinder-n.cas.org/>, substance detail downloaded to PDF.

CAS Registry No. 1221411-67-1 [online database], STN Entry Date May 5, 2010 [retrieved on Sep. 16, 2022], Retrieved from SciFinder <https://scifinder-n.cas.org/>, substance detail downloaded to PDF.

CAS Registry No. 1221411-70-6 [online database], STN Entry Date May 5, 2010 [retrieved on Sep. 16, 2022], Retrieved from SciFinder <https://scifinder-n.cas.org/>, substance detail downloaded to PDF.

CAS Registry No. 1347499-81-3 [online database], STN Entry Date Dec. 2, 2011 [retrieved on Sep. 21, 2022], Retrieved from SciFinder <https://scifinder-n.cas.org/>, substance detail downloaded to PDF.

CAS Registry No. 1348234-90-1 [online database], STN Entry Date Dec. 4, 2011 [retrieved on Sep. 21, 2022], Retrieved from SciFinder <https://scifinder-n.cas.org/>, substance detail downloaded to PDF.

CAS Registry No. 1348857-03-3 [online database], STN Entry Date Dec. 5, 2011 [retrieved on Sep. 21, 2022], Retrieved from SciFinder <https://scifinder-n.cas.org/>, substance detail downloaded to PDF.

CAS Registry No. 1349215-63-9 [online database], STN Entry Date Dec. 5, 2011 [retrieved on Sep. 21, 2022], Retrieved from SciFinder <https://scifinder-n.cas.org/>, substance detail downloaded to PDF.

CAS Registry No. 1421694-45-2 [online database], STN Entry Date Feb. 22, 2013 [retrieved on Sep. 16, 2022], Retrieved from SciFinder <https://scifinder-n.cas.org/>, substance detail downloaded to PDF.

CAS Registry No. 1471306-25-8 [online database], STN Entry Date Nov. 11, 2013 [retrieved on Sep. 16, 2022], Retrieved from SciFinder <https://scifinder-n.cas.org/>, substance detail downloaded to PDF.

CAS Registry No. 1471306-27-0 [online database], STN Entry Date Nov. 11, 2013 [retrieved on Sep. 16, 2022], Retrieved from SciFinder <https://scifinder-n.cas.org/>, substance detail downloaded to PDF.

CAS Registry No. 1471306-29-2 [online database], STN Entry Date Nov. 11, 2013 [retrieved on Sep. 16, 2022], Retrieved from SciFinder <https://scifinder-n.cas.org/>, substance detail downloaded to PDF.

CAS Registry No. 1471306-31-6 [online database], STN Entry Date Nov. 11, 2013 [retrieved on Sep. 16, 2022], Retrieved from SciFinder <https://scifinder-n.cas.org/>, substance detail downloaded to PDF.

CAS Registry No. 1471306-33-8 [online database], STN Entry Date Nov. 11, 2013 [retrieved on Sep. 16, 2022], Retrieved from SciFinder <https://scifinder-n.cas.org/>, substance detail downloaded to PDF.

CAS Registry No. 1471306-35-0 [online database], STN Entry Date Nov. 11, 2013 [retrieved on Sep. 16, 2022], Retrieved from SciFinder <https://scifinder-n.cas.org/>, substance detail downloaded to PDF.

CAS Registry No. 1471306-37-2 [online database], STN Entry Date Nov. 11, 2013 [retrieved on Sep. 16, 2022], Retrieved from SciFinder <https://scifinder-n.cas.org/>, substance detail downloaded to PDF.

CAS Registry No. 1471306-39-4 [online database], STN Entry Date Nov. 11, 2013 [retrieved on Sep. 16, 2022], Retrieved from SciFinder <https://scifinder-n.cas.org/>, substance detail downloaded to PDF.

CAS Registry No. 1611464-74-4 [online database], STN Entry Date Jun. 20, 2014 [retrieved on Oct. 25, 2022], Retrieved from SciFinder <https://scifinder-n.cas.org/>, substance detail downloaded to PDF.

CAS Registry No. 1714959-81-5 [online database], STN Entry Date May 28, 2015 [retrieved on Sep. 16, 2022], Retrieved from SciFinder <https://scifinder-n.cas.org/>, substance detail downloaded to PDF.

CAS Registry No. 1714959-82-6 [online database], STN Entry Date May 28, 2015 [retrieved on Sep. 16, 2022], Retrieved from SciFinder <https://scifinder-n.cas.org/>, substance detail downloaded to PDF.

CAS Registry No. 1714959-83-7 [online database], STN Entry Date May 28, 2015 [retrieved on Sep. 16, 2022], Retrieved from SciFinder <https://scifinder-n.cas.org/>, substance detail downloaded to PDF.

CAS Registry No. 1714959-86-0 [online database], STN Entry Date May 28, 2015 [retrieved on Sep. 16, 2022], Retrieved from SciFinder <https://scifinder-n.cas.org/>, substance detail downloaded to PDF.

CAS Registry No. 1714959-92-8 [online database], STN Entry Date May 28, 2015 [retrieved on Sep. 16, 2022], Retrieved from SciFinder <https://scifinder-n.cas.org/>, substance detail downloaded to PDF.

CAS Registry No. 1714959-93-9 [online database], STN Entry Date May 28, 2015 [retrieved on Sep. 16, 2022], Retrieved from SciFinder <https://scifinder-n.cas.org/>, substance detail downloaded to PDF.

CAS Registry No. 1714959-95-1 [online database], STN Entry Date May 28, 2015 [retrieved on Sep. 16, 2022], Retrieved from SciFinder <https://scifinder-n.cas.org/>, substance detail downloaded to PDF.

CAS Registry No. 1714959-96-2 [online database], STN Entry Date May 28, 2015 [retrieved on Sep. 16, 2022], Retrieved from SciFinder <https://scifinder-n.cas.org/>, substance detail downloaded to PDF.

CAS Registry No. 1714961-85-9 [online database], STN Entry Date May 28, 2015 [retrieved on Sep. 16, 2022], Retrieved from SciFinder <https://scifinder-n.cas.org/>, substance detail downloaded to PDF.

CAS SciFinder Search Result on Jan. 27, 2022, at 5:14 pm (2 results)—1-Preparation of thienopyridines and related compounds, their compositions and methods of modulating short-chain dehydrogenase activity (WO 2018/218251);—2-Compositions and methods of modulating short-chain dehydrogenase activity (WO 2016/168472).

CAS SciFinder Search Result on Jan. 27, 2022, at 11:52 am (1 result)—1-Preparation of thienopyridines and similar bicyclic heterocyclic compounds as modulators of 15-hydroxyprostaglandin dehydrogenase type I for therapy (WO 2015/065716).

CAS SciFinder Search Result on Jan. 27, 2022, at 3:02 pm (2 results)—1-Preparation of thienopyridines and similar bicyclic heterocyclic compounds as modulators of 15-hydroxyprostaglandin dehydrogenase type I for therapy (WO 2015/065716);—2-Preparation of thienopyridines and related compounds, their compositions and methods of modulating short-chain dehydrogenase activity (WO 2018/218251).

CAS SciFinder Search Result on Jan. 27, 2022, at 3:25 pm (1 result)—1-Preparation of thienopyridines and similar bicyclic heterocyclic compounds as modulators of 15-hydroxyprostaglandin dehydrogenase type I for therapy (WO 2015/065716).

CAS SciFinder Search Result on Jan. 27, 2022, at 3:30 pm (2 results)—1-Preparation of thienopyridines and similar bicyclic heterocyclic compounds as modulators of 15-hydroxyprostaglandin dehydrogenase type I for therapy (WO 2015/065716);—2-Preparation of thienopyridines and related compounds, their compositions and methods of modulating short-chain dehydrogenase activity (WO 2018/218251).

CAS SciFinder Search Result on Jan. 27, 2022, at 4:08 pm (2 results)—1-Preparation of thienopyridines and similar bicyclic heterocyclic compounds as modulators of 15-hydroxyprostaglandin dehydrogenase type I for therapy (WO 2015/065716);—2-Preparation of thienopyridines and related compounds, their compositions and methods of modulating short-chain dehydrogenase activity (WO 2018/218251).

CAS SciFinder Search Result on Jan. 27, 2022, at 4:11 pm (2 results)—1-Preparation of thienopyridines and similar bicyclic het-

(56) References Cited

OTHER PUBLICATIONS erocyclic compounds as modulators of 15-hydroxyprostaglandin dehydrogenase type I for therapy (WO 2015/065716);—2-Preparation of thienopyridines and related compounds, their compositions and methods of modulating short-chain dehydrogenase activity (WO 2018/218251).
CAS SciFinder Search Result on Jan. 27, 2022, at 4:14 pm (2 results)—1-Preparation of thienopyridines and similar bicyclic heterocyclic compounds as modulators of 15-hydroxyprostaglandin dehydrogenase type I for therapy (WO 2015/065716);—2-Preparation of thienopyridines and related compounds, their compositions and methods of modulating short-chain dehydrogenase activity (WO 2018/218251).
CAS SciFinder Search Result on Jan. 27, 2022, at 4:16 pm (2 results)—1-Preparation of thienopyridines and similar bicyclic heterocyclic compounds as modulators of 15-hydroxyprostaglandin dehydrogenase type I for therapy (2015/065716);—2-Preparation of thienopyridines and related compounds, their compositions and methods of modulating short-chain dehydrogenase activity (WO 2018/218251).
CAS SciFinder Search Result on Jan. 27, 2022, at 4:50 pm (2 results)—1-Preparation of thienopyridines and similar bicyclic heterocyclic compounds as modulators of 15-hydroxyprostaglandin dehydrogenase type I for therapy (WO 2015/065716);—2-Preparation of thienopyridines and related compounds, their compositions and methods of modulating short-chain dehydrogenase activity (WO 2018/218251).
CAS SciFinder Search Result on Jan. 27, 2022, at 5:09 pm (2 results)—1-Preparation of thienopyridines and similar bicyclic heterocyclic compounds as modulators of 15-hydroxyprostaglandin dehydrogenase type I for therapy (WO 2015/065716);—2-Preparation of thienopyridines and related compounds, their compositions and methods of modulating short-chain dehydrogenase activity (WO 2018/218251).
CAS SciFinder Search Result on Jan. 27, 2022, at 5:52 pm (2 results)—1-Preparation of thienopyridines and related compounds, their compositions and methods of modulating short-chain dehydrogenase activity (WO 2018/218251);—2-Compositions and methods of modulating short-chain dehydrogenase activity (WO 2016/168472).
CAS SciFinder Search Result on Jan. 27, 2022, at 5:58 pm (2 results)—1-Preparation of thienopyridines and related compounds, their compositions and methods of modulating short-chain dehydrogenase activity (WO 2018/218251);—2-Compositions and methods of modulating short-chain dehydrogenase activity (WO 2016/168472).
CAS SciFinder Search Result on Jan. 27, 2022, at 6:03 pm (6 results)—1-Preparation of thienopyridines and similar bicyclic heterocyclic compounds as modulators of 15-hydroxyprostaglandin dehydrogenase type I for therapy (WO 2015/065716);—2-Inhibitors of 15-Prostaglandin Dehydrogenase To Potentiate Tissue Repair (Antczak et al.);—3-Compositions and methods of modulating short-chain dehydrogenase activity (WO 2016/168472);—4-Preparation of thienopyridines and related compounds, their compositions and methods of modulating short-chain dehydrogenase activity (WO 2018/218251);—5-Preparation of alkylsulfinyl-, alkylsulfonyl- and alkylthio-thieno[2,3-b]pyridinamines as inhibitors of short-chain dehydrogenase activity for promoting neurogenesis and inhibiting nerve cell death (WO 2018/017582);—6-Preparation of thienopyridine compounds having sulfur-containing substituent as inhibitors of short-chain dehydrogenase activity for treating fibrosis (WO 2016/144958).
CAS SciFinder Search Result on Jan. 27, 2022, at 7:17 pm (6 results)—1-Compositions and methods of modulating short-chain dehydrogenase activity (WO 2016/168472);—2-Preparation of thienopyridines and similar bicyclic heterocyclic compounds as modulators of 15-hydroxyprostaglandin dehydrogenase type I for therapy (WO 2015/065716);—3-Inhibitors of 15-Prostaglandin Dehydrogenase To Potentiate Tissue Repair (Antczak et al.);—4-Preparation of thienopyridines and related compounds, their compositions and methods of modulating short-chain dehydrogenase activity (WO 2018/218251);—5-Preparation of alkylsulfinyl-, alkylsulfonyl- and alkylthio-thieno[2,3-b]pyridinamines as inhibitors of short-chain dehydrogenase activity for promoting neurogenesis and inhibiting nerve cell death (WO 2018/017582);—6-Preparation of thienopyridine compounds having sulfur-containing substituent as inhibitors of short-chain dehydrogenase activity for treating fibrosis (WO 2016/144958).
CAS SciFinder Search Result on Jan. 27, 2022, at 7:21 pm (2 results)—1-Preparation of thienopyridines and similar bicyclic heterocyclic compounds as modulators of 15-hydroxyprostaglandin dehydrogenase type I for therapy (WO 2015/065716);—2-Preparation of thienopyridines and related compounds, their compositions and methods of modulating short-chain dehydrogenase activity (WO 2018/218251).
CAS SciFinder Search Result on Jan. 27, 2022, at 7:30 pm (1 result)—1-Preparation of thienopyridines and similar bicyclic heterocyclic compounds as modulators of 15-hydroxyprostaglandin dehydrogenase type I for therapy (WO 2015/065716).
CAS SciFinder Search Result on Jan. 27, 2022, at 7:31 pm (1 result)—1-Preparation of thienopyridines and similar bicyclic heterocyclic compounds as modulators of 15-hydroxyprostaglandin dehydrogenase type I for therapy (WO 2015/065716).
CAS SciFinder Search Result on Jan. 27, 2022, at 7:32 pm (1 result)—1-Preparation of thienopyridines and similar bicyclic heterocyclic compounds as modulators of 15-hydroxyprostaglandin dehydrogenase type I for therapy (WO 2015/065716).
CAS SciFinder Search Result on Jan. 27, 2022, at 7:39 pm (6 results)—1-Preparation of thienopyridines and similar bicyclic heterocyclic compounds as modulators of 15-hydroxyprostaglandin dehydrogenase type I for therapy (WO 2015/065716);—2-Inhibitors of 15-Prostaglandin Dehydrogenase To Potentiate Tissue Repair (Antczak et al.);—3-Compositions and methods of modulating short-chain dehydrogenase activity (WO 2016/168472);—4-Preparation of thienopyridines and related compounds, their compositions and methods of modulating short-chain dehydrogenase activity (WO 2018/218251);—5-Preparation of alkylsulfinyl-, alkylsulfonyl- and alkylthio-thieno[2,3-b]pyridinamines as inhibitors of short-chain dehydrogenase activity for promoting neurogenesis and inhibiting nerve cell death (WO 2018/017582);—6-Preparation of thienopyridine compounds having sulfur-containing substituent as inhibitors of short-chain dehydrogenase activity for treating fibrosis (WO 2016/144958).
CAS SciFinder Search Result on Jan. 27, 2022, at 7:47 pm (2 results)—1-Preparation of thienopyridines and similar bicyclic heterocyclic compounds as modulators of 15-hydroxyprostaglandin dehydrogenase type I for therapy (WO 2015/065716);—2-Preparation of thienopyridines and related compounds, their compositions and methods of modulating short-chain dehydrogenase activity (WO 2018/218251).
CAS SciFinder Search Result on Jan. 27, 2022, at 7:50 pm (2 results)—1-Preparation of thienopyridines and similar bicyclic heterocyclic compounds as modulators of 15-hydroxyprostaglandin dehydrogenase type I for therapy;—2-Preparation of thienopyridines and related compounds, their compositions and methods of modulating short-chain dehydrogenase activity.
CAS SciFinder Search Result on Jan. 27, 2022, at 7:52 pm (2 results)—1-Preparation of thienopyridines and related compounds, their compositions and methods of modulating short-chain dehydrogenase activity (WO 2015/065716);—2-Preparation of thienopyridines and similar bicyclic heterocyclic compounds as modulators of 15-hydroxyprostaglandin dehydrogenase type I for therapy (WO 2018/218251).
CAS SciFinder Search Result on Jan. 27, 2022, at 7:55 pm (2 results)—1-Preparation of thienopyridines and related compounds, their compositions and methods of modulating short-chain dehydrogenase activity (WO 2018/218251);—2-Preparation of thienopyridines and similar bicyclic heterocyclic compounds as modulators of 15-hydroxyprostaglandin dehydrogenase type I for therapy (WO 2015/065716).
CAS SciFinder Search Result on Jan. 27, 2022, at 3:28 pm (0 results).

(56) References Cited

OTHER PUBLICATIONS

NCBI Database Accession No. CID 3337839 [online database], create date Sep. 7, 2005, modify date Sep. 10, 2022, [retrieved on Sep. 15, 2022], Retrieved from PubChem <https://pubchem.ncbi.nlm.nih.gov>, compound summary printed to pdf.
NCBI Database Accession No. CID 3337991 [online database], create date Sep. 7, 2005, modify date Sep. 17, 2022, [retrieved on Sep. 19, 2022], Retrieved from PubChem <https://pubchem.ncbi.nlm.nih.gov>, compound summary printed to pdf.
NCBI Database Accession No. CID 3337992 [online database], create date Sep. 7, 2005, modify date Sep. 17, 2022, [retrieved on Sep. 19, 2022], Retrieved from PubChem <https://pubchem.ncbi.nlm.nih.gov>, compound summary printed to pdf.
NCBI Database Accession No. CID 3337993 [online database], create date Sep. 7, 2005, modify date Sep. 17, 2022, [retrieved on Sep. 19, 2022], Retrieved from PubChem <https://pubchem.ncbi.nlm.nih.gov>, compound summary printed to pdf.
NCBI Database Accession No. CID 3337994 [online database], create date Sep. 7, 2005, modify date Sep. 10, 2022, [retrieved on Sep. 15, 2022], Retrieved from PubChem <https://pubchem.ncbi.nlm.nih.gov>, compound summary printed to pdf.
NCBI Database Accession No. CID 3337995 [online database], create date Sep. 7, 2005, modify date Sep. 10, 2022, [retrieved on Sep. 15, 2022], Retrieved from PubChem <https://pubchem.ncbi.nlm.nih.gov>, compound summary printed to pdf.
NCBI Database Accession No. CID 3337996 [online database], create date Sep. 7, 2005, modify date Sep. 10, 2022, [retrieved on Sep. 16, 2022], Retrieved from PubChem <https://pubchem.ncbi.nlm.nih.gov>, compound summary printed to pdf.
NCBI Database Accession No. CID 3337997 [online database], create date Sep. 7, 2005, modify date Sep. 10, 2022, [retrieved on Sep. 15, 2022], Retrieved from PubChem <https://pubchem.ncbi.nlm.nih.gov>, compound summary printed to pdf.
NCBI Database Accession No. CID 3337998 [online database], create date Sep. 7, 2005, modify date Sep. 10, 2022, [retrieved on Sep. 15, 2022], Retrieved from PubChem <https://pubchem.ncbi.nlm.nih.gov>, compound summary printed to pdf.
NCBI Database Accession No. CID 46864148 [online database], create date Sep. 7, 2005, modify date Sep. 10, 2022, [retrieved on Sep. 15, 2022], Retrieved from PubChem <https://pubchem.ncbi.nlm.nih.gov>, compound summary printed to pdf.
NCBI Database Accession No. CID 52943190 [online database], create date Jun. 16, 2011, modify date Sep. 10, 2022, [retrieved on Sep. 15, 2022], Retrieved from PubChem <https://pubchem.ncbi.nlm.nih.gov>, compound summary printed to pdf.
NCBI Database Accession No. CID 72188203 [online database], create date Dec. 9, 2013, modify date Sep. 10, 2022, [retrieved on Sep. 15, 2022], Retrieved from PubChem <https://pubchem.ncbi.nlm.nih.gov>, compound summary printed to pdf.
NCBI Database Accession No. CID 72188204 [online database], create date Dec. 9, 2013, modify date Sep. 10, 2022, [retrieved on Sep. 15, 2022], Retrieved from PubChem <https://pubchem.ncbi.nlm.nih.gov>, compound summary printed to pdf.
NCBI Database Accession No. CID 92272562 [online database], create date Dec. 10, 2015, modify date Sep. 10, 2022, [retrieved on Sep. 15, 2022], Retrieved from PubChem <https://pubchem.ncbi.nlm.nih.gov>, compound summary printed to pdf.
NCBI Database Accession No. CID 92272564 [online database], create date Dec. 10, 2015, modify date Sep. 10, 2022, [retrieved on Sep. 16, 2022], Retrieved from PubChem <https://pubchem.ncbi.nlm.nih.gov>, compound summary printed to pdf.
NCBI Database Accession No. CID 118050369 [online database], create date Feb. 23, 2016, modify date Sep. 10, 2022, [retrieved on Sep. 15, 2022], Retrieved from PubChem <https://pubchem.ncbi.nlm.nih.gov>, compound summary printed to pdf.
NCBI Database Accession No. CID 118050655 [online database], create date Feb. 23, 2016, modify date Sep. 10, 2022, [retrieved on Sep. 15, 2022], Retrieved from PubChem <https://pubchem.ncbi.nlm.nih.gov>, compound summary printed to pdf.
NCBI Database Accession No. CID 118050656 [online database], create date Feb. 23, 2016, modify date Sep. 10, 2022, [retrieved on Sep. 15, 2022], Retrieved from PubChem <https://pubchem.ncbi.nlm.nih.gov>, compound summary printed to pdf.
NCBI Database Accession No. CID 118050707 [online database], create date Feb. 23, 2016, modify date Sep. 10, 2022, [retrieved on Sep. 15, 2022], Retrieved from PubChem <https://pubchem.ncbi.nlm.nih.gov>, compound summary printed to pdf.
NCBI Database Accession No. CID 118050770 [online database], create date Feb. 23, 2016, modify date Sep. 10, 2022, [retrieved on Sep. 15, 2022], Retrieved from PubChem <https://pubchem.ncbi.nlm.nih.gov>, compound summary printed to pdf.
NCBI Database Accession No. CID 118050833 [online database], create date Feb. 23, 2016, modify date Sep. 10, 2022, [retrieved on Sep. 15, 2022], Retrieved from PubChem <https://pubchem.ncbi.nlm.nih.gov>, compound summary printed to pdf.
NCBI Database Accession No. CID 118050838 [online database], create date Feb. 23, 2016, modify date Sep. 10, 2022, [retrieved on Sep. 15, 2022], Retrieved from PubChem <https://pubchem.ncbi.nlm.nih.gov>, compound summary printed to pdf.
NCBI Database Accession No. CID 118050952 [online database], create date Feb. 23, 2016, modify date Sep. 10, 2022, [retrieved on Sep. 15, 2022], Retrieved from PubChem <https://pubchem.ncbi.nlm.nih.gov>, compound summary printed to pdf.
NCBI Database Accession No. CID 118051074 [online database], create date Feb. 23, 2016, modify date Sep. 10, 2022, [retrieved on Sep. 15, 2022], Retrieved from PubChem <https://pubchem.ncbi.nlm.nih.gov>, compound summary printed to pdf.
NCBI Database Accession No. CID 118051078 [online database], create date Feb. 23, 2016, modify date Sep. 10, 2022, [retrieved on Sep. 15, 2022], Retrieved from PubChem <https://pubchem.ncbi.nlm.nih.gov>, compound summary printed to pdf.
NCBI Database Accession No. CID 118059027 [online database], create date Feb. 23, 2016, modify date Sep. 10, 2022, [retrieved on Sep. 15, 2022], Retrieved from PubChem <https://pubchem.ncbi.nlm.nih.gov>, compound summary printed to pdf.
NCBI Database Accession No. CID 118059055 [online database], create date Feb. 23, 2016, modify date Sep. 10, 2022, [retrieved on Sep. 15, 2022], Retrieved from PubChem <https://pubchem.ncbi.nlm.nih.gov>, compound summary printed to pdf.
NCBI Database Accession No. CID 118059089 [online database], create date Feb. 23, 2016, modify date Sep. 10, 2022, [retrieved on Sep. 15, 2022], Retrieved from PubChem <https://pubchem.ncbi.nlm.nih.gov>, compound summary printed to pdf.
NCBI Database Accession No. CID 118059090 [online database], create date Feb. 23, 2016, modify date Sep. 10, 2022, [retrieved on Sep. 15, 2022], Retrieved from PubChem <https://pubchem.ncbi.nlm.nih.gov>, compound summary printed to pdf.
NCBI Database Accession No. CID 118059098 [online database], create date Feb. 23, 2016, modify date Sep. 10, 2022, [retrieved on Sep. 15, 2022], Retrieved from PubChem <https://pubchem.ncbi.nlm.nih.gov>, compound summary printed to pdf.
NCBI Database Accession No. CID 122624302 [online database], create date Dec. 8, 2016, modify date Sep. 10, 2022, [retrieved on Sep. 15, 2022], Retrieved from PubChem <https://pubchem.ncbi.nlm.nih.gov>, compound summary printed to pdf.
NCBI Database Accession No. CID 123677271 [online database], create date Jan. 25, 2017, modify date Sep. 10, 2022, [retrieved on Sep. 15, 2022], Retrieved from PubChem <https://pubchem.ncbi.nlm.nih.gov>, compound summary printed to pdf.
NCBI Database Accession No. CID 129266585 [online database], create date Aug. 4, 2017, modify date Sep. 10, 2022, [retrieved on Sep. 15, 2022], Retrieved from PubChem <https://pubchem.ncbi.nlm.nih.gov>, compound summary printed to pdf.
NCBI Database Accession No. CID 129266602 [online database], create date Aug. 4, 2017, modify date Sep. 10, 2022, [retrieved on Sep. 15, 2022], Retrieved from PubChem <https://pubchem.ncbi.nlm.nih.gov>, compound summary printed to pdf.
NCBI Database Accession No. CID 130296193 [online database], create date Oct. 7, 2017, modify date Sep. 10, 2022, [retrieved on Sep. 15, 2022], Retrieved from PubChem <https://pubchem.ncbi.nlm.nih.gov>, compound summary printed to pdf.

(56) References Cited

OTHER PUBLICATIONS

NCBI Database Accession No. CID 130296194 [online database], create date Oct. 7, 2017, modify date Sep. 10, 2022, [retrieved on Sep. 15, 2022], Retrieved from PubChem <https://pubchem.ncbi.nlm.nih.gov>, compound summary printed to pdf.

NCBI Database Accession No. CID 132012504 [online database], create date Jan. 29, 2018, modify date Sep. 10, 2022, [retrieved on Sep. 15, 2022], Retrieved from PubChem <https://pubchem.ncbi.nlm.nih.gov>, compound summary printed to pdf.

NCBI Database Accession No. CID 134314069 [online database], create date Jun. 23, 2018, modify date Sep. 10, 2022, [retrieved on Sep. 15, 2022], Retrieved from PubChem <https://pubchem.ncbi.nlm.nih.gov>, compound summary printed to pdf.

NCBI Database Accession No. CID 134474501 [online database], create date Jun. 23, 2018, modify date Sep. 10, 2022, [retrieved on Sep. 15, 2022], Retrieved from PubChem <https://pubchem.ncbi.nlm.nih.gov>, compound summary printed to pdf.

NCBI Database Accession No. CID 134576829 [online database], create date Jun. 23, 2018, modify date Sep. 10, 2022, [retrieved on Sep. 16, 2022], Retrieved from PubChem <https://pubchem.ncbi.nlm.nih.gov>, compound summary printed to pdf.

NCBI Database Accession No. CID 135387726 [online database], create date Dec. 15, 2018, modify date Sep. 10, 2022, [retrieved on Sep. 16, 2022], Retrieved from PubChem <https://pubchem.ncbi.nlm.nih.gov>, compound summary printed to pdf.

NCBI Database Accession No. CID 135387830 [online database], create date Dec. 15, 2018, modify date Sep. 10, 2022, [retrieved on Sep. 16, 2022], Retrieved from PubChem <https://pubchem.ncbi.nlm.nih.gov>, compound summary printed to pdf.

NCBI Database Accession No. CID 139476465 [online database], create date Nov. 2, 2019, modify date Sep. 17, 2022, [retrieved on Sep. 19, 2022], Retrieved from PubChem <https://pubchem.ncbi.nlm.nih.gov>, compound summary printed to pdf.

NCBI Database Accession No. CID 142484843 [online database], create date Dec. 6, 2019, modify date Sep. 17, 2022, [retrieved on Sep. 19, 2022], Retrieved from PubChem <https://pubchem.ncbi.nlm.nih.gov>, compound summary printed to pdf.

NCBI Database Accession No. CID 142485754 [online database], create date Dec. 6, 2019, modify date Sep. 17, 2022, [retrieved on Sep. 19, 2022], Retrieved from PubChem <https://pubchem.ncbi.nlm.nih.gov>, compound summary printed to pdf.

NCBI Database Accession No. CID 142485836 [online database], create date Dec. 6, 2019, modify date Sep. 17, 2022, [retrieved on Sep. 19, 2022], Retrieved from PubChem <https://pubchem.ncbi.nlm.nih.gov>, compound summary printed to pdf.

NCBI Database Accession No. CID 142485845 [online database], create date Dec. 6, 2019, modify date Sep. 17, 2022, [retrieved on Sep. 19, 2022], Retrieved from PubChem <https://pubchem.ncbi.nlm.nih.gov>, compound summary printed to pdf.

NCBI Database Accession No. CID 142485847 [online database], create date Dec. 6, 2019, modify date Sep. 17, 2022, [retrieved on Sep. 19, 2022], Retrieved from PubChem <https://pubchem.ncbi.nlm.nih.gov>, compound summary printed to pdf.

NCBI Database Accession No. CID 142485863 [online database], create date Dec. 6, 2019, modify date Sep. 17, 2022, [retrieved on Sep. 19, 2022], Retrieved from PubChem <https://pubchem.ncbi.nlm.nih.gov>, compound summary printed to pdf.

NCBI Database Accession No. CID 142485864 [online database], create date Dec. 6, 2019, modify date Sep. 17, 2022, [retrieved on Sep. 19, 2022], Retrieved from PubChem <https://pubchem.ncbi.nlm.nih.gov>, compound summary printed to pdf.

NCBI Database Accession No. CID 142485868 [online database], create date Dec. 6, 2019, modify date Sep. 17, 2022, [retrieved on Sep. 19, 2022], Retrieved from PubChem <https://pubchem.ncbi.nlm.nih.gov>, compound summary printed to pdf.

NCBI Database Accession No. CID 142485879 [online database], create date Dec. 6, 2019, modify date Sep. 17, 2022, [retrieved on Sep. 19, 2022], Retrieved from PubChem <https://pubchem.ncbi.nlm.nih.gov>, compound summary printed to pdf.

NCBI Database Accession No. CID 142485866 [online database], create date Dec. 6, 2019, modify date Sep. 17, 2022, [retrieved on Sep. 19, 2022], Retrieved from PubChem <https://pubchem.ncbi.nlm.nih.gov>, compound summary printed to pdf.

NCBI Database Accession No. CID 142485929 [online database], create date Dec. 6, 2019, modify date Sep. 17, 2022, [retrieved on Sep. 19, 2022], Retrieved from PubChem <https://pubchem.ncbi.nlm.nih.gov>, compound summary printed to pdf.

NCBI Database Accession No. CID 142485938 [online database], create date Dec. 6, 2019, modify date Sep. 17, 2022, [retrieved on Sep. 19, 2022], Retrieved from PubChem <https://pubchem.ncbi.nlm.nih.gov>, compound summary printed to pdf.

NCBI Database Accession No. CID 142485953 [online database], create date Dec. 6, 2019, modify date Sep. 17, 2022, [retrieved on Sep. 19, 2022], Retrieved from PubChem <https://pubchem.ncbi.nlm.nih.gov>, compound summary printed to pdf.

NCBI Database Accession No. CID 142485954 [online database], create date Dec. 6, 2019, modify date Sep. 17, 2022, [retrieved on Sep. 19, 2022], Retrieved from PubChem <https://pubchem.ncbi.nlm.nih.gov>, compound summary printed to pdf.

NCBI Database Accession No. CID 144839639 [online database], create date Dec. 7, 2019, modify date Sep. 17, 2022, [retrieved on Sep. 19, 2022], Retrieved from PubChem <https://pubchem.ncbi.nlm.nih.gov>, compound summary printed to pdf.

NCBI Database Accession No. CID 145656773 [online database], create date Dec. 12, 2019, modify date Sep. 17, 2022, [retrieved on Sep. 19, 2022], Retrieved from PubChem <https://pubchem.ncbi.nlm.nih.gov>, compound summary printed to pdf.

NCBI Database Accession No. CID 145656809 [online database], create date Dec. 12, 2019, modify date Sep. 17, 2022, [retrieved on Sep. 19, 2022], Retrieved from PubChem <https://pubchem.ncbi.nlm.nih.gov>, compound summary printed to pdf.

NCBI Database Accession No. CID 146410683 [online database], create date Jun. 27, 2020, modify date Sep. 17, 2022, [retrieved on Sep. 19, 2022], Retrieved from PubChem <https://pubchem.ncbi.nlm.nih.gov>, compound summary printed to pdf.

NCBI Database Accession No. CID 146580152 [online database], create date Jun. 27, 2020, modify date Sep. 17, 2022, [retrieved on Sep. 19, 2022], Retrieved from PubChem <https://pubchem.ncbi.nlm.nih.gov>, compound summary printed to pdf.

NCBI Database Accession No. CID 146580711 [online database], create date Jun. 27, 2020, modify date Sep. 17, 2022, [retrieved on Sep. 19, 2022], Retrieved from PubChem <https://pubchem.ncbi.nlm.nih.gov>, compound summary printed to pdf.

NCBI Database Accession No. CID 146602898 [online database], create date Jun. 27, 2020, modify date Sep. 17, 2022, [retrieved on Sep. 19, 2022], Retrieved from PubChem <https://pubchem.ncbi.nlm.nih.gov>, compound summary printed to pdf.

NCBI Database Accession No. CID 146602900 [online database], create date Jun. 27, 2020, modify date Sep. 17, 2022, [retrieved on Sep. 19, 2022], Retrieved from PubChem <https://pubchem.ncbi.nlm.nih.gov>, compound summary printed to pdf.

NCBI Database Accession No. CID 146731064 [online database], create date Aug. 12, 2020, modify date Sep. 17, 2022, [retrieved on Sep. 19, 2022], Retrieved from PubChem <https://pubchem.ncbi.nlm.nih.gov>, compound summary printed to pdf.

NCBI Database Accession No. CID 146835156 [online database], create date Aug. 12, 2020, modify date Sep. 17, 2022, [retrieved on Sep. 19, 2022], Retrieved from PubChem <https://pubchem.ncbi.nlm.nih.gov>, compound summary printed to pdf.

NCBI Database Accession No. CID 147432252 [online database], create date Aug. 12, 2020, modify date Sep. 17, 2022, [retrieved on Sep. 19, 2022], Retrieved from PubChem <https://pubchem.ncbi.nlm.nih.gov>, compound summary printed to pdf.

NCBI Database Accession No. CID 147594754 [online database], create date Aug. 12, 2020, modify date Sep. 17, 2022, [retrieved on Sep. 19, 2022], Retrieved from PubChem <https://pubchem.ncbi.nlm.nih.gov>, compound summary printed to pdf.

NCBI Database Accession No. CID 148490795 [online database], create date Aug. 12, 2020, modify date Sep. 17, 2022, [retrieved on Sep. 19, 2022], Retrieved from PubChem <https://pubchem.ncbi.nlm.nih.gov>, compound summary printed to pdf.

(56) References Cited

OTHER PUBLICATIONS

NCBI Database Accession No. CID 149178699 [online database], create date Aug. 12, 2020, modify date Sep. 17, 2022, [retrieved on Sep. 19, 2022], Retrieved from PubChem <https://pubchem.ncbi.nlm.nih.gov>, compound summary printed to pdf.
NCBI Database Accession No. CID 152798992 [online database], create date Aug. 13, 2020, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 153596863 [online database], create date Aug. 13, 2020, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 153596870 [online database], create date Aug. 13, 2020, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 153596898 [online database], create date Aug. 13, 2020, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 153596904 [online database], create date Aug. 13, 2020, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 153596919 [online database], create date Aug. 13, 2020, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 153596924 [online database], create date Aug. 13, 2020, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 153596928 [online database], create date Aug. 13, 2020, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 153596948 [online database], create date Aug. 13, 2020, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 153596953 [online database], create date Aug. 13, 2020, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 153596968 [online database], create date Aug. 13, 2020, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 153596975 [online database], create date Aug. 13, 2020, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 153597016 [online database], create date Aug. 13, 2020, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 153597047 [online database], create date Aug. 13, 2020, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 153597069 [online database], create date Aug. 13, 2020, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 153597090 [online database], create date Aug. 13, 2020, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 153597104 [online database], create date Aug. 13, 2020, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 153597123 [online database], create date Aug. 13, 2020, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 153597128 [online database], create date Aug. 13, 2020, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 153597141 [online database], create date Aug. 13, 2020, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 153597150 [online database], create date Aug. 13, 2020, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 153597177 [online database], create date Aug. 13, 2020, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 153597180 [online database], create date Aug. 13, 2020, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 153597205 [online database], create date Aug. 13, 2020, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 153597208 [online database], create date Aug. 13, 2020, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 153597214 [online database], create date Aug. 13, 2020, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 153597233 [online database], create date Aug. 13, 2020, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 155786794 [online database], create date Feb. 22, 2021, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 156156400 [online database], create date Aug. 21, 2021, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 156837702 [online database], create date Nov. 10, 2021, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 156837721 [online database], create date Nov. 10, 2021, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 156837722 [online database], create date Nov. 10, 2021, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 156837731 [online database], create date Nov. 10, 2021, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 156837741 [online database], create date Nov. 10, 2021, modify date Sep. 17, 2022, [retrieved on Sep. 22, 2022], Retrieved from PubChem <https://pubchem.ncbi.nlm.nih.gov>, compound summary printed to pdf.

(56) References Cited

OTHER PUBLICATIONS

NCBI Database Accession No. CID 156837742 [online database], create date Nov. 10, 2021, modify date Sep. 17, 2022, [retrieved on Sep. 22, 2022], Retrieved from PubChem <https://pubchem.ncbi.nlm.nih.gov>, compound summary printed to pdf.

NCBI Database Accession No. CID 157158417 [online database], create date Dec. 3, 2021, modify date Sep. 17, 2022, [retrieved on Sep. 22, 2022], Retrieved from PubChem <https://pubchem.ncbi.nlm.nih.gov>, compound summary printed to pdf.

NCBI Database Accession No. CID 157167058 [online database], create date Dec. 3, 2021, modify date Sep. 17, 2022, [retrieved on Sep. 22, 2022], Retrieved from PubChem <https://pubchem.ncbi.nlm.nih.gov>, compound summary printed to pdf.

NCBI Database Accession No. CID 157167059 [online database], create date Dec. 3, 2021, modify date Sep. 17, 2022, [retrieved on Sep. 22, 2022], Retrieved from PubChem <https://pubchem.ncbi.nlm.nih.gov>, compound summary printed to pdf.

NCBI Database Accession No. CID 157167060 [online database], create date Dec. 3, 2021, modify date Sep. 17, 2022, [retrieved on Sep. 22, 2022], Retrieved from PubChem <https://pubchem.ncbi.nlm.nih.gov>, compound summary printed to pdf.

NCBI Database Accession No. CID 157213480 [online database], create date Dec. 3, 2021, modify date Sep. 17, 2022, [retrieved on Sep. 22, 2022], Retrieved from PubChem <https://pubchem.ncbi.nlm.nih.gov>, compound summary printed to pdf.

NCBI Database Accession No. CID 157216800 [online database], create date Dec. 3, 2021, modify date Sep. 17, 2022, [retrieved on Sep. 22, 2022], Retrieved from PubChem <https://pubchem.ncbi.nlm.nih.gov>, compound summary printed to pdf.

NCBI Database Accession No. CID 157257517 [online database], create date Dec. 3, 2021, modify date Sep. 17, 2022, [retrieved on Sep. 22, 2022], Retrieved from PubChem <https://pubchem.ncbi.nlm.nih.gov>, compound summary printed to pdf.

NCBI Database Accession No. CID 157294602 [online database], create date Dec. 3, 2021, modify date Sep. 17, 2022, [retrieved on Sep. 22, 2022], Retrieved from PubChem <https://pubchem.ncbi.nlm.nih.gov>, compound summary printed to pdf.

NCBI Database Accession No. CID 157302941 [online database], create date Dec. 3, 2021, modify date Sep. 17, 2022, [retrieved on Sep. 22, 2022], Retrieved from PubChem <https://pubchem.ncbi.nlm.nih.gov>, compound summary printed to pdf.

NCBI Database Accession No. CID 157386272 [online database], create date Dec. 3, 2021, modify date Sep. 17, 2022, [retrieved on Sep. 22, 2022], Retrieved from PubChem <https://pubchem.ncbi.nlm.nih.gov>, compound summary printed to pdf.

NCBI Database Accession No. CID 157400808 [online database], create date Dec. 3, 2021, modify date Sep. 17, 2022, [retrieved on Sep. 22, 2022], Retrieved from PubChem <https://pubchem.ncbi.nlm.nih.gov>, compound summary printed to pdf.

NCBI Database Accession No. CID 157440570 [online database], create date Dec. 3, 2021, modify date Sep. 17, 2022, [retrieved on Sep. 22, 2022], Retrieved from PubChem <https://pubchem.ncbi.nlm.nih.gov>, compound summary printed to pdf.

NCBI Database Accession No. CID 157440572 [online database], create date Dec. 3, 2021, modify date Sep. 17, 2022, [retrieved on Sep. 22, 2022], Retrieved from PubChem <https://pubchem.ncbi.nlm.nih.gov>, compound summary printed to pdf.

NCBI Database Accession No. CID 157456496 [online database], create date Dec. 3, 2021, modify date Sep. 17, 2022, [retrieved on Sep. 22, 2022], Retrieved from PubChem <https://pubchem.ncbi.nlm.nih.gov>, compound summary printed to pdf.

NCBI Database Accession No. CID 157498212 [online database], create date Dec. 3, 2021, modify date Sep. 17, 2022, [retrieved on Sep. 22, 2022], Retrieved from PubChem <https://pubchem.ncbi.nlm.nih.gov>, compound summary printed to pdf.

NCBI Database Accession No. CID 157526683 [online database], create date Dec. 3, 2021, modify date Sep. 17, 2022, [retrieved on Sep. 22, 2022], Retrieved from PubChem <https://pubchem.ncbi.nlm.nih.gov>, compound summary printed to pdf.

NCBI Database Accession No. CID 157600443 [online database], create date Dec. 3, 2021, modify date Sep. 17, 2022, [retrieved on Sep. 22, 2022], Retrieved from PubChem <https://pubchem.ncbi.nlm.nih.gov>, compound summary printed to pdf.

NCBI Database Accession No. CID 157604959 [online database], create date Dec. 3, 2021, modify date Sep. 17, 2022, [retrieved on Sep. 22, 2022], Retrieved from PubChem <https://pubchem.ncbi.nlm.nih.gov>, compound summary printed to pdf.

NCBI Database Accession No. CID 157688874 [online database], create date Dec. 3, 2021, modify date Sep. 17, 2022, [retrieved on Sep. 22, 2022], Retrieved from PubChem <https://pubchem.ncbi.nlm.nih.gov>, compound summary printed to pdf.

NCBI Database Accession No. CID 157717185 [online database], create date Dec. 3, 2021, modify date Sep. 17, 2022, [retrieved on Sep. 22, 2022], Retrieved from PubChem <https://pubchem.ncbi.nlm.nih.gov>, compound summary printed to pdf.

NCBI Database Accession No. CID 157767490 [online database], create date Dec. 3, 2021, modify date Sep. 17, 2022, [retrieved on Sep. 22, 2022], Retrieved from PubChem <https://pubchem.ncbi.nlm.nih.gov>, compound summary printed to pdf.

NCBI Database Accession No. CID 157848053 [online database], create date Dec. 3, 2021, modify date Sep. 17, 2022, [retrieved on Sep. 22, 2022], Retrieved from PubChem <https://pubchem.ncbi.nlm.nih.gov>, compound summary printed to pdf.

NCBI Database Accession No. CID 157864542 [online database], create date Dec. 3, 2021, modify date Sep. 17, 2022, [retrieved on Sep. 22, 2022], Retrieved from PubChem <https://pubchem.ncbi.nlm.nih.gov>, compound summary printed to pdf.

NCBI Database Accession No. CID 157864543 [online database], create date Dec. 3, 2021, modify date Sep. 17, 2022, [retrieved on Sep. 22, 2022], Retrieved from PubChem <https://pubchem.ncbi.nlm.nih.gov>, compound summary printed to pdf.

NCBI Database Accession No. CID 157872044 [online database], create date Dec. 3, 2021, modify date Sep. 17, 2022, [retrieved on Sep. 22, 2022], Retrieved from PubChem <https://pubchem.ncbi.nlm.nih.gov>, compound summary printed to pdf.

NCBI Database Accession No. CID 157901254 [online database], create date Dec. 3, 2021, modify date Sep. 17, 2022, [retrieved on Sep. 22, 2022], Retrieved from PubChem <https://pubchem.ncbi.nlm.nih.gov>, compound summary printed to pdf.

NCBI Database Accession No. CID 157944805 [online database], create date Dec. 3, 2021, modify date Sep. 17, 2022, [retrieved on Sep. 22, 2022], Retrieved from PubChem <https://pubchem.ncbi.nlm.nih.gov>, compound summary printed to pdf.

NCBI Database Accession No. CID 157949758 [online database], create date Dec. 3, 2021, modify date Sep. 17, 2022, [retrieved on Sep. 22, 2022], Retrieved from PubChem <https://pubchem.ncbi.nlm.nih.gov>, compound summary printed to pdf.

NCBI Database Accession No. CID 157955983 [online database], create date Dec. 3, 2021, modify date Sep. 17, 2022, [retrieved on Sep. 22, 2022], Retrieved from PubChem <https://pubchem.ncbi.nlm.nih.gov>, compound summary printed to pdf.

NCBI Database Accession No. CID 158049978 [online database], create date Dec. 3, 2021, modify date Sep. 17, 2022, [retrieved on Sep. 22, 2022], Retrieved from PubChem <https://pubchem.ncbi.nlm.nih.gov>, compound summary printed to pdf.

NCBI Database Accession No. CID 158088730 [online database], create date Dec. 3, 2021, modify date Sep. 17, 2022, [retrieved on Sep. 22, 2022], Retrieved from PubChem <https://pubchem.ncbi.nlm.nih.gov>, compound summary printed to pdf.

NCBI Database Accession No. CID 158134580 [online database], create date Dec. 3, 2021, modify date Sep. 17, 2022, [retrieved on Sep. 22, 2022], Retrieved from PubChem <https://pubchem.ncbi.nlm.nih.gov>, compound summary printed to pdf.

NCBI Database Accession No. CID 158145130 [online database], create date Dec. 3, 2021, modify date Sep. 17, 2022, [retrieved on Sep. 22, 2022], Retrieved from PubChem <https://pubchem.ncbi.nlm.nih.gov>, compound summary printed to pdf.

NCBI Database Accession No. CID 158221946 [online database], create date Dec. 3, 2021, modify date Sep. 17, 2022, [retrieved on Sep. 22, 2022], Retrieved from PubChem <https://pubchem.ncbi.nlm.nih.gov>, compound summary printed to pdf.

(56) References Cited

OTHER PUBLICATIONS

NCBI Database Accession No. CID 158221947 [online database], create date Dec. 3, 2021, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 158258231 [online database], create date Dec. 3, 2021, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 158329834 [online database], create date Dec. 3, 2021, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 158370045 [online database], create date Dec. 3, 2021, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 158404656 [online database], create date Dec. 3, 2021, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 158415066 [online database], create date Dec. 3, 2021, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 158432471 [online database], create date Dec. 3, 2021, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 158531185 [online database], create date Dec. 3, 2021, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 158540614 [online database], create date Dec. 3, 2021, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 158568511 [online database], create date Dec. 3, 2021, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 158628602 [online database], create date Dec. 3, 2021, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 158653266 [online database], create date Dec. 3, 2021, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 158660366 [online database], create date Dec. 3, 2021, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 158784514 [online database], create date Dec. 3, 2021, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 158829687 [online database], create date Dec. 3, 2021, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 158910891 [online database], create date Dec. 3, 2021, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 159056851 [online database], create date Dec. 3, 2021, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 159130668 [online database], create date Dec. 3, 2021, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 159144809 [online database], create date Dec. 3, 2021, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 159154352 [online database], create date Dec. 3, 2021, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 159191585 [online database], create date Dec. 3, 2021, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 159215478 [online database], create date Dec. 3, 2021, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 159233281 [online database], create date Dec. 3, 2021, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 159233282 [online database], create date Dec. 3, 2021, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 159474011 [online database], create date Dec. 3, 2021, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 159590113 [online database], create date Dec. 3, 2021, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 159820000 [online database], create date Dec. 3, 2021, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 159891397 [online database], create date Dec. 3, 2021, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 160071422 [online database], create date Dec. 3, 2021, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 160071423 [online database], create date Dec. 3, 2021, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 160155004 [online database], create date Dec. 3, 2021, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 160156242 [online database], create date Dec. 3, 2021, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 161100344 [online database], create date Dec. 3, 2021, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 162062070 [online database], create date Dec. 3, 2021, modify date Sep. 17, 2022, [retrieved on Sep. 22, 2022], Retrieved from PubChem <https://pubchem.ncbi.nlm.nih.gov>, compound summary printed to pdf.
NCBI Database Accession No. CID 162728470 [online database], create date Apr. 5, 2022, modify date Sep. 17, 2022, [retrieved on Sep. 22, 2022], Retrieved from PubChem <https://pubchem.ncbi.nlm.nih.gov>, compound summary printed to pdf.
U.S. Appl. No. 17/926,214, filed Nov. 18, 2022, Pending.

(56) References Cited

OTHER PUBLICATIONS

U.S. Appl. No. 17/296,055, US 2023-0039604 A1, filed May 21, 2021, Feb. 9, 2023, Pending.
U.S. Appl. No. 15/359,330, US 2017-0165241 A1 now U.S. Pat. No. 10,301,320, filed Nov. 22, 2016, Jun. 15, 2017 May 28, 2019, Issued.
U.S. Appl. No. 16/421,867, US 2020-0140453 A1, filed May 24, 2019, May 7, 2020, Abandoned.
U.S. Appl. No. 16/943,932, US-2021-0032265 A1, filed Oct. 12, 2020, Feb. 4, 2021, Pending.
U.S. Appl. No. 14/395,021, US-2015-0072998 A1 now U.S. Pat. No. 9,790,233, filed Oct. 16, 2014, Mar. 12, 2015 Oct 17, 2017, Issued.
U.S. Appl. No. 17/879,379, filed Aug. 2, 2022, Pending.
U.S. Appl. No. 17/898,776, US 2023/0116062 A1, filed Aug. 30, 2022, Apr. 13, 2023, Pending.
U.S. Appl. No. 18/117,257, filed Mar. 3, 2023, Pending.
U.S. Appl. No. 15/347,587, US-2017-0216265 now U.S. Pat. No. 9,801,863, filed Nov. 9, 2016, Aug 3, 2017 Oct 31, 2017, Issued.
U.S. Appl. No. 15/785,259, US 2019-0365769 A1 now U.S. Pat. No. 10,869,871, filed Oct. 16, 2017, Dec. 5, 2019 Dec. 22, 2020, Issued.
U.S. Appl. No. 15/799,307, US 2018-0125829 A1 now U.S. Pat. No. 10,420,752, filed Oct. 31, 2017, May 10, 2018 Sep. 24, 2019, Issued.
U.S. Appl. No. 16/581,024, US 2020-0147063 A1, filed Sep. 24, 2019, May 14, 2020, Abandoned.
U.S. Appl. No. 16/997,273, US 2021-0106587 A1, filed Aug. 19, 2020, Apr. 15, 2021, Abandoned.
U.S. Appl. No. 15/029,943, US 2017-0173028 A1 now U.S. Pat. No. 9,789,116, filed Apr. 15, 2016, Jun. 22, 2017 Oct 17, 2017, Issued.
U.S. Appl. No. 17/131,911, US-2021-0283113-A1, filed Dec. 23, 2020, Sep. 16, 2021, Pending.
U.S. Appl. No. 15/556,972, US 2018-0064694 A1 now U.S. Pat. No. 10,945,998, filed Sep. 8, 2017, Mar. 8, 2018 Mar. 16, 2021, Issued.
U.S. Appl. No. 16/869,879, US 2021-0094968 A1, filed May 8, 2020, Apr. 1, 2021, Pending.
U.S. Appl. No. 15/566,637, US 2018-0118756 A1, filed Oct. 13, 2017, May 3, 2018, Abandoned.
U.S. Appl. No. 16/995,878, US 2021-0100778 A1, filed Aug. 18, 2020, Apr. 8, 2021, Pending.
U.S. Appl. No. 16/319,159, US 2019-0275014 A1, filed Jan. 18, 2019, Sep. 12, 2019, Abandoned.
U.S. Appl. No. 16/465,500, US 2020-0061073 A1, filed May 30, 2019, Feb. 27, 2020, Pending.
U.S. Appl. No. 16/484,045, US 2020-0095206 A1, filed Aug. 6, 2019, Mar. 26, 2020, Pending.
U.S. Appl. No. 17/893,777, filed Aug. 23, 2022, Pending.
U.S. Appl. No. 16/603,544, US 2020-0030348 A1 now U.S. Pat. No. 11,426,420, filed Oct. 7, 2019, Jan. 30, 2020 Aug. 30, 2022, Issued.
U.S. Appl. No. 16/617,137, US 2021-0317132 A1, filed Nov. 26, 2019, Oct. 14, 2021, Abandoned.
U.S. Appl. No. 18/057,589, filed Nov. 21, 2022, Pending.
U.S. Appl. No. 17/044,888, US 2021-0100779A1, filed Oct. 2, 2020, Apr. 8, 2021, Pending.
U.S. Appl. No. 18/128,075, filed Mar. 29, 2023, Pending.
U.S. Appl. No. 17/892,585, US 2023-0052363 A1, filed Aug. 22, 2022, Feb. 16, 2023, Pending.
U.S. Appl. No. 18/020,202, filed Feb. 7, 2023, Pending.
Applicant: Case Western Reserve University; Japanese Application No. 2019-528506; Decision of Rejection—Japanese Office Action, Aug. 16, 2022; 8 pgs.
First Named Inventor: Sanford Markowitz; U.S. Appl. No. 16/465,500, filed May 30, 2019; U.S. Final OA dated Sep. 23, 2022; 11 pgs.
Na; Biochemical Pharmacology 2011, 82, 1352-1360. https://doi.org/10.1016/j.bcp.2011.08.005 (Year: 2011).
Nakanishi; Semin Immunopathol 2013, 35, 123-137. https://doi.org/10.1007/s00281-012-0342-8 (Year: 2013).
Tong, M., & Tai, H.-H. (2005). 15-Hydroxyprostaglandin dehydrogenase can be induced by dexamethasone and other glucocorticoids at the therapeutic level in A549 human lung adenocarcinoma cells. Archives of Biochemistry and Biophysics, 435(1), 50-55. doi:10.1016/j.abb.2004.11.031.
Yan; Proc Natl Acad Sci USA 2009, 106, 9409-9413. https://doi.org/10.1073/pnas.0902367106 (Year: 2009).
Chinese Application No. 201880028200.4, Decision of Rejection dated Jan. 15, 2024.
Saudi Arabia Application No. 523450532, Examination Report dated Mar. 26, 2025.
Australian Application No. 2021224268, Examination Report dated Nov. 19, 2025.

* cited by examiner

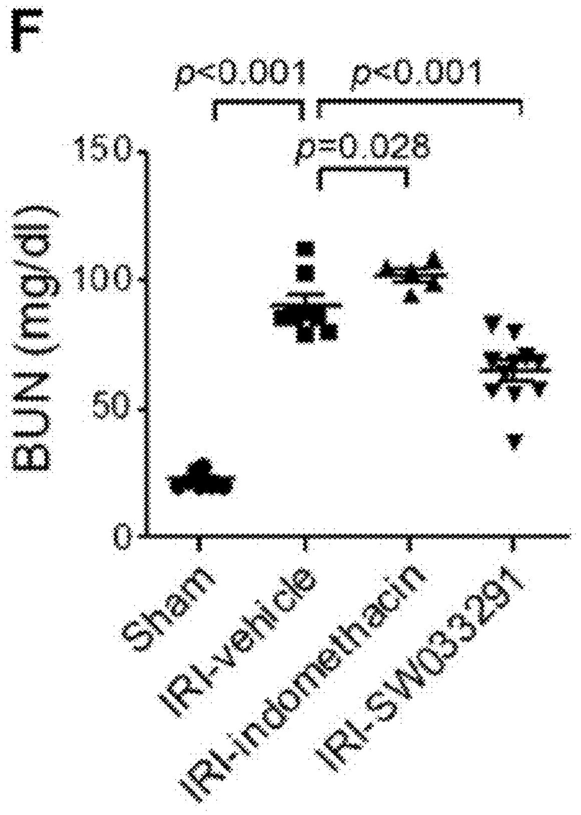
Fig. 1F
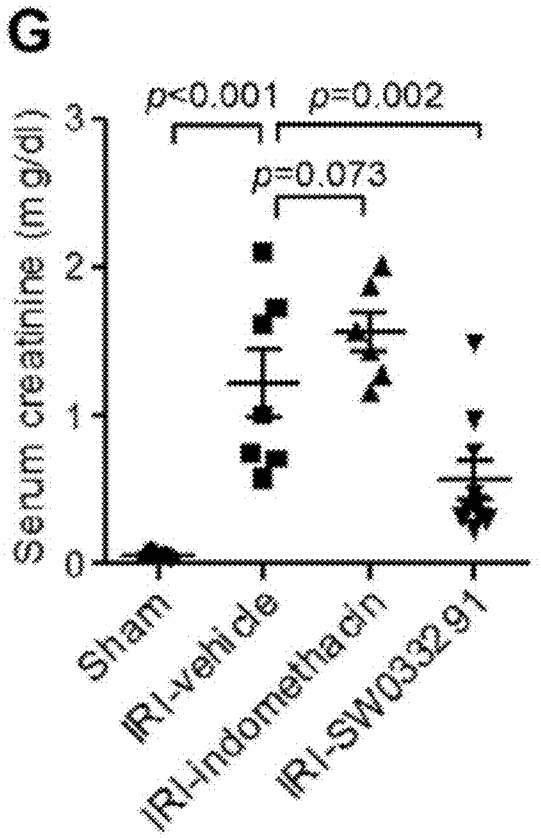
Fig. 1G
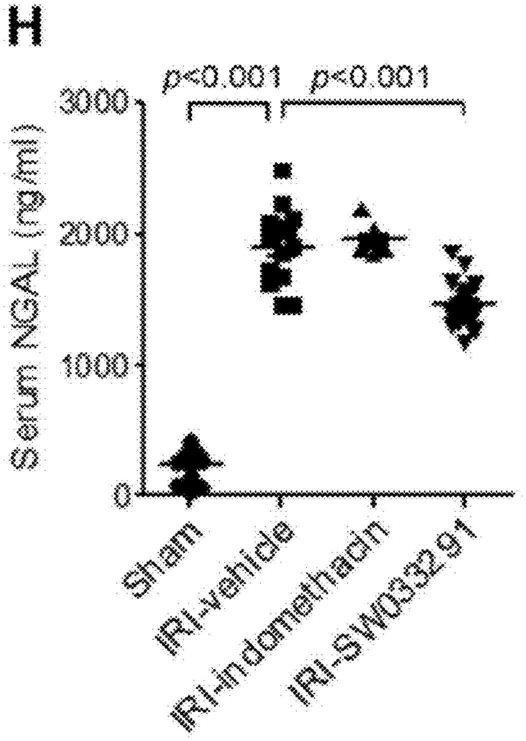
Fig. 1H
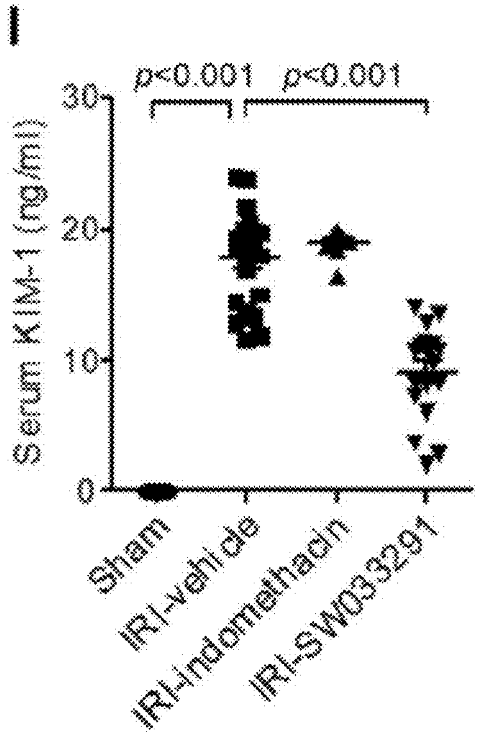
Fig, 1I (A)
| CM | Iodine Con. | Viscosity (mPa.s, 37℃) | Osmolality (mOsm/kg $H_2O$) | Hydrophilicity (OH-number) |
|---|---|---|---|---|
| Iodixanol (Visipaque) | 320 | 11.8 | 290 | 9 |
| Iobitridol (Xenetix) | 300 | 6.0 | 695 | 6 |
Fig. 10A
(B)
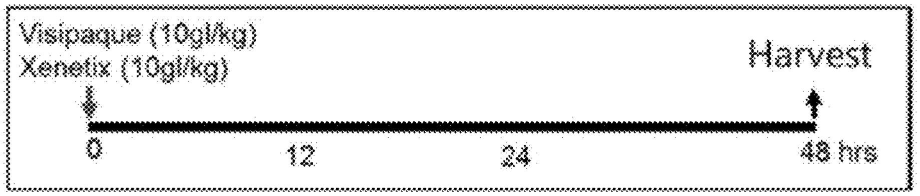
Fig. 10B
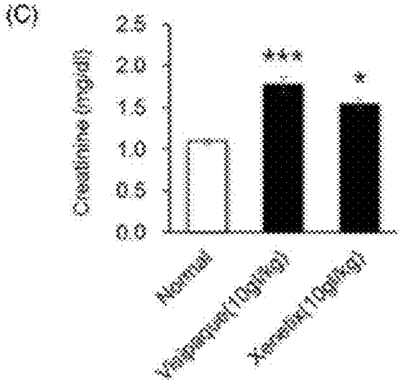
Fig. 10C
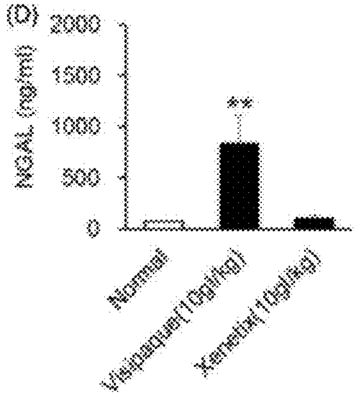
Fig. 10D
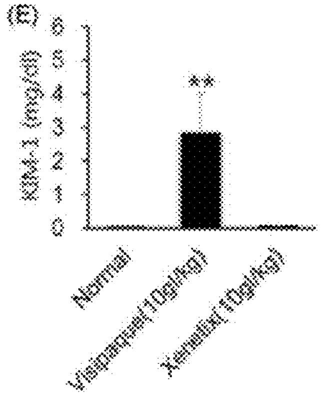
Fig. 10E

COMPOSITIONS AND METHODS FOR TREATING RENAL INJURY

RELATED APPLICATION

This application is a Continuation-in-Part of PCT/US2021/019084, filed Feb. 22, 2021, which claims priority from U.S. Provisional Application No. 62/979,813 filed Feb. 21, 2020, and is Continuation-in-Part of PCT/US2019/025812, filed Apr. 4, 2019, the subject matter of which are incorporated herein by reference in their entirety.

GOVERNMENT FUNDING

This invention was made with government support under grant CA197442 awarded by the National Institutes of Health. The government has certain rights in the invention.

BACKGROUND

Acute kidney injury (AKI) is an important clinical problem associated with high rates of morbidity and mortality (1.7 million deaths annually). Considerable effort has been directed toward the development of preventive strategies for AKI using various agents and animal models. Despite advances in prevention strategies, no specific treatment for AKI has yet been developed.

The main causes of AKI are hypoxia and oxidative stress due to renal ischemic reperfusion injury (IRI). During periods of transient reduction in renal blood flow (RBF), an insufficient oxygen supply can cause energy impairment (ATP depletion) in the renal outer medulla, resulting in the injury and death of the tubular epithelial cells due to acute tubular necrosis (ATN) and apoptosis. The inflammation due to oxygen-free radicals after reperfusion leads to the extension phase of ischemic AKI. Resistance to hypoxia and the reduction of oxidative stress are treatment targets for ischemic AKI.

SUMMARY

Embodiments described herein relate to compositions and methods of preventing, treating, or reducing the severity of a renal disorder, disease, and/or injury. It was found that administration of a 15-PGDH inhibitor to a subject prior to and/or after renal injury can induce renal vasodilation, and enhance resistance to hypoxia resulting in a prophylactic and protective effect against renal injury. These benefits can be associated with a prophylactic use of as little as a single dose of a 15-PGDH inhibitor. Administration of a 15-PGDH inhibitor to a subject having or at risk of a renal injury improved renal hemodynamics, decreased induction of oxidative stress, reduced induction of inflammation, attenuated multiple markers of renal damage and preserved renal function. Moreover, administration of a 15-PGDH inhibitor before and/or after administration of a contrast media was found to prevent and/or treat contrast-induced acute kidney injury (CIAKI). Accordingly, in some embodiments, compositions and methods of inhibiting 15-PDGH activity can be used to prevent, treat, or reduce the severity of a renal disorder, disease, and/or injury in a subject and/or kidney of a subject in need thereof.

Examples of renal disorders, diseases, and/or injuries that can be treated include hypotensive injury to the kidney; hypertensive renal disease; diabetic renal disease and diabetic nephropathy; renal disease from vasculitis and autoimmune diseases, including but not limited to lupus erythematosis, polyarteritis, Wegeners' Granulomatosis, and mixed connective tissue disease; ischemic renal injury; acute renal failure; chronic renal failure; glomerulonephritis; nephrotic syndrome; acute tubular necrosis; nephrosclerosis; gomerulosclerosis; minimal change disease; idiopathic membranous nephropathy; membranoproliferative glomerulonephritis; Berger's disease; mesangial proliferative glomerulonephritis; chronic glomerulonephritis; focal glomerulosclerosis; renal effects of Sjogren's syndrome; renal effects of scleroderma; interstitial nephritis; and renal injury to a kidney donor, transplant recipient, and/or transplanted kidney following kidney transplant.

In other embodiments, the 15-PGDH inhibitor can prevent or treat acute kidney injury (AKI) associated with renal ischemia reperfusion injury (IRI).

In some embodiments, the amount of 15-PGDH inhibitor administered to a subject can be an amount effective to induce endogenous renal PGE2 levels of the subject.

In other embodiments, the amount of 15-PGDH inhibitor administered to a subject can be an amount effective to induce renal vasodilatation, enhance resistance to hypoxia, improve renal hemodynamics, decrease renal oxidative stress, reduce renal inflammation, and preserve renal function.

In other embodiments, the amount of 15-PGDH inhibitor administered to a subject is an amount effective to reduce malondialdehyde (MDA) and NGAL levels, attenuate medulla tubular damage, reduce medulla acute tubular necrosis (ATN) and apoptosis, reduce induction of high-mobility group box 1 (HMGB1) and proinflammatory cytokines, induce renal EP4 PGE2 receptors and A2A adenosine receptors in vascular smooth muscle cells that regulate renal arterioles, increase renal cAMP, AMP, and adenosine levels, and/or inhibit induction of creatinine and KIM-1.

In other embodiments, the 15-PGDH inhibitor can be administered to a subject before a renal injury. For example, the 15-PGDH inhibitor can be administered at a range of about 1 minute to about 72 hours, about 10 minutes to about 48 hours, or about 30 minutes to about 36 hours before a renal disorder, disease, and/or injury.

In other embodiments, the 15-PGDH inhibitor can be administered at a time selected from less than about 2 hours, less than about 8 hours, less than about 24 hours, and less than about 26 hours before the renal disorder, disease, and/or injury.

In some embodiments, the renal disorder, disease, and/or injury is associated with an organ transplant, such as a kidney transplant, in the subject.

In other embodiments, the renal disorder, disease, and/or injury is associated with cardiovascular surgery or sepsis.

In some embodiments, the renal disorder, disease, and/or injury is a contrast-induced acute kidney injury (CIAKI).

In some embodiments, the 15-PGDH inhibitor can include a compound having the following formula (V):

(V)

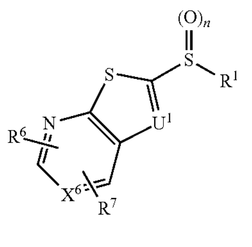

or a pharmaceutically acceptable salt, tautomer, or solvate thereof, wherein n is 0-2

$X^6$ is independently is N or $CR^c$ $R^1$, $R^6$, $R^7$, and $R^c$ are the same or different each independently hydrogen or a substituted or unsubstituted group selected from $C_1$-$C_{24}$ alkyl, $C_2$-$C_{24}$ alkenyl, $C_2$-$C_{24}$ alkynyl, $C_3$-$C_{20}$ aryl, heteroaryl, heterocycloalkenyl containing from 5-6 ring atoms, $C_6$-$C_{24}$ alkaryl, $C_6$—$C_{24}$ aralkyl, halo, —Si($C_1$-$C_3$ alkyl)$_3$, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl, acyloxy, $C_2$-$C_{24}$ alkoxycarbonyl, $C_6$-$C_{20}$ aryloxycarbonyl, $C_2$-$C_{24}$ alkylcarbonato, $C_6$-$C_{20}$ arylcarbonato, carboxy, carboxylato, carbamoyl, $C_1$-$C_{24}$ alkyl-carbamoyl, aryl-carbamoyl, thiocarbamoyl, carbamido, cyano, isocyano, cyanato, isocyanato, isothiocyanato, azido, formyl, thioformyl, amino, $C_1$-$C_{24}$ alkyl amino, $C_5$-$C_{20}$ aryl amino, $C_2$-$C_{24}$ alkylamido, $C_2$-$C_{24}$ alkylamido substituted with a hydroxyl, $C_6$-$C_{20}$ arylamido, imino, alkylimino, arylimino, nitro, nitroso, sulfo, sulfonato, $C_1$-$C_{24}$ alkylsulfanyl, arylsulfanyl, $C_1$-$C_{24}$ alkylsulfinyl, $C_5$-$C_{20}$ arylsulfinyl, $C_1$-$C_{24}$ alkylsulfonyl, $C_5$-$C_{20}$ arylsulfonyl, sulfonamide, phosphono, phosphonato, phosphinato, phospho, phosphino, polyalkylethers, phosphates, and phosphate esters, groups incorporating amino acids or other moieties expected to bear positive or negative charge at physiological pH, and combinations thereof, and wherein $R^6$ and $R^7$ may be linked to form a cyclic or polycyclic ring, wherein the ring is a substituted or unsubstituted aryl, a substituted or unsubstituted heteroaryl, a substituted or unsubstituted cycloalkyl, and a substituted or unsubstituted heterocyclyl; and $U^1$ is N, C—$R^2$, or C—$NR^3R^4$, wherein $R^2$ is selected from the group consisting of a H, a lower alkyl group, O, $(CH_2)_{n1}$OR' (wherein n1=1, 2, or 3), $CF_3$, $CH_2$—$CH_2X$, O—$CH_2$—$CH_2X$, $CH_2$—$CH_2$—$CH_2X$, O—$CH_2$—$CH_2X$, X, (wherein X=H, F, Cl, Br, or I), CN, (C=O)—R', (C=O)N(R')$_2$, O(CO)R', COOR' (wherein R' is H or a lower alkyl group), and wherein $R^1$ and $R^2$ may be linked to form a cyclic or polycyclic ring, wherein $R^3$ and $R^4$ are the same or different and are each selected from the group consisting of H, a lower alkyl group, O, $(CH_2)_{n1}$OR' (wherein n1=1, 2, or 3), $CF_3$, $CH_2$—$CH_2X$, $CH_2$—$CH_2$—$CH_2X$, (wherein X=H, F, Cl, Br, or I), CN, (C=O)—R', (C=O)N(R')$_2$, COOR' (wherein R' is H or a lower alkyl group), and $R^3$ or $R^4$ may be absent.

In some embodiments, the 15-PGDH inhibitor can inhibit the enzymatic activity of recombinant 15-PGDH at an $IC_{50}$ of less than 1 μM, or preferably at an $IC_{50}$ of less than 250 nM, or more preferably at an $IC_{50}$ of less than 50 nM, or more preferably at an $IC_{50}$ of less than 10 nM, or more preferably at an $IC_{50}$ of less than 5 nM at a recombinant 15-PGDH concentration of about 5 nM to about 10 nM.

BRIEF DESCRIPTION OF THE DRAWINGS

FIG. 10 (A-E) illustrate a table, schematic, and graphs showing an establishment of contrast induced acute kidney injury (CIAKI).

DETAILED DESCRIPTION

Figure 1A:
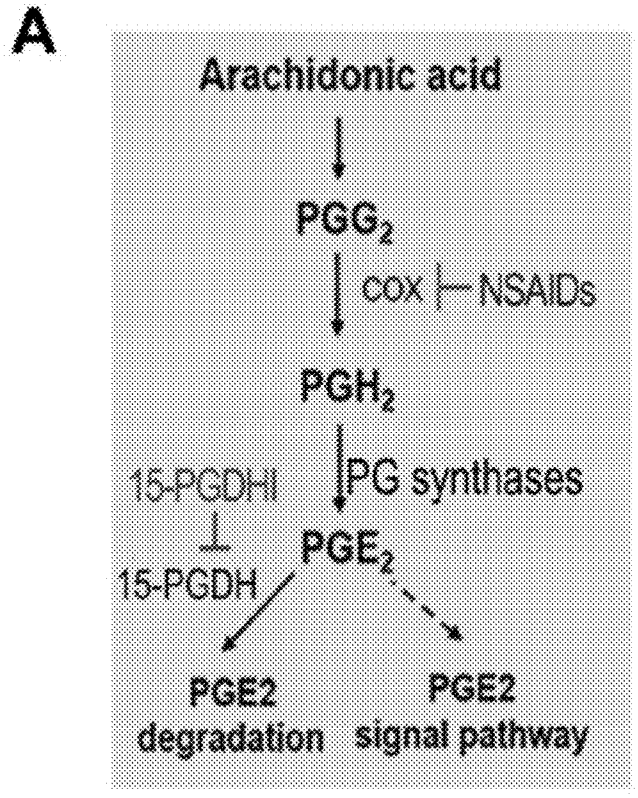
FIGS. 1(A-I) illustrate a schematic and plots showing 15-hydoxyprostaglandin dehydrogenase (15-PGDH) inhibition with renal ischemia-reperfusion (I/R) injury (IRI) decreases levels of renal injury biomarkers. A: the arachidonic acid prostaglandin (PG) biosynthesis pathway and biological activity of 15-PGDH inhibitor. Cox, cyclooxygenase; NSAIDs, nonsteroidal anti-inflammatory drugs. B: chemical structure of SW033291. C: pharmacological inhibition of 15-PGDH with SW033291 was confirmed by endogenous $PGE_2$ levels in kidney tissue at 3 h after intraperitoneal injection of 2.5 or 5 mg/kg SW033291 or vehicle. D: $PGE_2$ levels in kidney tissue at 1 and 3 h after intraperitoneal injection of 5 mg/kg SW033291 or vehicle. E: experimental setup. Mice were subjected to bilateral renal IRI for 30 min and were injected with vehicle, SW033291, or indo-methacin at 1 h before, immediately after, and 12 h after renal IRI. F I: serum levels of blood urea nitrogen (BUN; F), creatinine (G), neutrophil gelatinase-associated lipocalin (NGAL; H), and kidney injury molecule 1 (KIM-1; I). Renal function was evaluated at 24 h after renal IRI. n=8-15 animals/group. Data are presented as means±SE. Analysis was performed using Student's t test.

While the following terms are believed to be well understood by one of ordinary skill in the art, the following definitions are set forth to facilitate explanation of the presently disclosed subject matter.

As used herein, the verb "comprise" as is used in this description and in the claims and its conjugations are used in its non-limiting sense to mean that items following the word are included, but items not specifically mentioned are not excluded. The present invention may suitably "comprise", "consist of", or "consist essentially of", the steps, elements, and/or reagents described in the claims.

It is further noted that the claims may be drafted to exclude any optional element. As such, this statement is intended to serve as antecedent basis for use of such exclusive terminology as "solely", "only" and the like in connection with the recitation of claim elements, or the use of a "negative" limitation.

The term "pharmaceutically acceptable" means suitable for use in contact with the tissues of humans and animals without undue toxicity, irritation, allergic response, and the like, commensurate with a reasonable benefit/risk ratio, and effective for their intended use within the scope of sound medical judgment.

The term "pharmaceutically acceptable salt" include those obtained by reacting the active compound functioning as a base, with an inorganic or organic acid to form a salt, for example, salts of hydrochloric acid, sulfuric acid, phosphoric acid, methanesulfonic acid, camphorsulfonic acid, oxalic acid, maleic acid, succinic acid, citric acid, formic acid, hydrobromic acid, benzoic acid, tartaric acid, fumaric acid, salicylic acid, mandelic acid, carbonic acid, etc. Those skilled in the art will further recognize that acid addition salts may be prepared by reaction of the compounds with the appropriate inorganic or organic acid via any of a number of known methods. The term "pharmaceutically acceptable salts" also includes those obtained by reacting the active compound functioning as an acid, with an inorganic or organic base to form a salt, for example salts of ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris-(hydroxymethyl)-aminomethane, tetramethylammonium hydroxide, triethylamine, dibenzylamine, ephenamine, dehydroabietylamine, N-ethylpiperidine, benzylamine, tetramethylammonium, tetraethylammonium, methylamine, dimethylamine, trimethylamine, ethylamine, basic amino acids, and the like. Non limiting examples of inorganic or metal salts include lithium, sodium, calcium, potassium, magnesium salts and the like.

Additionally, the salts of the compounds described herein, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

The term "solvates" means solvent addition forms that contain either stoichiometric or non-stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

The compounds and salts described herein can exist in several tautomeric forms, including the enol and imine form, and the keto and enamine form and geometric isomers and mixtures thereof. Tautomers exist as mixtures of a tautomeric set in solution. In solid form, usually one tautomer predominates. Even though one tautomer may be described, the present application includes all tautomers of the present compounds. A tautomer is one of two or more structural isomers that exist in equilibrium and are readily converted from one isomeric form to another. This reaction results in the formal migration of a hydrogen atom accompanied by a switch of adjacent conjugated double bonds. In solutions where tautomerization is possible, a chemical equilibrium of the tautomers will be reached. The exact ratio of the tautomers depends on several factors, including temperature, solvent, and pH. The concept of tautomers that are interconvertable by tautomerizations is called tautomerism.

Of the various types of tautomerism that are possible, two are commonly observed. In keto-enol tautomerism a simultaneous shift of electrons and a hydrogen atom occurs.

Tautomerizations can be catalyzed by: Base: 1. deprotonation; 2. formation of a delocalized anion (e.g., an enolate); 3. protonation at a different position of the anion; Acid: 1. protonation; 2. formation of a delocalized cation; 3. deprotonation at a different position adjacent to the cation.

The terms below, as used herein, have the following meanings, unless indicated otherwise:

"Amino" refers to the $-NH_2$ radical.

"Cyano" refers to the —CN radical.

"Halo" or "halogen" refers to bromo, chloro, fluoro or iodo radical.

"Hydroxy" or "hydroxyl" refers to the —OH radical.

"Imino" refers to the =NH substituent.

"Nitro" refers to the —$NO_2$ radical.

"Oxo" refers to the =O substituent.

"Thioxo" refers to the =S substituent.

"Alkyl" or "alkyl group" refers to a fully saturated, straight or branched hydrocarbon chain radical having from one to twelve carbon atoms, and which is attached to the rest of the molecule by a single bond. Alkyls comprising any number of carbon atoms from 1 to 12 are included. An alkyl comprising up to 12 carbon atoms is a $C_1$-$C_{12}$ alkyl, an alkyl comprising up to 10 carbon atoms is a $C_1$-$C_{10}$ alkyl, an alkyl comprising up to 6 carbon atoms is a $C_1$-$C_6$ alkyl and an alkyl comprising up to 5 carbon atoms is a $C_1$-$C_5$ alkyl. A $C_1$-$C_5$ alkyl includes $C_5$ alkyls, $C_4$ alkyls, $C_3$ alkyls, $C_2$ alkyls and $C_1$ alkyl (i.e., methyl). A $C_1$-$C_6$ alkyl includes all moieties described above for $C_1$-$C_5$ alkyls but also includes $C_6$ alkyls. A $C_1$-$C_{10}$ alkyl includes all moieties described above for $C_1$-$C_5$ alkyls and $C_1$-$C_6$ alkyls, but also includes $C_7$, $C_8$, $C_9$ and $C_{10}$ alkyls. Similarly, a $C_1$-$C_{12}$ alkyl includes all the foregoing moieties, but also includes $C_{11}$ and $C_{12}$ alkyls. Non-limiting examples of $C_1$-$C_{12}$ alkyl include methyl, ethyl, n-propyl, i-propyl, sec-propyl, n-butyl, i-butyl, sec-butyl, t-butyl, n-pentyl, t-amyl, n-hexyl, n-heptyl, n-octyl, n-nonyl, n-decyl, n-undecyl, and n-dodecyl. Unless stated otherwise specifically in the specification, an alkyl group can be optionally substituted.

"Alkylene" or "alkylene chain" refers to a fully saturated, straight or branched divalent hydrocarbon chain radical, and having from one to twelve carbon atoms. Non-limiting examples of $C_1$-$C_{12}$ alkylene include methylene, ethylene, propylene, n-butylene, ethenylene, propenylene, n-butenylene, propynylene, n-butynylene, and the like. The alkylene chain is attached to the rest of the molecule through a single bond and to the radical group through a single bond. The points of attachment of the alkylene chain to the rest of the molecule and to the radical group can be through one carbon or any two carbons within the chain. Unless stated otherwise specifically in the specification, an alkylene chain can be optionally substituted.

"Alkenyl" or "alkenyl group" refers to a straight or branched hydrocarbon chain radical having from two to twelve carbon atoms, and having one or more carbon-carbon double bonds. Each alkenyl group is attached to the rest of the molecule by a single bond. Alkenyl group comprising any number of carbon atoms from 2 to 12 are included. An alkenyl group comprising up to 12 carbon atoms is a $C_2$-$C_{12}$ alkenyl, an alkenyl comprising up to 10 carbon atoms is a $C_2$-$C_{10}$ alkenyl, an alkenyl group comprising up to 6 carbon atoms is a $C_2$-$C_6$ alkenyl and an alkenyl comprising up to 5 carbon atoms is a $C_2$-$C_5$ alkenyl. A $C_2$-$C_5$ alkenyl includes $C_5$ alkenyls, $C_4$ alkenyls, $C_3$ alkenyls, and $C_2$ alkenyls. A $C_2$-$C_6$ alkenyl includes all moieties described above for $C_2$-$C_5$ alkenyls but also includes $C_6$ alkenyls. A $C_2$-$C_{10}$ alkenyl includes all moieties described above for $C_2$-$C_5$ alkenyls and $C_2$-$C_6$ alkenyls, but also includes $C_7$, $C_8$, $C_9$ and $C_{10}$ alkenyls. Similarly, a $C_2$-$C_{12}$ alkenyl includes all the foregoing moieties, but also includes $C_{11}$ and $C_{12}$ alkenyls. Non-limiting examples of $C_2$-$C_{12}$ alkenyl include ethenyl (vinyl), 1-propenyl, 2-propenyl (allyl), iso-propenyl, 2-methyl-1-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, 1-heptenyl, 2-heptenyl, 3-heptenyl, 4-heptenyl, 5-heptenyl, 6-heptenyl, 1-octenyl, 2-octenyl, 3-octenyl, 4-octenyl, 5-octenyl, 6-octenyl, 7-octenyl, 1-nonenyl, 2-nonenyl, 3-nonenyl, 4-nonenyl, 5-nonenyl, 6-nonenyl, 7-nonenyl, 8-nonenyl, 1-decenyl, 2-decenyl, 3-decenyl, 4-decenyl, 5-decenyl, 6-decenyl, 7-decenyl, 8-decenyl, 9-decenyl, 1-undecenyl, 2-undecenyl, 3-undecenyl, 4-undecenyl, 5-undecenyl, 6-undecenyl, 7-undecenyl, 8-undecenyl, 9-undecenyl, 10-undecenyl, 1-dodecenyl, 2-dodecenyl, 3-dodecenyl, 4-dodecenyl, 5-dodecenyl, 6-dodecenyl, 7-dodecenyl, 8-dodecenyl, 9-dodecenyl, 10-dodecenyl, and 11-dodecenyl. Unless stated otherwise specifically in the specification, an alkyl group can be optionally substituted.

"Alkenylene" or "alkenylene chain" refers to a straight or branched divalent hydrocarbon chain radical, having from two to twelve carbon atoms, and having one or more carbon-carbon double bonds. Non-limiting examples of $C_2$-$C_{12}$ alkenylene include ethene, propene, butene, and the like. The alkenylene chain is attached to the rest of the molecule through a single bond and to the radical group through a single bond. The points of attachment of the alkenylene chain to the rest of the molecule and to the radical group can be through one carbon or any two carbons within the chain. Unless stated otherwise specifically in the specification, an alkenylene chain can be optionally substituted.

"Alkynyl" or "alkynyl group" refers to a straight or branched hydrocarbon chain radical having from two to twelve carbon atoms, and having one or more carbon-carbon triple bonds. Each alkynyl group is attached to the rest of the molecule by a single bond. Alkynyl group comprising any number of carbon atoms from 2 to 12 are included. An alkynyl group comprising up to 12 carbon atoms is a $C_2$-$C_{12}$ alkynyl, an alkynyl comprising up to 10 carbon atoms is a $C_2$-$C_{10}$ alkynyl, an alkynyl group comprising up to 6 carbon atoms is a $C_2$-$C_6$ alkynyl and an alkynyl comprising up to 5 carbon atoms is a $C_2$-$C_5$ alkynyl. A $C_2$-$C_5$ alkynyl includes $C_5$ alkynyls, $C_4$ alkynyls, $C_3$ alkynyls, and $C_2$ alkynyls. A $C_2$-$C_6$ alkynyl includes all moieties described above for $C_2$-$C_5$ alkynyls but also includes $C_6$ alkynyls. A $C_2$-$C_{10}$ alkynyl includes all moieties described above for $C_2$-$C_5$ alkynyls and $C_2$-$C_6$ alkynyls, but also includes $C_7$, $C_8$, $C_9$ and $C_{10}$ alkynyls. Similarly, a $C_2$-$C_{12}$ alkynyl includes all the foregoing moieties, but also includes $C_{11}$ and $C_{12}$ alkynyls. Non-limiting examples of $C_2$-$C_{12}$ alkenyl include ethynyl, propynyl, butynyl, pentynyl and the like. Unless stated otherwise specifically in the specification, an alkyl group can be optionally substituted.

"Alkynylene" or "alkynylene chain" refers to a straight or branched divalent hydrocarbon chain radical, having from two to twelve carbon atoms, and having one or more carbon-carbon triple bonds. Non-limiting examples of $C_2$-$C_{12}$ alkynylene include ethynylene, propargylene and the like. The alkynylene chain is attached to the rest of the molecule through a single bond and to the radical group through a single bond. The points of attachment of the alkynylene chain to the rest of the molecule and to the radical group can be through one carbon or any two carbons within the chain. Unless stated otherwise specifically in the specification, an alkynylene chain can be optionally substituted.

"Alkoxy" refers to a radical of the formula —$OR_a$ where $R_a$ is an alkyl, alkenyl or alknyl radical as defined above containing one to twelve carbon atoms. Unless stated otherwise specifically in the specification, an alkoxy group can be optionally substituted.

"Alkylamino" refers to a radical of the formula —$NHR_a$ or —$NR_aR_a$ where each $R_a$ is, independently, an alkyl, alkenyl or alkynyl radical as defined above containing one to twelve carbon atoms. Unless stated otherwise specifically in the specification, an alkylamino group can be optionally substituted.

"Alkylcarbonyl" refers to the —C(═O)$R_a$ moiety, wherein $R_a$ is an alkyl, alkenyl or alkynyl radical as defined above. A non-limiting example of an alkyl carbonyl is the methyl carbonyl ("acetal") moiety. Alkylcarbonyl groups can also be referred to as "$C_w$-$C_z$ acyl" where w and z depicts the range of the number of carbon in $R_a$, as defined above. For example, "$C_1$-$C_{10}$ acyl" refers to alkylcarbonyl group as defined above, where $R_a$ is $C_1$-$C_{10}$ alkyl, $C_2$-$C_{10}$ alkenyl, or $C_2$-$C_{10}$ alkynyl radical as defined above. Unless stated otherwise specifically in the specification, an alkyl carbonyl group can be optionally substituted.

"Aryl" refers to a hydrocarbon ring system radical comprising hydrogen, 6 to 18 carbon atoms and at least one aromatic ring. For purposes of this invention, the aryl radical can be a monocyclic, bicyclic, tricyclic or tetracyclic ring system, which can include fused or bridged ring systems. Aryl radicals include, but are not limited to, aryl radicals derived from phenyl (benzene), aceanthrylene, acenaphthylene, acephenanthrylene, anthracene, azulene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, the term "aryl" is meant to include aryl radicals that are optionally substituted.

"Aralkyl" or "arylalkyl" refers to a radical of the formula —$R_b$—$R_c$ where $R_b$ is an alkylene group as defined above and $R_c$ is one or more aryl radicals as defined above. Aralkyl radicals include, but are not limited to, benzyl, diphenylmethyl and the like. Unless stated otherwise specifically in the specification, an aralkyl group can be optionally substituted.

"Aralkenyl" or "arylalkenyl" refers to a radical of the formula —$R_b$—$R_c$ where $R_b$ is an alkenylene group as defined above and $R_c$ is one or more aryl radicals as defined above. Unless stated otherwise specifically in the specification, an aralkenyl group can be optionally substituted.

"Aralkynyl" or "arylalkynyl" refers to a radical of the formula —$R_b$—$R_c$ where $R_b$ is an alkynylene group as defined above and $R_c$ is one or more aryl radicals as defined above. Unless stated otherwise specifically in the specification, an aralkynyl group can be optionally substituted.

"Carbocyclyl," "carbocyclic ring" or "carbocycle" refers to a ring structure, wherein the atoms which form the ring are each carbon. Carbocyclic rings can comprise from 3 to 20 carbon atoms in the ring. Carbocyclic rings include aryls and cycloalkyl. Cycloalkenyl and cycloalkynyl as defined herein. Unless stated otherwise specifically in the specification, a carbocyclyl group can be optionally substituted.

"Cycloalkyl" refers to a stable non-aromatic monocyclic or polycyclic fully saturated hydrocarbon radical consisting solely of carbon and hydrogen atoms, which can include fused, bridged, or spiral ring systems, having from three to twenty carbon atoms, preferably having from three to ten carbon atoms, and which is attached to the rest of the molecule by a single bond. Monocyclic cycloalkyl radicals include, for example, cyclopropyl, cyclobutyl, cyclopentyl, cyclohexyl, cycloheptyl, and cyclooctyl. Polycyclic cycloalkyl radicals include, for example, adamantyl, norbornyl, decalinyl, 7,7-dimethyl-bicyclo[2.2.1]heptanyl, and the like. Unless otherwise stated specifically in the specification, a cycloalkyl group can be optionally substituted.

"Cycloalkenyl" refers to a stable non-aromatic monocyclic or polycyclic hydrocarbon radical consisting solely of carbon and hydrogen atoms, having one or more carbon-carbon double bonds, which can include fused, bridged, or spiral ring systems, having from three to twenty carbon atoms, preferably having from three to ten carbon atoms, and which is attached to the rest of the molecule by a single bond. Monocyclic cycloalkenyl radicals include, for example, cyclopentenyl, cyclohexenyl, cycloheptenyl, cycloctenyl, and the like. Polycyclic cycloalkenyl radicals include, for example, bicyclo[2.2.1]hept-2-enyl and the like. Unless otherwise stated specifically in the specification, a cycloalkenyl group can be optionally substituted.

"Cycloalkynyl" refers to a stable non-aromatic monocyclic or polycyclic hydrocarbon radical consisting solely of carbon and hydrogen atoms, having one or more carbon-carbon triple bonds, which can include fused, bridged, or spiral ring systems, having from three to twenty carbon atoms, preferably having from three to ten carbon atoms, and which is attached to the rest of the molecule by a single bond. Monocyclic cycloalkynyl radicals include, for example, cycloheptynyl, cyclooctynyl, and the like. Unless otherwise stated specifically in the specification, a cycloalkynyl group can be optionally substituted.

"Cycloalkylalkyl" refers to a radical of the formula —$R_b$—$R_d$ where $R_b$ is an alkylene, alkenylene, or alkynylene group as defined above and $R_d$ is a cycloalkyl, cycloalkenyl, cycloalkynyl radical as defined above. Unless stated otherwise specifically in the specification, a cycloalkylalkyl group can be optionally substituted.

"Haloalkyl" refers to an alkyl radical, as defined above, that is substituted by one or more halo radicals, as defined above, e.g., trifluoromethyl, difluoromethyl, trichloromethyl, 2,2,2-trifluoroethyl, 1,2-difluoroethyl, 3-bromo-2-fluoropropyl, 1,2-dibromoethyl, and the like. Unless stated otherwise specifically in the specification, a haloalkyl group can be optionally substituted.

"Haloalkenyl" refers to an alkenyl radical, as defined above, that is substituted by one or more halo radicals, as defined above, e.g., 1-fluoropropenyl, 1,1-difluorobutenyl, and the like. Unless stated otherwise specifically in the specification, a haloalkenyl group can be optionally substituted.

"Haloalkynyl" refers to an alkynyl radical, as defined above, that is substituted by one or more halo radicals, as defined above, e.g., 1-fluoropropynyl, 1-fluorobutynyl, and the like. Unless stated otherwise specifically in the specification, a haloalkynyl group can be optionally substituted.

"Heterocyclyl," "heterocyclic ring" or "heterocycle" refers to a stable 3- to 20-membered non-aromatic, partially aromatic, or aromatic ring radical which consists of two to twelve carbon atoms and from one to six heteroatoms selected from the group consisting of nitrogen, oxygen and sulfur. Heterocyclycl or heterocyclic rings include heteroaryls as defined below. Unless stated otherwise specifically in the specification, the heterocyclyl radical can be a monocyclic, bicyclic, tricyclic or tetracyclic ring system, which can include fused, bridged, and spiral ring systems; and the nitrogen, carbon or sulfur atoms in the heterocyclyl radical can be optionally oxidized; the nitrogen atom can be optionally quaternized; and the heterocyclyl radical can be partially or fully saturated. Examples of such heterocyclyl radicals include, but are not limited to, aziridinyl, oextanyl, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, 1,1-dioxo-thiomorpholinyl, pyridine-one, and the like. The point of attachment of the heterocyclyl, heterocyclic ring, or heterocycle to the rest of the molecule by a single bond is through a ring member atom, which can be carbon or nitrogen. Unless stated otherwise specifically in the specification, a heterocyclyl group can be optionally substituted.

"Heterocyclylalkyl" refers to a radical of the formula $—R_b—R_e$ where $R_b$ is an alkylene group as defined above and $R_e$ is a heterocyclyl radical as defined above. Unless stated otherwise specifically in the specification, a heterocyclylalkyl group can be optionally substituted.

"Heterocyclylalkenyl" refers to a radical of the formula $—R_b—R_e$ where $R_b$ is an alkenylene group as defined above and $R_e$ is a heterocyclyl radical as defined above. Unless stated otherwise specifically in the specification, a heterocyclylalkenyl group can be optionally substituted.

"Heterocyclylalkynyl" refers to a radical of the formula $—R_b—R_e$ where $R_b$ is an alkynylene group as defined above and $R_e$ is a heterocyclyl radical as defined above. Unless stated otherwise specifically in the specification, a heterocyclylalkynyl group can be optionally substituted.

"N-heterocyclyl" refers to a heterocyclyl radical as defined above containing at least one nitrogen and where the point of attachment of the heterocyclyl radical to the rest of the molecule is through a nitrogen atom in the heterocyclyl radical. Unless stated otherwise specifically in the specification, a N-heterocyclyl group can be optionally substituted.

"Heteroaryl" refers to a 5- to 20-membered ring system radical one to thirteen carbon atoms and one to six heteroatoms selected from the group consisting of nitrogen, oxygen and sulfur, as the ring member. For purposes of this invention, the heteroaryl radical can be a monocyclic, bicyclic, tricyclic or tetracyclic ring system, which can include fused or bridged ring systems, wherein at least one ring containing a heteroatom ring member is aromatic. The nitrogen, carbon or sulfur atoms in the heteroaryl radical can be optionally oxidized and the nitrogen atom can be optionally quaternized. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, pyrazolopyridine, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e., thienyl). Unless stated otherwise specifically in the specification, a heteroaryl group can be optionally substituted.

"N-heteroaryl" refers to a heteroaryl radical as defined above containing at least one nitrogen and where the point of attachment of the heteroaryl radical to the rest of the molecule is through a nitrogen atom in the heteroaryl radical. Unless stated otherwise specifically in the specification, an N-heteroaryl group can be optionally substituted.

"Heteroarylalkyl" refers to a radical of the formula $—R_b—R_f$ where $R_b$ is an alkylene chain as defined above and $R_f$ is a heteroaryl radical as defined above. Unless stated otherwise specifically in the specification, a heteroarylalkyl group can be optionally substituted.

"Heteroarylalkenyl" refers to a radical of the formula $—R_b—R_f$ where $R_b$ is an alkenylene, chain as defined above and $R_f$ is a heteroaryl radical as defined above. Unless stated otherwise specifically in the specification, a heteroarylalkenyl group can be optionally substituted.

"Heteroarylalkynyl" refers to a radical of the formula $—R_b—R_f$ where $R_b$ is an alkynylene chain as defined above and $R_f$ is a heteroaryl radical as defined above. Unless stated otherwise specifically in the specification, a heteroarylalkynyl group can be optionally substituted.

"Thioalkyl" refers to a radical of the formula $—SR_a$ where $R_a$ is an alkyl, alkenyl, or alkynyl radical as defined above containing one to twelve carbon atoms. Unless stated otherwise specifically in the specification, a thioalkyl group can be optionally substituted.

The term "substituted" used herein means any of the above groups (e.g., alkyl, alkylene, alkenyl, alkenylene, alkynyl, alkynylene, alkoxy, alkylamino, alkylcarbonyl, thioalkyl, aryl, aralkyl, carbocyclyl, cycloalkyl, cycloalkenyl, cycloalkynyl, cycloalkylalkyl, haloalkyl, heterocyclyl, N-heterocyclyl, heterocyclylalkyl, heteroaryl, N-heteroaryl, heteroarylalkyl, heteroarylalkenyl, heteroarylalkynyl, etc) wherein at least one hydrogen atom is replaced by a bond to a non-hydrogen atoms such as, but not limited to: a halogen atom such as F, Cl, Br, and I; an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with $—NR_gR_h$, $—NR_gC(=O)R_h$, $—NR_gC(=O)NR_gR_h$, $—NR_gC(=O)OR_h$, $—NR_gSO_2R_h$, $—OC(=O)NR_gR_h$, $—OR_g$, $—SR_g$, $—SOR_g$, $—SO_2R_g$, $—OSO_2R_g$, $—SO_2OR_g$, $=NSO_2R_g$, and $—SO_2NR_gR_h$. "Substituted" also means any of the above groups in which one or more hydrogen atoms are replaced with $—C(=O)R_g$, $—C(=O)OR_g$, $—C(=O)NR_gR_h$, $—CH_2SO_2R_g$, $—CH_2SO_2NR_gR_h$. In the foregoing, $R_g$ and $R_h$ are the same or different and independently hydrogen, alkyl, alkenyl, alkynyl, alkoxy, alkylamino, thioalkyl, aryl, aralkyl, cycloalkyl, cycloalkenyl, cycloalkynyl, cycloalkylalkyl, haloalkyl, haloalkenyl, haloalkynyl, heterocyclyl, N-heterocyclyl, heterocyclylalkyl, heteroaryl, N-heteroaryl and/or heteroarylalkyl. "Substituted" further means any of the above groups in which one or more hydrogen atoms are replaced by a bond to an amino, cyano, hydroxyl, imino, nitro, oxo, thioxo, halo, alkyl, alkenyl, alkynyl, alkoxy, alkylamino, thioalkyl, aryl, aralkyl, cycloalkyl, cycloalkenyl, cycloalkynyl, cycloalkylalkyl, haloalkyl, haloalkenyl, haloalkynyl, heterocyclyl, N-heterocyclyl, heterocyclylalkyl, heteroaryl, N-heteroaryl and/or heteroarylalkyl group. In addition, each of the foregoing substituents can also be optionally substituted with one or more of the above substituents.

As used herein, the symbol

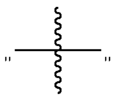

(hereinafter can be referred to as "a point of attachment bond") denotes a bond that is a point of attachment between two chemical entities, one of which is depicted as being attached to the point of attachment bond and the other of which is not depicted as being attached to the point of attachment bond. For example,

indicates that the chemical entity "A" is bonded to another chemical entity via the point of attachment bond. Furthermore, the specific point of attachment to the non-depicted chemical entity can be specified by inference. For example, the compound

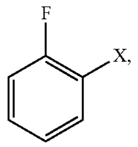

wherein X is

infers that the point of attachment bond is the bond by which X is depicted as being attached to the phenyl ring at the ortho position relative to fluorine.

The phrases "parenteral administration" and "administered parenterally" are art-recognized terms, and include modes of administration other than enteral and topical administration, such as injections, and include, without limitation, intravenous, intramuscular, intrapleural, intravascular, intrapericardial, intraarterial, intrathecal, intracapsular, intraorbital, intracardiac, intradermal, intraperitoneal, transtracheal, subcutaneous, subcuticular, intra-articular, subcapsular, subarachnoid, intraspinal and intrastemal injection and infusion.

The term "treating" is art-recognized and includes inhibiting a disease, disorder or condition in a subject, e.g., impeding its progress; and relieving the disease, disorder or condition, e.g., causing regression of the disease, disorder and/or condition. Treating the disease or condition includes ameliorating at least one symptom of the particular disease or condition, even if the underlying pathophysiology is not affected.

The term "preventing" is art-recognized and includes stopping a disease, disorder or condition from occurring in a subject, which may be predisposed to the disease, disorder and/or condition but has not yet been diagnosed as having it. Preventing a condition related to a disease includes stopping the condition from occurring after the disease has been diagnosed but before the condition has been diagnosed.

A "patient," "subject," or "host" to be treated by the subject method may mean either a human or non-human animal, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal. A patient refers to a subject afflicted with a disease or disorder.

The terms "prophylactic" or "therapeutic" treatment is art-recognized and includes administration to the host of one or more of the subject compositions. If it is administered prior to clinical manifestation of the unwanted condition (e.g., disease or other unwanted state of the host animal) then the treatment is prophylactic, i.e., it protects the host against developing the unwanted condition, whereas if it is administered after manifestation of the unwanted condition, the treatment is therapeutic (i.e., it is intended to diminish, ameliorate, or stabilize the existing unwanted condition or side effects thereof).

The terms "therapeutic agent", "drug", "medicament" and "bioactive substance" are art-recognized and include molecules and other agents that are biologically, physiologically, or pharmacologically active substances that act locally or systemically in a patient or subject to treat a disease or condition. The terms include without limitation pharmaceutically acceptable salts thereof and prodrugs. Such agents may be acidic, basic, or salts; they may be neutral molecules, polar molecules, or molecular complexes capable of hydrogen bonding; they may be prodrugs in the form of ethers, esters, amides and the like that are biologically activated when administered into a patient or subject.

The phrase "therapeutically effective amount" or "pharmaceutically effective amount" is an art-recognized term. In certain embodiments, the term refers to an amount of a therapeutic agent that produces some desired effect at a reasonable benefit/risk ratio applicable to any medical treatment. In certain embodiments, the term refers to that amount necessary or sufficient to eliminate, reduce or maintain a target of a particular therapeutic regimen. The effective amount may vary depending on such factors as the disease or condition being treated, the particular targeted constructs being administered, the size of the subject or the severity of the disease or condition. One of ordinary skill in the art may empirically determine the effective amount of a particular compound without necessitating undue experimentation. In certain embodiments, a therapeutically effective amount of a therapeutic agent for in vivo use will likely depend on a number of factors, including: the rate of release of an agent from a polymer matrix, which will depend in part on the chemical and physical characteristics of the polymer; the identity of the agent; the mode and method of administration; and any other materials incorporated in the polymer matrix in addition to the agent.

The term "ED50" is art-recognized. In certain embodiments, ED50 means the dose of a drug, which produces 50% of its maximum response or effect, or alternatively, the dose, which produces a pre-determined response in 50% of test subjects or preparations. The term "LD50" is art-recognized. In certain embodiments, LD50 means the dose of a drug, which is lethal in 50% of test subjects. The term "therapeutic index" is an art-recognized term, which refers to the therapeutic index of a drug, defined as LD50/ED50.

The terms "$IC_{50}$," or "half maximal inhibitory concentration" is intended to refer to the concentration of a substance (e.g., a compound or a drug) that is required for 50% inhibition of a biological process, or component of a process, including a protein, subunit, organelle, ribonucleoprotein, etc.

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present.

Throughout the description, where compositions are described as having, including, or comprising, specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the compositions and methods described herein remains operable. Moreover, two or more steps or actions can be conducted simultaneously.

All percentages and ratios used herein, unless otherwise indicated, are by weight.

The terms "gene expression" or "protein expression" includes any information pertaining to the amount of gene transcript or protein present in a sample, as well as information about the rate at which genes or proteins are produced or are accumulating or being degraded (e.g., reporter gene data, data from nuclear runoff experiments, pulse-chase data etc.). Certain kinds of data might be viewed as relating to both gene and protein expression. For example, protein levels in a cell are reflective of the level of protein as well as the level of transcription, and such data is intended to be included by the phrase "gene or protein expression information". Such information may be given in the form of amounts per cell, amounts relative to a control gene or protein, in unitless measures, etc.; the term "information" is not to be limited to any particular means of representation and is intended to mean any representation that provides relevant information. The term "expression levels" refers to a quantity reflected in or derivable from the gene or protein expression data, whether the data is directed to gene transcript accumulation or protein accumulation or protein synthesis rates, etc.

The terms "healthy" and "normal" are used interchangeably herein to refer to a subject or particular cell or tissue that is devoid (at least to the limit of detection) of a disease condition.

The term "nucleic acid" refers to polynucleotides such as deoxyribonucleic acid (DNA), and, where appropriate, ribonucleic acid (RNA). The term should also be understood to include analogues of either RNA or DNA made from nucleotide analogues, and, as applicable to the embodiment being described, single-stranded (such as sense or antisense) and double-stranded polynucleotides. In some embodiments, "nucleic acid" refers to inhibitory nucleic acids. Some categories of inhibitory nucleic acid compounds include antisense nucleic acids, RNAi constructs, and catalytic nucleic acid constructs. Such categories of nucleic acids are well-known in the art.

Embodiments described herein relate to compositions and methods of preventing, treating, or reducing the severity of a renal disorder, disease, and/or injury. It was found that administration of a 15-PGDH inhibitor to a subject prior to and/or after renal injury can induce renal vasodilation, and enhance resistance to hypoxia resulting in a prophylactic and protective effect against renal injury. These benefits can be associated with a prophylactic use of as little as a single dose of a 15-PGDH inhibitor. Administration of a 15-PGDH inhibitor to a subject having or at risk of a renal injury improved renal hemodynamics, decreased induction of oxidative stress, reduced induction of inflammation, attenuated multiple markers of renal damage and preserved renal function. Moreover, administration of a 15-PGDH inhibitor before and/or after administration of a contrast media was found to prevent and/or treat contrast-induced acute kidney injury (CIAKI). Advantageously, the administration of a 15-PGDH inhibitor systemically to generate endogenous renal PGE2 in a subject with a renal injury showed greater effectiveness in treating the renal injury than systemic administration of PGE1 or PGE2.

Accordingly, in some embodiments, compositions and methods of inhibiting 15-PDGH activity can be used to prevent, treat, or reduce the severity of a renal disorder, disease, and/or injury in a subject or kidney of a subject in need thereof. Examples of renal disorders, diseases, and/or injuries that can be treated include hypotensive injury to the kidney; hypertensive renal disease; diabetic renal disease and diabetic nephropathy; renal disease from vasculitis and autoimmune diseases, including but not limited to lupus erythematosis, polyarteritis, Wegeners' Granulomatosis, and mixed connective tissue disease; ischemic renal injury; acute renal failure; chronic renal failure; glomerulonephritis; nephrotic syndrome; acute tubular necrosis; nephrosclerosis; gomerulosclerosis; minimal change disease; idiopathic membranous nephropathy; membranoproliferative glomerulonephritis; Berger's disease; mesangial proliferative glomerulonephritis; chronic glomerulonephritis; focal glomerulosclerosis; renal effects of Sjogren's syndrome; renal effects of scleroderma; interstitial nephritis; and renal injury to a kidney donor, transplant recipient, and/or transplanted kidney following kidney transplant.

In certain embodiments, the subject has been identified as having an acute kidney injury (AKI) based on the Acute Kidney Injury Network (AKIN) criteria or Risk/Injury/Failure/Loss/ESRD (RIFLE) criteria.

In another embodiment, the subject has been identified as having an elevated level of serum creatinine, plasma creatinine, urine creatinine, or blood urea nitrogen (BUN), compared to a healthy control subject.

In another embodiment, the subject has been identified as having an elevated level of serum or urine neutrophil gelatinase-associated lipocalin, serum or urine interleukin-18, serum or urine cystatin C, or urine KIM-1, compared to a healthy control subject.

In some embodiments, the renal disorder, disease, and/or injury is an acute kidney injury. In other embodiments, the renal disorder, disease, and/or injury is an ischemic acute kidney injury. In one embodiment, the subject is a human who has been identified as having reduced effective arterial volume. In one embodiment, the subject has been identified as having intravascular volume depletion (e.g., due to hemorrhage, gastrointestinal loss, renal loss, skin and mucous membrane loss, nephrotic syndrome, cirrhosis, or capillary leak). In one embodiment, the subject has been identified as having reduced cardiac output (e.g., due to cardiogenic shock, pericardial disease, congestive heart failure, valvular heart disease, pulmonary disease, or sepsis). In one embodiment, the subject has been identified as having systemic vasodilation (e.g., caused by cirrhosis, anaphylaxis, or sepsis). In one embodiment, the subject has been identified as having renal vasoconstriction (e.g., caused by early sepsis, hepatorenal syndrome, acute hypercalcemia, a drug, or a radiocontrast agent).

In some embodiments, the renal disorder, disease, and/or injury is a nephrotoxic kidney injury. In one embodiment, the human subject has been exposed to a nephrotoxin. For example, the nephrotoxin can be a nephrotoxic drug selected from the group consisting of an antibiotic (e.g., an aminoglycoside), a chemotherapeutic agent (e.g., cis-platinum), a calcineurin inhibitor, amphotericin B, and a radiographic contrast agent, such as an iodinated contrast media (e.g., Iodixanol or Iobitridol). In another example, the nephrotoxin can be an illicit drug or a heavy metal.

In certain embodiments, the subject has undergone a trauma injury or a crush injury.

In certain embodiments, the subject will undergo or has undergone an organ transplant surgery (e.g., a kidney transplant surgery or heart transplant surgery).

In certain embodiments, the subject will undergo or has undergone a surgery complicated by hypoperfusion.

In certain embodiments, the subject will undergo or has undergone cardiothoracic surgery or a vascular surgery.

In certain embodiments, the subject will be taking or has taken medication (e.g., an anticholinergic) that interferes with normal emptying of the bladder.

In certain embodiments, the subject has benign prostatic hypertrophy or a cancer (e.g., prostate cancer, ovarian cancer, or colorectal cancer).

In certain embodiments, the subject has a kidney stone.

In certain embodiments, the subject has an obstructed urinary catheter.

In certain embodiments, the subject has taken a drug that causes or leads to crystalluria, a drug that causes or leads to myoglobinuria, or a drug that causes or leads to cystitis.

Other embodiments, described herein relate to a method for protecting a kidney from injury in a subject. The method involves administering to the subject an effective amount of 15-PGDH inhibitor to protect the subject's kidney from injury. In some embodiments, the subject has been or will be exposed to an ischemic or nephrotoxic insult. In some embodiments, the human subject has been exposed to oxidative damage (e.g., by free radicals such as reactive oxygen or nitrogen species.

Still further embodiments relate to a method for protecting a human subject's kidney from kidney injury during organ transplantation, such as kidney transplantation. The method involves administering to the kidney transplant donor, kidney transplant recipient, and/or transplanted kidney an effective amount of 15-PGDH inhibitor to protect the transplant donor, transplant recipient, and/or transplanted kidney from injury. In certain embodiments, the method further comprises administering to the human subject one or more doses of a 15-PGDH inhibitor before and/or after (e.g., 0.1, 0.2, 0.3, 0.4, 0.5, 1, 2, 3, 4, 5, 6, 7, 8, 9, 10, 11, 12, 24, 48, 72, 96, 168 hours, or 1 week, 2 weeks, 3 weeks or 1 month) the kidney transplantation. It will be appreciated that administration of the 15-PGDH inhibitor can protect the human subject's kidney from kidney injury during other non-kidney organ transplantation.

In some embodiments, 15-PGDH inhibitors potentially used in preventing, treating, or reducing the severity of the renal disorder, disease, and/or injury can be identified using assays in which putative inhibitor compounds are applied to cells expressing 15-PGDH and then the functional effects on 15-PGDH activity are determined. Samples or assays comprising 15-PGDH that are treated with a potential inhibitor are compared to control samples without the inhibitor to examine the extent of effect. Control samples (untreated with modulators) are assigned a relative 15-PGDH activity value of 100%. Inhibition of 15-PGDH is achieved when the 15-PGDH activity value relative to the control is about 80%, optionally 50% or 25%, 10%, 5% or 1%.

Agents tested as 15-PGDH inhibitors can be any small chemical molecule or compound. Typically, test compounds will be small chemical molecules, natural products, or peptides. The assays are designed to screen large chemical libraries by automating the assay steps and providing compounds from any convenient source to assays, which are typically run in parallel (e.g., in microtiter formats on microtiter plates in robotic assays).

In some embodiments, the 15-PGDH inhibitor can include a compound having the following formula (I):

(I)

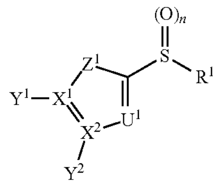

or a pharmaceutically acceptable salt, tautomer, or solvate thereof;

wherein n is 0-2;

$Y^1$, $Y^2$, and $R^1$ are the same or different and are independently hydrogen or a substituted or unsubstituted group selected from $C_1$-$C_{24}$ alkyl, $C_2$-$C_{24}$ alkenyl, $C_2$-$C_{24}$ alkynyl, $C_3$-$C_{20}$ aryl, heteroaryl, heterocycloalkenyl containing from 5-6 ring atoms, $C_6$-$C_{24}$ alkaryl, $C_6$-$C_{24}$ aralkyl, halo, —Si($C_1$-$C_3$ alkyl)$_3$, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl, acyloxy, $C_2$-$C_{24}$ alkoxycarbonyl, $C_6$-$C_{20}$ aryloxycarbonyl, $C_2$-$C_{24}$ alkylcarbonato, $C_6$-$C_{20}$ arylcarbonato, carboxy, carboxylato, carbamoyl, $C_1$-$C_{24}$ alkyl-carbamoyl, arylcarbamoyl, thiocarbamoyl, carbamido, cyano, isocyano, cyanato, isocyanato, isothiocyanato, azido, formyl, thioformyl, amino, $C_1$-$C_{24}$ alkyl amino, $C_5$-$C_{20}$ aryl amino, $C_2$-$C_{24}$ alkylamido, $C_6$-$C_{20}$ arylamido, imino, alkylimino, arylimino, nitro, nitroso, sulfo, sulfonato, $C_1$-$C_{24}$ alkylsulfanyl, arylsulfanyl, $C_1$-$C_{24}$ alkylsulfinyl, $C_5$-$C_{20}$ arylsulfinyl, $C_1$-$C_{24}$ alkylsulfonyl, $C_5$-$C_{20}$ arylsulfonyl, sulfonamide, phosphono, phosphonato, phosphinato, phospho, phosphino, polyalkylethers, phosphates, and phosphate esters, groups incorporating amino acids or other moieties expected to bear positive or negative charge at physiological pH, and combinations thereof, and wherein $Y^1$ and $Y^2$ may be linked to form a cyclic or polycyclic ring, wherein the ring is a substituted or unsubstituted aryl, a substituted or unsubstituted heteroaryl, a substituted or unsubstituted cycloalkyl, and a substituted or unsubstituted heterocyclyl;

$U^1$ is N, C—$R^2$, or C—$NR^3R^4$, wherein $R^2$ is selected from the group consisting of a H, a lower alkyl group, O, $(CH_2)_{n1}OR'$ (wherein n1=1, 2, or 3), $CF_3$, $CH_2$—$CH_2X$, O—$CH_2$—$CH_2X$, $CH_2$—$CH_2$—$CH_2X$, O—$CH_2$—$CH_2X$, X, (wherein X═H, F, Cl, Br, or I), CN, (C═O)—R', (C═O)N$(R')_2$, O(CO)R', COOR' (wherein R' is H or a lower alkyl group), and wherein $R^1$ and $R^2$ may be linked to form a cyclic or polycyclic ring, wherein $R^3$ and $R^4$ are same or different and are each selected from the group consisting of H, a lower alkyl group, O, $(CH_2)_{n1}OR'$ (wherein n1=1, 2, or 3), $CF_3$, $CH_2$—$CH_2X$, $CH_2$—$CH_2$—$CH_2X$, (wherein X═H, F, Cl, Br, or I), CN, (C═O)—R', (C═O)N$(R')_2$, COOR' (wherein R' is H or a lower alkyl group), and $R^3$ or $R^4$ may be absent;

$X^1$ and $X^2$ are independently N or C, and wherein when $X^1$ and/or $X^2$ are N, $Y^1$ and/or $Y^2$, respectively, are absent; and $Z^1$ is O, S, $CR^aR^b$ or $NR^a$, wherein $R^a$ and $R^b$ are independently H or a $C_{1-8}$ alkyl, which is linear, branched, or cyclic, and which is unsubstituted or substituted.

In other embodiments, the 15-PGDH inhibitor can include a compound having the following formula (II):

(II)

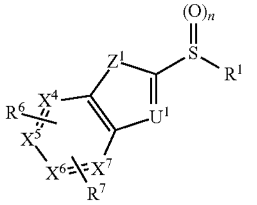

or a pharmaceutically acceptable salt, tautomer, or solvate thereof;

wherein n is 0-2

$X^4$, $X^5$, $X^6$, and $X^7$ are independently N or $CR^c$;

$R^1$, $R^6$, $R^7$, and $R^c$ are the same or different and independently hydrogen or a substituted or unsubstituted group selected from $C_1$-$C_{24}$ alkyl, $C_2$-$C_{24}$ alkenyl, $C_2$-$C_{24}$ alkynyl, $C_3$-$C_{20}$ aryl, heteroaryl, heterocycloalkenyl containing from 5-6 ring atoms, $C_6$-$C_{24}$ alkaryl, $C_6$-$C_{24}$ aralkyl, halo, —Si($C_1$-$C_3$ alkyl)$_3$, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl, acyloxy, $C_2$-$C_{24}$ alkoxycarbonyl, $C_6$-$C_{20}$ aryloxycarbonyl, $C_2$-$C_{24}$ alkylcarbonato, $C_6$-$C_{20}$ arylcarbonato, carboxy, carboxylato, carbamoyl, $C_1$-$C_{24}$ alkyl-carbamoyl, arylcarbamoyl, thiocarbamoyl, carbamido, cyano, isocyano, cyanato, isocyanato, isothiocyanato, azido, formyl, thioformyl, amino, $C_1$-$C_{24}$ alkyl amino, $C_5$-$C_{20}$ aryl amino, $C_2$-$C_{24}$ alkylamido, $C_2$-$C_{24}$ alkylamido substituted with a hydroxyl, $C_6$-$C_{20}$ arylamido, imino, alkylimino, arylimino, nitro, nitroso, sulfo, sulfonato, $C_1$-$C_{24}$ alkylsulfanyl, arylsulfanyl, $C_1$-$C_{24}$ alkylsulfinyl, $C_5$-$C_{20}$ arylsulfinyl, $C_1$-$C_{24}$ alkylsulfonyl, $C_5$-$C_{20}$ arylsulfonyl, sulfonamide, phosphono, phosphonato, phosphinato, phospho, phosphino, polyalkylethers, phosphates, and phosphate esters, groups incorporating amino acids or other moieties expected to bear positive or negative charge at physiological pH, and combinations thereof, and wherein $R^6$ and $R^7$ may be linked to form a cyclic or polycyclic ring, wherein the ring is a substituted or unsubstituted aryl, a substituted or unsubstituted heteroaryl, a substituted or unsubstituted cycloalkyl, and a substituted or unsubstituted heterocyclyl;

$U^1$ is N, C—$R^2$, or C—$NR^3R^4$, wherein $R^2$ is selected from the group consisting of a H, a lower alkyl group, O, $(CH_2)_{n1}OR'$ (wherein n1=1, 2, or 3), $CF_3$, $CH_2$—$CH_2X$, O—$CH_2$—$CH_2X$, $CH_2$—$CH_2$—$CH_2X$, O—$CH_2$—$CH_2X$, X, (wherein X═H, F, Cl, Br, or I), CN, (C═O)—R', (C═O)N$(R')_2$, O(CO)R', COOR' (wherein R' is H or a lower alkyl group), and wherein $R^1$ and $R^2$ may be linked to form a cyclic or polycyclic ring, wherein $R^3$ and $R^4$ are the same or different and are each selected from the group consisting of H, a lower alkyl group, O, $(CH_2)_{n1}OR'$ (wherein n1=1, 2, or 3), $CF_3$, $CH_2$—$CH_2X$, $CH_2$—$CH_2$—$CH_2X$, (wherein X═H, F, Cl, Br, or I), CN, (C═O)—R', (C═O)N$(R')_2$, COOR' (wherein R' is H or a lower alkyl group), and $R^3$ or $R^4$ may be absent; and $Z^1$ is O, S, $CR^aR^b$ or $NR^a$, wherein $R^a$ and $R^b$ are independently H or a $C_{1-8}$ alkyl, which is linear, branched, or cyclic, and which is unsubstituted or substituted.

In yet other embodiments, the 15-PGDH inhibitor can include a compound having the following formula (III) or (IV):

(III)

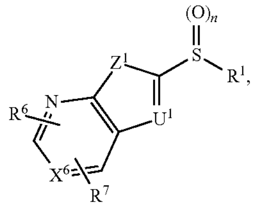

(IV)

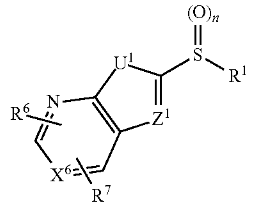

or a pharmaceutically acceptable salt, tautomer, or solvate thereof;

wherein n is 0-2

$X^6$ is independently is N or $CR^c$;

$R^1$, $R^6$, $R^7$, and $R^c$ are the same or different and independently hydrogen or a substituted or unsubstituted group selected from $C_1$-$C_{24}$ alkyl, $C_2$-$C_{24}$ alkenyl, $C_2$-$C_{24}$ alkynyl, $C_3$-$C_{20}$ aryl, heteroaryl, heterocycloalkenyl containing from 5-6 ring atoms, $C_6$-$C_{24}$ alkaryl, $C_6$-$C_{24}$ aralkyl, halo, —Si($C_1$-$C_3$ alkyl)$_3$, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl, acyloxy, $C_2$-$C_{24}$ alkoxycarbonyl, $C_6$-$C_{20}$ aryloxycarbonyl, $C_2$-$C_{24}$ alkylcarbonato, $C_6$-$C_{20}$ arylcarbonato, carboxy, carboxylato, carbamoyl, $C_1$-$C_{24}$ alkyl-carbamoyl, arylcarbamoyl, thiocarbamoyl, carbamido, cyano, isocyano, cyanato, isocyanato, isothiocyanato, azido, formyl, thioformyl, amino, $C_1$-$C_{24}$ alkyl amino, $C_2$-$C_{24}$ alkylamido substituted with a hydroxyl, $C_5$-$C_{20}$ aryl amino, $C_2$-$C_{24}$ alkylamido, $C_6$-$C_{20}$ arylamido, imino, alkylimino, arylimino, nitro, nitroso, sulfo, sulfonato, $C_1$-$C_{24}$ alkylsulfanyl, arylsulfanyl, $C_1$-$C_{24}$ alkylsulfinyl, $C_5$-$C_{20}$ arylsulfinyl, $C_1$-$C_{24}$ alkylsulfonyl, $C_5$-$C_{20}$ arylsulfonyl, sulfonamide, phosphono, phosphonato, phosphinato, phospho, phosphino, polyalkylethers, phosphates, and phosphate esters, groups incorporating amino acids or other moieties expected to bear positive or negative charge at physiological pH, and combinations thereof, and wherein $R^6$ and $R^7$ may be linked to form a cyclic or polycyclic ring, wherein the ring is a substituted or unsubstituted aryl, a substituted or unsubstituted heteroaryl, a substituted or unsubstituted cycloalkyl, and a substituted or unsubstituted heterocyclyl;

$U^1$ is N, C—$R^2$, or C—$NR^3R^4$, wherein $R^2$ is selected from the group consisting of a H, a lower alkyl group, O, $(CH_2)_{n1}OR'$ (wherein n1=1, 2, or 3), $CF_3$, $CH_2$—$CH_2X$, O—$CH_2$—$CH_2X$, $CH_2$—$CH_2$—$CH_2X$, O—$CH_2$—$CH_2X$, X, (wherein X═H, F, Cl, Br, or I), CN, (C═O)—R', (C═O)N(R')$_2$, O(CO)R', COOR' (wherein R' is H or a lower alkyl group), and wherein $R^1$ and $R^2$ may be linked to form a cyclic or polycyclic ring, wherein $R^3$ and $R^4$ are the same or different and are each selected from the group consisting of H, a lower alkyl group, O, $(CH_2)_{n1}OR'$ (wherein n1=1, 2, or 3), $CF_3$, $CH_2$—$CH_2X$, $CH_2$—$CH_2$—$CH_2X$, (wherein X═H, F, Cl, Br, or I), CN, (C═O)—R', (C═O)N(R')$_2$, COOR' (wherein R' is H or a lower alkyl group), and $R^3$ or $R^4$ may be absent;

$Z^1$ is O, S, $CR^aR^b$ or $NR^a$, wherein $R^a$ and $R^b$ are independently H or a $C_{1-8}$ alkyl, which is linear, branched, or cyclic, and which is unsubstituted or substituted.

In some embodiments, $R^1$ is selected from the group consisting of branched, linear, or cyclic alkyl,

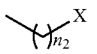

wherein $n_2$=0-6 and X is any of the following: $CF_yH_z$ (y+z=3), $CCl_yH_z$ (y+z 3), OH, OAc, OMe, $R^{71}$, $OR^{72}$, CN, $N(R^{73})_2$,

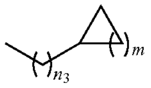

($n_3$=0-5, m=1-5), and

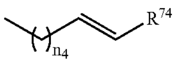

($n_4$=0-5).

In other embodiments, $R^6$ and $R^7$ can each independently be one of the following:

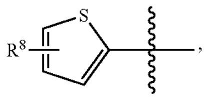,

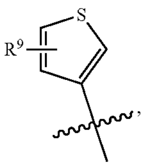,

-continued

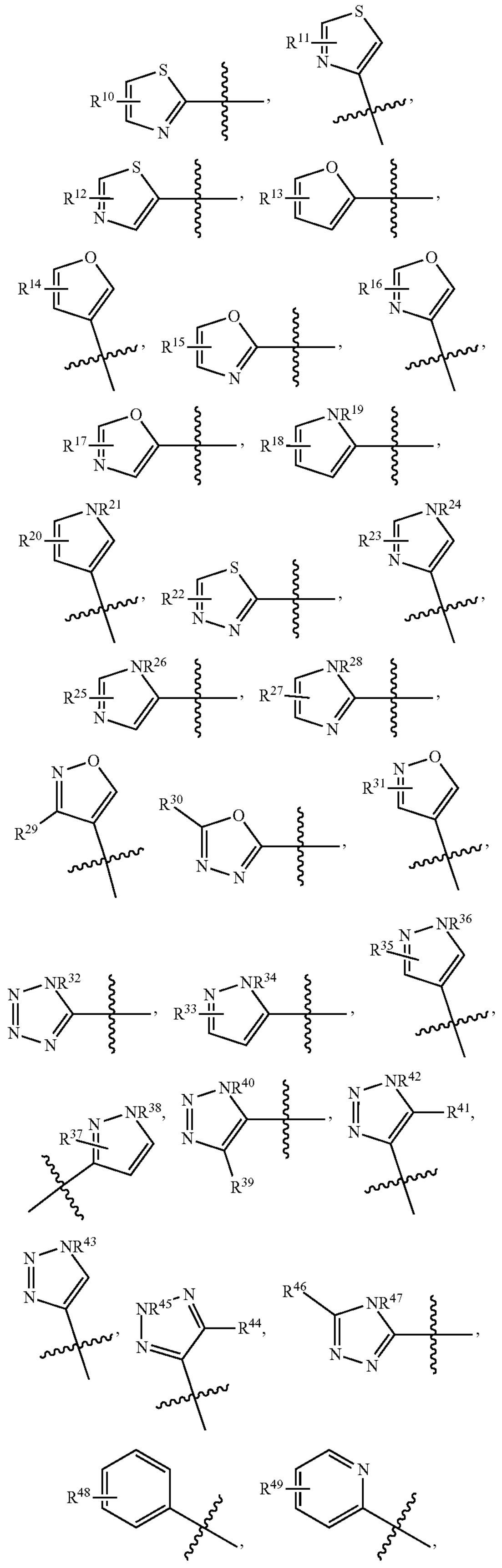

-continued

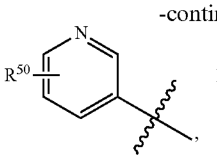, 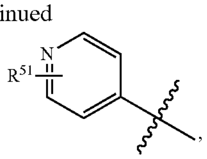,

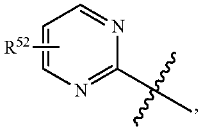, 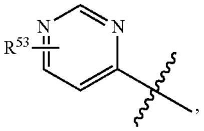,

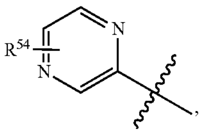, 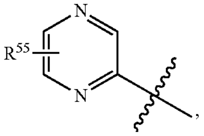,

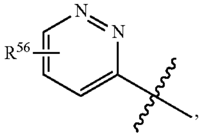, 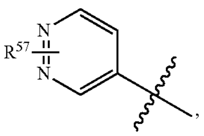,

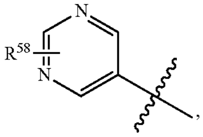, 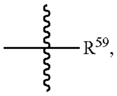, 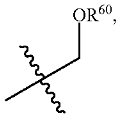,

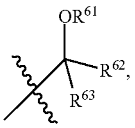, 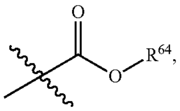, 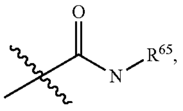,

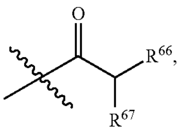, 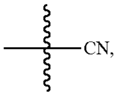, 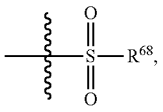,

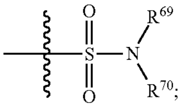;

each $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$, $R^{45}$, $R^{46}$, $R^{47}$, $R^{48}$, $R^{49}$, $R^{50}$, $R^{51}$, $R^{52}$, $R^{53}$, $R^{54}$, $R^{55}$, $R^{56}$, $R^{57}$, $R^{58}$, $R^{59}$, $R^{60}$, $R^{61}$, $R^{62}$, $R^{63}$, $R^{64}$, $R^{65}$, $R^{66}$, $R^{67}$, $R^{68}$, $R^{69}$, $R^{70}$, $R^{71}$, $R^{72}$, $R^{73}$, and $R^{74}$ are the same or different and are independently selected from the group consisting of hydrogen, substituted or unsubstituted $C_1$-$C_{24}$ alkyl, $C_2$-$C_{24}$ alkenyl, $C_2$-$C_{24}$ alkynyl, $C_3$-$C_{20}$ aryl, heterocycloalkenyl containing from 5-6 ring atoms, (wherein from 1-3 of the ring atoms is independently selected from N, NH, $N(C_1$-$C_6$ alkyl), $NC(O)(C_1$-$C_6$ alkyl), O, and S), heteroaryl or heterocyclyl containing from 5-14 ring atoms, (wherein from 1-6 of the ring atoms is independently selected from N, NH, $N(C_1$-$C_3$ alkyl), O, and S), $C_6$-$C_{24}$ alkaryl, $C_6$-$C_{24}$ aralkyl, halo, silyl, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO—), carbamoyl (—(CO)—$NH_2$), $C_1$-$C_{24}$ alkyl-carbamoyl (—(CO)—NH($C_1$-$C_{24}$ alkyl)), arylcarbamoyl (—(CO)—NH-aryl), thiocarbamoyl (—(CS)—$NH_2$), carbamido (—NH—(CO)—$NH_2$), cyano(—CN), isocyano (—$N^+C^-$), cyanato (—O—CN), isocyanato (—O—$N^+$=$C^-$), isothiocyanato (—S—CN), azido (—N=$N^+$=$N^-$), formyl (—(CO)—H), thioformyl (—(CS)—H), amino (—$NH_2$), $C_1$-$C_{24}$ alkyl amino, $C_1$-$C_{24}$ alkyl amino substituted with hydroxyl, $C_5$-$C_{20}$ aryl amino, $C_2$-$C_{24}$ alkylamido (—NH—(CO)-alkyl), $C_6$-$C_{20}$ arylamido (—NH—(CO)-aryl), sulfanamido (—$SO_2N(R)_2$ where R is independently H, alkyl, aryl or heteroaryl), imino (—CR=NH where R is hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR=N(alkyl), where R=hydrogen, alkyl, aryl, alkaryl, aralkyl, etc.), arylimino (—CR=N(aryl), where R=hydrogen, alkyl, aryl, alkaryl, etc.), nitro (—$NO_2$), nitroso (—NO), sulfo (—$SO_2$—OH), sulfonato (—$SO_2$—O—), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—$SO_2$-alkyl), $C_5$-$C_{20}$ arylsulfonyl (—$SO_2$-aryl), sulfonamide (—$SO_2$—$NH_2$, —$SO_2NY_2$ (wherein Y is independently H, arlyl or alkyl), phosphono (—$P(O)(OH)_2$), phosphonato (—P(O)(O—$)_2$), phosphinato (—P(O)(O—)), phospho (—$PO_2$), phosphino (—$PH_2$), polyalkyl ethers (—$[(CH_2)_nO]_m$), phosphates, phosphate esters [—$OP(O)(OR)_2$ where R=H, methyl or other alkyl], groups incorporating amino acids or other moieties expected to bear positive or negative charge at physiological pH, and combinations thereof, or a pharmaceutically acceptable salt, tautomer, or solvate thereof.

In still other embodiments, $R^6$ and $R^7$ can independently be a group that improves aqueous solubility, for example, a phosphate ester (—$OPO_3H_2$), a phenyl ring linked to a phosphate ester (—$OPO_3H_2$), a phenyl ring substituted with one or more methoxyethoxy groups, or a morpholine, or an aryl or heteroaryl ring substituted with such a group.

In other embodiments, the 15-PGDH inhibitor can include a compound having the following formula (V):

(V)

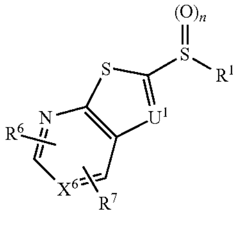

or a pharmaceutically acceptable salt, tatomer, or solvate thereof;

wherein n is 0-2

$X^6$ is independently is N or $CR^c$ $R^1$, $R^6$, $R^7$, and $R^c$ are the same or different each independently hydrogen or a substituted or unsubstituted group selected from $C_1$-$C_{24}$ alkyl, $C_2$-$C_{24}$ alkenyl, $C_2$-$C_{24}$ alkynyl, $C_3$-$C_{20}$ aryl, heteroaryl, heterocycloalkenyl containing from 5-6 ring atoms, $C_6$-$C_{24}$ alkaryl, $C_6$-$C_{24}$ aralkyl, halo, —Si($C_1$-$C_3$ alkyl)$_3$, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl, acyloxy, $C_2$-$C_{24}$ alkoxycarbonyl, $C_6$-$C_{20}$ aryloxycarbonyl, $C_2$-$C_{24}$ alkylcarbonato, $C_6$-$C_{20}$ arylcarbonato, carboxy, carboxylato, carbamoyl, $C_1$-$C_{24}$ alkyl-carbamoyl, arylcarbamoyl, thiocarbamoyl, carbamido, cyano, isocyano, cyanato, isocyanato, isothiocyanato, azido, formyl, thioformyl, amino, $C_1$-$C_{24}$ alkyl amino, $C_5$-$C_{20}$ aryl amino, $C_2$-$C_{24}$ alkylamido, $C_2$-$C_{24}$ alkylamido substituted with a hydroxyl, $C_6$-$C_{20}$ arylamido, imino, alkylimino, arylimino, nitro, nitroso, sulfo, sulfonato, $C_1$-$C_{24}$ alkylsulfanyl, arylsulfanyl, $C_1$-$C_{24}$ alkylsulfinyl, $C_5$-$C_{20}$ arylsulfinyl, $C_1$-$C_{24}$ alkylsulfonyl, $C_5$-$C_{20}$ arylsulfonyl, sulfonamide, phosphono, phosphonato, phosphinato, phospho, phosphino, polyalkylethers, phosphates, and phosphate esters, groups incorporating amino acids or other moieties expected to bear positive or negative charge at physiological pH, and combinations thereof, and wherein $R^6$ and $R^7$ may be linked to form a cyclic or polycyclic ring, wherein the ring is a substituted or unsubstituted aryl, a substituted or unsubstituted heteroaryl, a substituted or unsubstituted cycloalkyl, and a substituted or unsubstituted heterocyclyl; and $U^1$ is N, C—$R^2$, or C—$NR^3R^4$, wherein $R^2$ is selected from the group consisting of a H, a lower alkyl group, O, $(CH_2)_{n1}$OR' (wherein n1=1, 2, or 3), $CF_3$, $CH_2$—$CH_2X$, O—$CH_2$—$CH_2X$, $CH_2$—$CH_2$—$CH_2X$, O—$CH_2$—$CH_2X$, X, (wherein X=H, F, Cl, Br, or I), CN, (C=O)—R', (C=O)N(R')$_2$, O(CO)R', COOR' (wherein R' is H or a lower alkyl group), and wherein $R^1$ and $R^2$ may be linked to form a cyclic or polycyclic ring, wherein $R^3$ and $R^4$ are the same or different and are each selected from the group consisting of H, a lower alkyl group, O, $(CH_2)_{n1}$OR' (wherein n1=1, 2, or 3), $CF_3$, $CH_2$—$CH_2X$, $CH_2$—$CH_2$—$CH_2X$, (wherein X=H, F, Cl, Br, or I), CN, (C=O)—R', (C=O)N(R')$_2$, COOR' (wherein R' is H or a lower alkyl group), and $R^3$ or $R^4$ may be absent.

In some embodiments, $R^1$ is selected from the group consisting of branched, linear, or cyclic alkyl,

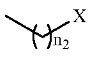

wherein $n_2$=0-6 and X is any of the following: $CF_yH_z$ (y+z=3), $CCl_yH_z$ (y+z=3), OH, OAc, OMe, $R^{71}$, $OR^{72}$, CN, $N(R^{73})_2$,

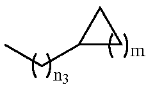

($n_3$=0-5, m=1-5), and

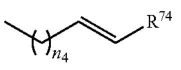

($n_4$=0-5).

In other embodiments, $R^6$ and $R^7$ can each independently be one of the following:

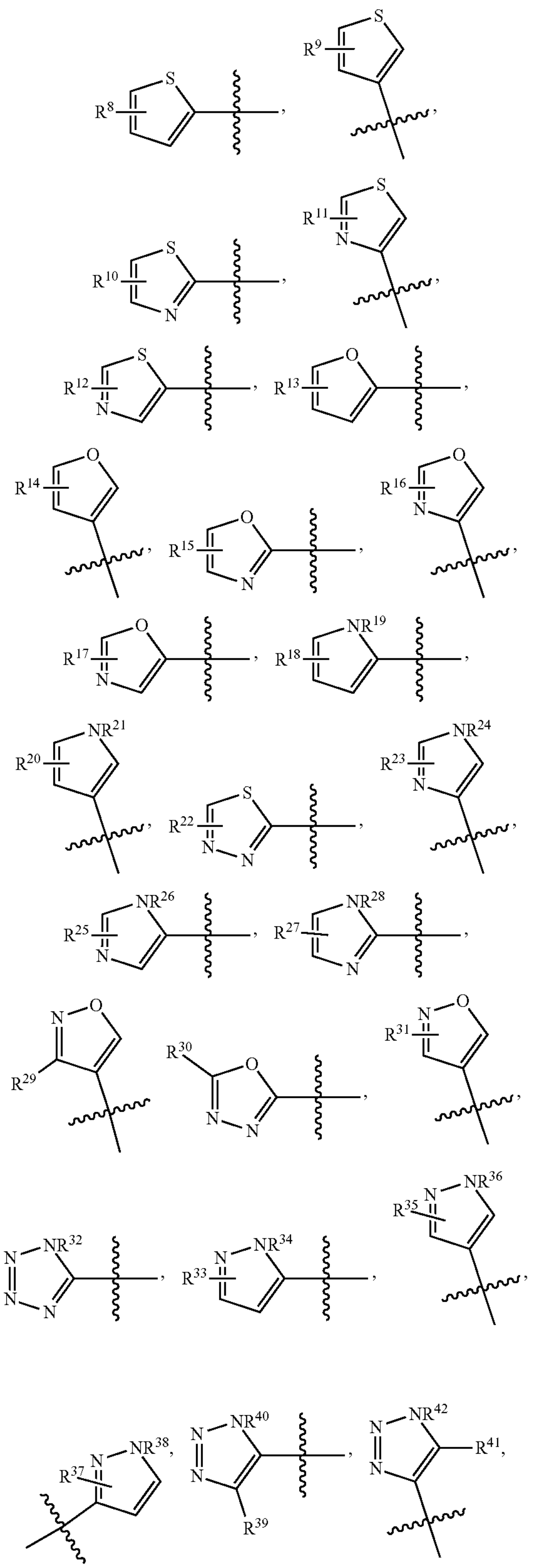

-continued

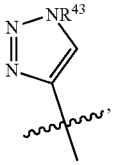 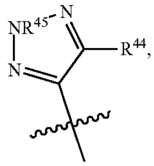, 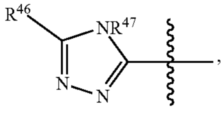,

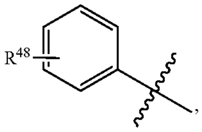, 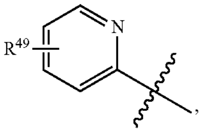,

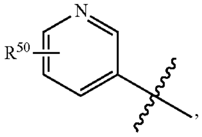, 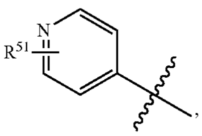,

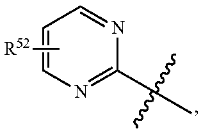, 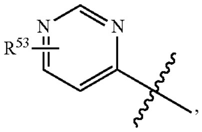,

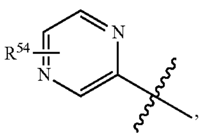, 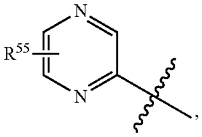,

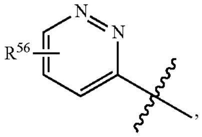, 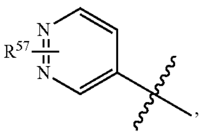,

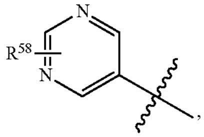, 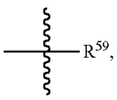, 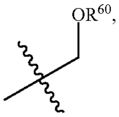,

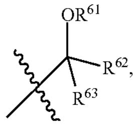, 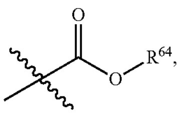, 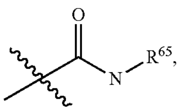,

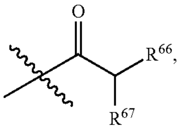, 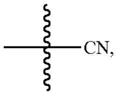, 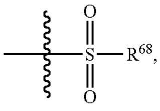,

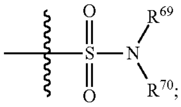;

each $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$, $R^{45}$, $R^{46}$, $R^{47}$, $R^{48}$, $R^{49}$, $R^{50}$, $R^{51}$, $R^{52}$, $R^{53}$, $R^{54}$, $R^{55}$, $R^{56}$, $R^{57}$, $R^{58}$, $R^{59}$, $R^{60}$, $R^{61}$, $R^{62}$, $R^{63}$, $R^{64}$, $R^{65}$, $R^{66}$, $R^{67}$, $R^{68}$, $R^{69}$, $R^{70}$, $R^{71}$, $R^{72}$, $R^{73}$, and $R^{74}$, are the same or different and are independently selected from the group consisting of hydrogen, substituted or unsubstituted $C_1$-$C_{24}$ alkyl, $C_2$-$C_{24}$ alkenyl, $C_2$-$C_{24}$ alkynyl, $C_3$-$C_{20}$ aryl, heterocycloalkenyl containing from 5-6 ring atoms, (wherein from 1-3 of the ring atoms is independently selected from N, NH, N($C_1$-$C_6$ alkyl), NC(O)($C_1$-$C_6$ alkyl), O, and S), heteroaryl or heterocyclyl containing from 5-14 ring atoms, (wherein from 1-6 of the ring atoms is independently selected from N, NH, N($C_1$-$C_3$ alkyl), O, and S), $C_6$-$C_{24}$ alkaryl, $C_6$-$C_{24}$ aralkyl, halo, silyl, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO—), carbamoyl (—(CO)—$NH_2$), $C_1$-$C_{24}$ alkyl-carbamoyl (—(CO)—NH($C_1$-$C_{24}$ alkyl)), arylcarbamoyl (—(CO)—NH-aryl), thiocarbamoyl (—(CS)—$NH_2$), carbamido (—NH—(CO)—$NH_2$), cyano(—CN), isocyano (—$N^+C^-$), cyanato (—O—CN), isocyanato (—O—$N^+$═$C^-$), isothiocyanato (—S—CN), azido (—N═$N^+$═$N^-$), formyl (—(CO)—H), thioformyl (—(CS)—H), amino (—$NH_2$), $C_1$-$C_{24}$ alkyl amino, $C_1$-$C_{24}$ alkyl amino substituted with hydroxyl, $C_5$-$C_{20}$ aryl amino, $C_2$-$C_{24}$ alkylamido (—NH—(CO)-alkyl), $C_6$-$C_{20}$ arylamido (—NH—(CO)-aryl), sulfanamido (—$SO_2N(R)_2$ where R is independently H, alkyl, aryl or heteroaryl), imino (—CR═NH where R is hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR═N(alkyl), where R=hydrogen, alkyl, aryl, alkaryl, aralkyl, etc.), arylimino (—CR═N(aryl), where R=hydrogen, alkyl, aryl, alkaryl, etc.), nitro (—$NO_2$), nitroso (—NO), sulfo (—$SO_2$—OH), sulfonato (—$SO_2$—O—), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—$SO_2$-alkyl), $C_5$-$C_{20}$ arylsulfonyl (—$SO_2$-aryl), sulfonamide (—$SO_2$—$NH_2$, —$SO_2NY_2$ (wherein Y is independently H, aryl or alkyl), phosphono (—$P(O)(OH)_2$), phosphonato (—P(O)(O—$)_2$), phosphinato (—P(O)(O—)), phospho (—$PO_2$), phosphino (—$PH_2$), polyalkyl ethers (—$[(CH_2)_nO]_m$), phosphates, phosphate esters [—$OP(O)(OR)_2$ where R═H, methyl or other alkyl], groups incorporating amino acids or other moieties expected to bear positive or negative charge at physiological pH, and combinations thereof, or a pharmaceutically acceptable salt, tautomer, or solvate thereof.

In still other embodiments, $R^6$ and $R^7$ can independently be a group that improves aqueous solubility, for example, a phosphate ester (—$OPO_3H_2$), a phenyl ring linked to a phosphate ester (—$OPO_3H_2$), a phenyl ring substituted with one or more methoxyethoxy groups, or a morpholine, or an aryl or heteroaryl ring substituted with such a group.

In other embodiments, the 15-PGDH inhibitor can include a compound having a structure of formula (IA):

(IA)

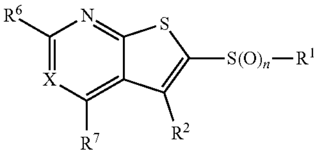

or a pharmaceutically acceptable salt, tautomer, or solvate thereof, wherein:

$R^1$ is alkyl, haloalkyl, cycloalkyl, alkylene-cycloalkyl, alkylene-alkoxy, heterocyclyl, or alkylene-heterocyclyl;

$R^2$ is —$NH_2$, CN, or —NHC(O)alkyl;

$R^6$ is heterocyclyl or heteroaryl, each of which is optionally substituted with one or more $R^3$;

$R^7$ is alkyl, haloalkyl, cycloalkyl, aryl, heterocyclyl, heteroaryl, —C(O)-alkyl, —C(O)O-alkyl, or —C(O)$NR^5$-alkyl, each of which is optionally substituted with one or more $R^4$;

$R^3$ is oxo, —OH, —O-alkylene-OH, —O-alkylene-$N(R^5)_2$, —$N(R^5)_2$, —$N(R^5)$(alkylene-OH), —$N(R^5)$(alkylene-O-alkyl), alkyl, -alkylene-OH, haloalkyl, cycloalkyl, heterocyclyl, —C(O)$N(R^5)_2$, —C(O)$N(R^5)$(alkylene-OH), —C(O)-alkyl, —C(O)O-alkyl, or —$S(O)_m$-alkyl, wherein the cycloalkyl and the heterocyclyl is each optionally substituted with $R^{10}$;

$R^4$ is oxo, halogen, —CN, —$N(R^5)_2$, —OH, —O-alkylene-OH, —$S(O)_m$-alkyl, —C(O)— alkyl, —C(O)-cycloalkyl, alkyl, -alkylene-O-alkyl, alkoxy, haloalkyl, cycloalkyl, heterocyclyl, or -alkylene-aryl optionally substituted with $R^8$;

each $R^5$ is independently, H, alkyl, -alkylene-OH optionally substituted with —OH, -alkylene-$NH_2$, -alkylene-$N(R^9)_2$, -alkylene-O-alkylene-OH, -alkylene-O-alkylene-$NH_2$, —C(O)-alkyl, —C(O)O-alkyl, -alkylene-COOH, or —$S(O)_m$-alkyl;

or alternatively, two $R^5$ together with the N atom to which they are attached can form a 4- to 7-membered heterocycle, optionally containing an additional heteroatom selected from O, S, or N, and wherein the heterocycle is optionally substituted with $R^8$;

$R^8$ is halogen, alkyl, or alkoxy;

$R^9$ is H or alkyl, or two $R^9$ together with the N atom to which they are attached can form a 4- to 7-membered heterocycle, optionally containing an additional heteroatom selected from O, $S(O)_t$, or N;

$R^{10}$ is —OH, halogen, alkyl, or alkoxy;

X is N or CH;

m is 0, 1, or 2;

n is 0, 1, or 2; and t is 0, 1, or 2.

In some embodiment, the 15-PGDH inhibitor can include a compound having a structure of formula (IIA):

(IIA)

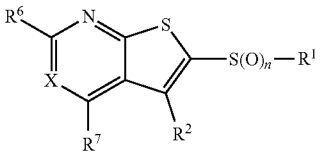

or a pharmaceutically acceptable salt, tautomer, or solvate thereof, wherein:

$R^1$ is alkyl, haloalkyl, cycloalkyl, alkylene-cycloalkyl, alkylene-alkoxy, heterocyclyl, or alkylene-heterocyclyl;

$R^2$ is —$NH_2$, CN, or —NHC(O)alkyl;

$R^6$ is heterocyclyl or heteroaryl, each of which is optionally substituted with one or more $R^3$; $R^7$ is alkyl, haloalkyl, cycloalkyl, aryl, heterocyclyl, heteroaryl, —C(O)-alkyl, —C(O)O-alkyl, or —C(O)$NR^5$-alkyl, each of which is optionally substituted with one or more $R^4$;

$R^3$ is oxo, —OH, —O-alkylene-$N(R^5)_2$, —$N(R^5)_2$, —$N(R^5)$(alkylene-OH), alkyl, haloalkyl, cycloalkyl, heterocyclyl, —C(O)$N(R^5)_2$, —C(O)$N(R^5)$(alkylene-OH), —C(O)-alkyl, —C(O)O-alkyl, or —$S(O)_m$-alkyl;

$R^4$ is oxo, halogen, —CN, —$N(R^5)_2$, —OH, —O-alkylene-OH, —$S(O)_m$-alkyl, —C(O)— alkyl, —C(O)-cycloalkyl, alkyl, alkoxy, haloalkyl, cycloalkyl, heterocyclyl, or -alkylene-aryl optionally substituted with $R^8$;

each $R^5$ is independently, H, alkyl, -alkylene-OH optionally substituted with —OH, -alkylene-$NH_2$, -alkylene-$N(R^9)_2$, -alkylene-O-alkylene-OH, -alkylene-O-alkylene-$NH_2$, —C(O)-alkyl, —C(O)O-alkyl, -alkylene-COOH, or —$S(O)_m$-alkyl;

or alternatively, two $R^5$ together with the N atom to which they are attached can form a 4- to 7-membered heterocycle, optionally containing an additional heteroatom selected from O, S, or N, and wherein the heterocycle is optionally substituted with $R^8$;

$R^8$ is halogen, alkyl, or alkoxy;

$R^9$ is H or alkyl, or two $R^9$ together with the N atom to which they are attached can form a 4- to 7-membered heterocycle, optionally containing an additional heteroatom selected from O, $S(O)_t$, or N;

X is N or CH;

m is 0, 1, or 2;

n is 0, 1, or 2; and t is 0, 1, or 2.

In some embodiments, $R^1$ is $C_1$-$C_6$ alkyl, $C_1$-$C_6$ haloalkyl, 3- to 6-membered cycloalkyl, —($C_1$-$C_6$ alkylene)-(3- to 6-membered cycloalkyl), —($C_1$-$C_6$ alkylene)-($C_1$-$C_6$ alkoxy), 3- to 6-membered heterocyclyl, or —($C_1$-$C_6$ alkylene)-(3- to 6-membered heterocyclyl).

In other embodiments, $R^1$ is cyclopropyl, cyclobutyl, cyclopentyl, cyclohexyl, —$(CH_2)_p$-cyclopropyl, —$(CH_2)_p$-cyclobutyl, —$(CH_2)_p$-cyclopentyl, or —$(CH_2)_p$-cyclohexyl; wherein p is 1, 2, or 3.

In still other embodiments, $R^2$ is —$NH_2$.

In some embodiments, $R^6$ is 5- to 6-membered heterocyclyl or 5- to 10-membered heteroaryl, each of which is optionally substituted with one or more $R^3$.

In other embodiments, $R^6$ is 5- to 6-membered heteroaryl optionally substituted with one or more $R^3$.

In still other embodiments, $R^6$ is 8- to 10-membered bicyclic heteroaryl optionally substituted with one or more $R^3$.

In some embodiments, $R^7$ is $C_1$-$C_6$ alkyl, $C_1$-$C_6$ haloalkyl, 3- to 6-membered cycloalkyl, 6- to 10-membered aryl, 3- to 6-membered heterocyclyl, 5- to 10-membered heteroaryl, —C(O)($C_1$-$C_6$ alkyl), —C(O)O($C_1$-$C_6$ alkyl), or —C(O)$NR^5$($C_1$-$C_6$ alkyl), each of which is optionally substituted with one or more $R^4$.

In other embodiments, $R^7$ is $C_1$-$C_6$ alkyl, $C_1$-$C_6$ haloalkyl, 3- to 6-membered cycloalkyl, phenyl, 3- to 6-membered heterocyclyl, or 5- to 10-membered heteroaryl, each of which is optionally substituted with one or more $R^4$.

In still other embodiments, $R^7$ is $C_1$-$C_6$ haloalkyl, 3- to 6-membered cycloalkyl, phenyl, 5- to 10-membered heteroaryl each of which is optionally substituted with one or more $R^4$.

In some embodiments, $R^3$ is —O—($C_1$-$C_6$ alkylene)-$N(R^5)_2$, —$N(R^5)_2$, —$N(R^5)$($C_1$-$C_6$ alkylene-OH), —C(O)$N(R^5)_2$, —C(O)$N(R^5)$($C_1$-$C_6$ alkylene-OH), —C(O)($C_1$-$C_6$ alkyl), —C(O)O($C_1$-$C_6$ alkyl), or —$S(O)_m$($C_1$-$C_6$ alkyl).

In other embodiments, $R^3$ is —($C_1$-$C_3$ alkyl)OH, —$NH_2$, —N($C_1$-$C_3$ alkyl)$_2$, —$NHCH_2CH_2OH$, —N($C_1$-$C_3$ alkyl)$CH_2CH_2OH$, N($CH_2CH_2OH$)$_2$, —$NHCH_2CH(CH_2OH)_2$, —N($C_1$-$C_3$ alkyl)$CH_2CH(CH_2OH)_2$, —$NHCH_2CH_2OCH_2CH_2OH$, —$NHCH_2CH_2OCH_2CH_2NH_2$, —$NHCH_2CH_2NH_2$, —N($C_1$-$C_3$ alkyl)$CH_2CH_2NH_2$, —$NHCH_2CH_2NH$($C_1$-$C_3$ alkyl), —$NHCH_2CH_2N$($C_1$-$C_3$ alkyl)$_2$, —N($C_1$-$C_3$ alkyl)$CH_2CH_2NH$($C_1$-$C_3$ alkyl), —N($C_1$-$C_3$ alkyl)$CH_2CH_2N$($C_1$-$C_3$ alkyl)$_2$, —$NHSO_2CH_3$, —N($C_1$-$C_3$ alkyl)$SO_2CH_3$, —$OCH_2CH_2OH$, —$OCH_2CH_2NH_2$, —$OCH_2CH_2NH$($C_1$-$C_3$ alkyl), or —$OCH_2CH_2N$($C_1$-$C_3$ alkyl)$_2$.

In other embodiments, $R^3$ is —$NH_2$, —N($C_1$-$C_3$ alkyl)$_2$, —$NHCH_2CH_2OH$, —N($C_1$-$C_3$ alkyl)$CH_2CH_2OH$, N($CH_2CH_2OH$)$_2$, —$NHCH_2CH(CH_2OH)_2$, —N($C_1$-$C_3$ alkyl)$CH_2CH(CH_2OH)_2$, —$NHCH_2CH_2OCH_2CH_2OH$, —$NHCH_2CH_2OCH_2CH_2NH_2$, —$NHCH_2CH_2NH_2$, —N($C_1$-$C_3$ alkyl)$CH_2CH_2NH_2$, —$NHCH_2CH_2NH$($C_1$-$C_3$ alkyl), —$NHCH_2CH_2N$($C_1$-$C_3$ alkyl)$_2$, —N($C_1$-$C_3$ alkyl)$CH_2CH_2NH$($C_1$-$C_3$ alkyl), —N($C_1$-$C_3$ alkyl)$CH_2CH_2N$($C_1$-$C_3$ alkyl)$_2$, —$NHSO_2CH_3$, —N($C_1$-$C_3$ alkyl)$SO_2CH_3$, —$OCH_2CH_2OH$, —$OCH_2CH_2NH_2$, —$OCH_2CH_2NH$($C_1$-$C_3$ alkyl), or —$OCH_2CH_2N$($C_1$-$C_3$ alkyl)$_2$.

In still other embodiments, $R^3$ is —$NHCH_2CH_2OH$ or —N($CH_3$)$CH_2CH_2OH$.

In some embodiments, $R^4$ is halogen, —CN, —N($R^5$)$_2$, —OH, —O—($C_1$-$C_6$ alkylene)-OH, —S(O)$_m$($C_1$-$C_6$ alkyl), —C(O)($C_1$-$C_6$ alkyl), —C(O)-(3- to 6-membered cycloalkyl), $C_1$-$C_6$ alkyl, $C_1$-$C_6$haloalkyl, 3- to 6-membered cycloalkyl, or 3- to 6-membered heterocyclyl.

In some embodiments, n is 1.

In other embodiments, the compound has the structure of formula (IIIA):

(IIIA)

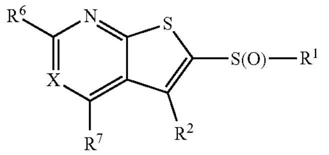

or a pharmaceutically acceptable salt, tautomer, or solvate thereof, wherein:

$R^1$ is 3- to 6-membered cycloalkyl, —($C_1$-$C_6$ alkylene)-(3- to 6-membered cycloalkyl), 3- to 6-membered heterocyclyl, or —($C_1$-$C_6$ alkylene)-(3- to 6-membered heterocyclyl);

$R^2$ is —$NH_2$, CN, or —NHC(O)alkyl;

$R^6$ is heterocyclyl or heteroaryl, each of which is optionally substituted with one or more $R^3$;

$R^7$ is alkyl, haloalkyl, cycloalkyl, aryl, heterocyclyl, heteroaryl, —C(O)-alkyl, —C(O)O-alkyl, or —C(O)N$R^5$-alkyl, each of which is optionally substituted with one or more $R^4$;

$R^3$ is oxo, —OH, —O-alkylene-N($R^5$)$_2$, —N($R^5$)$_2$, —N($R^5$)(alkylene-OH), alkyl, haloalkyl, cycloalkyl, heterocyclyl, —C(O)N($R^5$)$_2$, —C(O)N($R^5$)(alkylene-OH), —C(O)-alkyl, —C(O)O-alkyl, or —S(O)$_m$-alkyl, $R^4$ is oxo, halogen, —CN, —N($R^5$)$_2$, —OH, —O-alkylene-OH, —S(O)$_m$-alkyl, —C(O)— alkyl, —C(O)-cycloalkyl, alkyl, haloalkyl, cycloalkyl, heterocyclyl, or -alkylene-aryl optionally substituted with $R^8$;

each $R^5$ is independently, H, alkyl, -alkylene-OH optionally substituted with —OH, -alkylene-$NH_2$, -alkylene-N($R^9$)$_2$, -alkylene-O-alkylene-OH, -alkylene-O-alkylene-$NH_2$, —C(O)-alkyl, —C(O)O-alkyl, -alkylene-COOH, or —S(O)$_m$-alkyl;

or alternatively, two $R^5$ together with the N atom to which they are attached can form a 4- to 7-membered heterocycle, optionally containing an additional heteroatom selected from O, S, or N, and wherein the heterocycle is optionally substituted with $R^8$;

$R^8$ is halogen, alkyl, or alkoxy;

$R^9$ is H or alkyl, or two $R^9$ together with the N atom to which they are attached can form a 4- to 7-membered heterocycle, optionally containing an additional heteroatom selected from O, S(O)$_t$, or N;

X is N or CH;

m is 0, 1, or 2; and t is 0, 1, or 2.

In some embodiments, $R^1$ is 3- to 5-membered cycloalkyl or —($C_1$-$C_6$ alkylene)-(3- to 5-membered cycloalkyl).

In other embodiments, $R^1$ is cyclobutyl.

In still other embodiments, $R^1$ is a bicyclic 4- to 6-membered cycloalkyl.

In some embodiments, $R^7$ is $C_1$-$C_6$ alkyl, $C_1$-$C_6$ haloalkyl, 3- to 6-membered cycloalkyl, 6- to 10-membered aryl, 3- to 6-membered heterocyclyl, 5- to 10-membered heteroaryl, —C(O)($C_1$-$C_6$ alkyl), —C(O)O($C_1$-$C_6$ alkyl), or —C(O)N$R^5$($C_1$-$C_6$ alkyl), each of which is optionally substituted with one or more $R^4$.

In other embodiments, $R^7$ is $C_1$-$C_4$ alkyl, $C_1$-$C_6$ haloalkyl, 3- to 6-membered cycloalkyl, phenyl, 3- to 6-membered heterocyclyl, or 5- to 10-membered heteroaryl, each of which is optionally substituted with one or more $R^4$. In other embodiments, $R^7$ is $C_1$-$C_6$ haloalkyl, 3- to 6-membered cycloalkyl, phenyl, 3- to 6-membered heterocyclyl, or 5- to 10-membered heteroaryl, each of which is optionally substituted with one or more $R^4$.

In other embodiments, $R^7$ is $C_1$-$C_3$ alkyl, $C_1$-$C_3$ haloalkyl, 3-membered cycloalkyl, phenyl, 4-membered heterocyclyl, or 5- to 6-membered heteroaryl, each of which is optionally substituted with one or more $R^4$. In other embodiments, $R^7$ is $C_1$-$C_3$ haloalkyl, 3-membered cycloalkyl, phenyl, 4-membered heterocyclyl, or 5- to 6-membered heteroaryl, each of which is optionally substituted with one or more $R^4$.

In other embodiments, $R^7$ is —$CF_3$, isopropyl, cyclopropyl, phenyl, pyridyl, pyrazole, or triazole, each of which is optionally substituted with one or more $R^4$. In other embodiments, $R^7$ is —$CF_3$, cyclopropyl, phenyl, pyridyl, pyrazole, or triazole, each of which is optionally substituted with one or more $R^4$.

In some embodiments, $R^3$ is —O—($C_1$-$C_6$ alkylene)-N($R^5$)$_2$, —N($R^5$)$_2$, —N($R^5$)($C_1$-$C_6$ alkylene-OH), —C(O)N($R^5$)$_2$, —C(O)N($R^5$)($C_1$-$C_6$ alkylene-OH), —C(O)($C_1$-$C_6$ alkyl), —C(O)O($C_1$-$C_6$ alkyl), or —S(O)$_m$($C_1$-$C_6$ alkyl).

In other embodiments, $R^3$ is —$NH_2$, —N($C_1$-$C_3$ alkyl)$_2$, —$NHCH_2CH_2OH$, —N($C_1$-$C_3$ alkyl)$CH_2CH_2OH$, N($CH_2CH_2OH$)$_2$, —$NHCH_2CH(CH_2OH)_2$, —N($C_1$-$C_3$ alkyl)$CH_2CH(CH_2OH)_2$, —$NHCH_2CH_2OCH_2CH_2OH$, —$NHCH_2CH_2OCH_2CH_2NH_2$, —$NHCH_2CH_2NH_2$, —N($C_1$-$C_3$ alkyl)$CH_2CH_2NH_2$, —$NHCH_2CH_2NH$($C_1$-$C_3$ alkyl), —$NHCH_2CH_2N$($C_1$-$C_3$ alkyl)$_2$, —N($C_1$-$C_3$ alkyl)$CH_2CH_2NH$($C_1$-$C_3$ alkyl), —N($C_1$-$C_3$ alkyl)$CH_2CH_2N$($C_1$-$C_3$ alkyl)$_2$, —$NHSO_2CH_3$, —N($C_1$-$C_3$ alkyl)$SO_2CH_3$, —$OCH_2CH_2OH$, —$OCH_2CH_2NH_2$, —$OCH_2CH_2NH$($C_1$-$C_3$ alkyl), or —$OCH_2CH_2N$($C_1$-$C_3$ alkyl)$_2$.

In still other embodiments, $R^3$ is —$NHCH_2CH_2OH$ or —N($CH_3$)$CH_2CH_2OH$.

In some embodiments and without being limited by theory, Applicants surprisingly and unexpectedly discovered that substituents at the $R^7$ position could be modified to improve hERG activity, including hERG inhibition ($IC_{50}$), blockade, and efflux ratio. For example, in some embodiments, certain 6- to 10-membered aryls (e.g., optionally substituted phenyl) and 5- to 10-membered heteroaryls (e.g., optionally substituted pyridyls, pyrazoles, and triazoles) were observed to have beneficial hERG properties. In some embodiments, certain $C_1$-$C_6$ haloalkyls (e.g., —$CF_3$) exhibited improved hERG inhibition (IC50), while also improving half-life and solubility.

In other embodiments, the compound has the structure of formula (IVA):

(IVA)

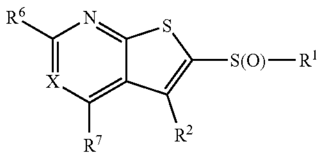

or a pharmaceutically acceptable salt, tautomer, or solvate thereof, wherein:

$R^1$ is cycloalkyl, alkylene-cycloalkyl, alkylene-alkoxy, heterocyclyl, or alkylene-heterocyclyl;

$R^2$ is —$NH_2$, CN, or —NHC(O)alkyl;

$R^6$ is heterocyclyl or heteroaryl, each of which is optionally substituted with one or more $R^3$;

$R^7$ is $C_1$-$C_6$ haloalkyl, aryl or heteroaryl, each of which is optionally substituted with one or more $R^4$;

$R^3$ is oxo, —OH, —O-alkylene-$N(R^5)_2$, —$N(R^5)_2$, —$N(R^5)$(alkylene-OH), alkyl, haloalkyl, cycloalkyl, heterocyclyl, —C(O)$N(R^5)_2$, —C(O)$N(R^5)$(alkylene-OH), —C(O)-alkyl, —C(O)O-alkyl, or —$S(O)_m$-alkyl;

each $R^5$ is independently, H, alkyl, -alkylene-OH optionally substituted with —OH, -alkylene-$NH_2$, -alkylene-$N(R^9)_2$, -alkylene-O-alkylene-OH, -alkylene-O-alkylene-$NH_2$, —C(O)-alkyl, -alkylene-COOH, —C(O)O-alkyl, or —$S(O)_m$-alkyl;

or alternative, two $R^5$ together with the N atom to which they are attached can form a 4- to 7-membered heterocycle, optionally containing an additional heteroatom selected from O, S, or N, and wherein the heterocycle is optionally substituted with $R^8$;

$R^4$ is halogen, alkyl, or alkoxy;

X is N or CH; and m is 0, 1, or 2.

In some embodiments, $R^7$ is —$CF_3$, pyridyl, pyrazole, phenyl, or triazole, each of which is optionally substituted with $R^4$.

In other embodiments, $R^7$ is —$CF_3$, pyridyl, fluorophenyl, or a triazole optionally substituted with halogen or methyl.

In other embodiments, $R^7$ is —$CF_3$,

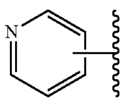,
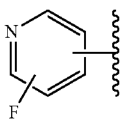,
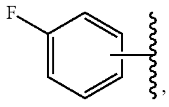,
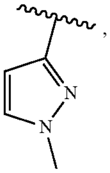,
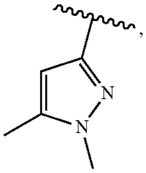,
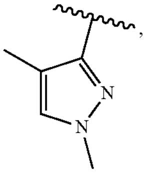,
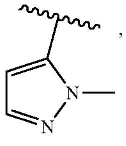, -continued

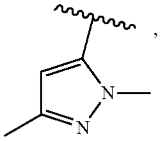,
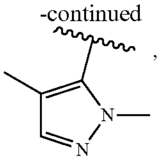,
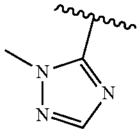 or
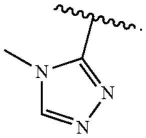.

In still other embodiments, $R^7$ is —$CF_3$.

In still other embodiments, $R^7$ is

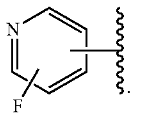.

In some embodiments, $R^7$ is

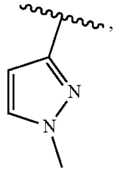,
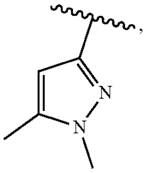,
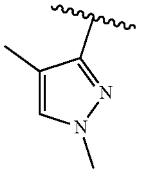,
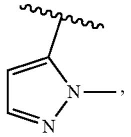,
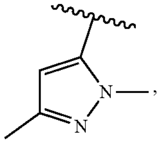,
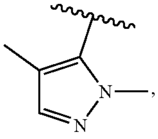,
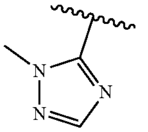 or
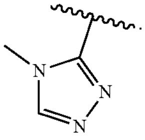.

In some embodiments, $R^7$ is

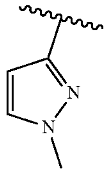,
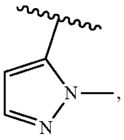,
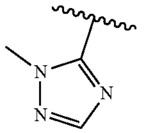 or
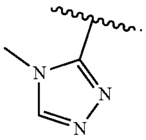.

In other embodiments, $R^6$ is 8- to 10-membered bicyclic heteroaryl optionally substituted with one or more $R^3$.

In some embodiments and without being limited by theory, Applicants surprisingly and unexpectedly discovered that 3- to 6-membered cycloalkyls at the $R^7$ position can improve solubility while maintaining PDGH activity.

In other embodiments, the compound has the structure of formula (VA):

(VA)

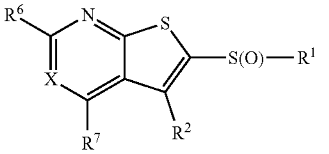

or a pharmaceutically acceptable salt, tautomer, or solvate thereof, wherein:

$R^1$ is cycloalkyl, -alkylene-cycloalkyl, -alkylene-alkoxy, heterocyclyl, or -alkylene-heterocyclyl;

$R^2$ is —$NH_2$, CN, or —NHC(O)alkyl;

$R^6$ is heterocyclyl or heteroaryl, each of which is optionally substituted with one or more $R^3$;

$R^7$ is 3- to 6-membered cycloalkyl, optionally substituted with one or more $R^4$;

$R^3$ is oxo, —OH, —O-alkylene-N($R^5$)$_2$, —N($R^5$)$_2$, —N($R^5$)(alkylene-OH), alkyl, haloalkyl, cycloalkyl, heterocyclyl, —C(O)N($R^5$)$_2$, —C(O)N($R^5$)(alkylene-OH), —C(O)-alkyl, —C(O)O-alkyl, or —S(O)$_m$-alkyl;

$R^4$ is halogen, —CN, —$NH_2$, —OH, or $C_1$-$C_3$ alkyl;

each $R^5$ is independently, H, alkyl, -alkylene-OH optionally substituted with —OH, -alkylene-$NH_2$, -alkylene-N($R^9$)$_2$, -alkylene-O-alkylene-OH, -alkylene-O-alkylene-$NH_2$, —C(O)-alkyl, -alkylene-COOH, —C(O)O-alkyl, or —S(O)$_m$-alkyl;

or alternative, two $R^5$ together with the N atom to which they are attached can form a 4- to 7-membered heterocycle, optionally containing an additional heteroatom selected from O, S, or N, and wherein the heterocycle is optionally substituted with $R^8$;

$R^8$ is halogen, alkyl, or alkoxy;

X is N or CH;

m is 0, 1, or 2.

In some embodiments, $R^7$ is cyclopropyl.

In other embodiments, $R^1$ is 3- to 6-membered cycloalkyl, —($C_1$-$C_6$ alkylene)-(3- to 6-membered cycloalkyl), —($C_1$-$C_6$ alkylene)-($C_1$-$C_6$ alkoxy), 3- to 6-membered heterocyclyl, or —($C_1$-$C_6$ alkylene)-(3- to 6-membered heterocyclyl).

In some embodiments, $R^1$ is cyclopropyl, cyclobutyl, cyclopentyl, cyclohexyl, —$(CH_2)_p$-cyclopropyl, —$(CH_2)_p$-cyclobutyl, —$(CH_2)_p$-cyclopentyl, or —$(CH_2)_p$-cyclohexyl; wherein p is 1, 2, or 3.

In some embodiments, $R^3$ is —O—($C_1$-$C_6$ alkylene)-N($R^5$)$_2$, —N($R^5$)$_2$, —N($R^5$)($C_1$-$C_6$ alkylene-OH), —C(O)N($R^5$)$_2$, —C(O)N($R^5$)($C_1$-$C_6$ alkylene-OH), —C(O)($C_1$-$C_6$ alkyl), —C(O)O($C_1$-$C_6$ alkyl), or —S(O)$_m$($C_1$-$C_6$ alkyl).

In some embodiments, $R^3$ is —$NH_2$, —N($C_1$-$C_3$ alkyl)$_2$, —$NHCH_2CH_2OH$, —N($C_1$-$C_3$ alkyl)$CH_2CH_2OH$, N$(CH_2CH_2OH)_2$, —$NHCH_2CH(CH_2OH)_2$, —N($C_1$-$C_3$ alkyl)$CH_2CH(CH_2OH)_2$, —$NHCH_2CH_2OCH_2CH_2OH$, —$NHCH_2CH_2OCH_2CH_2NH_2$, —$NHCH_2CH_2NH_2$, —N($C_1$-$C_3$ alkyl)$CH_2CH_2NH_2$, —$NHCH_2CH_2NH$($C_1$-$C_3$ alkyl), —$NHCH_2CH_2N$($C_1$-$C_3$ alkyl)$_2$, —N($C_1$-$C_3$ alkyl)$CH_2CH_2NH$($C_1$-$C_3$ alkyl), —N($C_1$-$C_3$ alkyl)$CH_2CH_2N$($C_1$-$C_3$ alkyl)$_2$, —$NHSO_2CH_3$, —N($C_1$-$C_3$ alkyl)$SO_2CH_3$, —$OCH_2CH_2OH$, —$OCH_2CH_2NH_2$, —$OCH_2CH_2NH$($C_1$-$C_3$ alkyl), or —$OCH_2CH_2N$($C_1$-$C_3$ alkyl)$_2$.

In other embodiments, $R^3$ is —$NHCH_2CH_2OH$ or —N$(CH_3)CH_2CH_2OH$.

In some embodiments and without being limited by theory, Applicants surprisingly and unexpectedly discovered that the $R^6$ position can be substituted with certain $R^3$ groups to improve solubility and activity.

In other embodiments, the compound has the structure of formula (VIA):

(VIA)

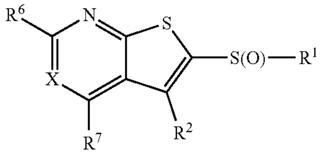

or a pharmaceutically acceptable salt, tautomer, or solvate thereof, wherein:

$R^1$ is cycloalkyl, -alkylene-cycloalkyl, -alkylene-alkoxy, heterocyclyl, or -alkylene-heterocyclyl;

$R^2$ is —$NH_2$, CN, or —NHC(O)alkyl;

$R^6$ is heterocyclyl or heteroaryl, each of which is substituted with one or more $R^3$;

$R^7$ is haloalkyl, cycloalkyl, aryl, heterocyclyl, heteroaryl, —C(O)-alkyl, —C(O)O— alkyl, or —C(O)N$R^5$-alkyl, each of which is optionally substituted with one or more $R^4$;

$R^3$ is —O—($C_1$-$C_6$ alkylene)-N($R^5$)$_2$, —N($R^5$)$_2$, —N($R^5$)($C_1$-$C_6$ alkylene-OH), —C(O)N($R^5$)$_2$, —C(O)N($R^5$)($C_1$-$C_6$ alkylene-OH), —C(O)($C_1$-$C_6$ alkyl), —C(O)O($C_1$-$C_6$ alkyl), or —S(O)$_m$($C_1$-$C_6$ alkyl);

$R^4$ is oxo, halogen, —CN, —N($R^5$)$_2$, —OH, —O-alkylene-OH, —S(O)$_m$-alkyl, —C(O)— alkyl, —C(O)-cycloalkyl, alkyl, haloalkyl, cycloalkyl, heterocyclyl, or -alkylene-aryl optionally substituted with $R^8$;

each $R^5$ is independently H, $C_1$-$C_6$ alkyl, —($C_1$-$C_6$ alkylene)-OH optionally substituted with —OH, -alkylene-$NH_2$, -alkylene-N($R^9$)$_2$, -alkylene-O-alkylene-OH, -alkylene-O-alkylene-$NH_2$, —C(O)($C_1$-$C_6$ alkyl), —C(O)O($C_1$-$C_6$ alkyl), alkylene-COOH, or —S(O)$_m$($C_1$-$C_6$ alkyl);

or alternative, two $R^5$ together with the N atom to which they are attached can form a 4- to 7-membered heterocycle, optionally containing an additional heteroatom selected from O, S, or N, and wherein the heterocycle is optionally substituted with $R^8$;

$R^8$ is halogen, alkyl, or alkoxy;

X is N or CH;

m is 0, 1, or 2.

In some embodiments, $R^3$ is —O—($C_1$-$C_6$ alkylene)-N($R^5$)$_2$, —N($R^5$)$_2$ or —N($R^5$)($C_1$-$C_6$ alkylene-OH).

In other embodiments, $R^5$ is H, $C_1$-$C_6$ alkyl, —($C_1$-$C_6$ alkylene)-OH, or —S(O)$_2$($C_1$-$C_3$ alkyl).

In some embodiments, $R^3$ is —$NH_2$, —N($C_1$-$C_3$ alkyl)$_2$, —$NHCH_2CH_2OH$, —N($C_1$-$C_3$ alkyl)$CH_2CH_2OH$, N$(CH_2CH_2OH)_2$, —$NHCH_2CH(CH_2OH)_2$, —N($C_1$-$C_3$ alkyl)$CH_2CH(CH_2OH)_2$, —$NHCH_2CH_2OCH_2CH_2OH$, —$NHCH_2CH_2OCH_2CH_2NH_2$, —$NHCH_2CH_2NH_2$, —N($C_1$-$C_3$ alkyl)$CH_2CH_2NH_2$, —$NHCH_2CH_2NH$($C_1$-$C_3$ alkyl), —$NHCH_2CH_2N$($C_1$-$C_3$ alkyl)$_2$, —N($C_1$-$C_3$ alkyl)$CH_2CH_2NH$($C_1$-$C_3$ alkyl), —N($C_1$-$C_3$ alkyl)$CH_2CH_2N$($C_1$-$C_3$ alkyl)$_2$, —$NHSO_2CH_3$, —N($C_1$-$C_3$ alkyl)$SO_2CH_3$, —$OCH_2CH_2OH$, —$OCH_2CH_2NH_2$, —$OCH_2CH_2NH$($C_1$-$C_3$ alkyl), or —$OCH_2CH_2N$($C_1$-$C_3$ alkyl)$_2$.

In other embodiments, $R^3$ is —$NHCH_2CH_2OH$ or —N$(CH_3)CH_2CH_2OH$.

In still other embodiments, $R^3$ is —$NHCH_2CH_2OH$.

In some embodiments, $R^6$ is 5- to 6-membered heterocyclyl or 5- to 10-membered heteroaryl, each of which is optionally substituted with one or more $R^3$.

In other embodiments, $R^6$ is 5- to 6-membered heteroaryl optionally substituted with one or more $R^3$.

In some embodiments, $R^6$ is furan, thiophene, pyrrole, thiazole, isothiazole, oxazole, isooxazole, pyrazole, imidazole, triazole, pyridine, pyrimidine, pyridazine, or pyrazine, each optionally substituted with one or more $R^3$.

In other embodiments, $R^6$ is thiazole, imidazole, oxazole, pyridine, or pyrimidine.

In some embodiments, $R^6$ is 8- to 10-membered bicyclic heteroaryl optionally substituted with one or more $R^3$.

In other embodiments, $R^6$ is 5- to 6-membered heterocyclyl, optionally substituted with one or more $R^3$, selected from morpholine, pyridine-one, or piperidine.

In some embodiments, $R^7$ is $C_1$-$C_3$ haloalkyl, 3-membered cycloalkyl, phenyl, 4-membered heterocyclyl, or 5- to 6-membered heteroaryl, each of which is optionally substituted with one or more $R^4$.

In other embodiments, $R^7$ is —$CF_3$, cyclopropyl, phenyl, pyrzole, pyridyl, or triazole, each of which is optionally substituted with one or more $R^4$.

In some embodiments, the compound has the structure of formula (VIIA):

(VIIA)

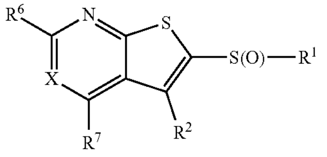

or a pharmaceutically acceptable salt, tautomer, or solvate thereof, wherein:

$R^1$ is cycloalkyl, alkylene-cycloalkyl, alkylene-alkoxy, heterocyclyl, or alkylene-heterocyclyl;

$R^2$ is —$NH_2$, CN, or —NHC(O)alkyl;

$R^6$ is fused bicyclic heterocyclyl or fused bicyclic heteroaryl, each of which is optionally substituted with one or more $R^3$;

$R^7$ is alkyl, haloalkyl, cycloalkyl, aryl, heterocyclyl, heteroaryl, —C(O)-alkyl, —C(O)O-alkyl, or —C(O)$NR^5$-alkyl, each of which is optionally substituted with one or more $R^4$;

$R^3$ is oxo, —OH, —O-alkylene-$N(R^5)_2$, —$N(R^5)_2$, —$N(R^5)$(alkylene-OH), alkyl, haloalkyl, cycloalkyl, heterocyclyl, —C(O)$N(R^5)_2$, —C(O)-alkyl, —C(O)O-alkyl, or —$S(O)_m$-alkyl;

$R^4$ is oxo, halogen, —CN, —$N(R^5)_2$, —OH, —O-alkylene-OH, —$S(O)_m$-alkyl, —C(O)— alkyl, —C(O)-cycloalkyl, alkyl, haloalkyl, cycloalkyl, heterocyclyl, or -alkylene-aryl optionally substituted with $R^8$;

each $R^5$ is independently, H, alkyl, -alkylene-OH optionally substituted with —OH, -alkylene-O-alkylene-OH, -alkylene-O-alkylene-$NH_2$, —C(O)-alkyl, —C(O)O-alkyl, or —$S(O)_m$-alkyl;

or alternatively, two $R^5$ together with the N atom to which they are attached can form a 4- to 7-membered heterocycle, optionally containing an additional heteroatom selected from O, S, or N, and wherein the heterocycle is optionally substituted with $R^8$;

$R^8$ is halogen, alkyl, or alkoxy;

X is N or CH; and m is 0, 1, or 2.

In some embodiments, $R^6$ is 8- to 10-membered fused bicyclic heteroaryl, each of which is optionally substituted with one or more $R^3$.

In some embodiments, $R^7$ is $C_1$-$C_6$ alkyl, $C_1$-$C_6$ haloalkyl, 3- to 6-membered cycloalkyl, 6- to 10-membered aryl, 3- to 6-membered heterocyclyl, 5- to 10-membered heteroaryl, —C(O)($C_1$-$C_6$ alkyl), —C(O)O($C_1$-$C_6$ alkyl), or —C(O)$NR^5$($C_1$-$C_6$ alkyl), each of which is optionally substituted with one or more $R^4$.

In other embodiments, $R^7$ is $C_1$-$C_4$ alkyl, $C_1$-$C_6$ haloalkyl, 3- to 6-membered cycloalkyl, phenyl, 3- to 6-membered heterocyclyl, or 5- to 10-membered heteroaryl, each of which is optionally substituted with one or more $R^4$. In other embodiments, $R^7$ is $C_1$-$C_6$ haloalkyl, 3- to 6-membered cycloalkyl, phenyl, 3- to 6-membered heterocyclyl, or 5- to 10-membered heteroaryl, each of which is optionally substituted with one or more $R^4$.

In still other embodiments, $R^7$ is $C_1$-$C_3$ alkyl, $C_1$-$C_6$ haloalkyl, 3- to 6-membered cycloalkyl, phenyl, 3- to 6-membered heterocyclyl, or 5- to 6-membered heteroaryl, each of which is optionally substituted with one or more $R^4$.

In other embodiments, $R^7$ is $C_1$-$C_3$ alkyl, $C_1$-$C_6$ haloalkyl, 3- to 6-membered cycloalkyl, phenyl, pyrazole, pyridyl, or triazole, each of which is optionally substituted with one or more $R^4$. In other embodiments, $R^7$ is $C_1$-$C_6$ haloalkyl, 3- to 6-membered cycloalkyl, phenyl, pyrazole, pyridyl, or triazole, each of which is optionally substituted with one or more $R^4$.

In other embodiments, $R^7$ is —$CF_3$, isopropyl, cyclopropyl, phenyl, pyridyl, or triazole, each of which is optionally substituted with one or more $R^4$. In other embodiments, $R^7$ is —$CF_3$, cyclopropyl, phenyl, pyridyl, or triazole, each of which is optionally substituted with one or more $R^4$.

In some embodiments, $R^1$ is $C_1$-$C_6$ alkyl, $C_1$-$C_6$ haloalkyl, 3- to 6-membered cycloalkyl, —($C_1$-$C_6$ alkylene)-(3- to 6-membered cycloalkyl), —($C_1$-$C_6$ alkylene)-($C_1$-$C_6$ alkoxy), 3- to 6-membered heterocyclyl, or —($C_1$-$C_6$ alkylene)-(3- to 6-membered heterocyclyl).

In other embodiments, $R^1$ is cyclopropyl, cyclobutyl, cyclopentyl, cyclohexyl, —$(CH_2)_p$-cyclopropyl, —$(CH_2)_p$-cyclobutyl, —$(CH_2)_p$-cyclopentyl, or —$(CH_2)_p$-cyclohexyl; wherein p is 1, 2, or 3.

In some embodiments, $R^3$ is —O—($C_1$-$C_6$ alkylene)-$N(R^5)_2$, —$N(R^5)_2$, —$N(R^5)$($C_1$-$C_6$ alkylene-OH), —C(O)$N(R^5)_2$, —C(O)$N(R^5)$($C_1$-$C_6$ alkylene-OH), —C(O)($C_1$-$C_6$ alkyl), —C(O)O($C_1$-$C_6$ alkyl), or —$S(O)_m$($C_1$-$C_6$ alkyl).

In other embodiments, $R^3$ is —$NH_2$, —$N(C_1$-$C_3$ alkyl$)_2$, —$NHCH_2CH_2OH$, —N($C_1$-$C_3$ alkyl)$CH_2CH_2OH$, $N(CH_2CH_2OH)_2$, —$NHCH_2CH(CH_2OH)_2$, —N($C_1$-$C_3$ alkyl)$CH_2CH(CH_2OH)_2$, —$NHCH_2CH_2OCH_2CH_2OH$, —$NHCH_2CH_2OCH_2CH_2NH_2$, —$NHCH_2CH_2NH_2$, —N($C_1$-$C_3$ alkyl)$CH_2CH_2NH_2$, —$NHCH_2CH_2NH$($C_1$-$C_3$ alkyl), —$NHCH_2CH_2N(C_1$-$C_3$ alkyl$)_2$, —N($C_1$-$C_3$ alkyl) $CH_2CH_2NH$($C_1$-$C_3$ alkyl), —N($C_1$-$C_3$ alkyl)$CH_2CH_2N(C_1$-$C_3$ alkyl$)_2$, —$NHSO_2CH_3$, —N($C_1$-$C_3$ alkyl)$SO_2CH_3$, —$OCH_2CH_2OH$, —$OCH_2CH_2NH_2$, —$OCH_2CH_2NH$($C_1$-$C_3$ alkyl), or —$OCH_2CH_2N(C_1$-$C_3$ alkyl$)_2$.

In some embodiments, $R^3$ is —$NHCH_2CH_2OH$ or —$N(CH_3)CH_2CH_2OH$.

In other embodiments, $R^4$ is halogen, —CN, —$N(R^5)_2$, —OH, —O—($C_1$-$C_6$ alkylene)-OH, —$S(O)_m$($C_1$-$C_6$ alkyl), —C(O)($C_1$-$C_6$ alkyl), —C(O)-(3- to 6-membered cycloalkyl), $C_1$-$C_6$ alkyl, $C_1$-$C_6$ haloalkyl, 3- to 6-membered cycloalkyl, or 3- to 6-membered heterocyclyl.

In some embodiments, the compound has the structure of formula (VIIIA):

(VIIIA)

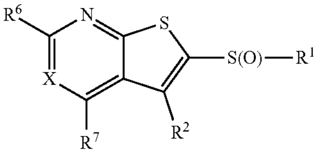

or a pharmaceutically acceptable salt, tautomer, or solvate thereof, wherein:

$R^1$ is cyclobutyl or —($C_1$-$C_4$ alkylene)-($C_1$-$C_3$ alkoxy);

$R^2$ is —$NH_2$, CN, or —NHC(O)alkyl;

$R^6$ is heterocyclyl or heteroaryl, each of which is optionally substituted with one or more $R^3$;

$R^7$ is —$CF_3$, isopropyl,

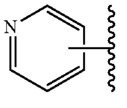, 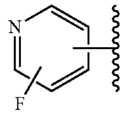, 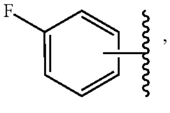,

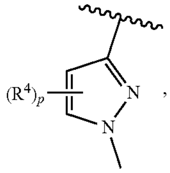, 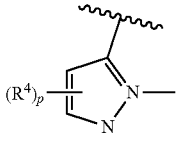,

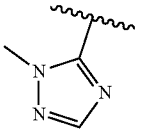 or 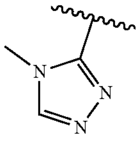;

$R^3$ is oxo, —OH, —O-alkylene-OH, —O-alkylene-N($R^5$)$_2$, —N($R^5$)$_2$, —N($R^5$)(alkylene-OH), —N($R^5$)(alkylene-O-alkyl), alkyl, -alkylene-OH, haloalkyl, cycloalkyl, heterocyclyl, —C(O)N($R^5$)$_2$, —C(O)N($R^5$)(alkylene-OH), —C(O)-alkyl, —C(O)O-alkyl, or —S(O)$_m$-alkyl, wherein the cycloalkyl and the heterocyclyl is each optionally substituted with $R^{10}$;

$R^4$ is $C_1$-$C_3$ alkyl;

each $R^5$ is independently, H, alkyl, -alkylene-OH optionally substituted with —OH, -alkylene-$NH_2$, -alkylene-N($R^9$)$_2$, -alkylene-O-alkylene-OH, -alkylene-O-alkylene-$NH_2$, —C(O)-alkyl, —C(O)O-alkyl, -alkylene-COOH, or —S(O)$_m$-alkyl;

or alternatively, two $R^5$ together with the N atom to which they are attached can form a 4- to 7-membered heterocycle, optionally containing an additional heteroatom selected from O, S, or N, and wherein the heterocycle is optionally substituted with $R^8$;

$R^8$ is halogen, alkyl, or alkoxy;

$R^9$ is H or alkyl, or two $R^9$ together with the N atom to which they are attached can form a 4- to 7-membered heterocycle, optionally containing an additional heteroatom selected from O, S(O)$_t$, or N;

$R^{10}$ is —OH, halogen, alkyl, or alkoxy;

X is N or CH;

m is 0, 1, or 2;

p is 0 or 1; and t is 0, 1, or 2.

In still other embodiments, $R^2$ is —$NH_2$.

In some embodiments, $R^6$ is 5- to 6-membered heterocyclyl or 5- to 10-membered heteroaryl, each of which is optionally substituted with one or more $R^3$.

In other embodiments, $R^6$ is 5- to 6-membered heteroaryl optionally substituted with one or more $R^3$.

In still other embodiments, $R^6$ is 8- to 10-membered bicyclic heteroaryl optionally substituted with one or more $R^3$.

In some embodiments, $R^3$ is —O—($C_1$-$C_6$ alkylene)-N($R^5$)$_2$, —N($R^5$)$_2$, —N($R^5$)($C_1$-$C_6$ alkylene-OH), —C(O)N($R^5$)$_2$, —C(O)N($R^5$)($C_1$-$C_6$ alkylene-OH), —C(O)($C_1$-$C_6$ alkyl), —C(O)O($C_1$-$C_6$ alkyl), or —S(O)$_m$($C_1$-$C_6$ alkyl).

In other embodiments, $R^3$ is —($C_1$-$C_3$ alkyl)OH, —$NH_2$, —N($C_1$-$C_3$ alkyl)$_2$, —$NHCH_2CH_2OH$, —N($C_1$-$C_3$ alkyl)$CH_2CH_2OH$, N($CH_2CH_2OH$)$_2$, —$NHCH_2CH(CH_2OH)_2$, —N($C_1$-$C_3$ alkyl)$CH_2CH(CH_2OH)_2$, —$NHCH_2CH_2OCH_2CH_2OH$, —$NHCH_2CH_2OCH_2CH_2NH_2$, —$NHCH_2CH_2NH_2$, —N($C_1$-$C_3$ alkyl)$CH_2CH_2NH_2$, —$NHCH_2CH_2NH$($C_1$-$C_3$ alkyl), —$NHCH_2CH_2N$($C_1$-$C_3$ alkyl)$_2$, —N($C_1$-$C_3$ alkyl)$CH_2CH_2NH$($C_1$-$C_3$ alkyl), —N($C_1$-$C_3$ alkyl)$CH_2CH_2N$($C_1$-$C_3$ alkyl)$_2$, —$NHSO_2CH_3$, —N($C_1$-$C_3$ alkyl)$SO_2CH_3$, —$OCH_2CH_2OH$, —$OCH_2CH_2NH_2$, —$OCH_2CH_2NH$($C_1$-$C_3$ alkyl), or —$OCH_2CH_2N$($C_1$-$C_3$ alkyl)$_2$.

In still other embodiments, $R^3$ is —$NHCH_2CH_2OH$ or —N($CH_3$)$CH_2CH_2OH$.

In some embodiments, $R^4$ is halogen, —CN, —N($R^5$)$_2$, —OH, —O—($C_1$-$C_6$ alkylene)-OH, —S(O)$_m$($C_1$-$C_6$ alkyl), —C(O)($C_1$-$C_6$ alkyl), —C(O)-(3- to 6-membered cycloalkyl), $C_1$-$C_6$ alkyl, $C_1$-$C_6$ haloalkyl, 3- to 6-membered cycloalkyl, or 3- to 6-membered heterocyclyl.

In some embodiments, n is 1.

In some embodiments, the compound has the structure of formula (IXA):

(IXA)

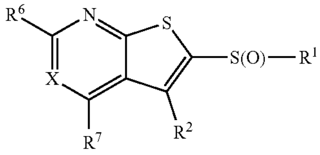

or a pharmaceutically acceptable salt, tautomer, or solvate thereof, wherein:

$R^1$ is cyclobutyl or —($C_1$-$C_4$ alkylene)-($C_1$-$C_3$ alkoxy);

$R^2$ is —$NH_2$, CN, or —NHC(O)alkyl;

$R^6$ is

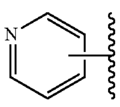, 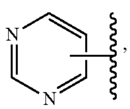, 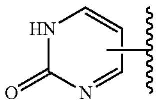,

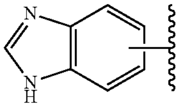, 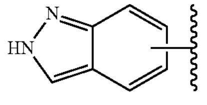, or

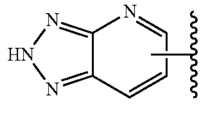, each of which is optionally substituted with one or more $R^3$;

$R^7$ is —$CF_3$, isopropyl, cyclopropyl, cyclobutyl,

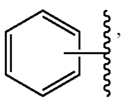, 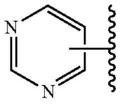, and 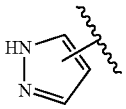, each of which is optionally substituted with one or more $R^4$;

$R^3$ is —$NH_2$, —NH($C_1$-$C_3$ alkyl), —NH($C_1$-$C_4$ alkylene)-OH, or $C_1$-$C_3$ alkyl;

$R^4$ is $C_1$-$C_3$ alkyl; and

X is N or CH.

In some embodiments of Formula (IXA), $R^1$ is cyclobutyl. In some embodiments of Formula (IXA), $R^1$—($C_1$-$C_4$ alkylene)-($C_1$-$C_3$ alkoxy). In some embodiments of Formula (IXA), the $R^1$—($C_1$-$C_4$ alkylene)-($C_1$-$C_3$ alkoxy) is —($C_2$-$C_3$ alkylene)-($C_1$ alkoxy).

In some embodiments of Formula (IXA), $R^2$ is —$NH_2$.

In some embodiments of Formula (IXA), $R^6$ is

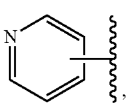, 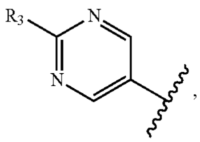, 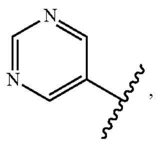,

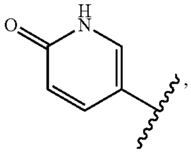, 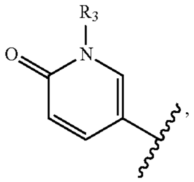,

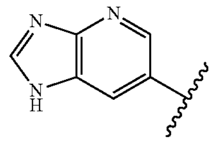, 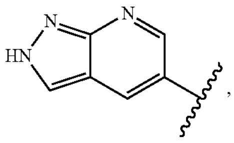,

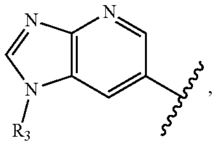, 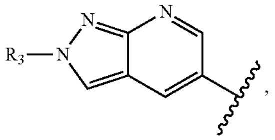,

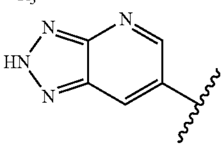, 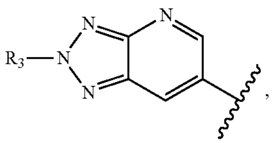,

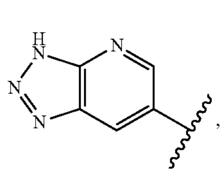, or 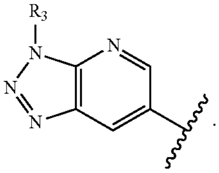.

In some embodiments of Formula (IXA), $R^3$ is —$NH_2$. In some embodiments of Formula (IXA), $R^3$ is —NH($C_1$-$C_3$ alkyl). In some embodiments of Formula (IXA), $R^3$ is —NH($C_1$-$C_4$ alkylene)-OH (e.g., —NH($C_2$-$C_4$ alkylene)-OH). In some embodiments of Formula (IXA), $R^3$ is $C_1$-$C_3$ alkyl (e.g., methyl or ethyl).

In some embodiments, of Formula (IXA), $R^7$ is —$CF_3$, isopropyl, cyclopropyl, or cyclobutyl. In some embodiments, of Formula (IXA), $R^7$ is isopropyl. In some embodiments of Formula (VII), $R^7$ is

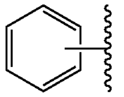, 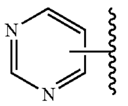, or 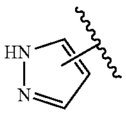, each of which is optionally substituted with one or more $R^4$. In some embodiments, each $R^4$ is independently selected from methyl or ethyl.

In some embodiments of Formula (IXA), X is —CH.

Examples of compounds having formulas (I), (II), (III), (IV), (V), (IA), (IIA), (IIIA), (IVA), (VA), (VIA), (VIIA), (VIIIA), and (IXA) are described in U.S. Patent Application Publication Nos. 2015/0072998, 2017/0165241, 2017/0173028, 2018/0118756, WO2018/218251, and WO2020/106998, all of which are incorporated herein by reference in their entirety.

For example, the 15-PGDH inhibitor can include a compound selected from:

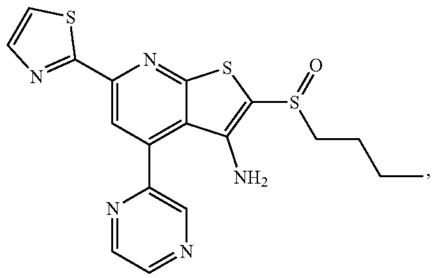

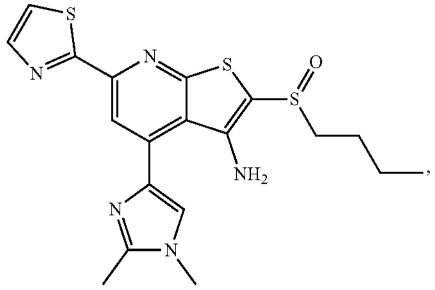

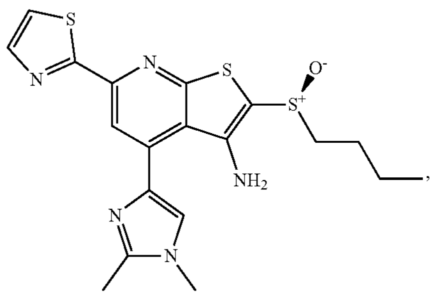

-continued
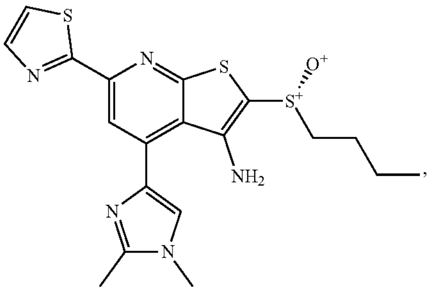
,
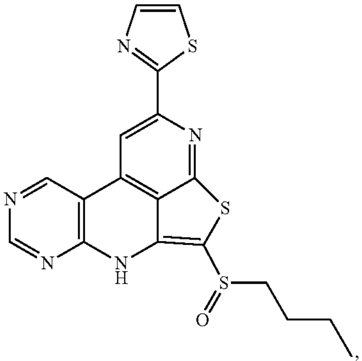
,
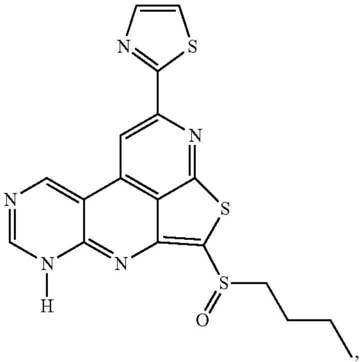
,
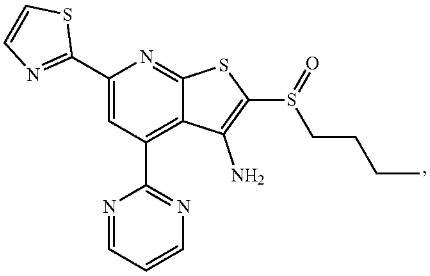
,
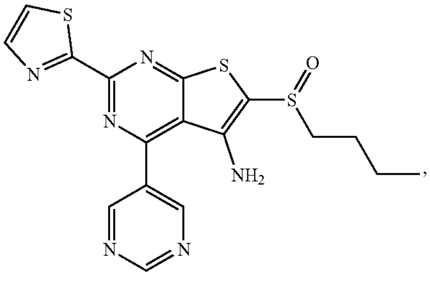
,
-continued
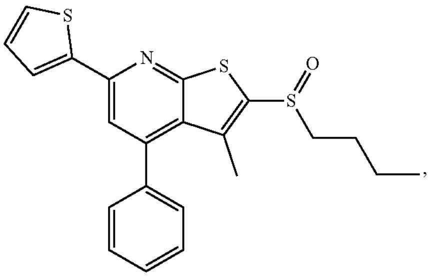
,
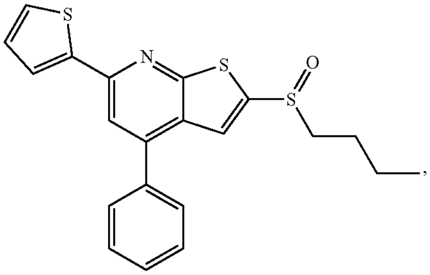
,
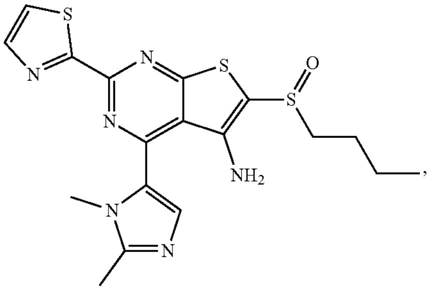
,
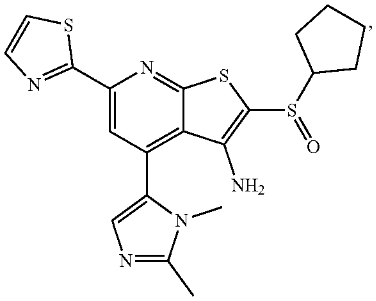
,
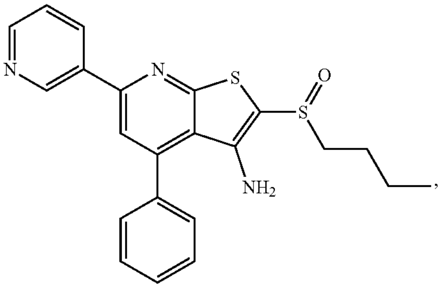
,
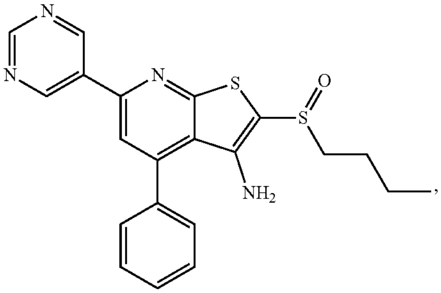
, -continued
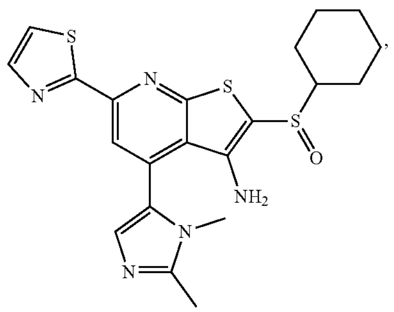
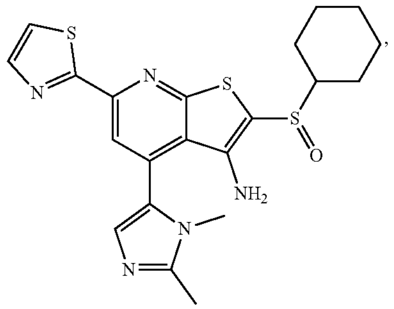
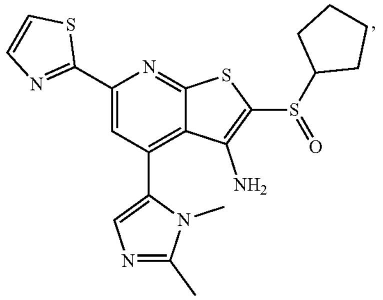
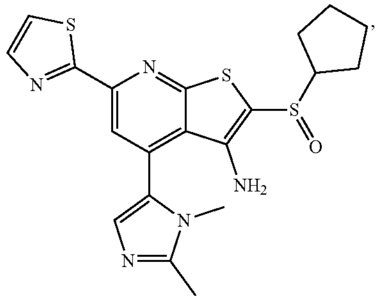
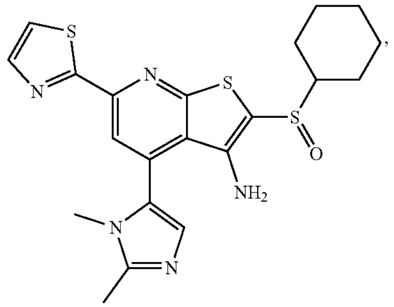
-continued
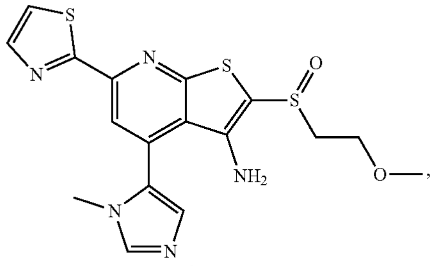
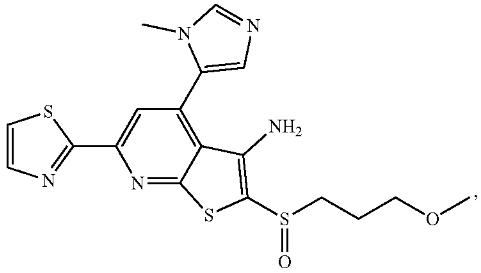
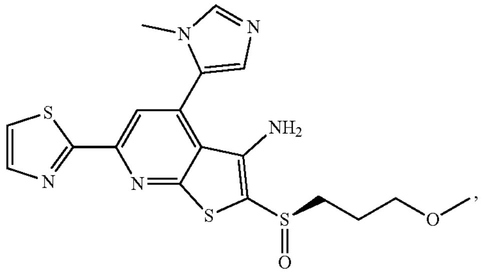
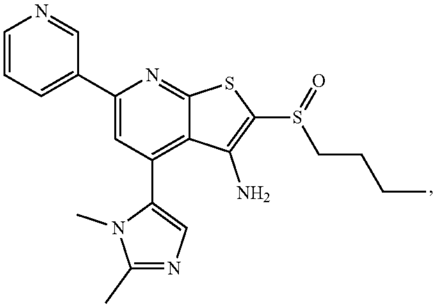
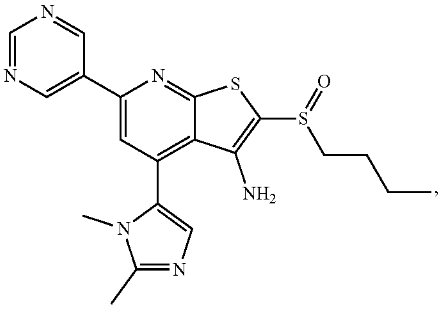
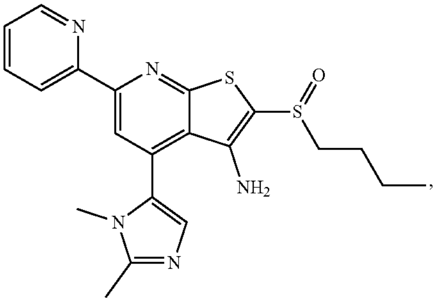

-continued
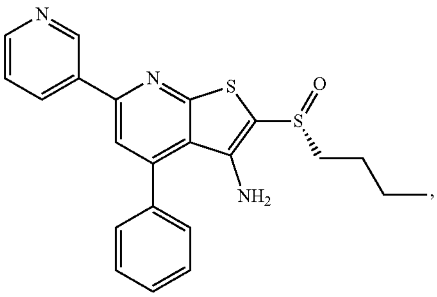
,
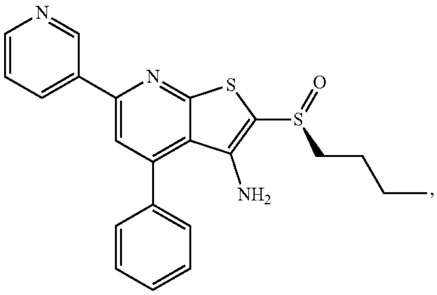
,
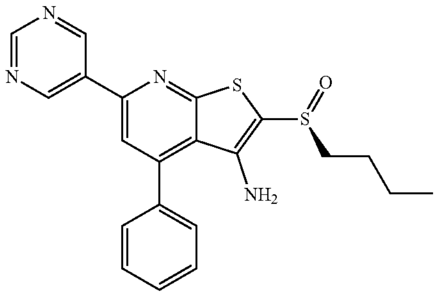
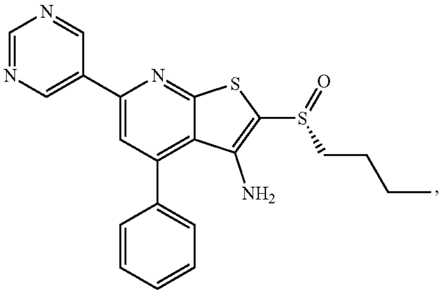
,
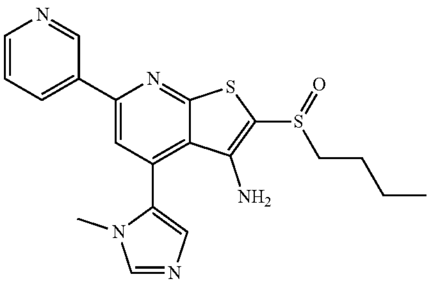
,
-continued
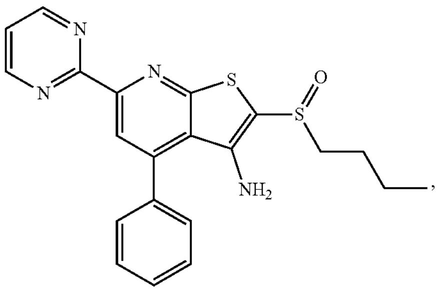
,
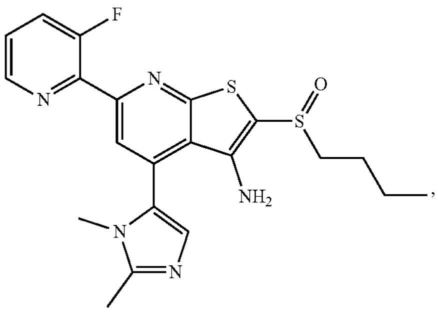
,
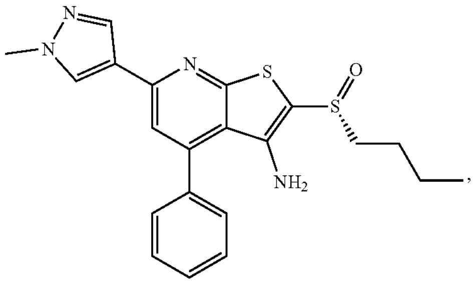
,
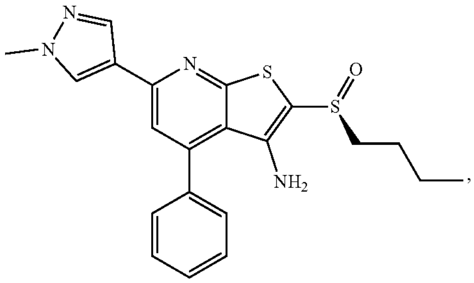
,
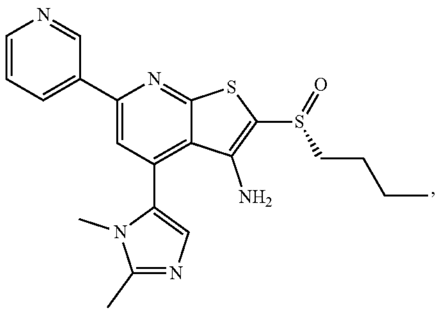
, -continued
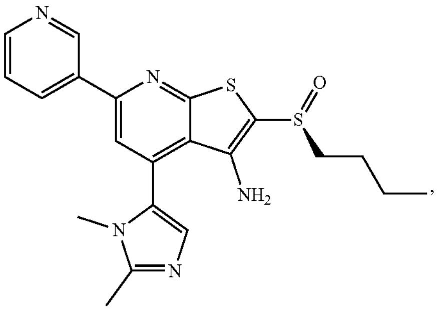
,
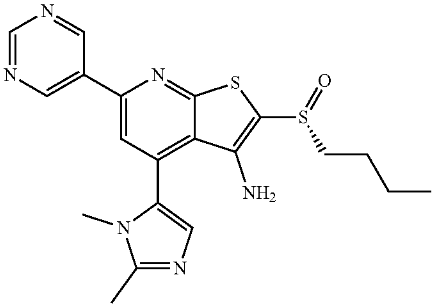
,
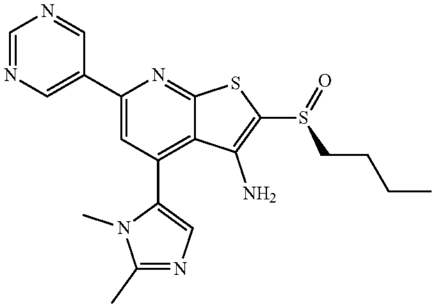
,
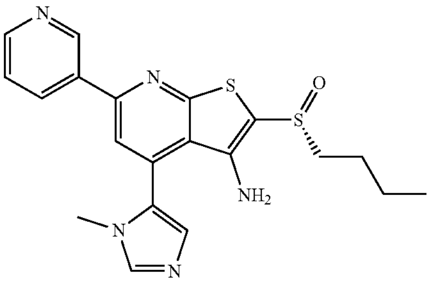
,
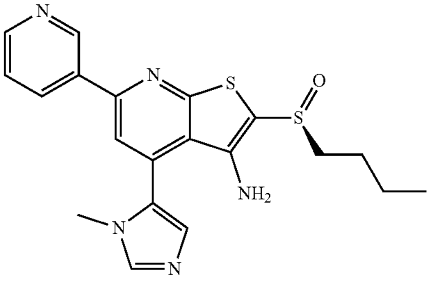
,
-continued
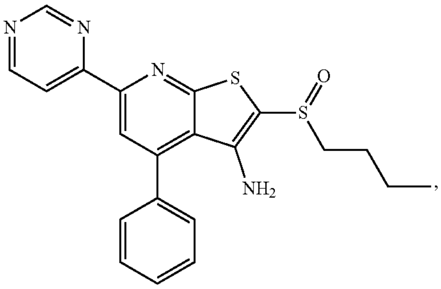
,
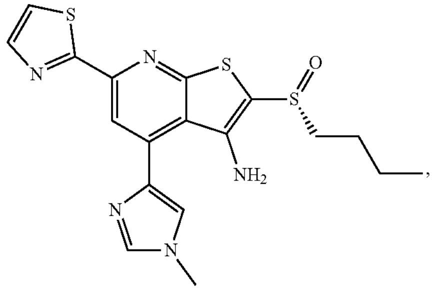
,
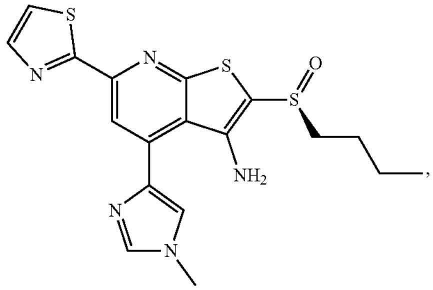
,
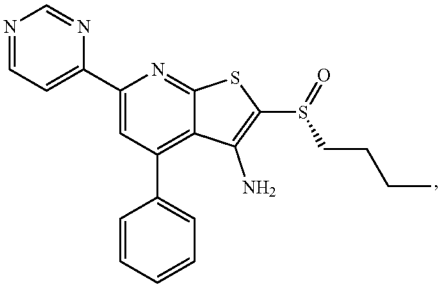
,
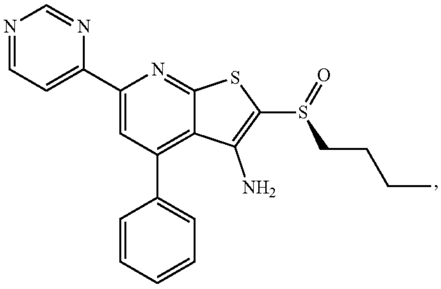
, -continued
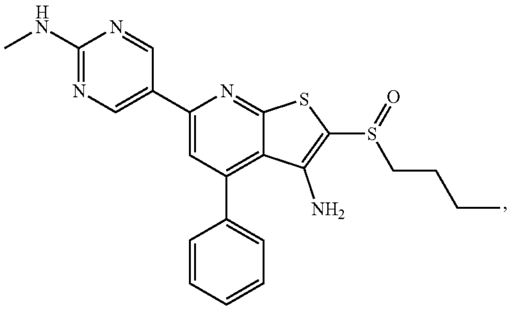
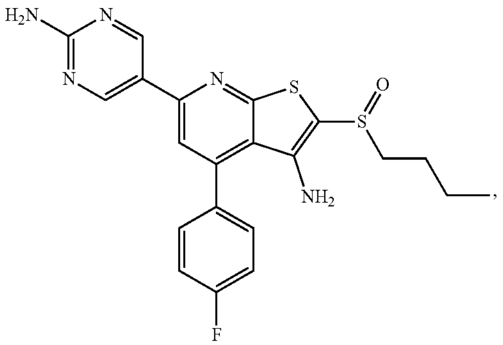
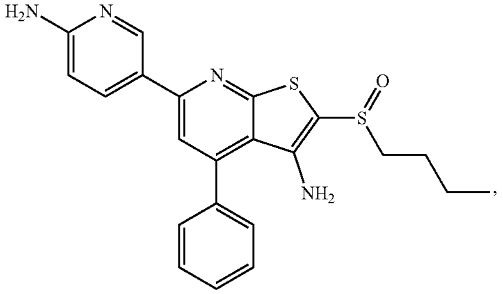
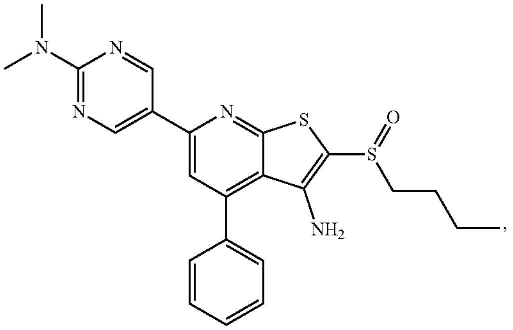
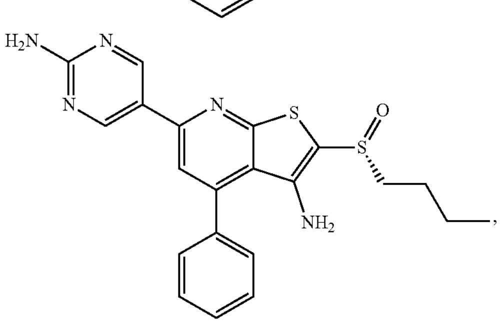
-continued
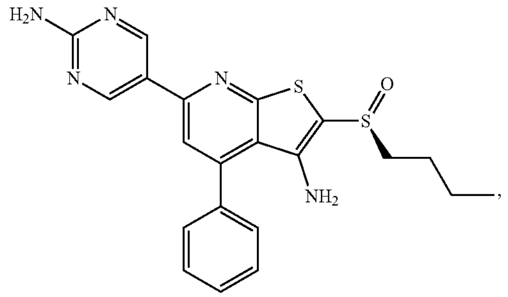
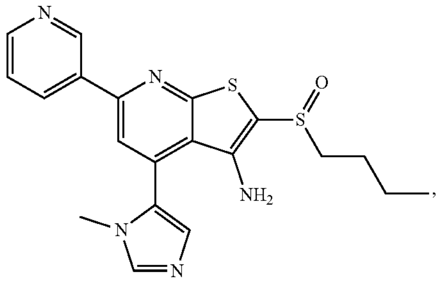
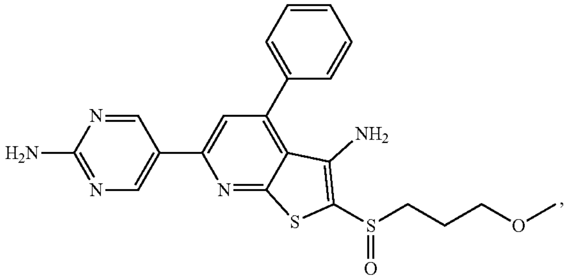
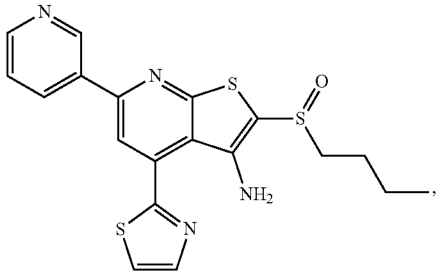
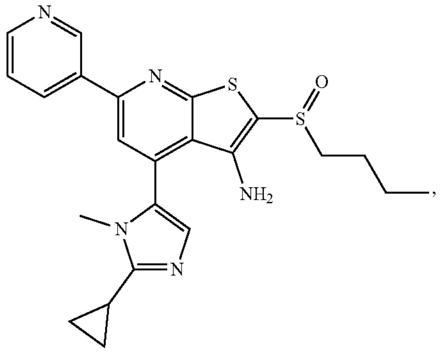

-continued
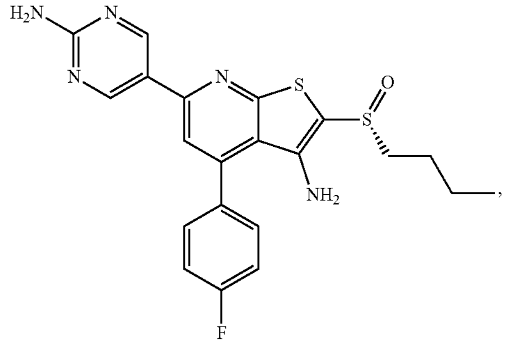
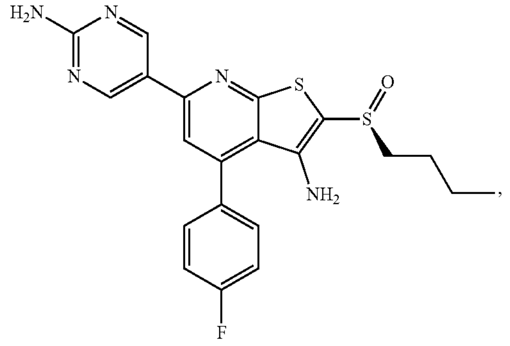
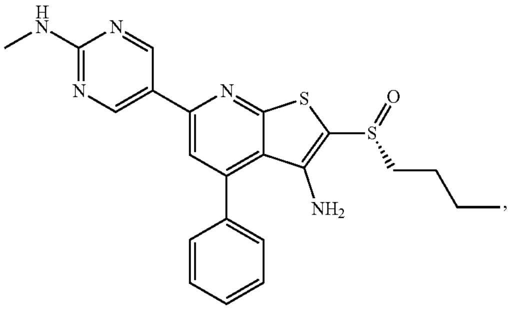
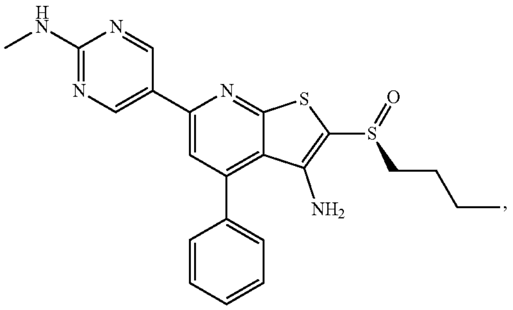
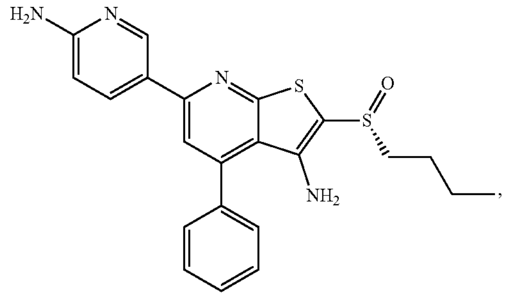
-continued
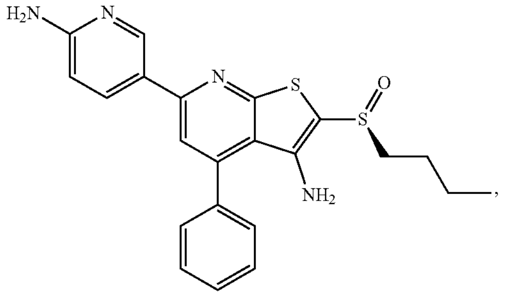
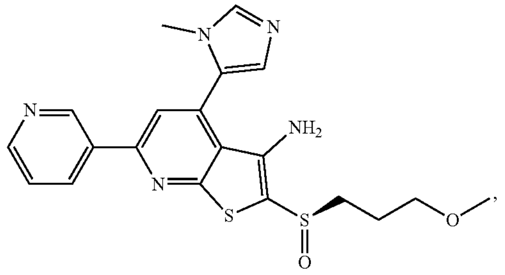
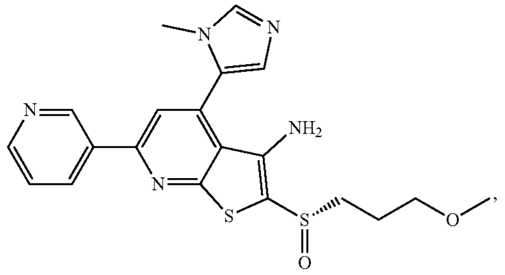
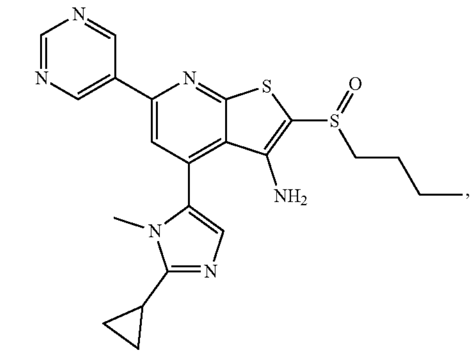
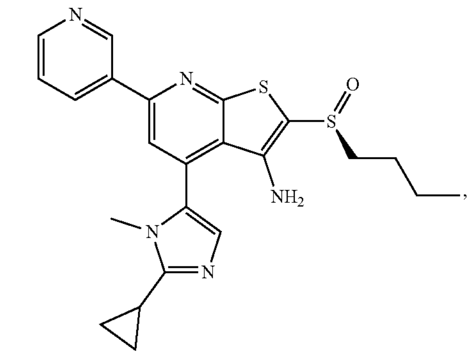

-continued
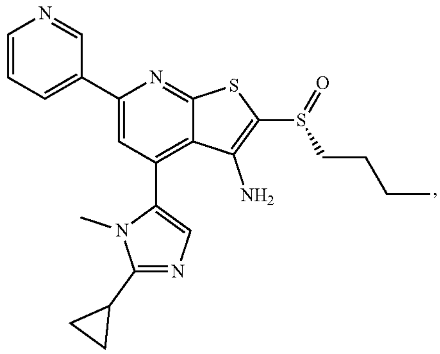
,
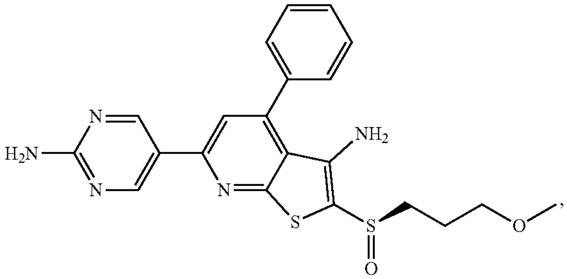
,
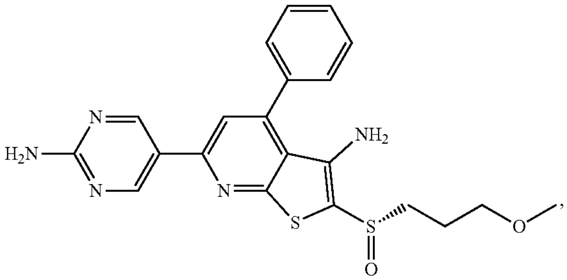
,
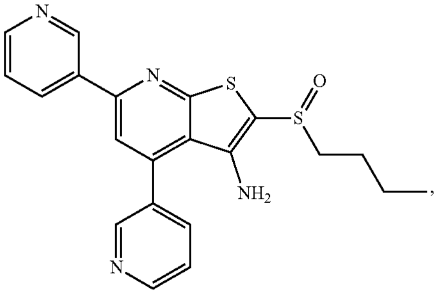
,
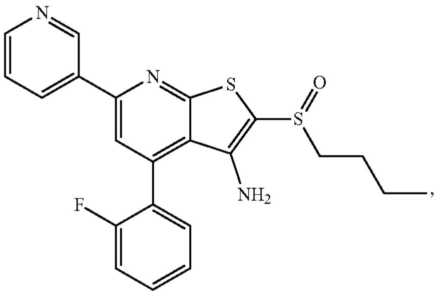
,
-continued
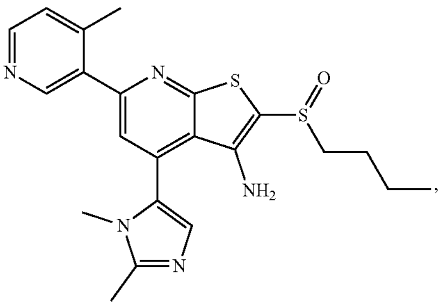
,
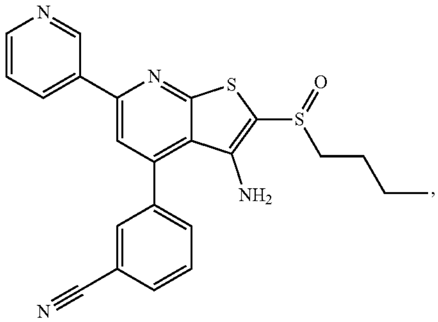
,
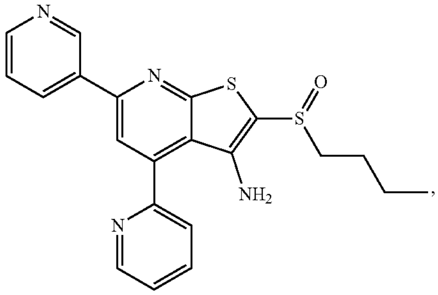
,
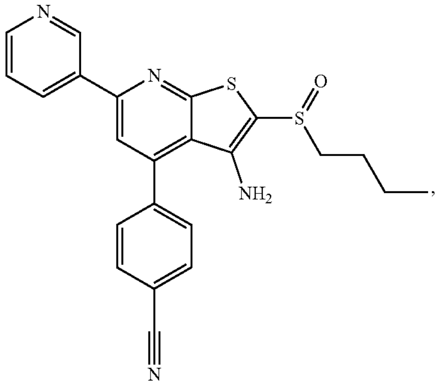
,
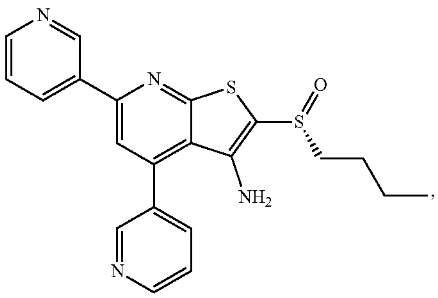
, -continued
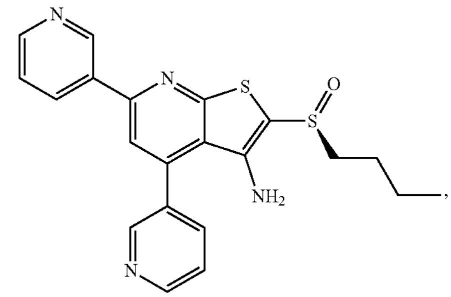
,
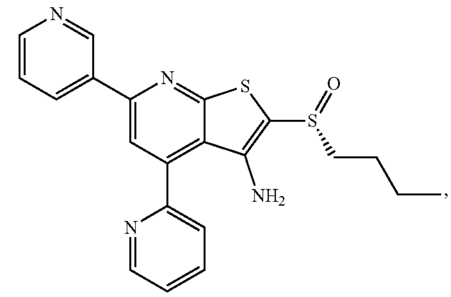
,
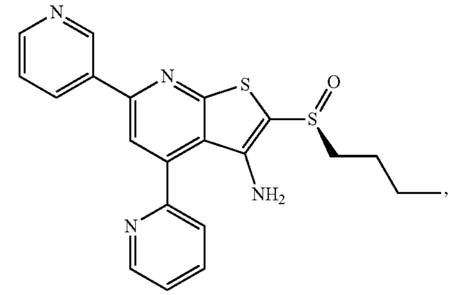
,
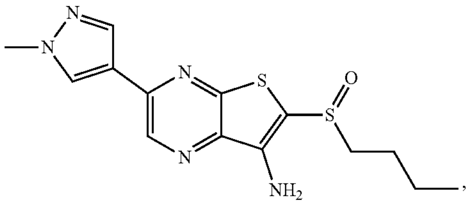
,
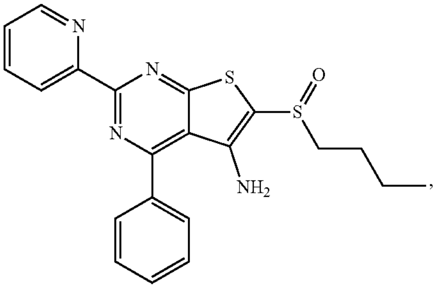
,
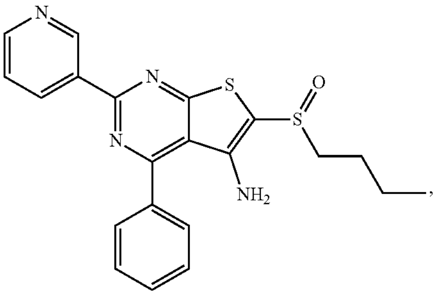
,
-continued
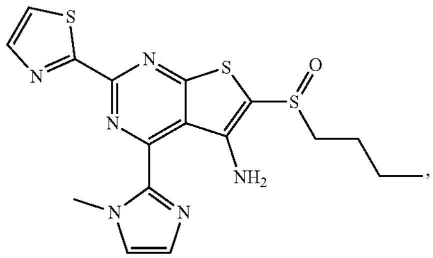
,
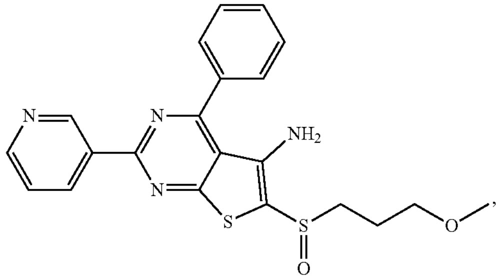
,
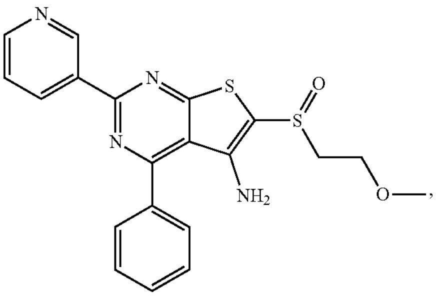
,
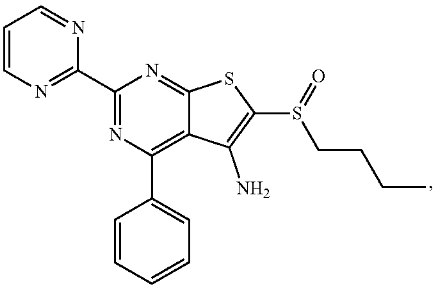
,
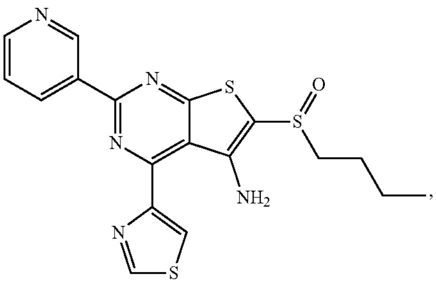
,
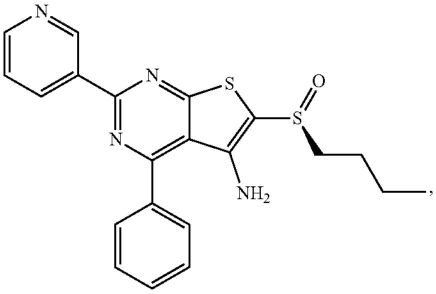
, -continued
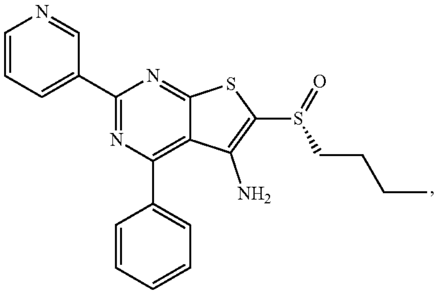
,
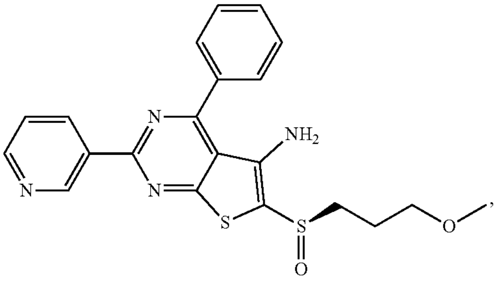
,
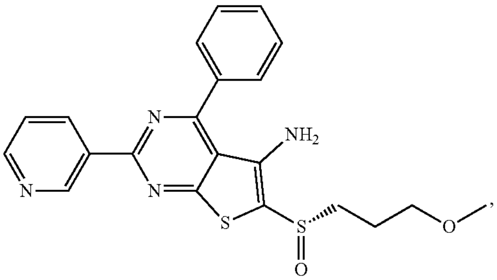
,
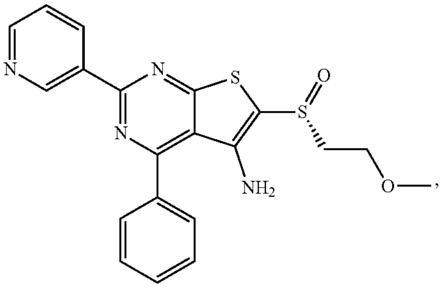
,
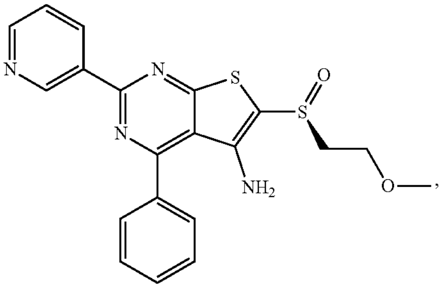
,
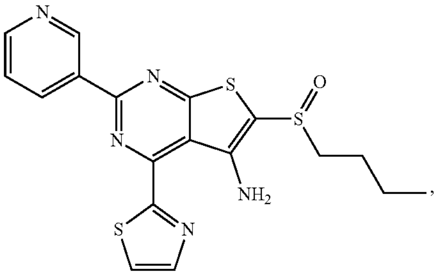
,
-continued
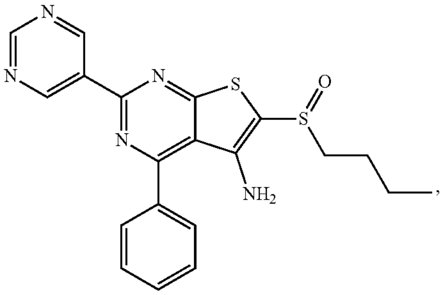
,
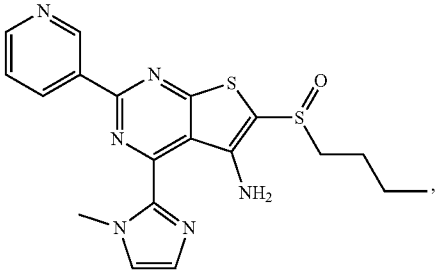
,
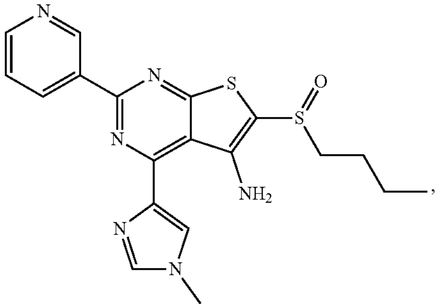
,
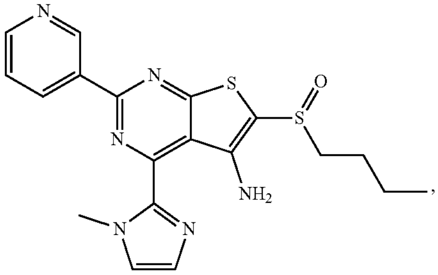
,
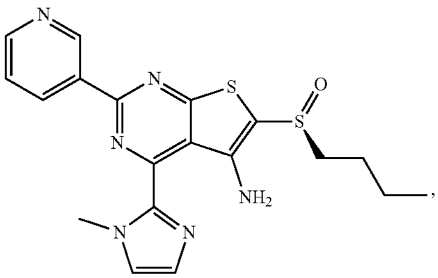
,
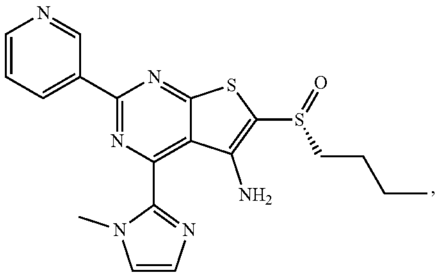
, -continued
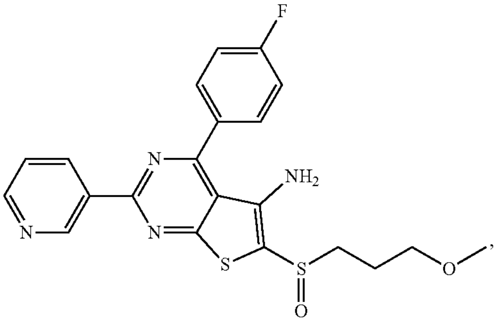
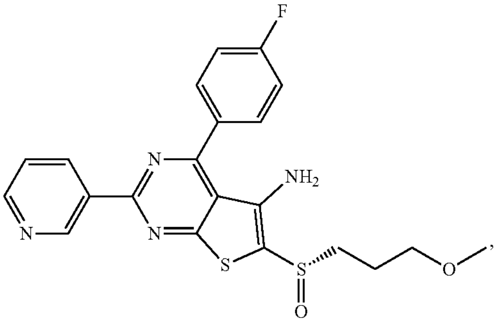
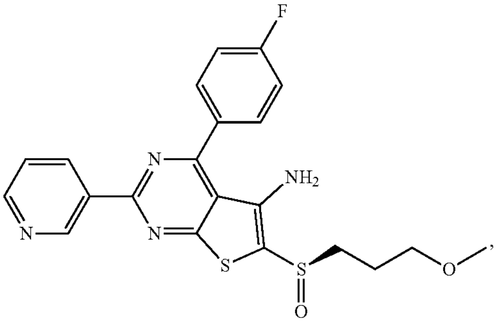
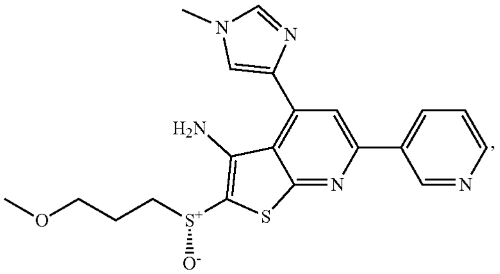
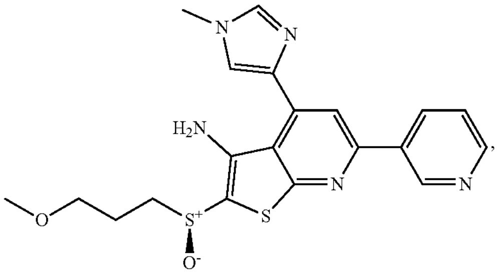
-continued
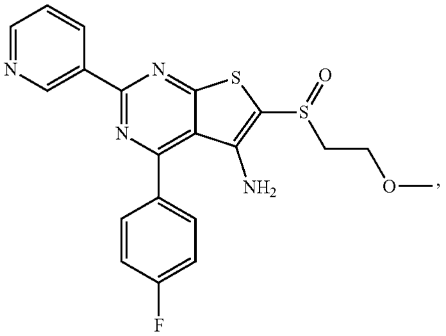
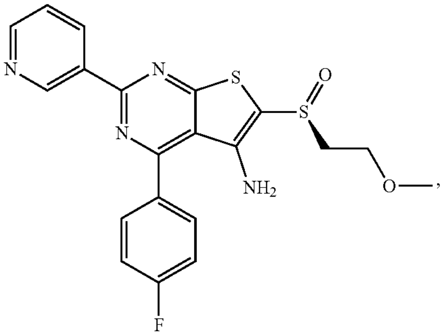
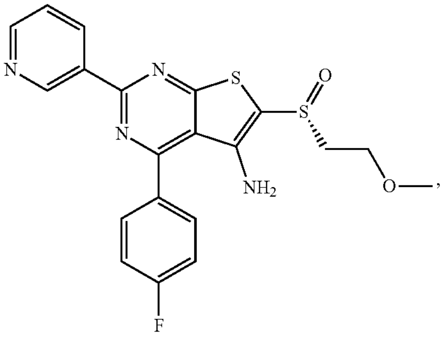
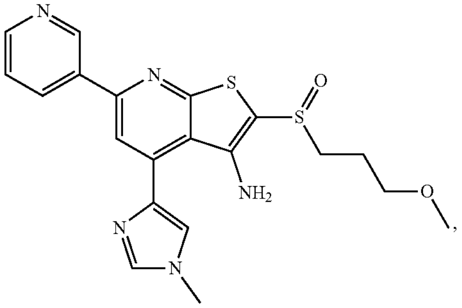
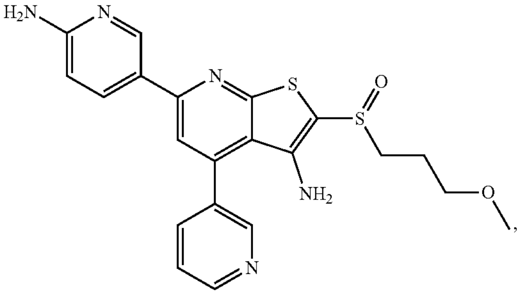

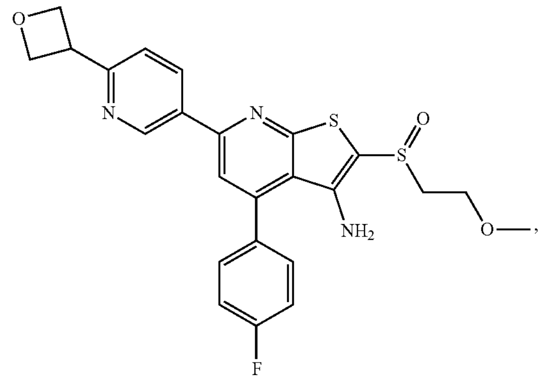
,
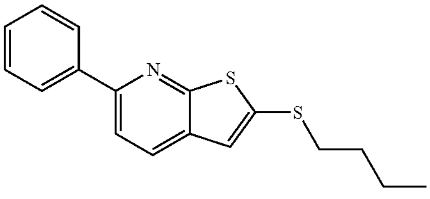
;
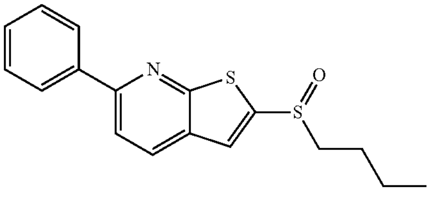
;
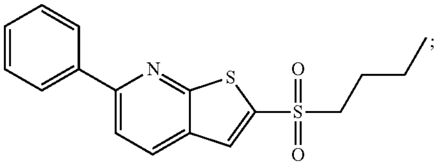
;
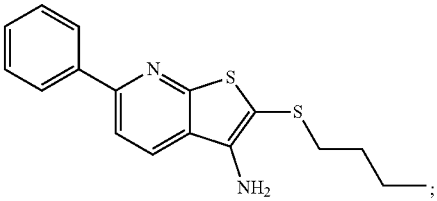
;
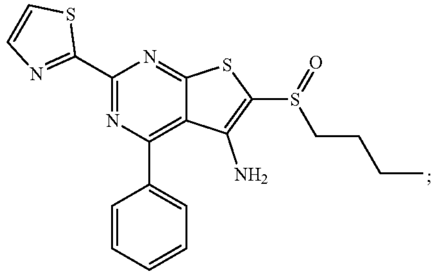
;
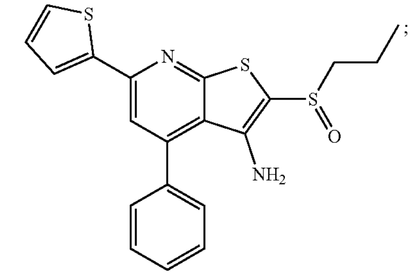
;
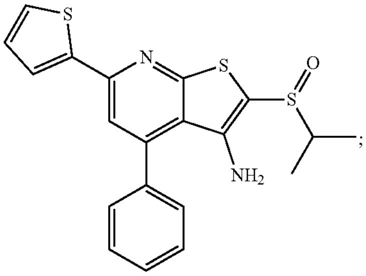
;
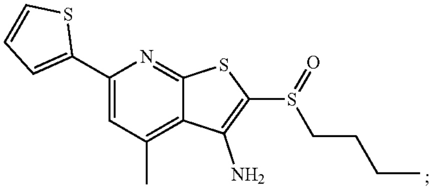
;
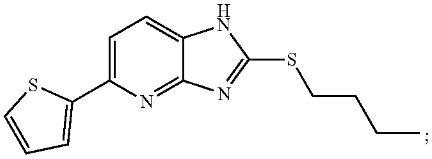
;
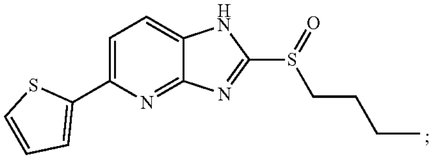
;
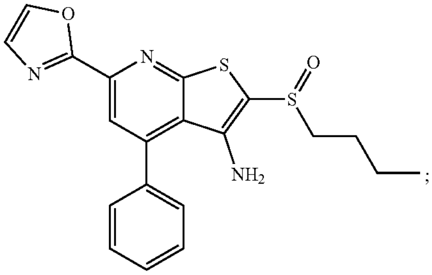
;
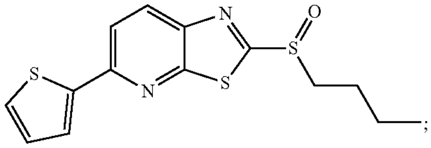
;

-continued
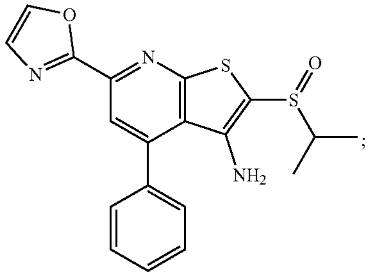
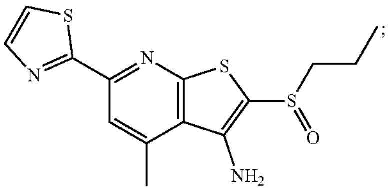
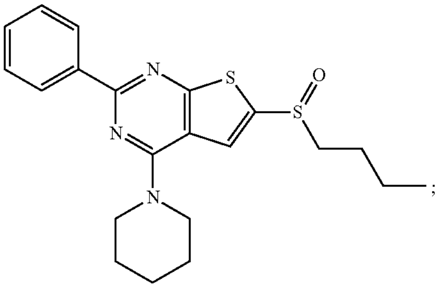
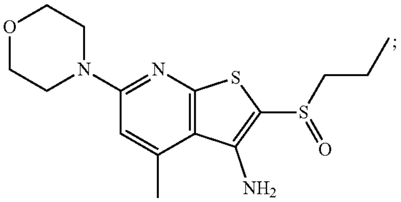
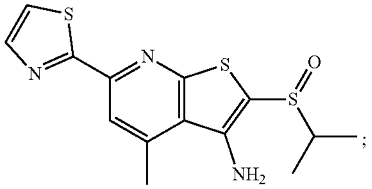
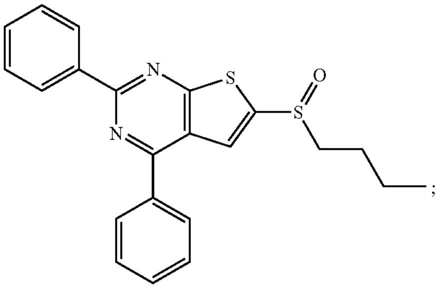
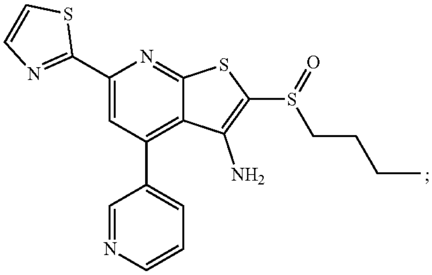
-continued
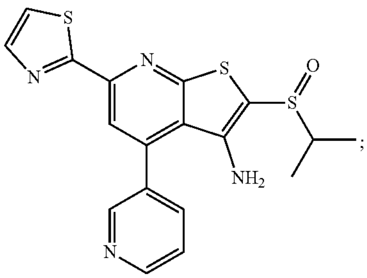
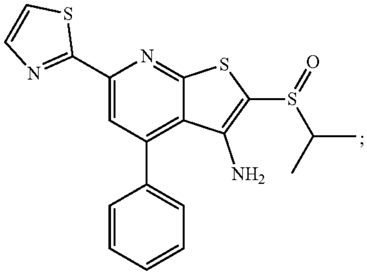
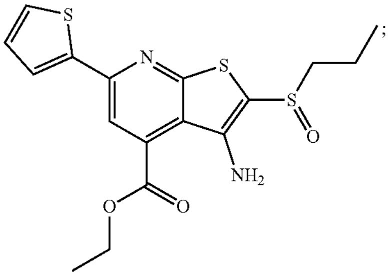
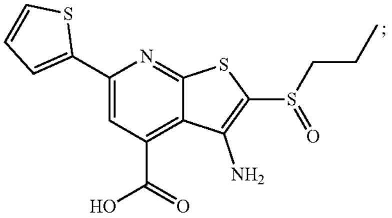
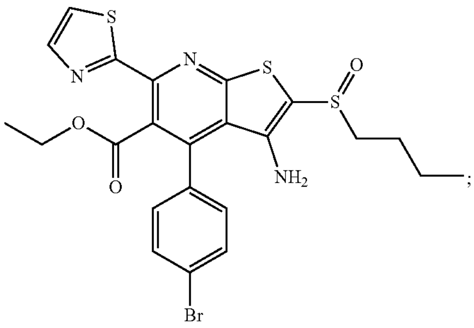
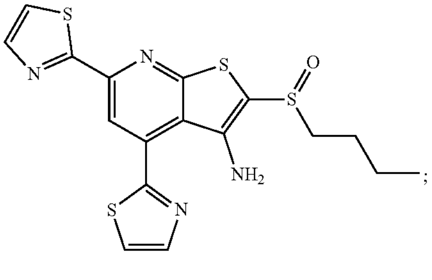

-continued
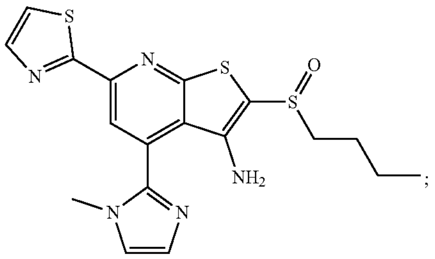
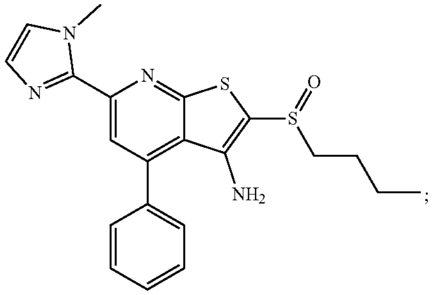
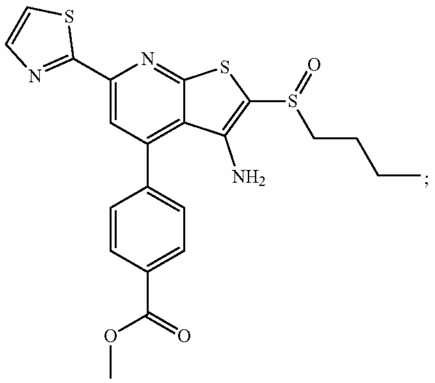
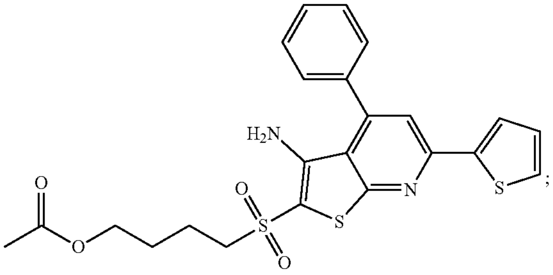
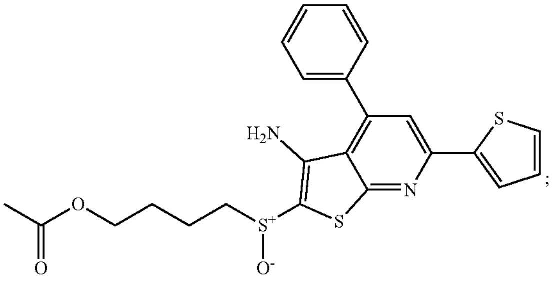
-continued
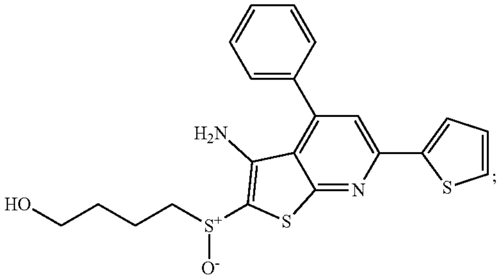
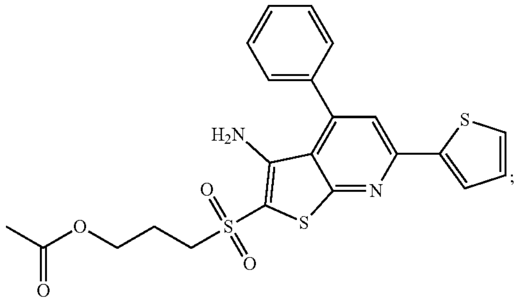
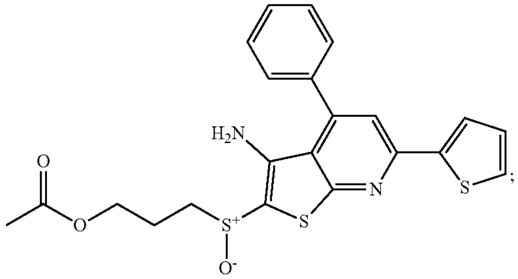
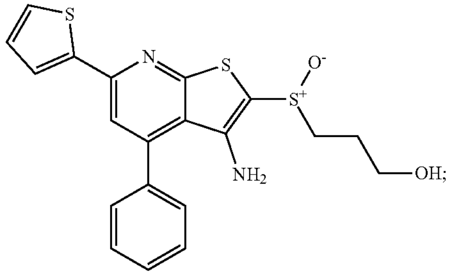
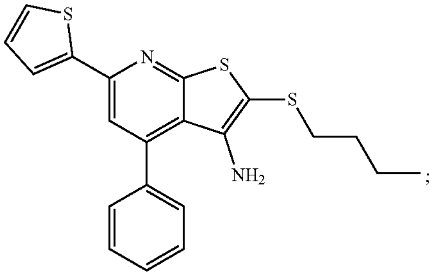
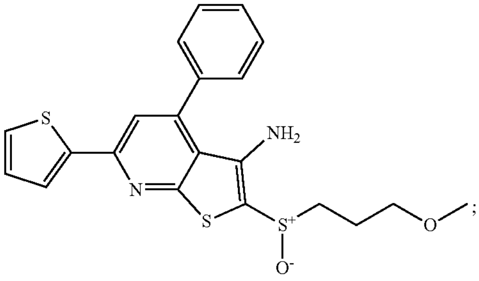

-continued
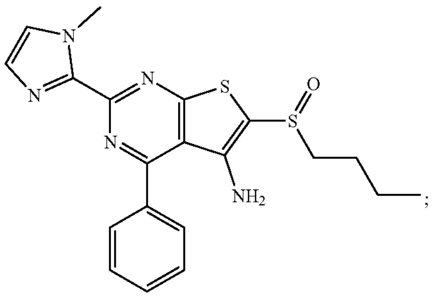
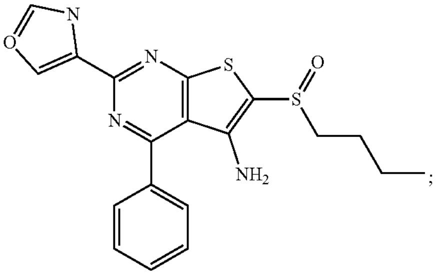
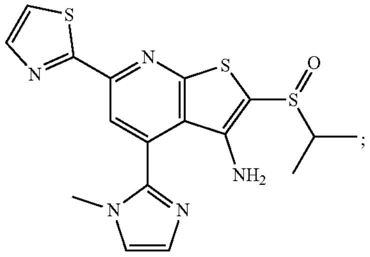
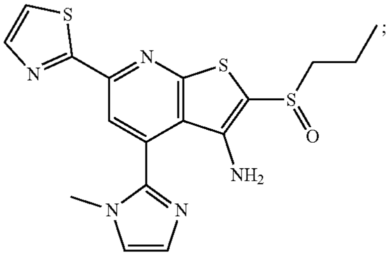
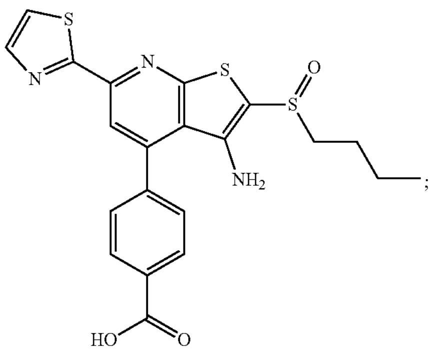
-continued
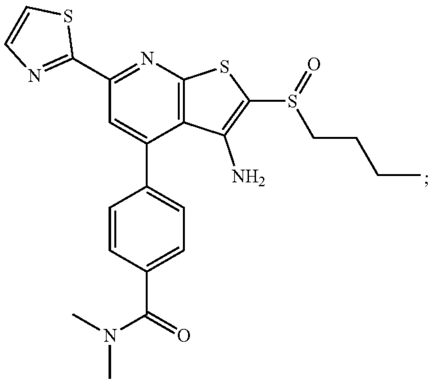
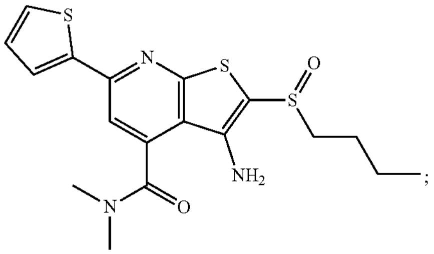
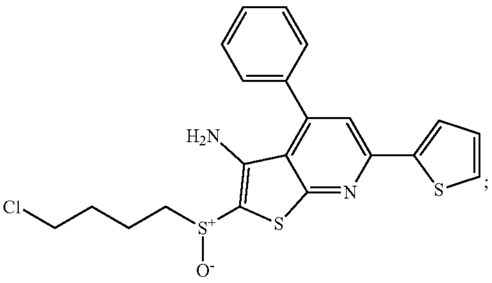
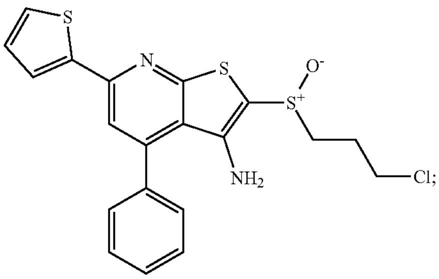
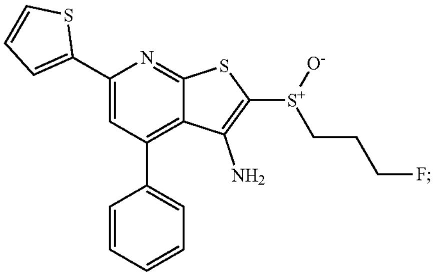

-continued
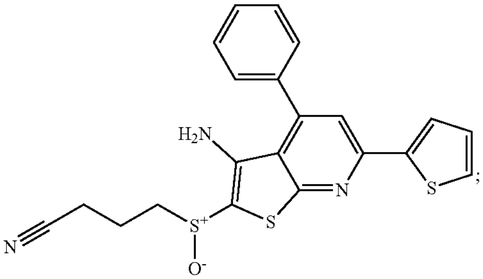
;
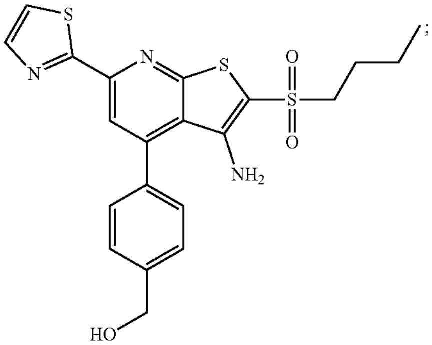
;
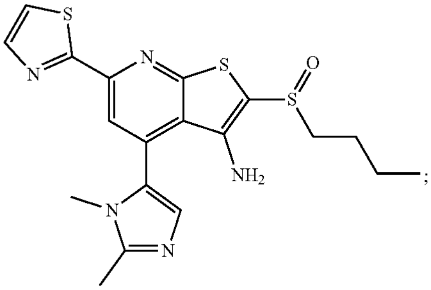
;
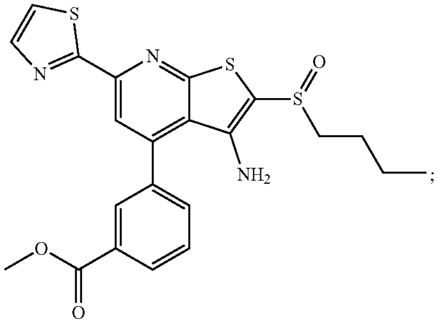
;
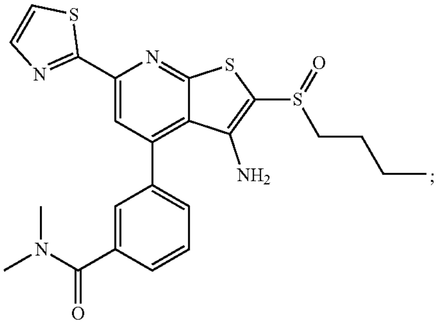
;
-continued
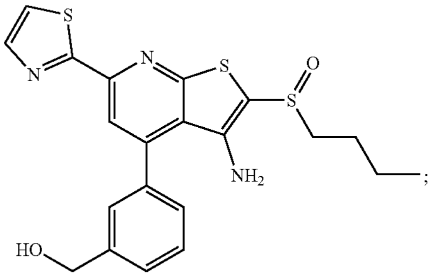
;
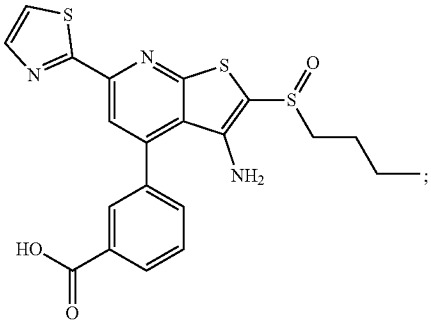
;
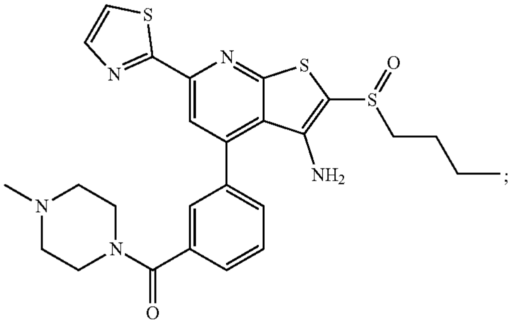
;
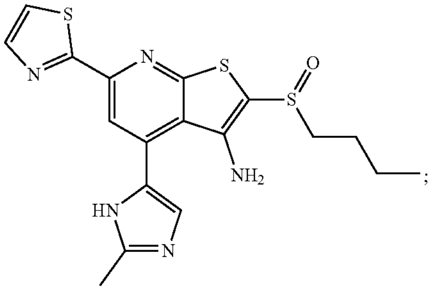
;
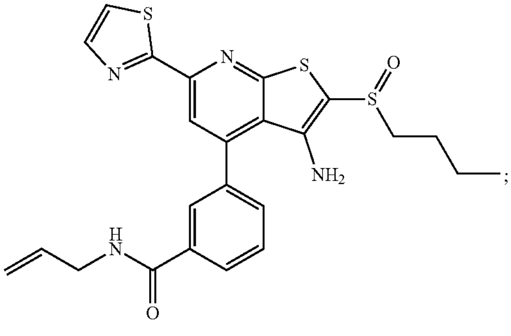
;

-continued
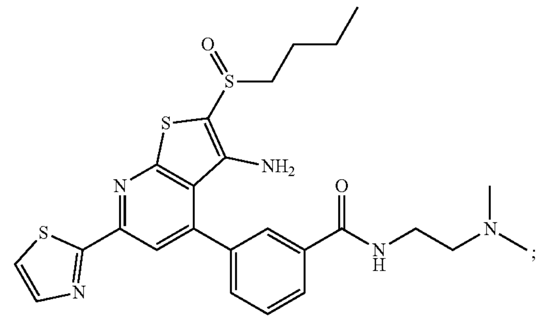
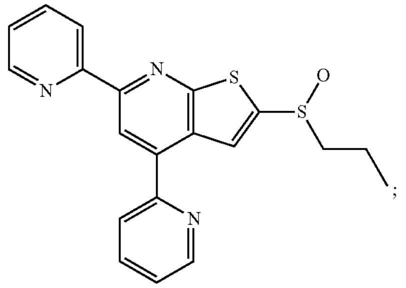
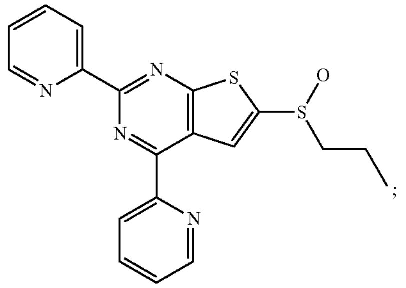
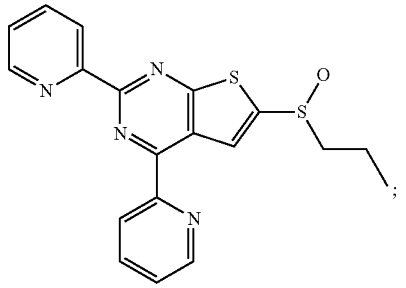
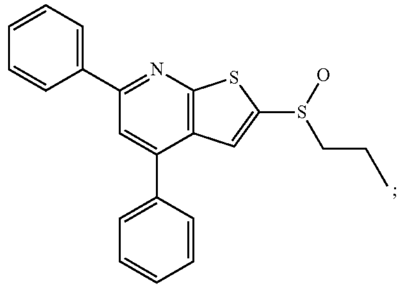
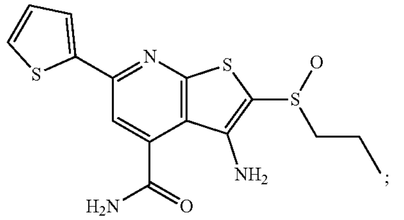
-continued
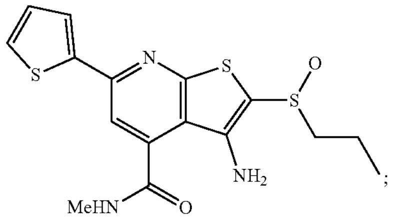
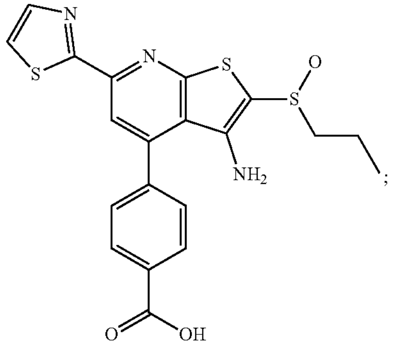
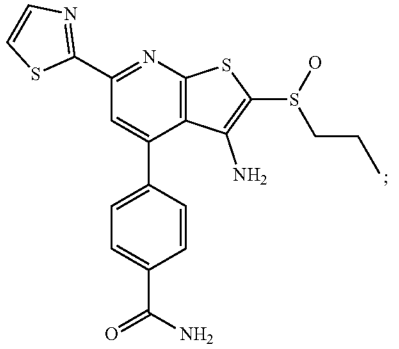
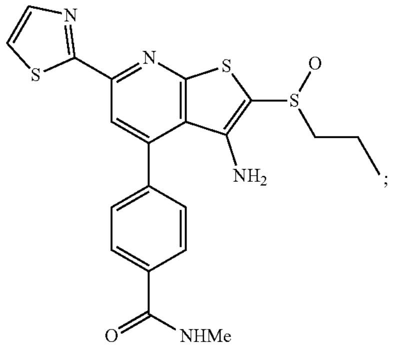
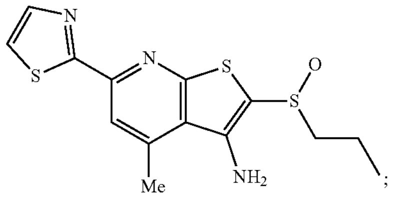
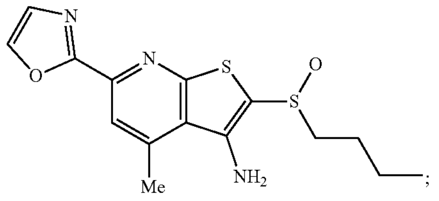

-continued
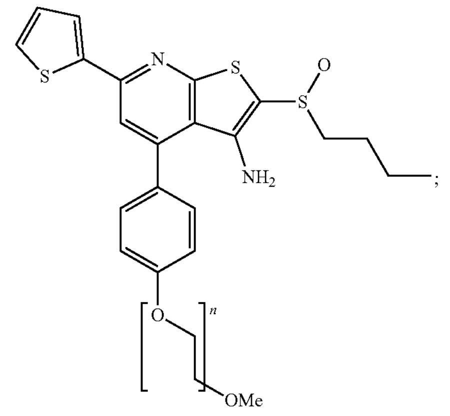
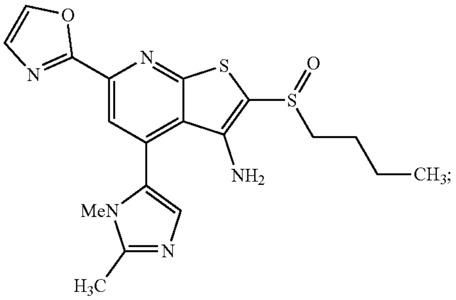
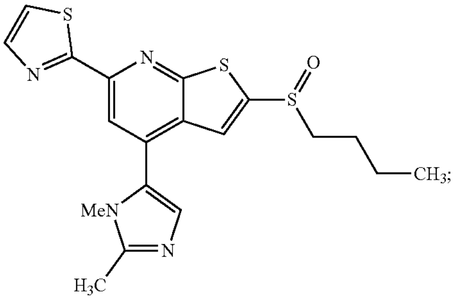
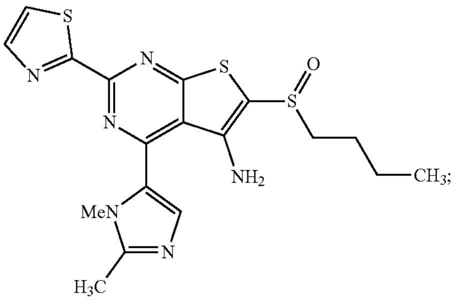
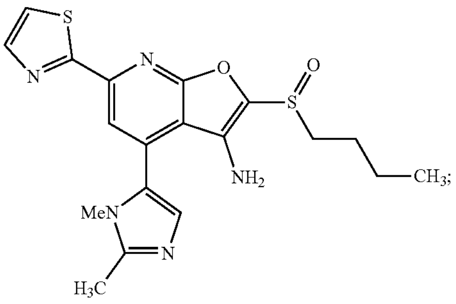
-continued
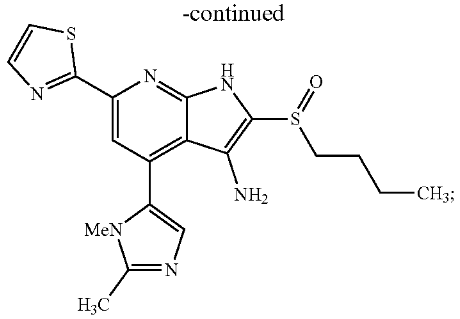
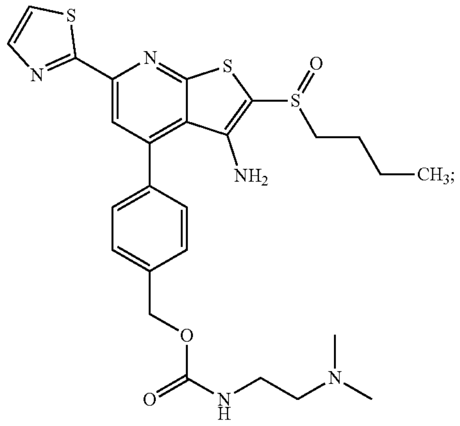
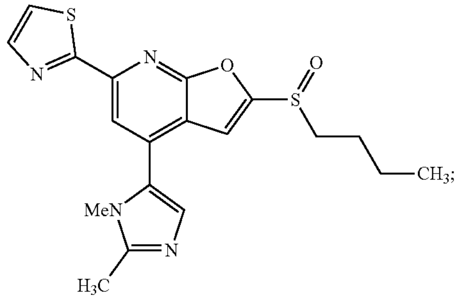
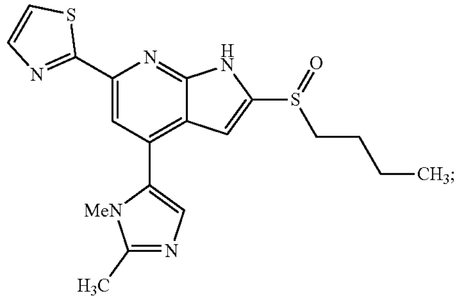
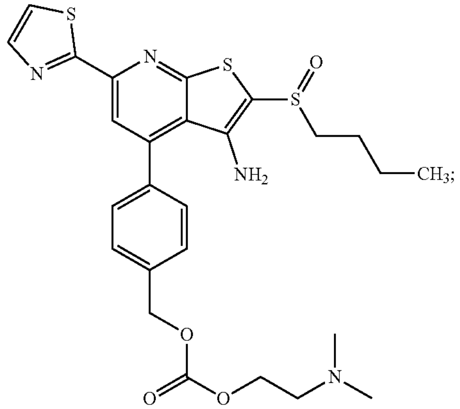

-continued
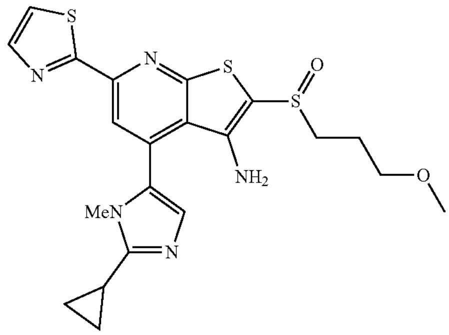
;
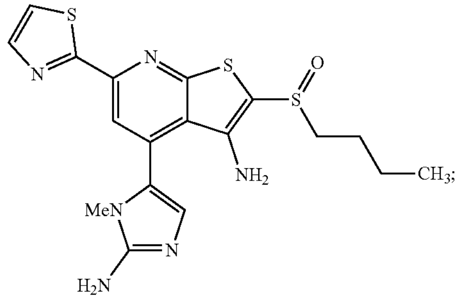
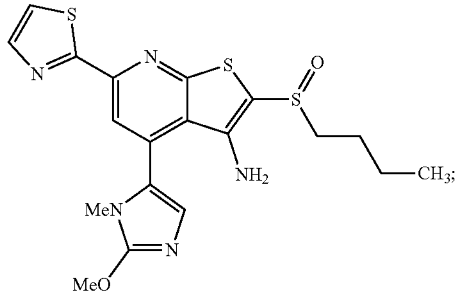
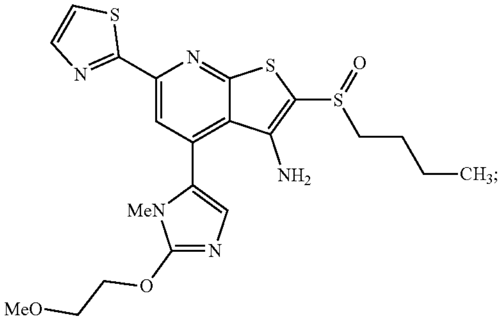
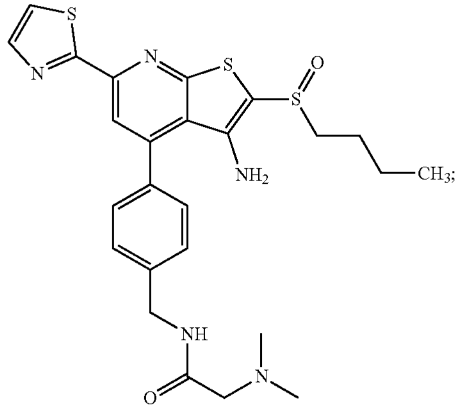
-continued
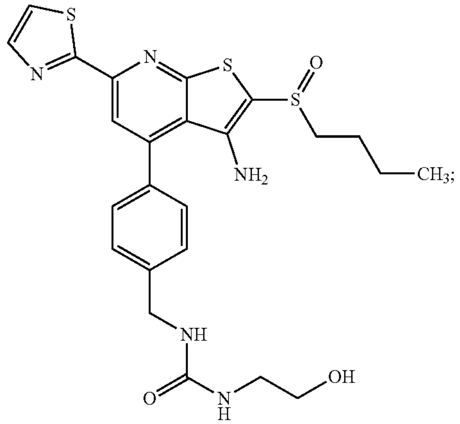
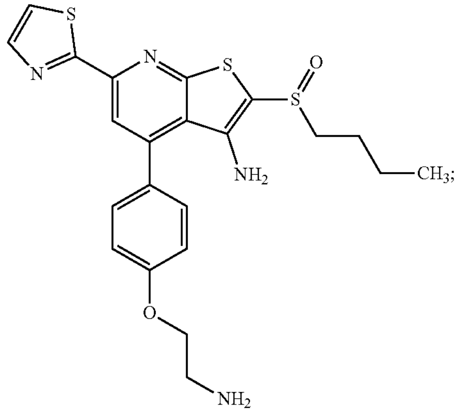
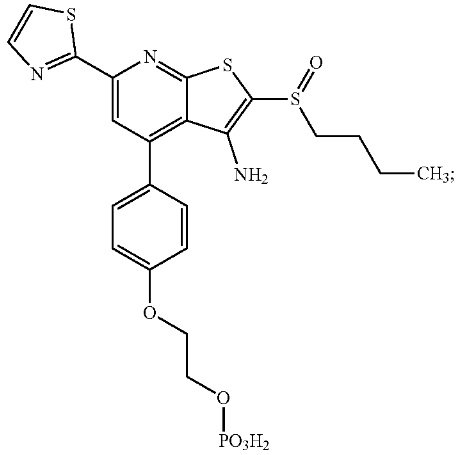

-continued
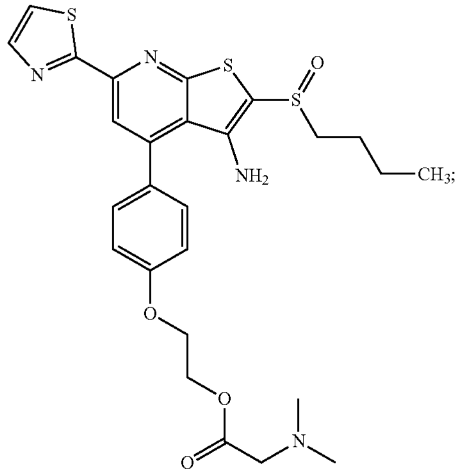
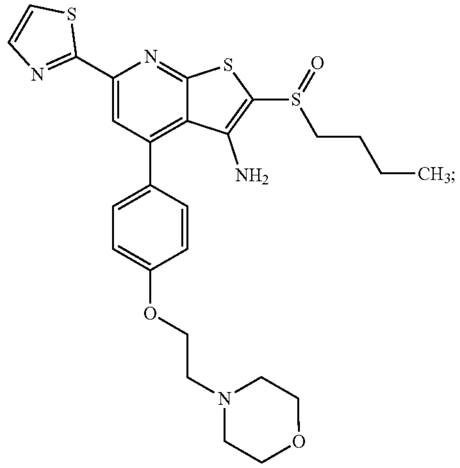
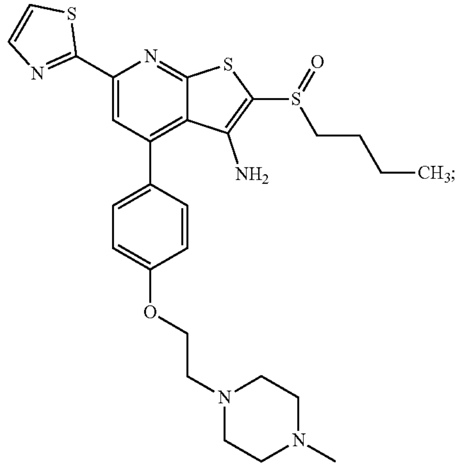
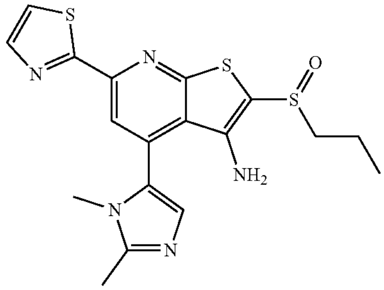
;
-continued
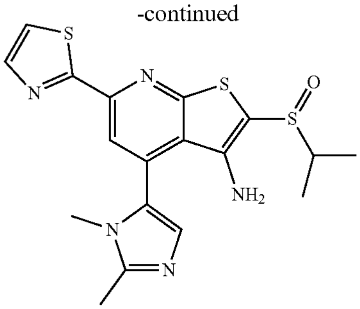
;
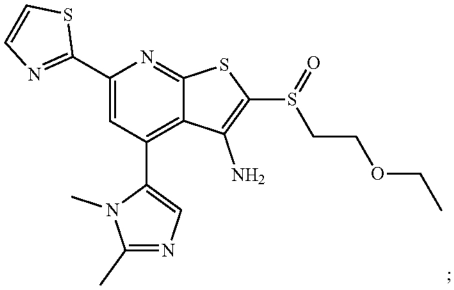
;
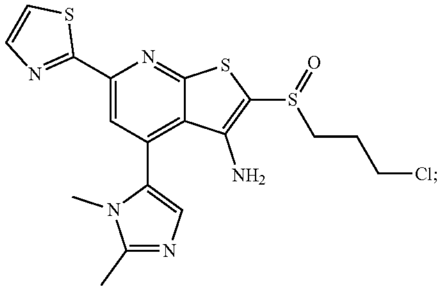
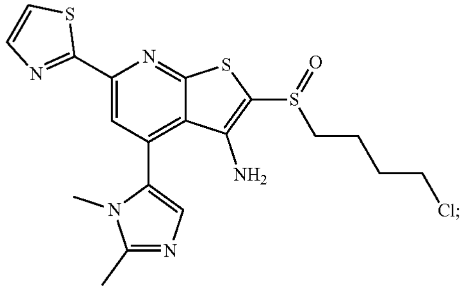
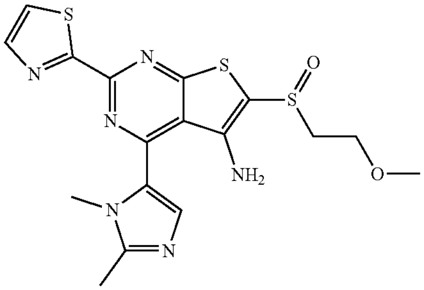
;
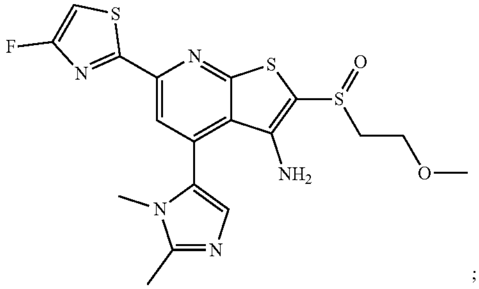
;

-continued
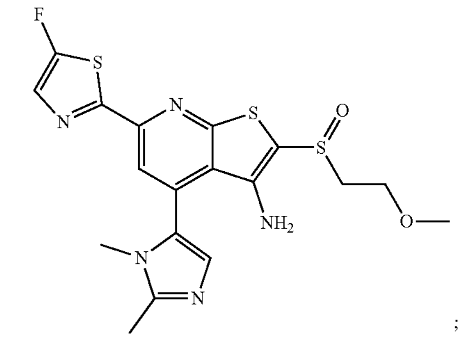
;
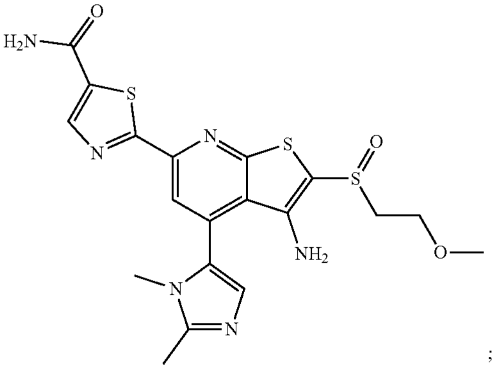
;
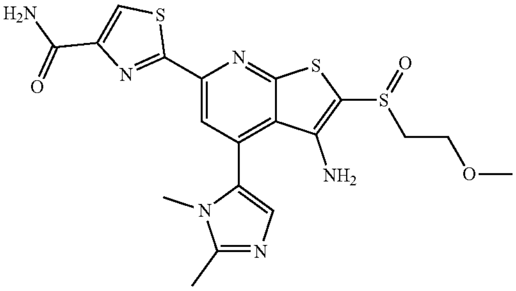
;
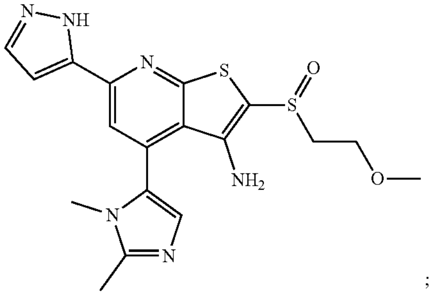
;
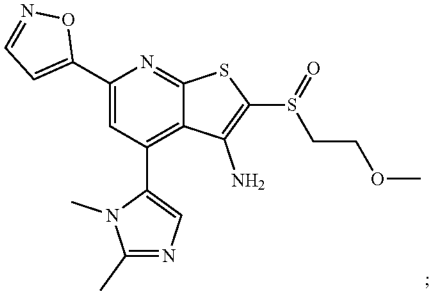
;
-continued
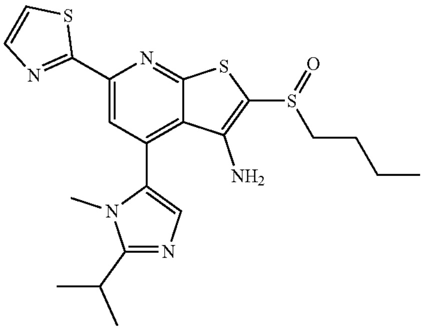
;
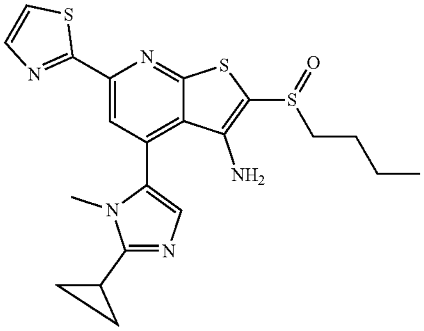
;
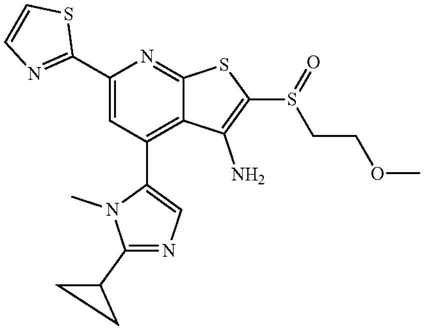
;
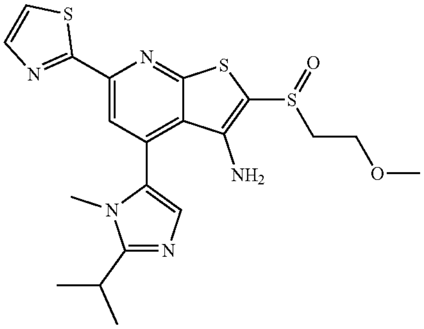
;

-continued
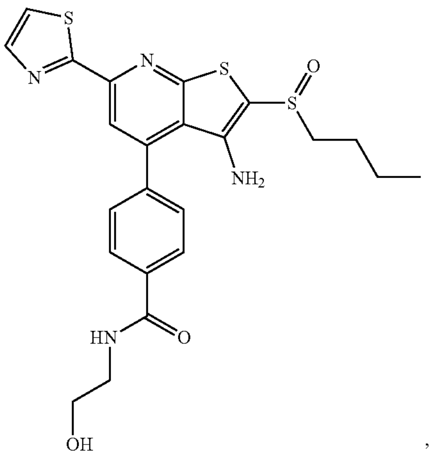
,
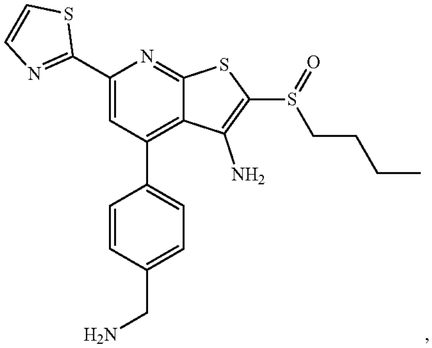
,
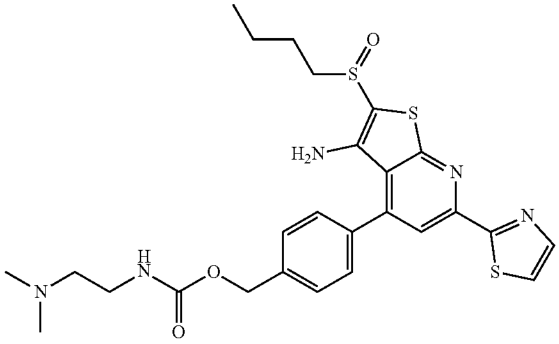
,
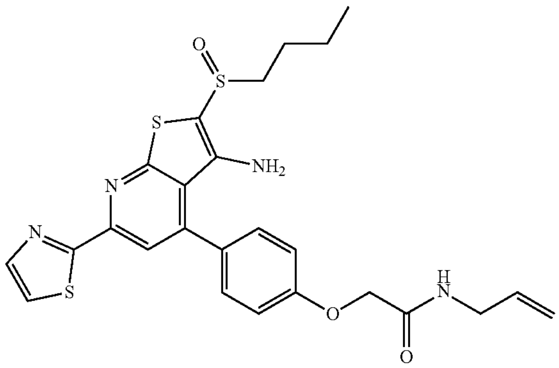
,
-continued
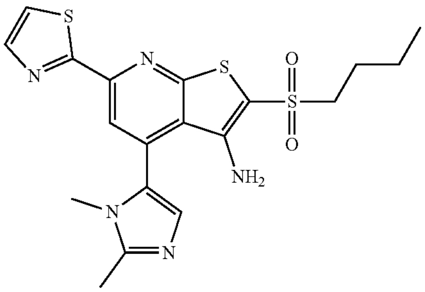
,
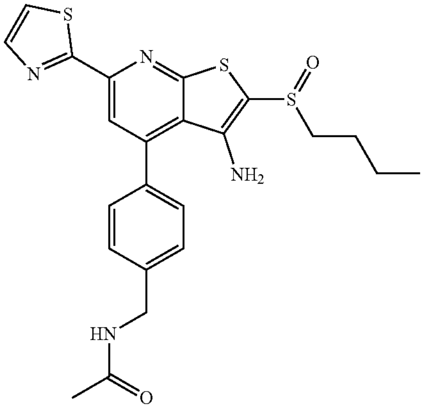
,
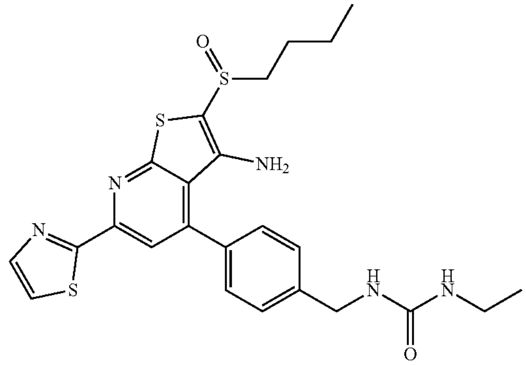
,
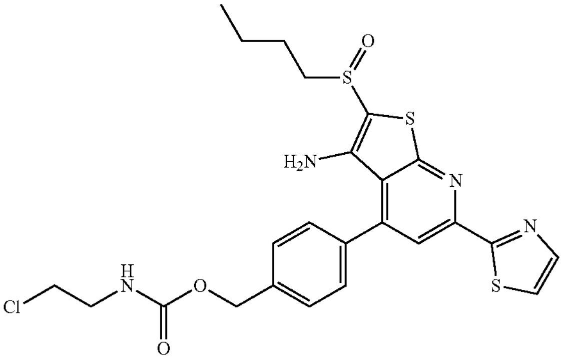
, -continued
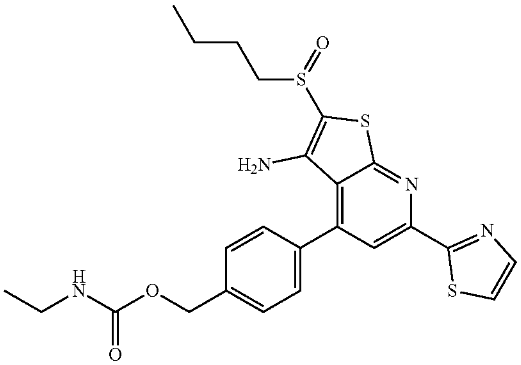
,
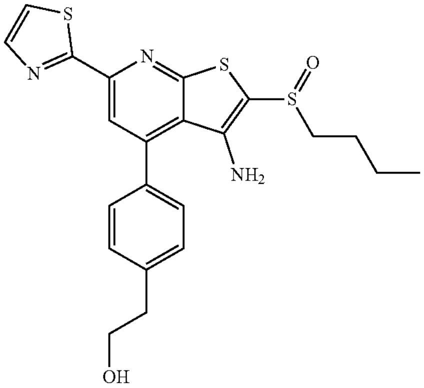
,
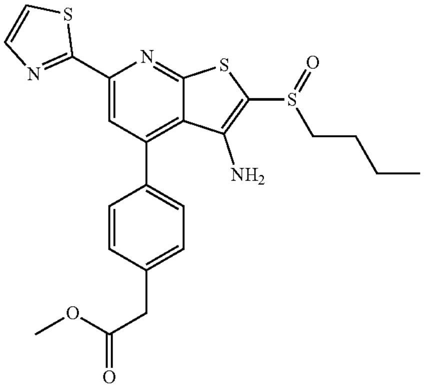
,
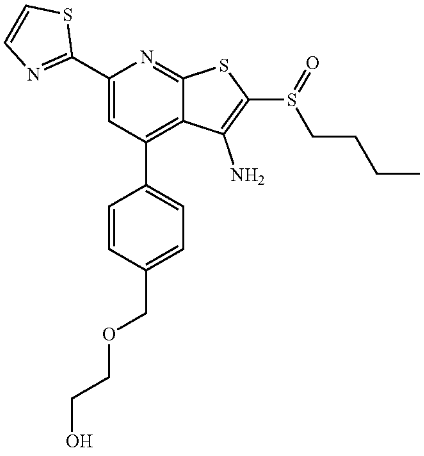
,
-continued
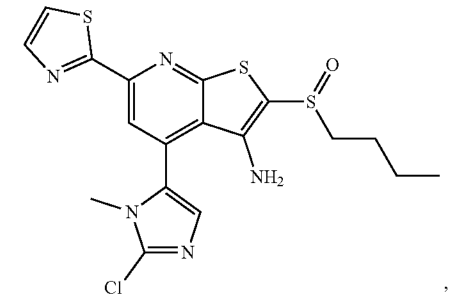
,
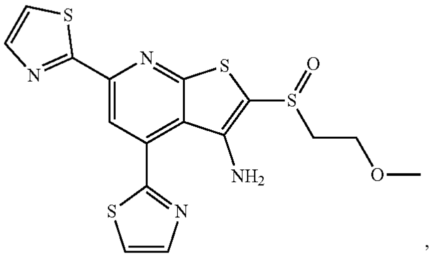
,
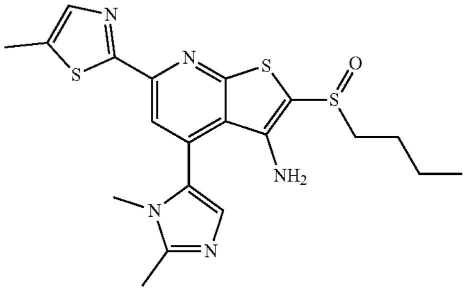
,
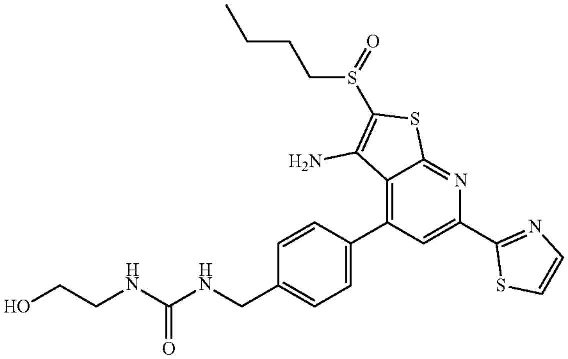
,
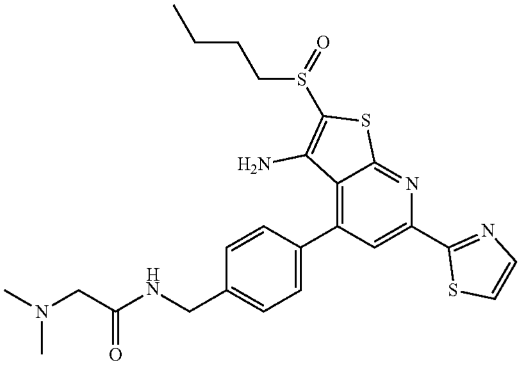
, -continued
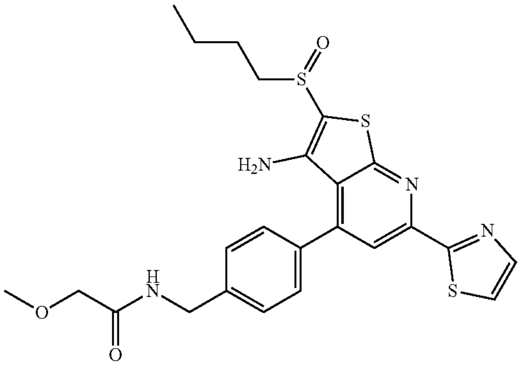
,
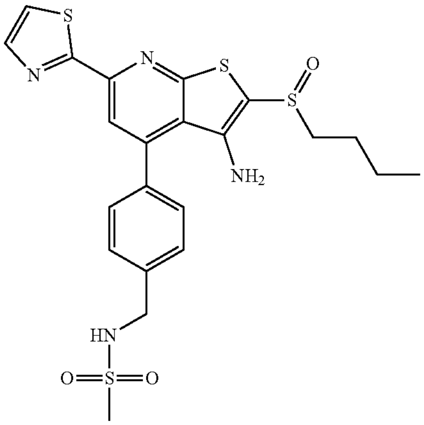
,
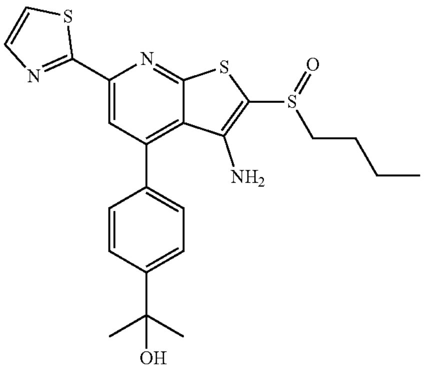
,
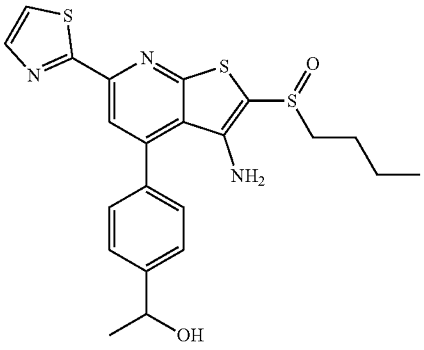
,
-continued
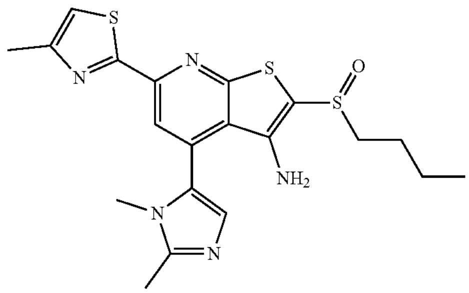
,
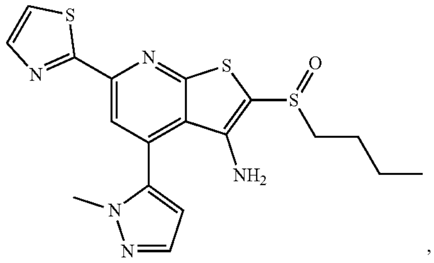
,
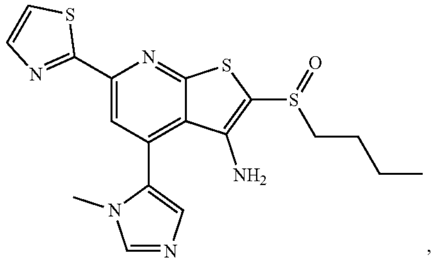
,
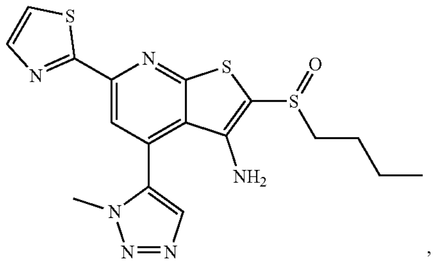
,
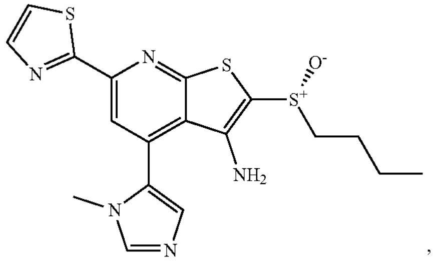
,
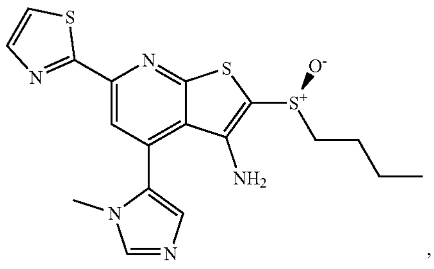
, -continued
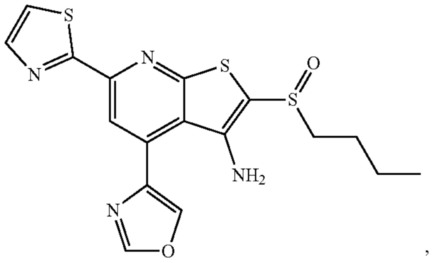
,
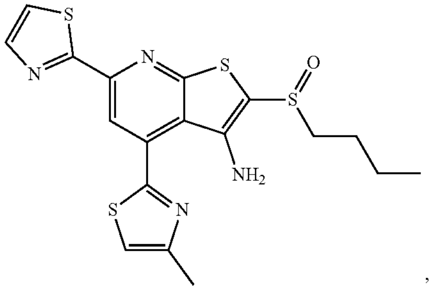
,
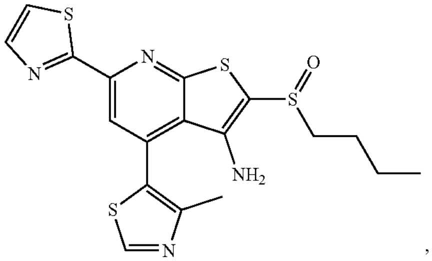
,
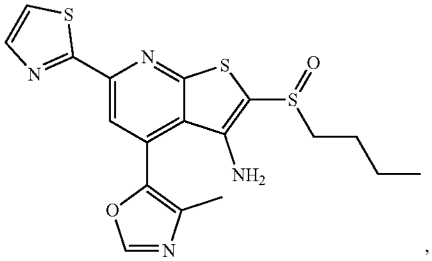
,
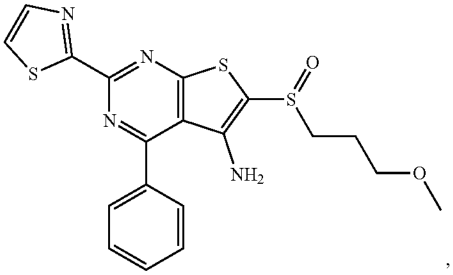
,
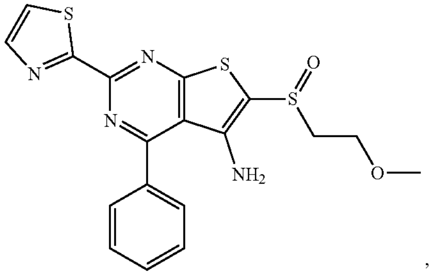
,
-continued
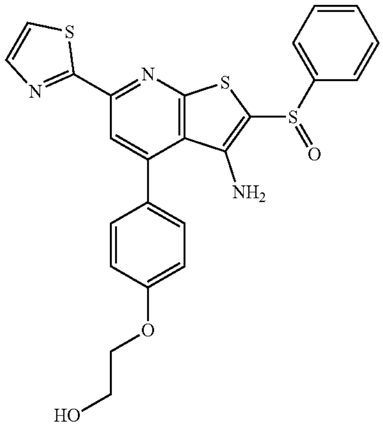
,
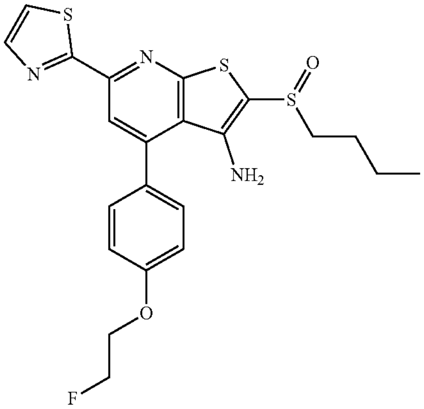
,
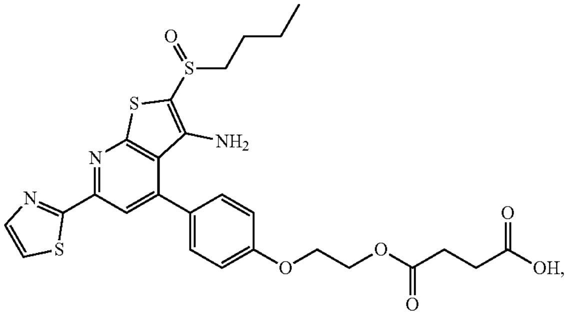
,
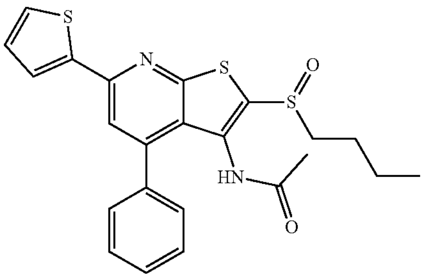
,
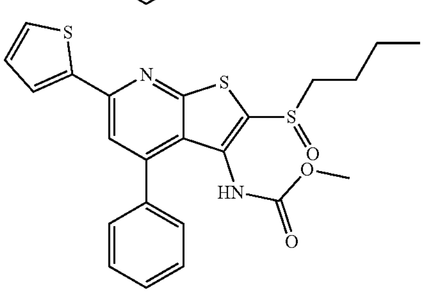
, -continued
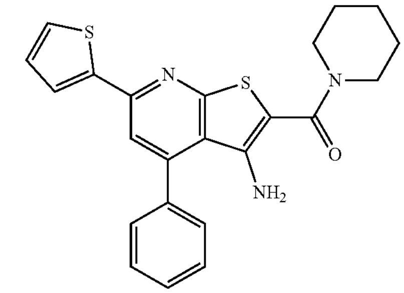
,
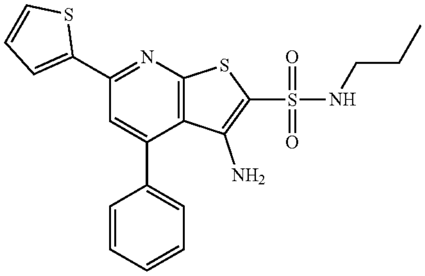
,
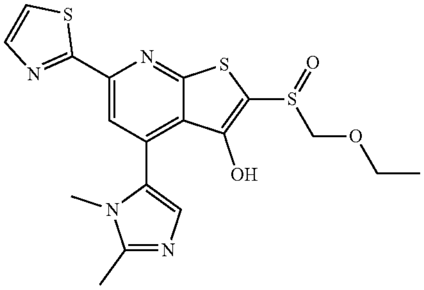
,
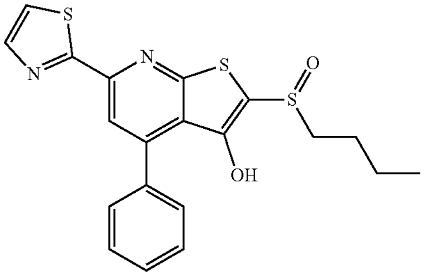
,
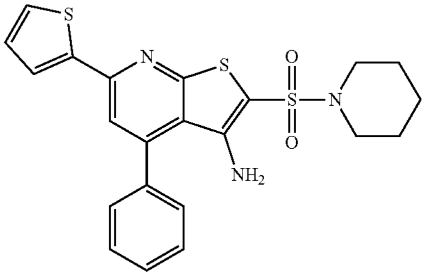
,
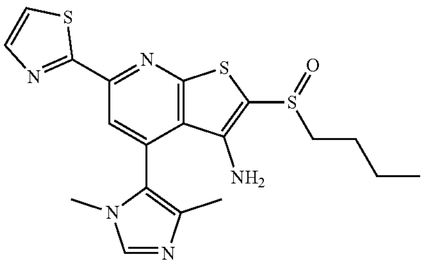
,
-continued
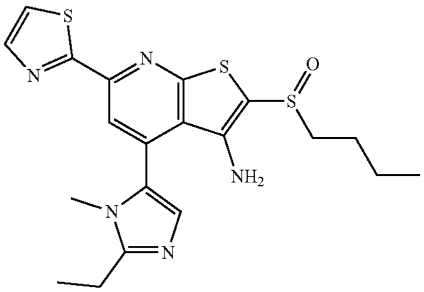
,
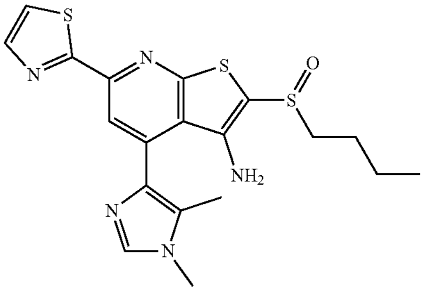
,
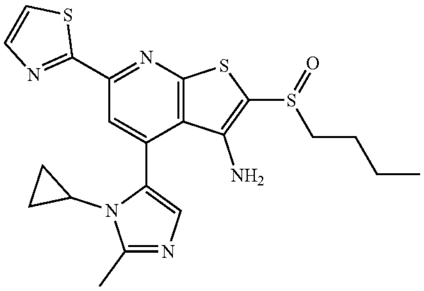
,
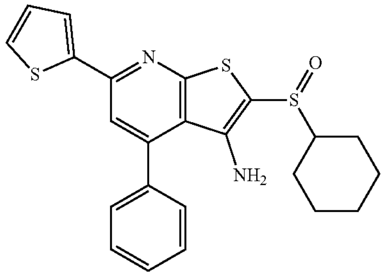
,
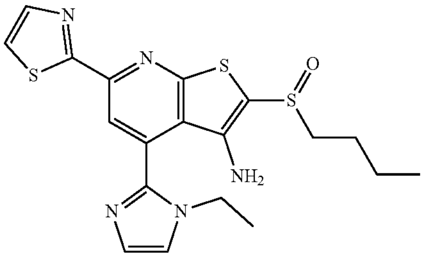
,
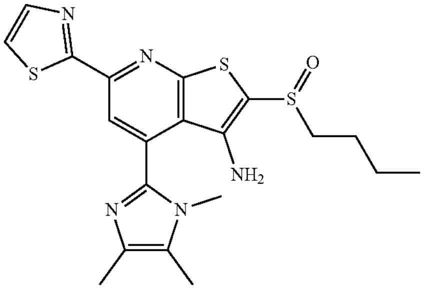
, -continued
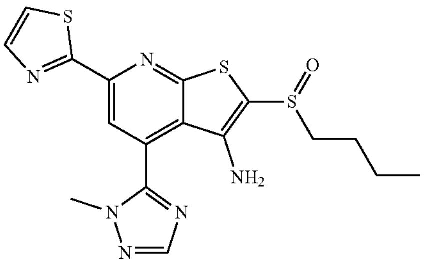
,
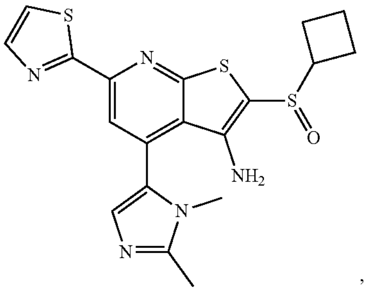
,
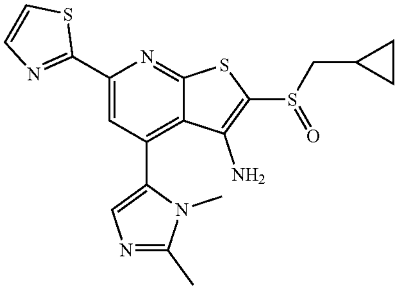
,
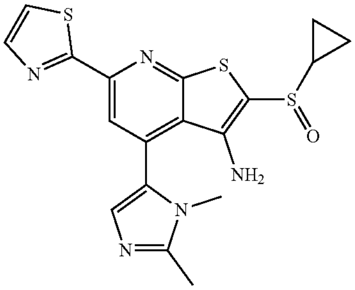
,
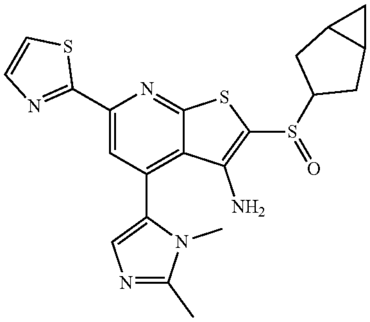
,
-continued
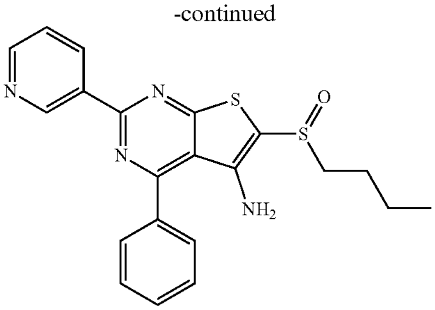
,
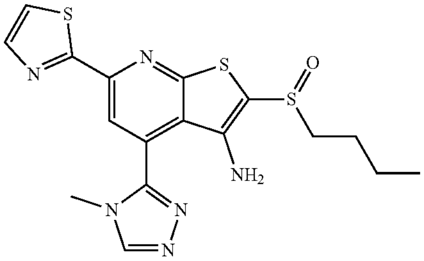
,
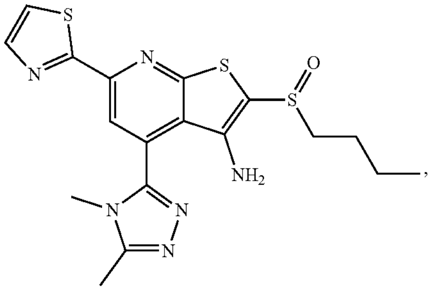
,
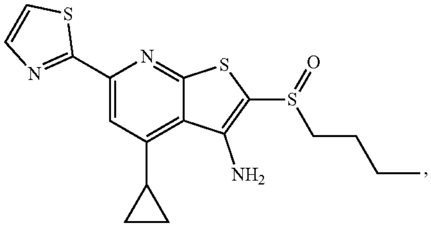
,
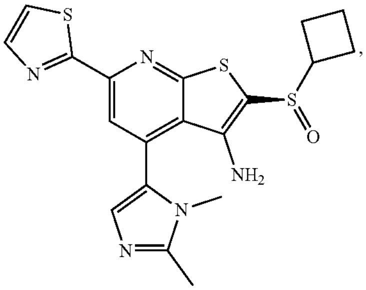
,
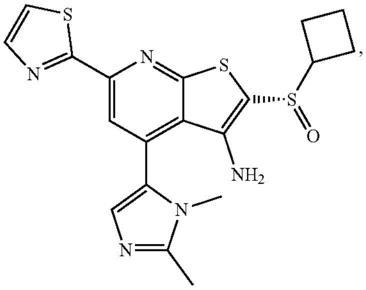
, -continued
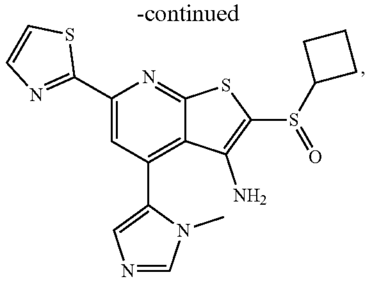
,
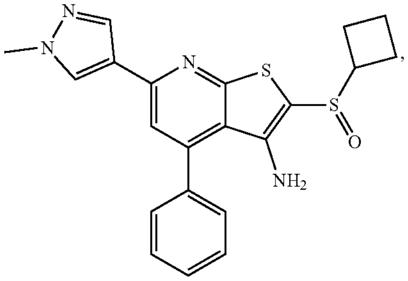
,
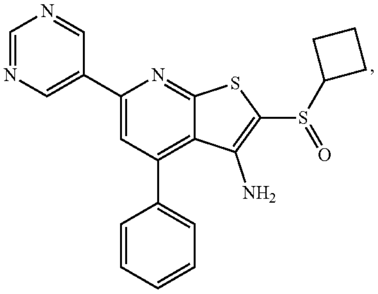
,
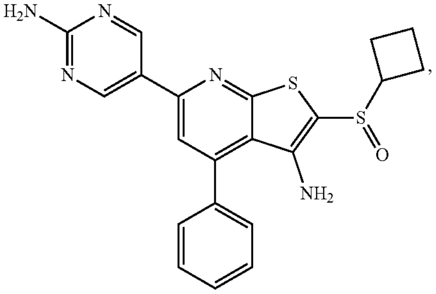
,
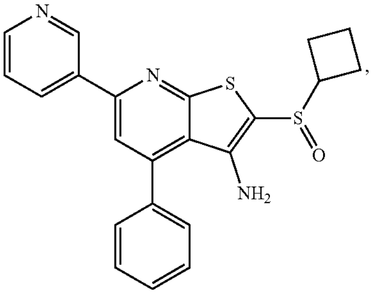
,
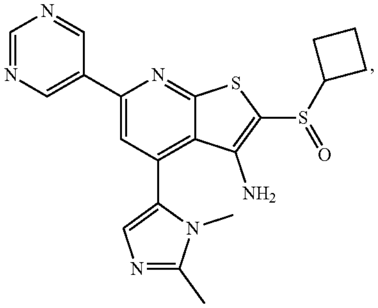
,
-continued
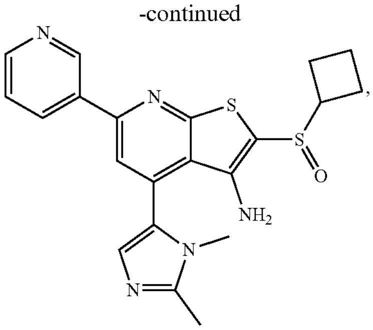
,
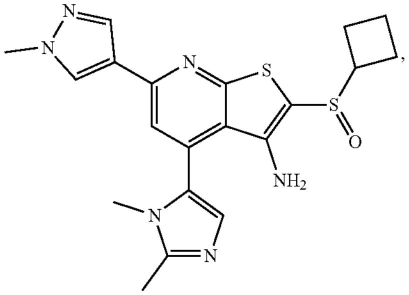
,
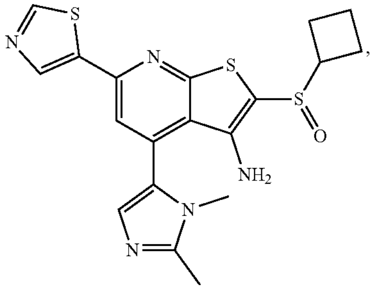
,
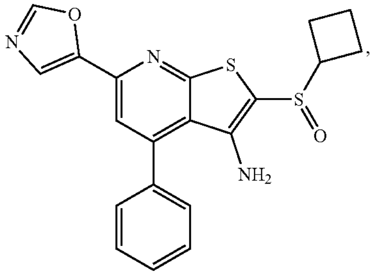
,
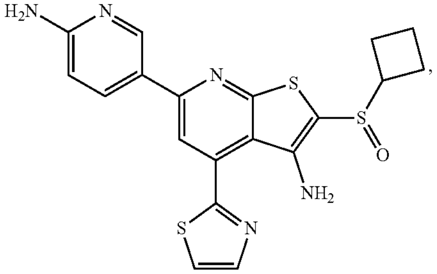
,
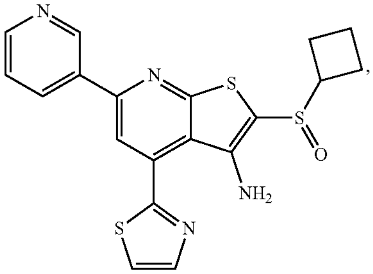
, -continued
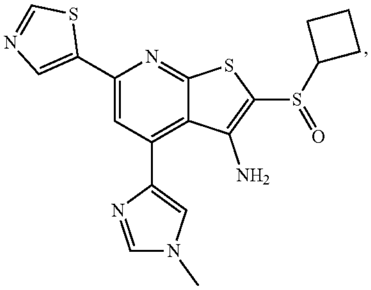
,
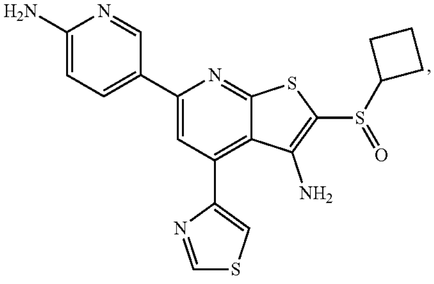
,
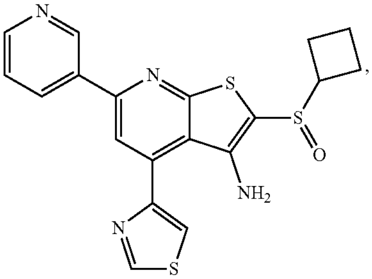
,
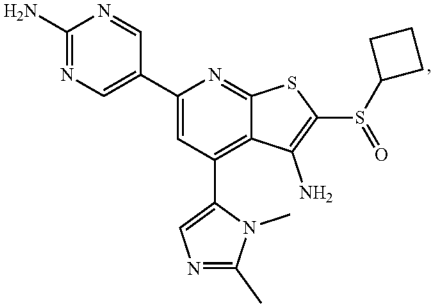
,
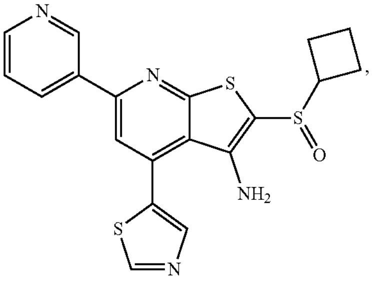
,
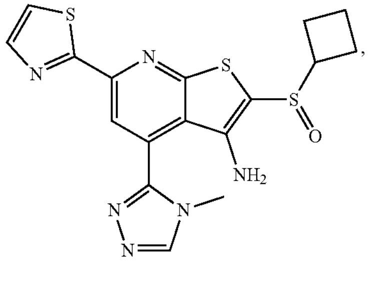
,
-continued
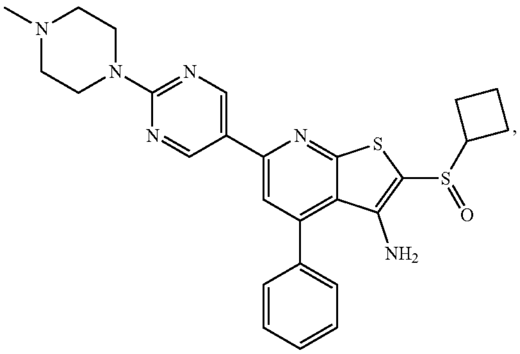
,
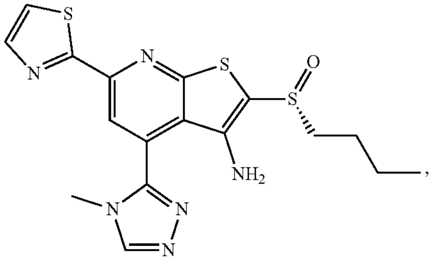
,
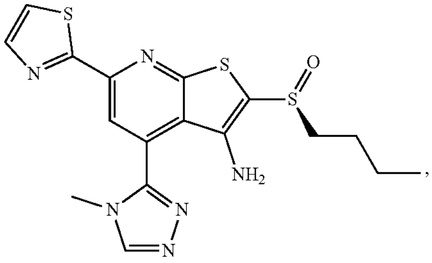
,
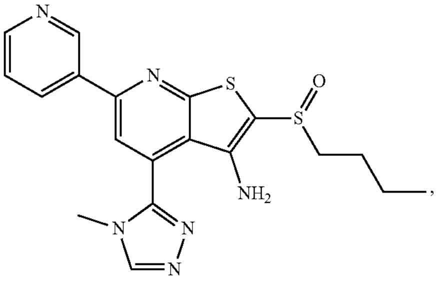
,
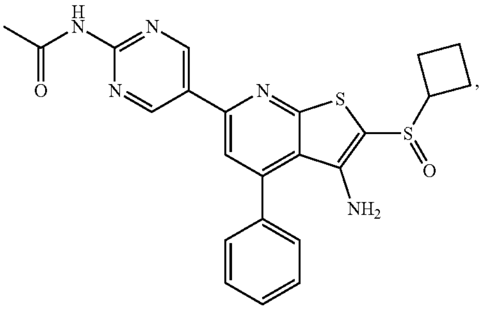
, -continued
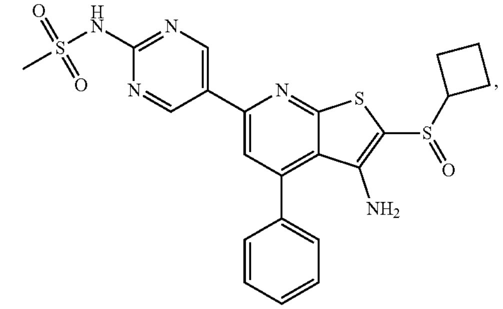,
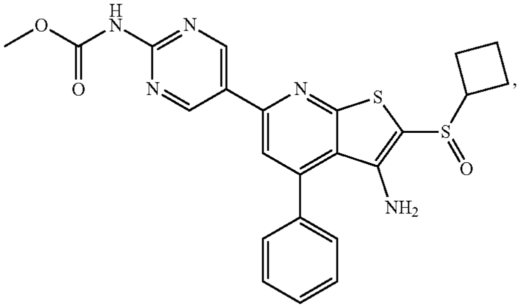,
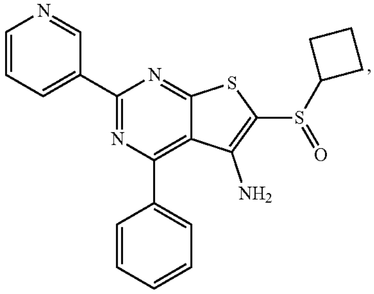,
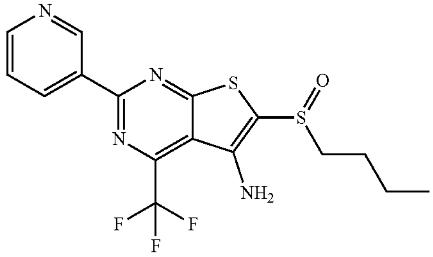,
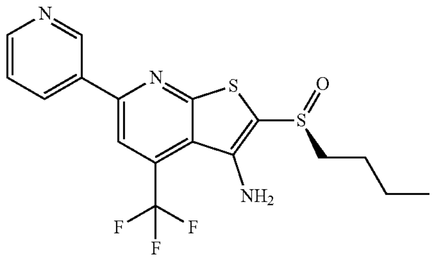,
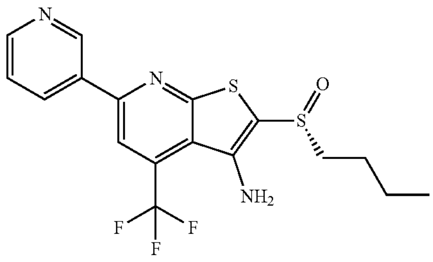,
-continued
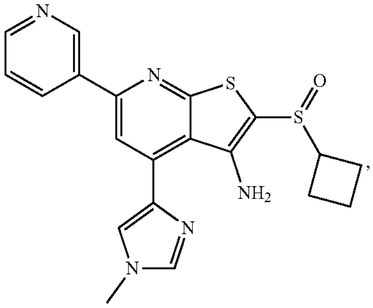,
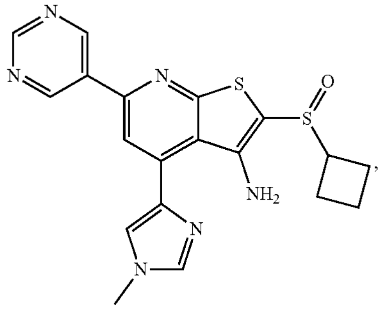,
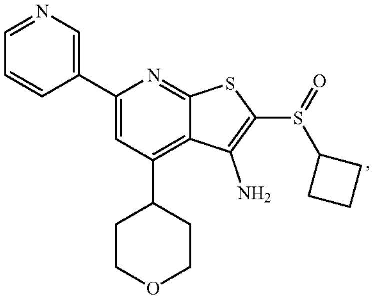,
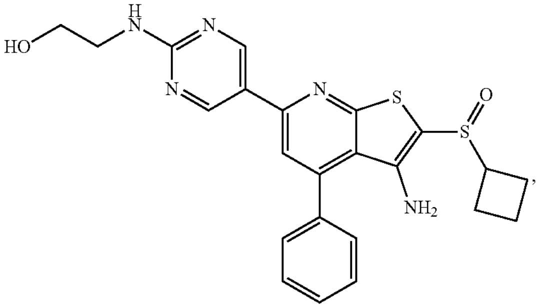,
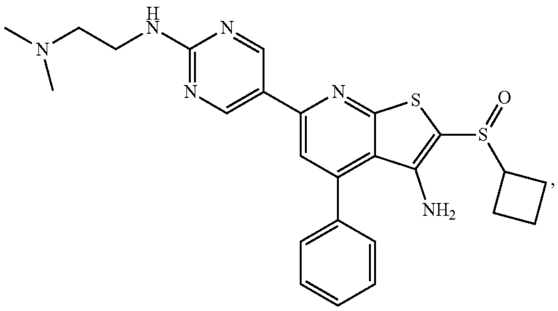, -continued
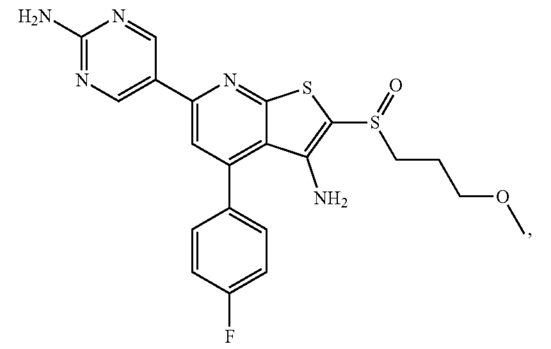
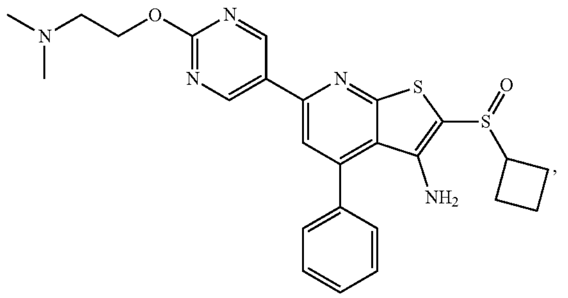
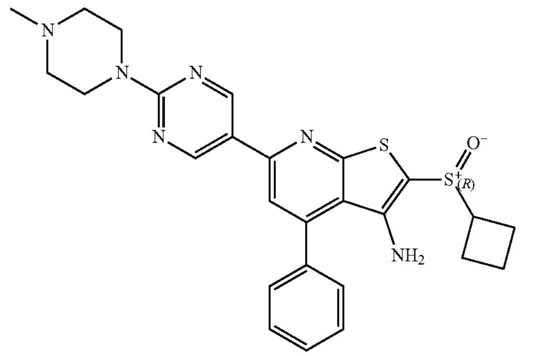
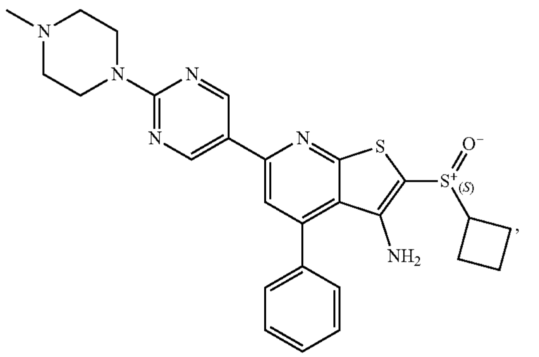
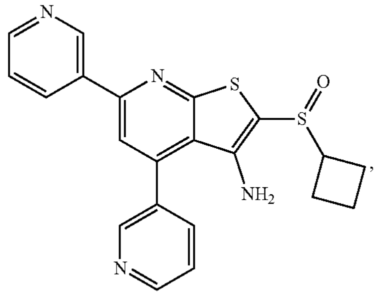
-continued
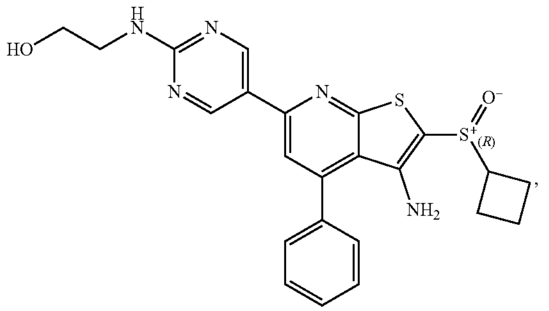
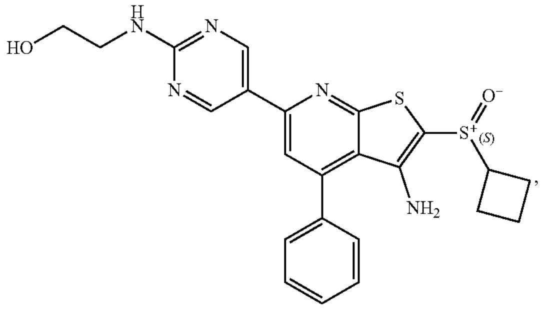
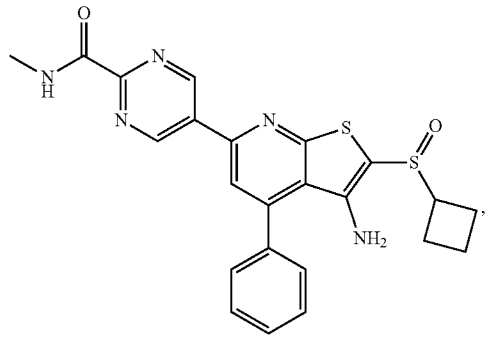
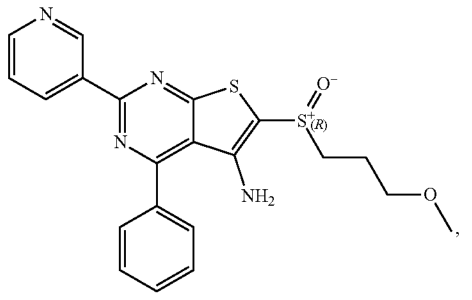
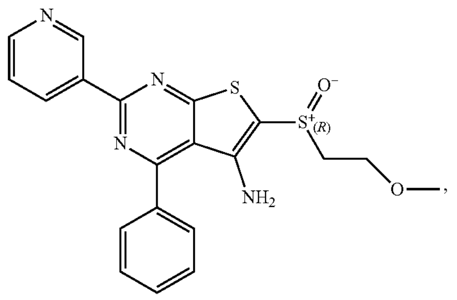

-continued
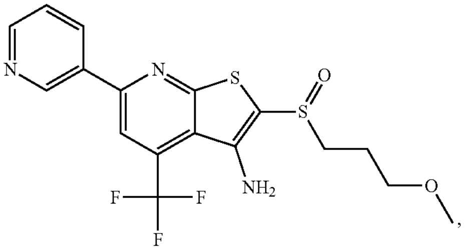
,
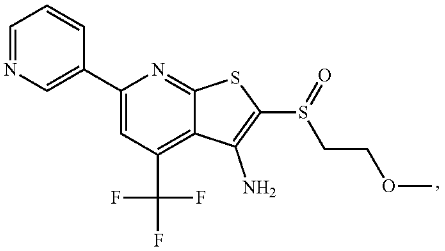
,
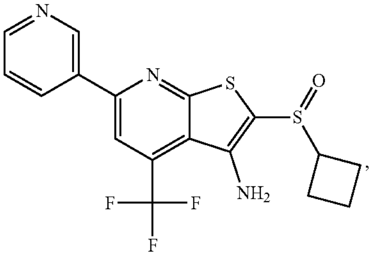
,
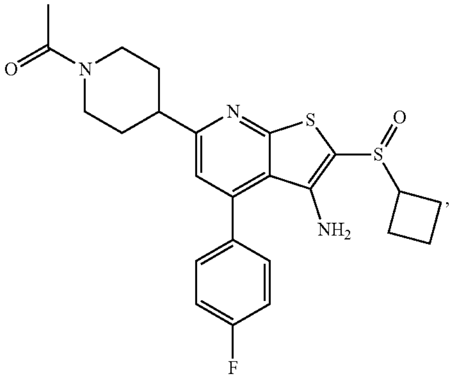
,
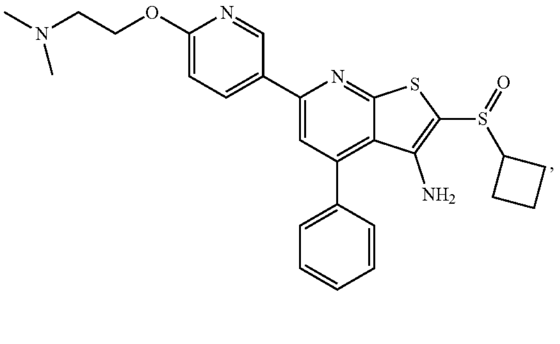
,
-continued
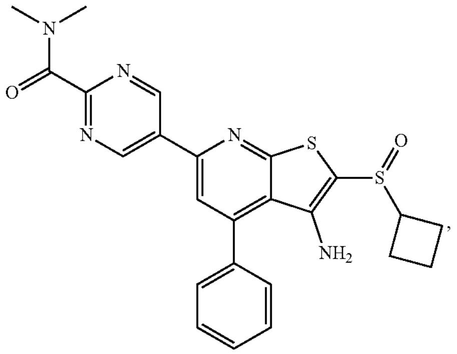
,
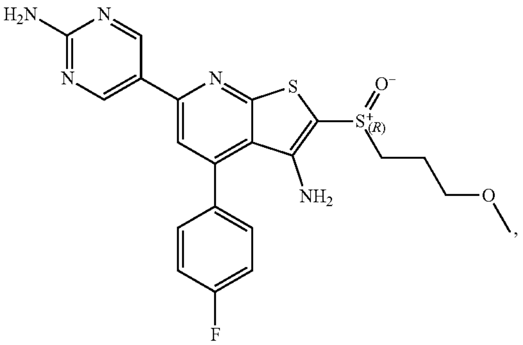
,
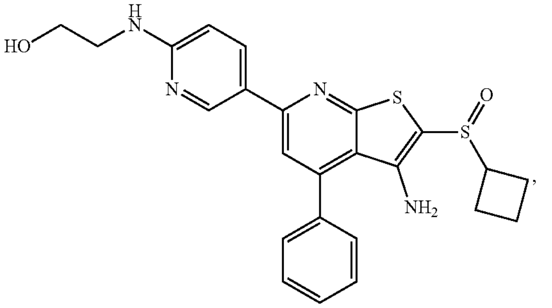
,
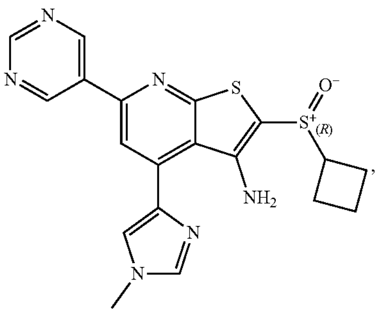
,
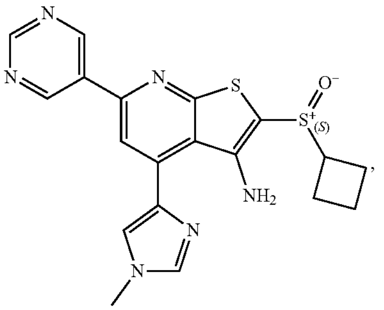
, -continued
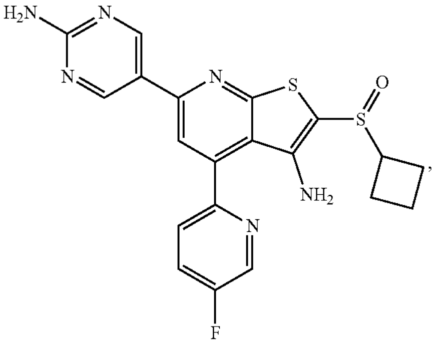
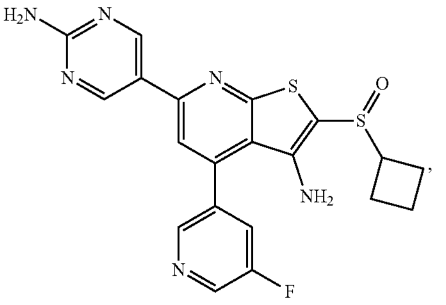
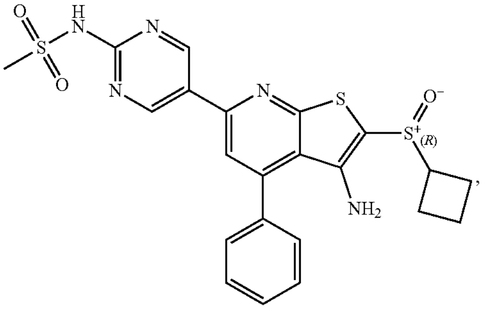
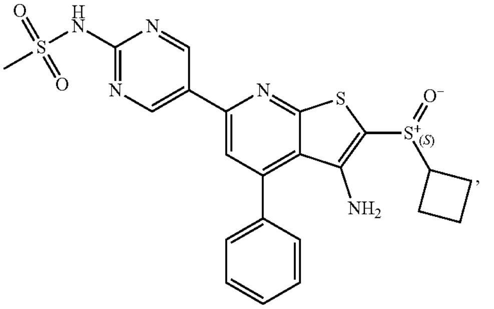
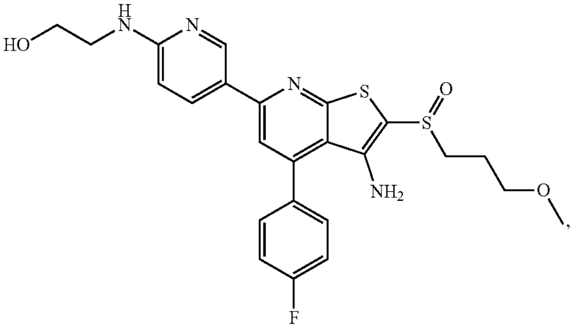
-continued
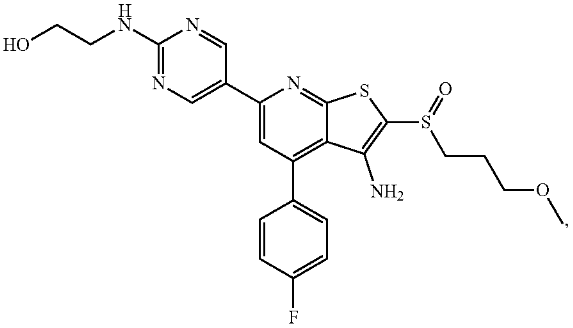
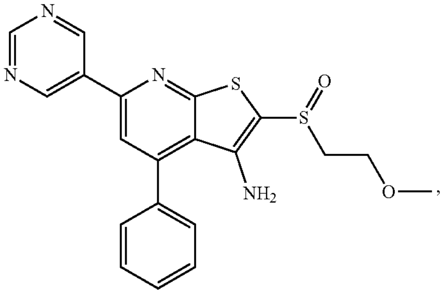
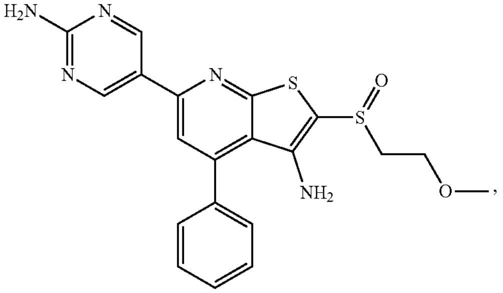
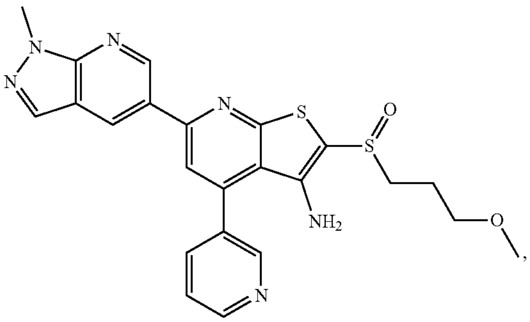
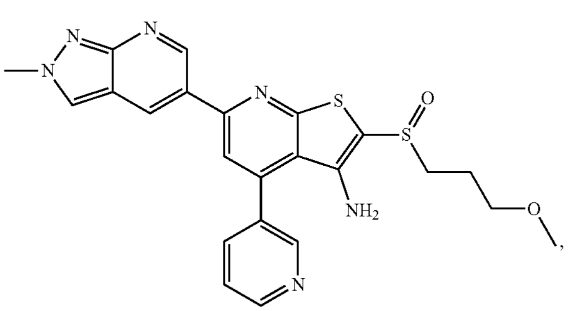

-continued
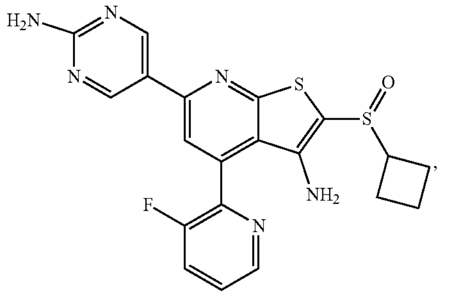
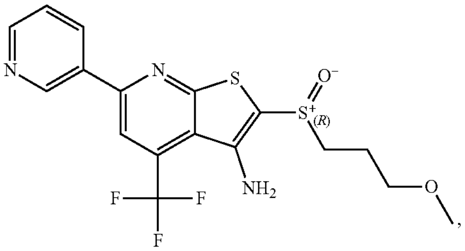
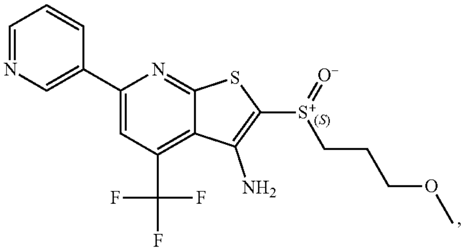
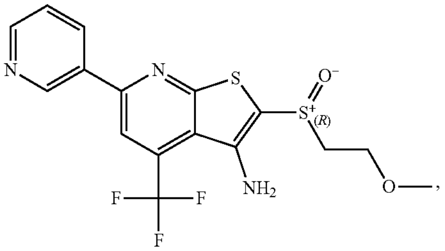
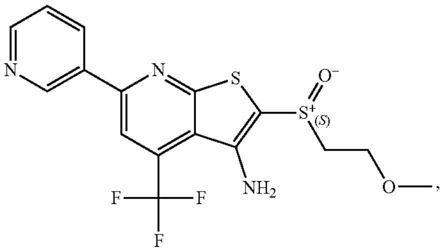
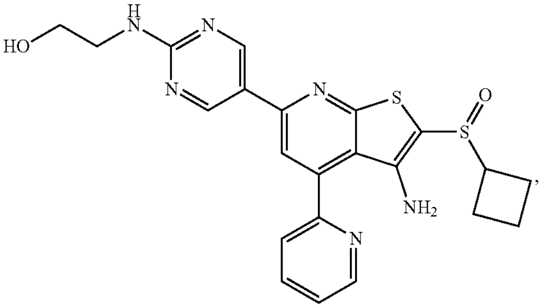
-continued
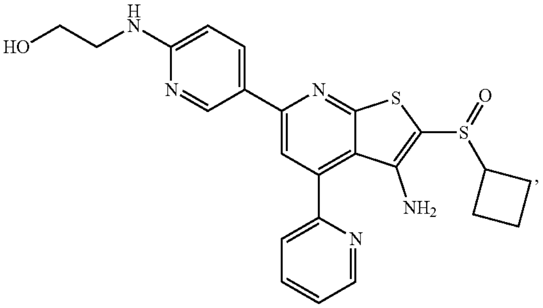
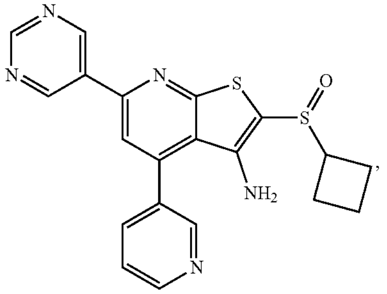
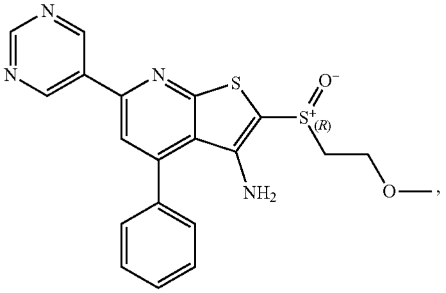
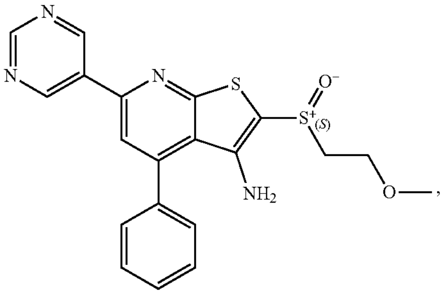
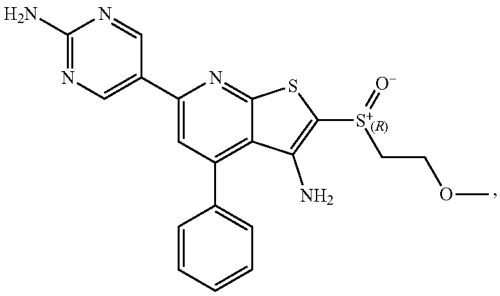

-continued
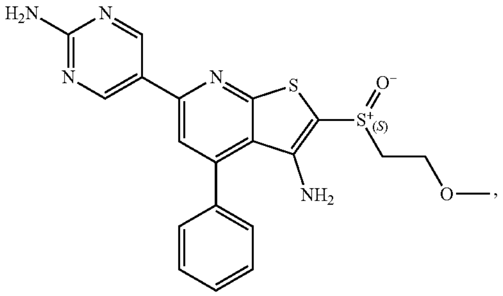
,
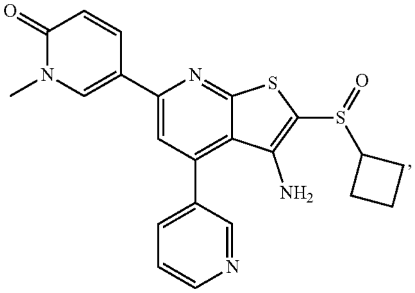
,
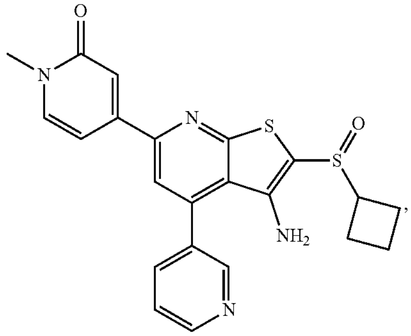
,
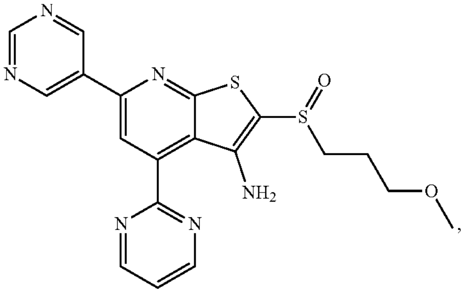
,
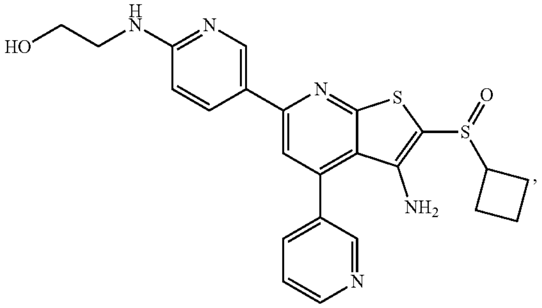
,
-continued
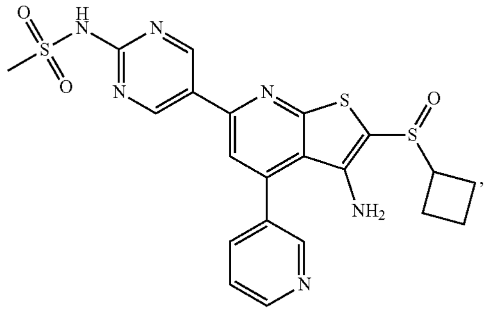
,
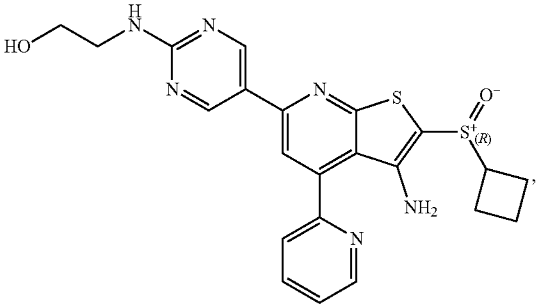
,
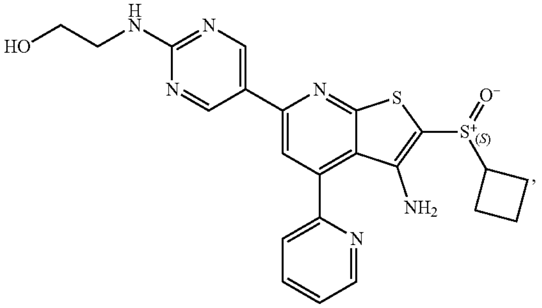
,
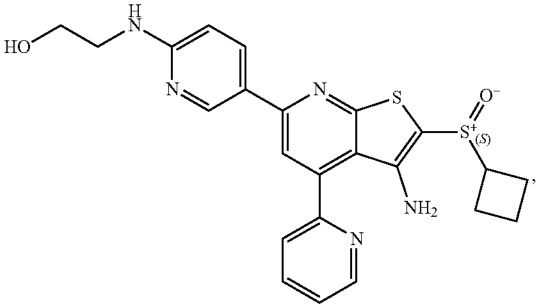
,
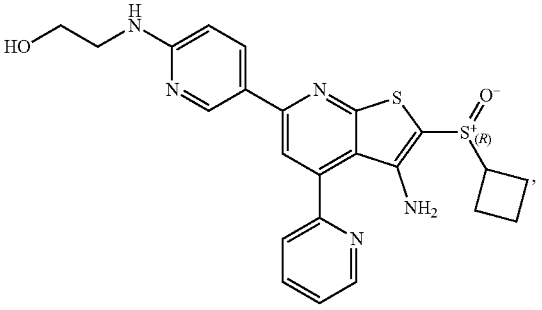
, -continued
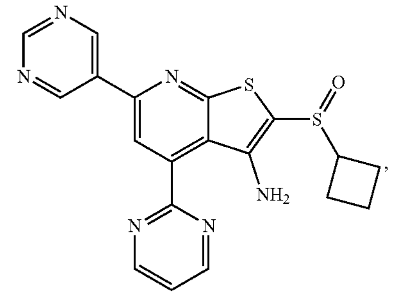
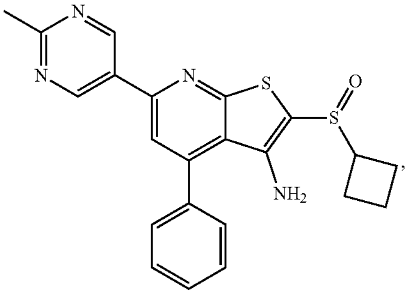
-continued
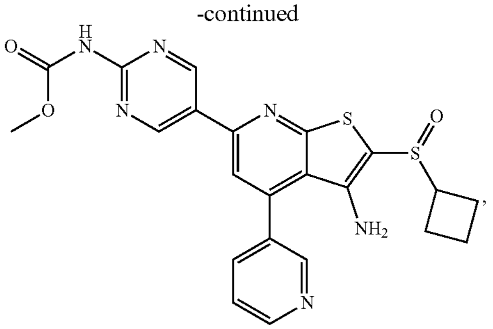
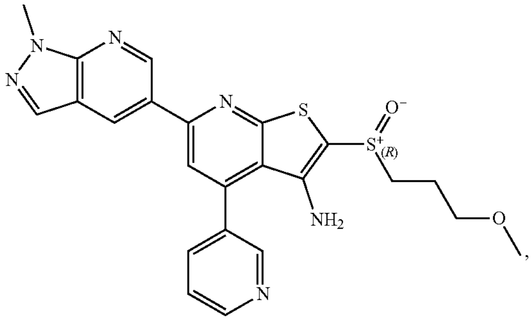
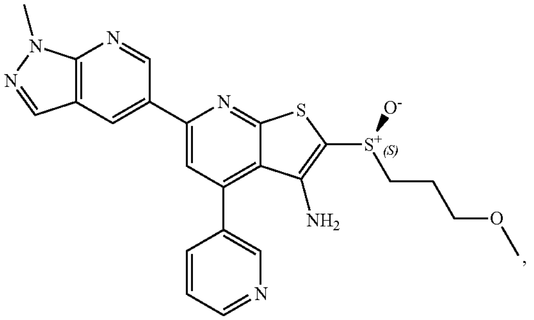
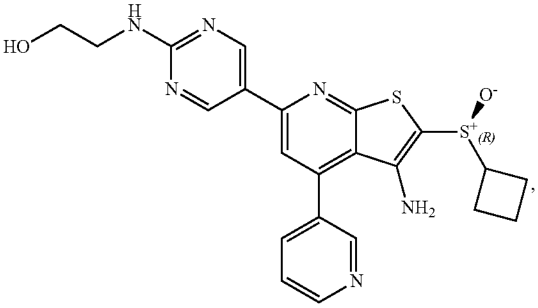
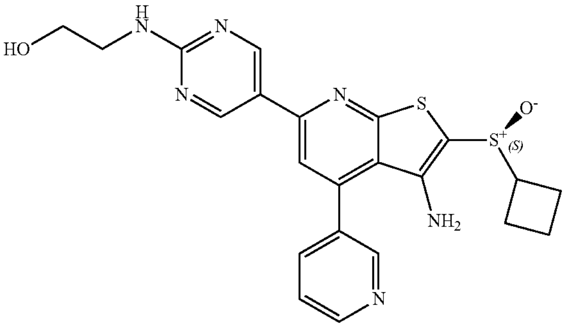

-continued
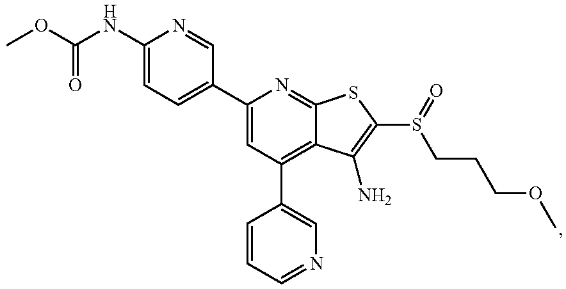
,
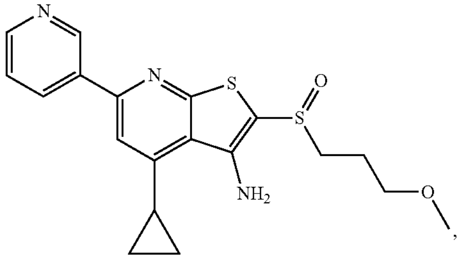
,
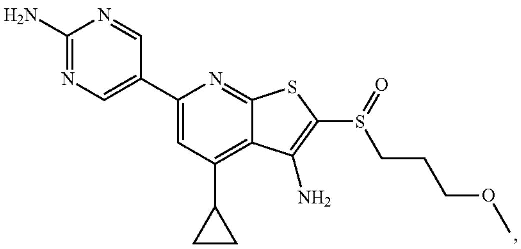
,
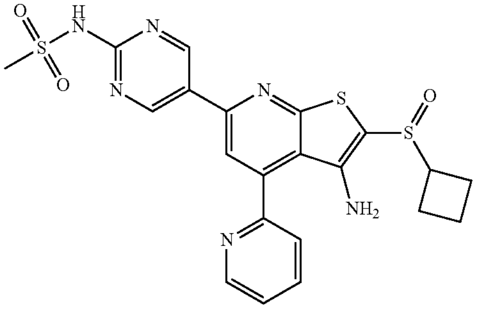
,
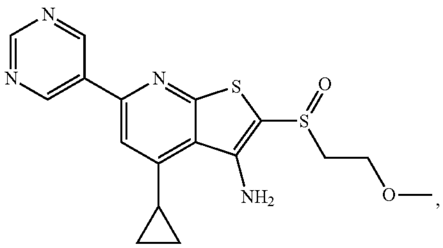
,
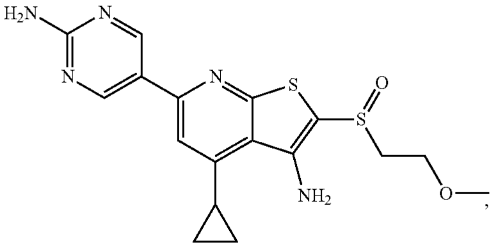
, -continued
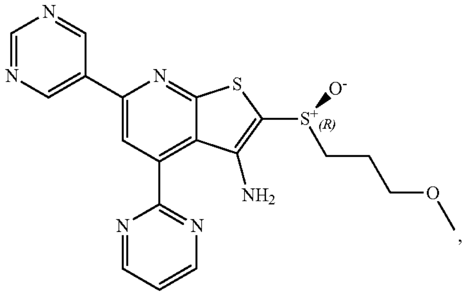
,
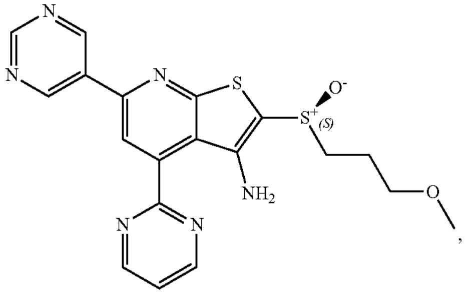
,
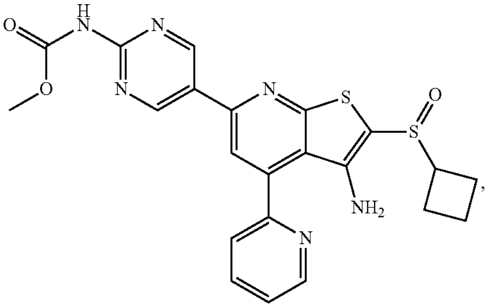
,
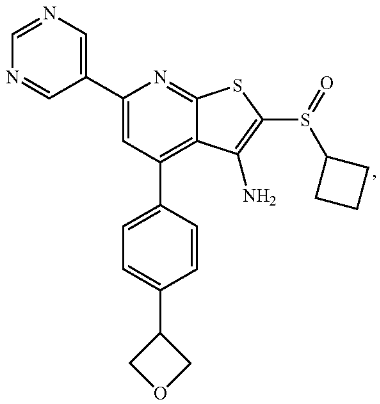
,
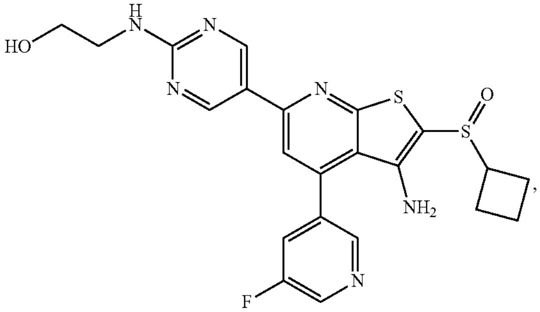
, -continued
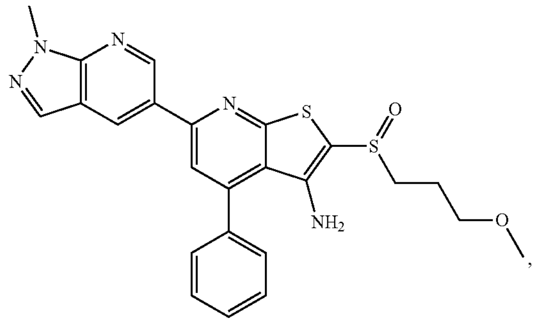
,
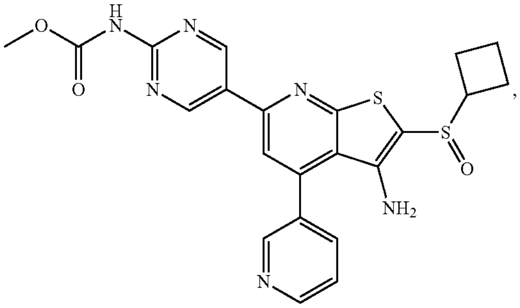
,
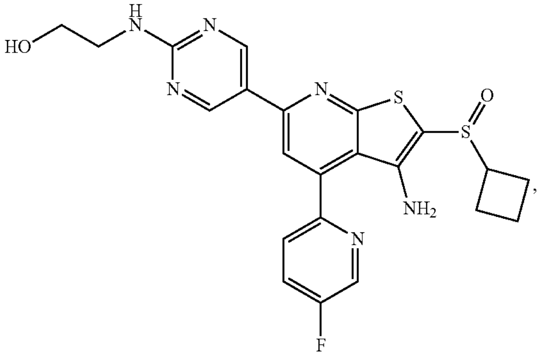
,
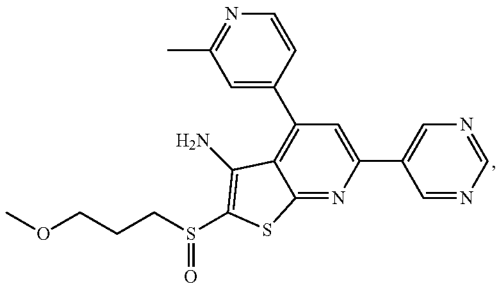
,
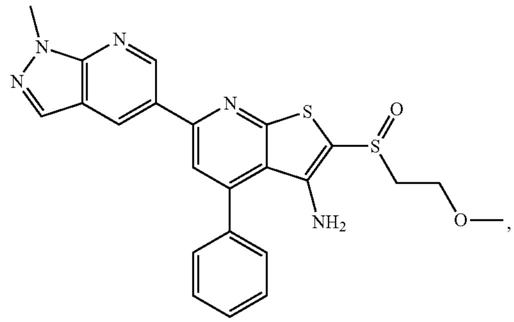
, -continued
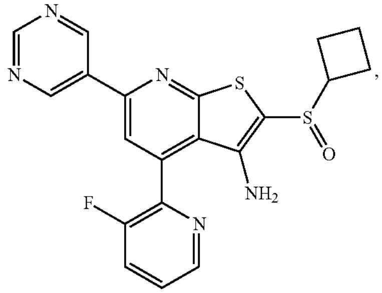
,
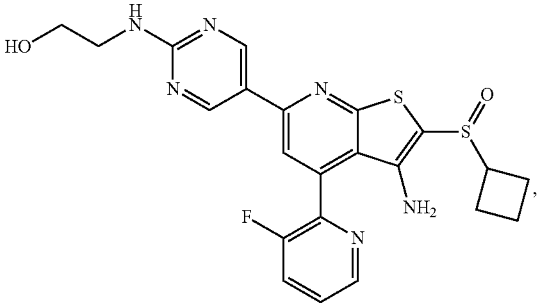
,
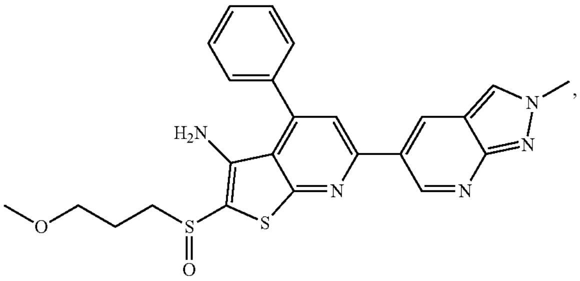
,
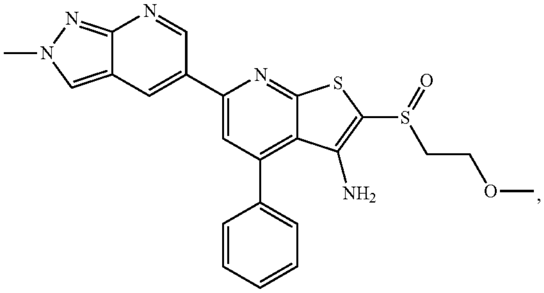
,
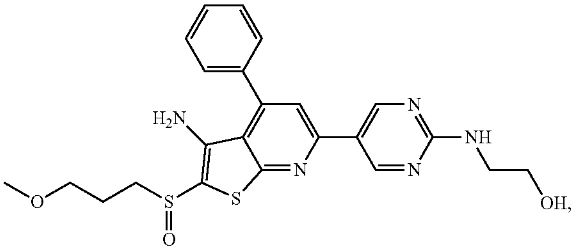
,
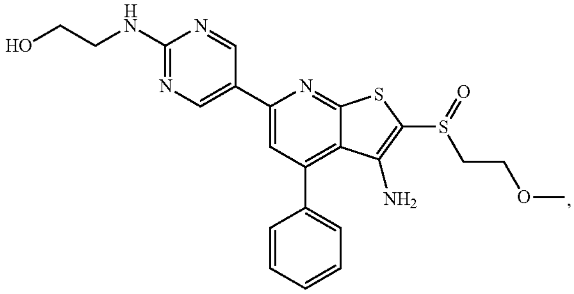
, -continued
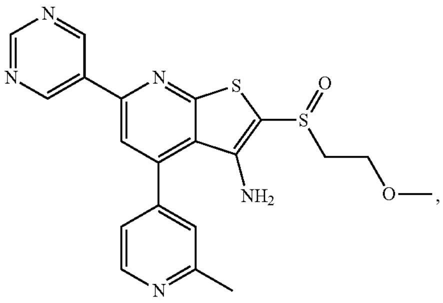
,
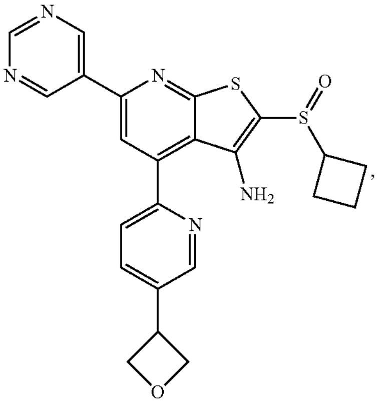
,
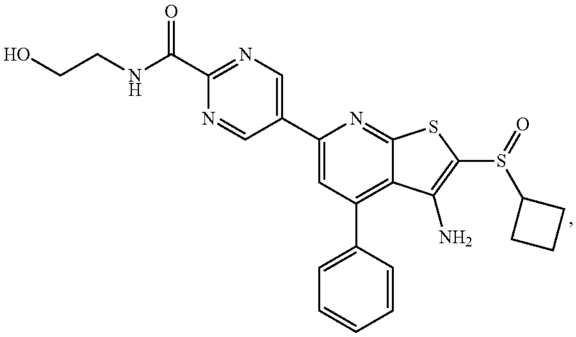
,
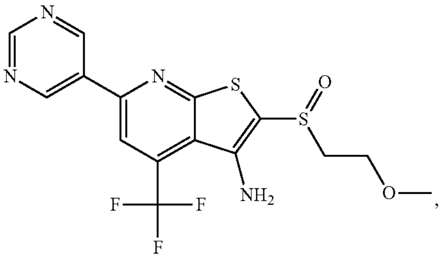
,
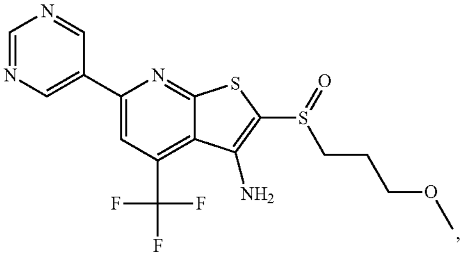
, -continued
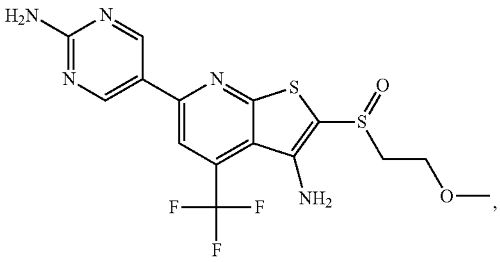,
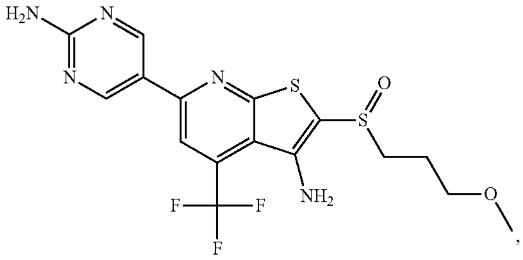,
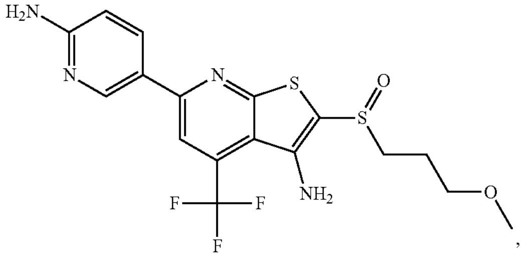,
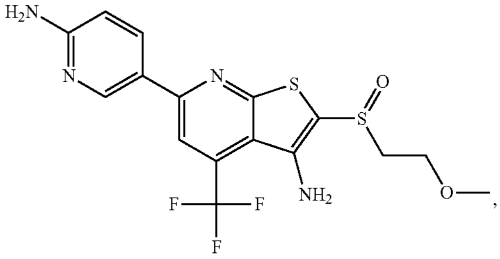,
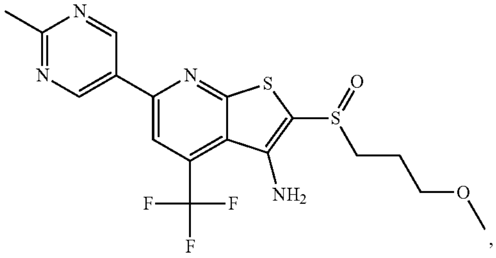,
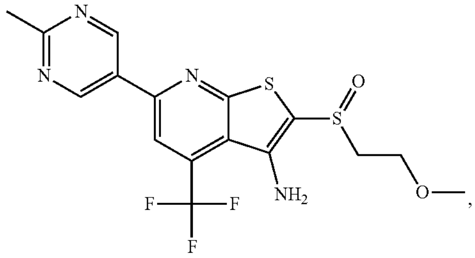, -continued
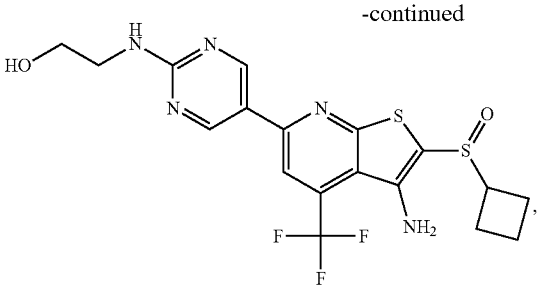
,
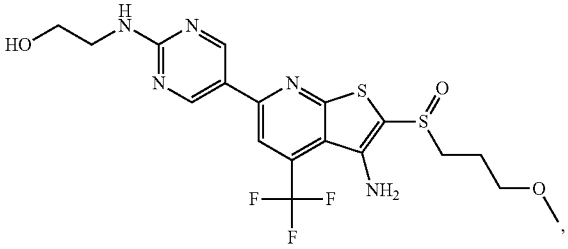
,
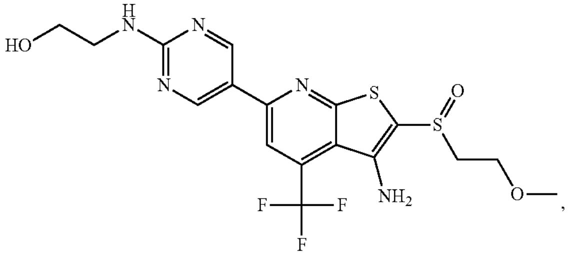
,
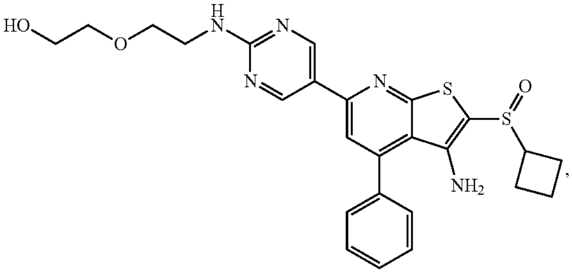
,
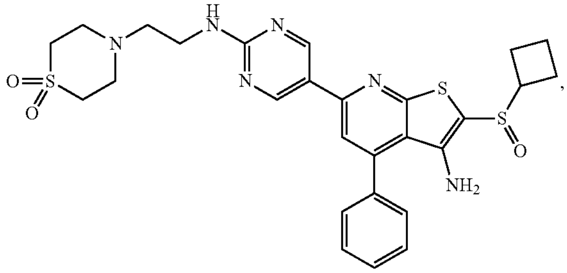
,
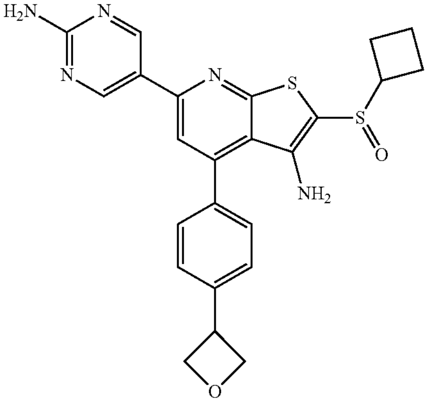

-continued
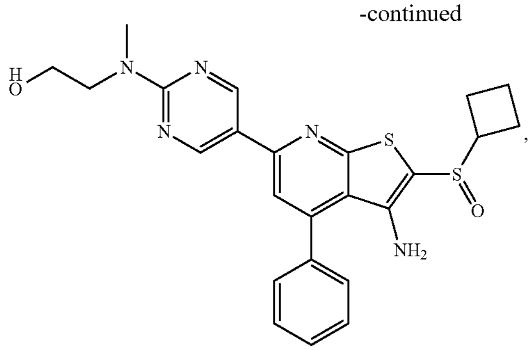
,
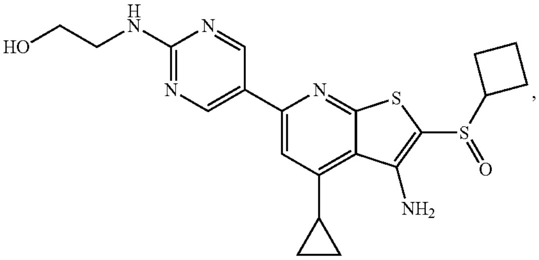
,
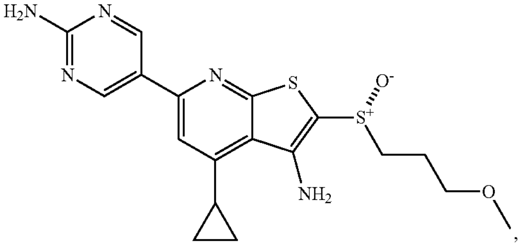
,
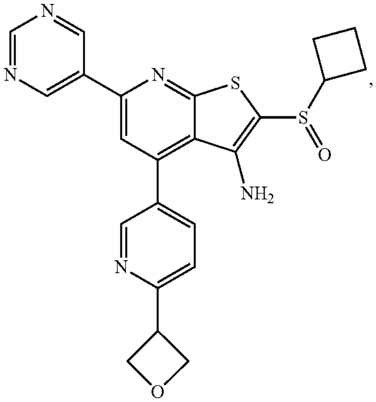
,
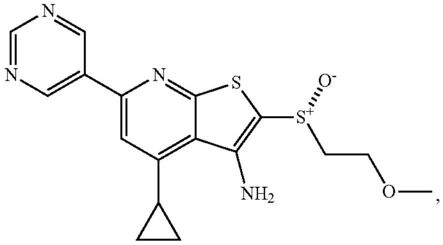
,
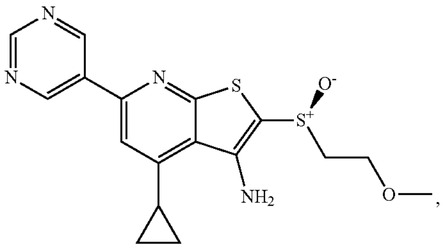
, -continued
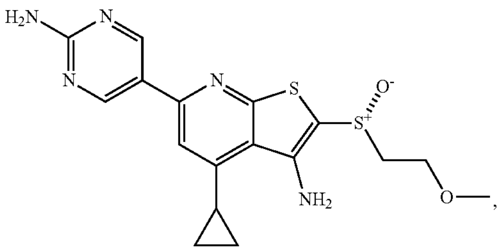
,
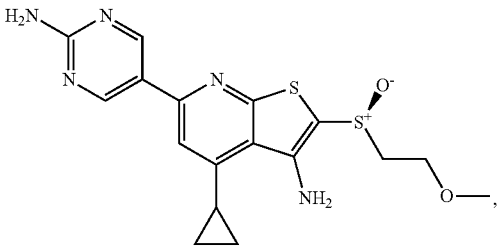
,
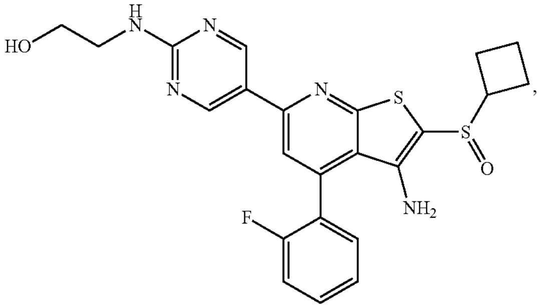
,
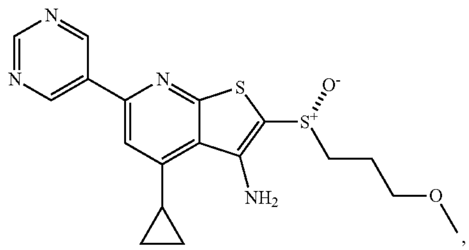
,
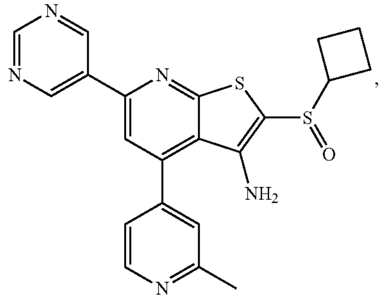
,
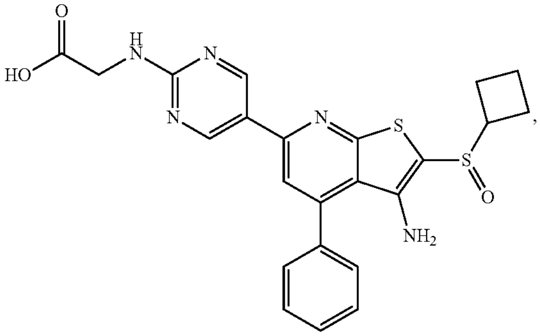
, -continued
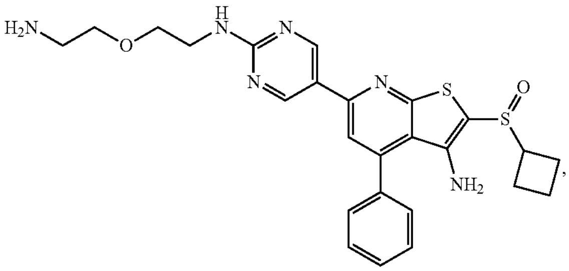
,
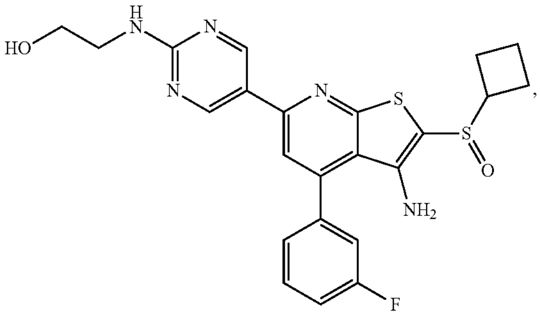
,
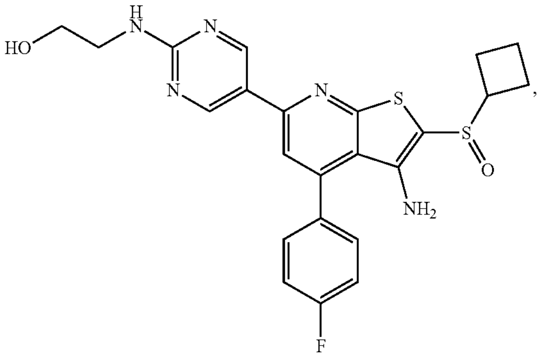
,
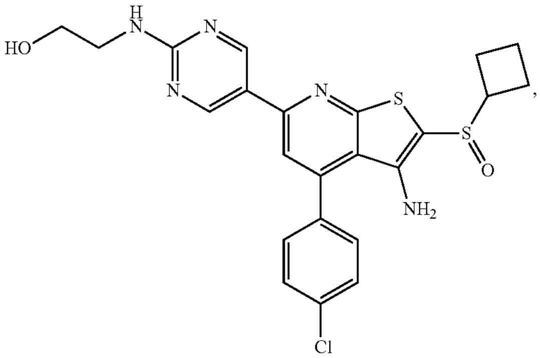
,
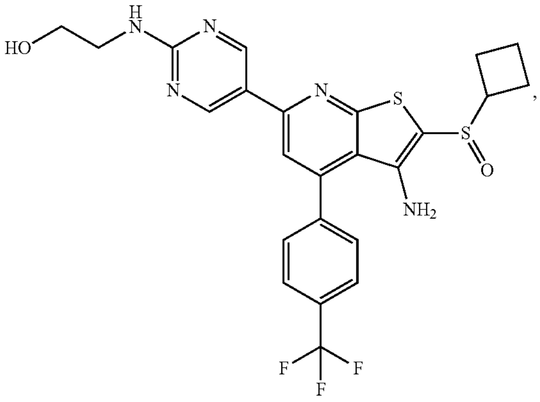
, -continued
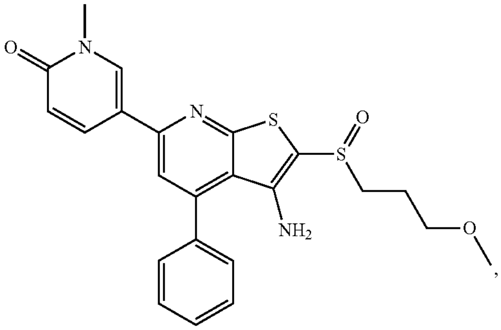
,
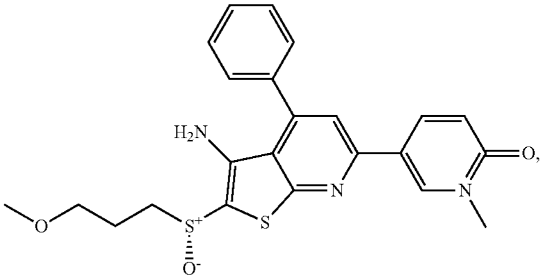
,
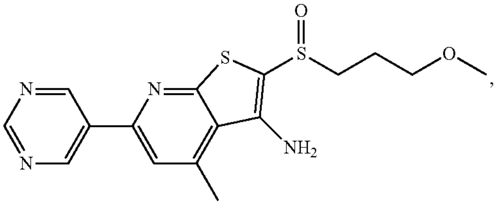
,
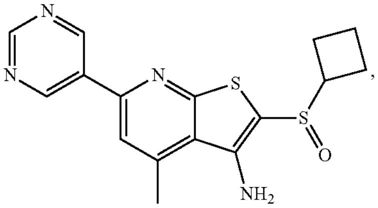
,
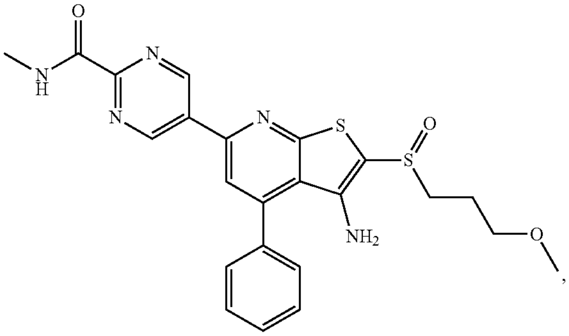
,
,
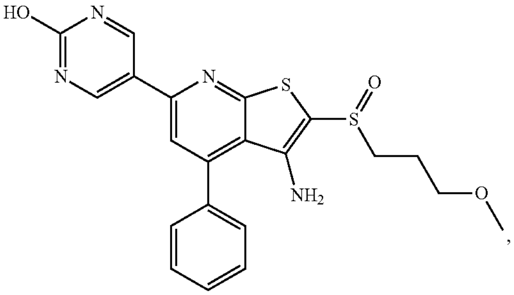
, -continued
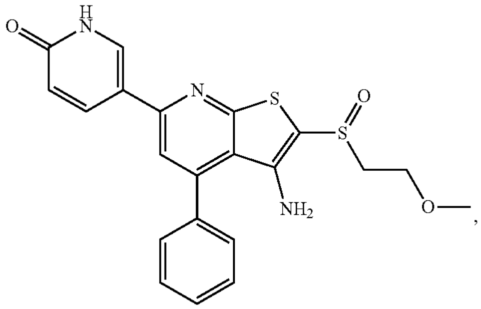
,
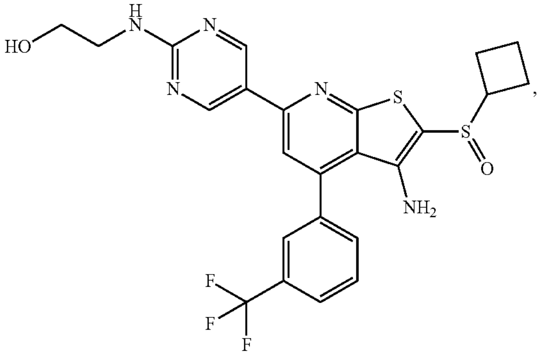
,
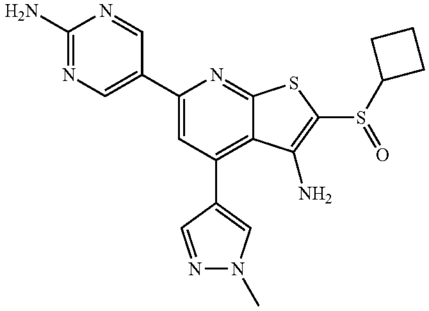
,
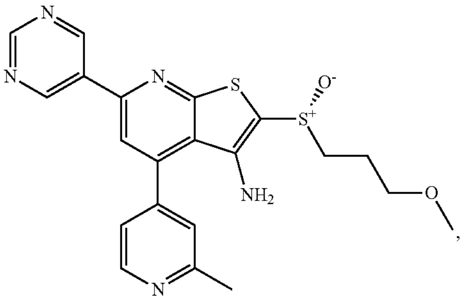
,
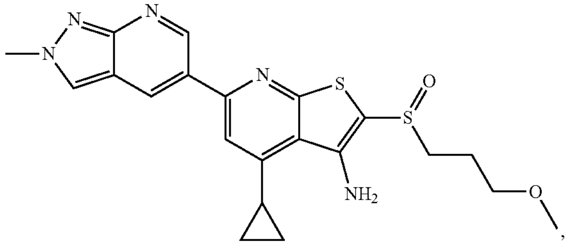
, -continued
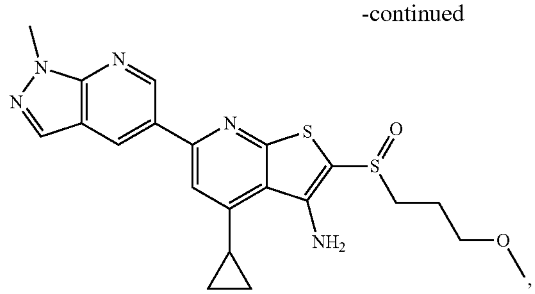
,
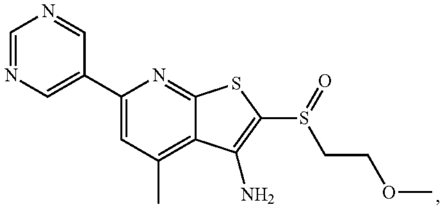
,
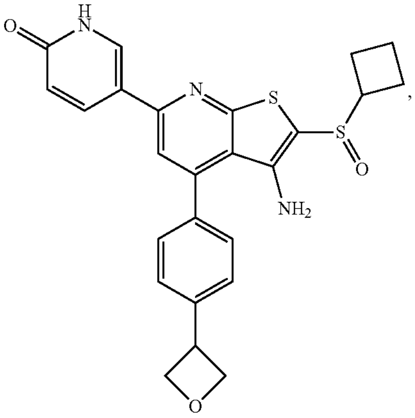
,
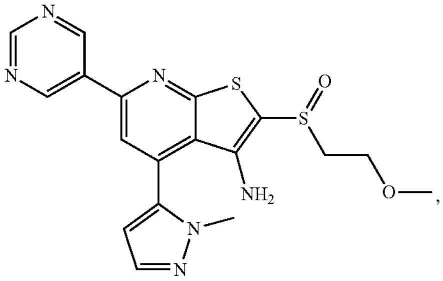
,
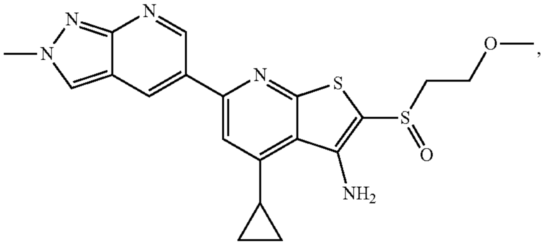
,
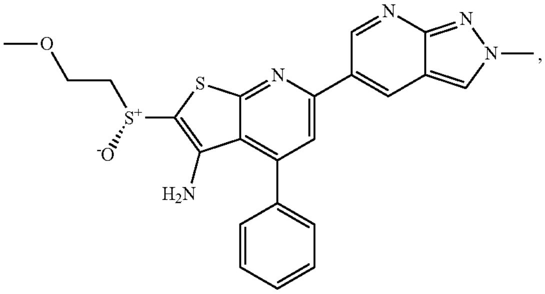
, -continued
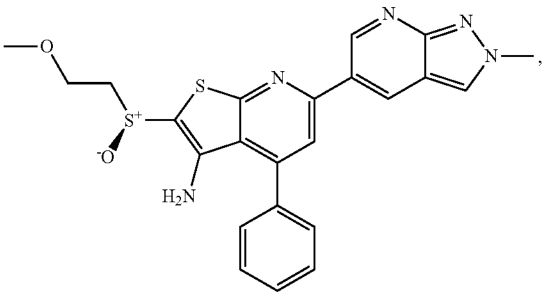
,
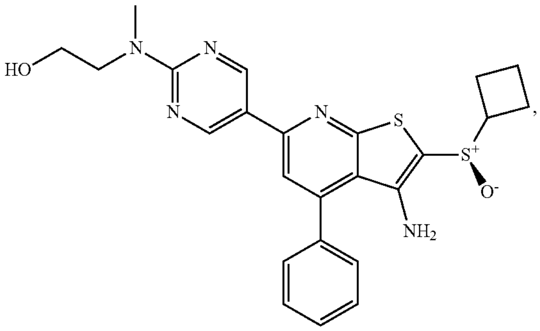
,
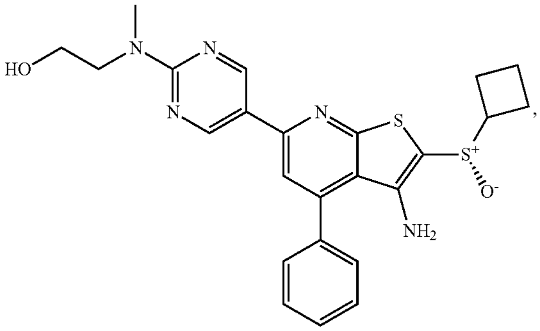
,
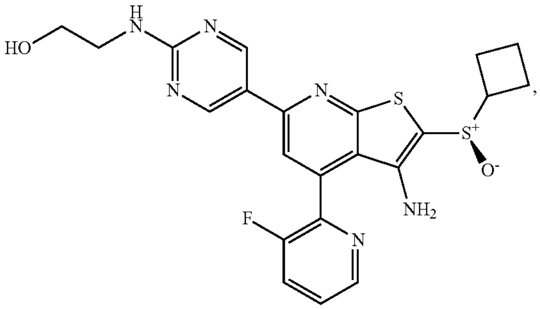
,
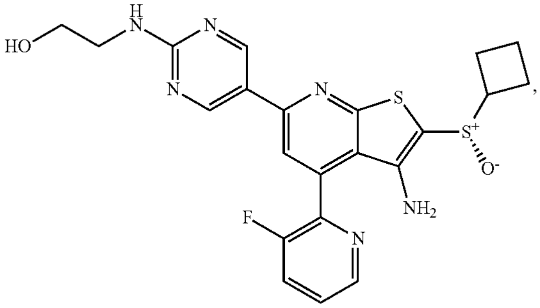
, -continued
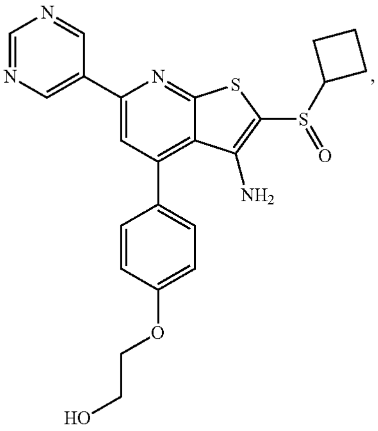
,
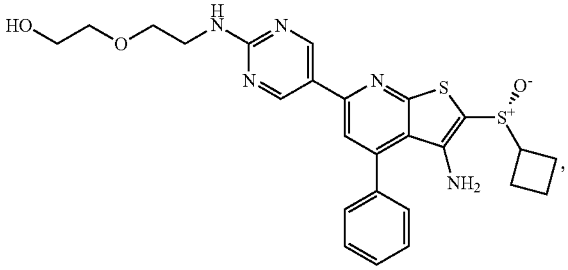
,
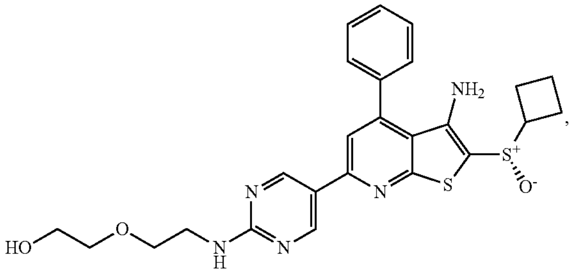
,
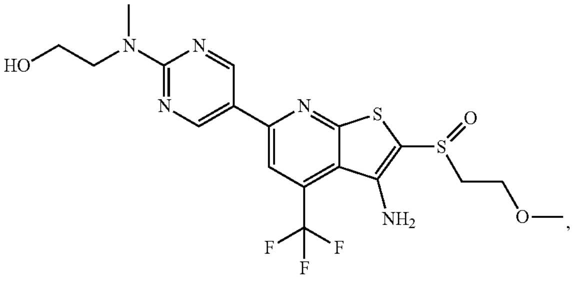
,
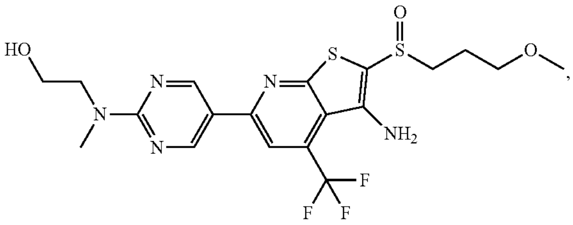
, -continued
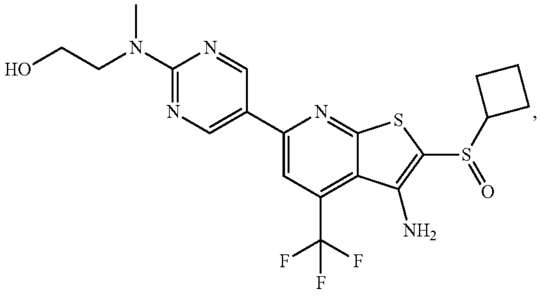
,
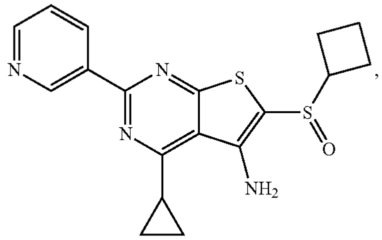
,
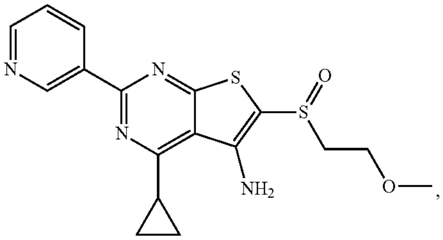
,
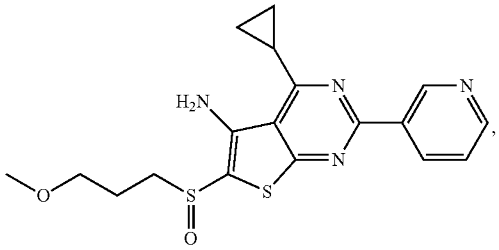
,
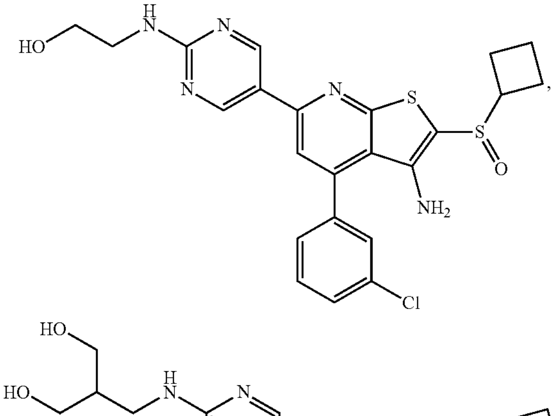
,
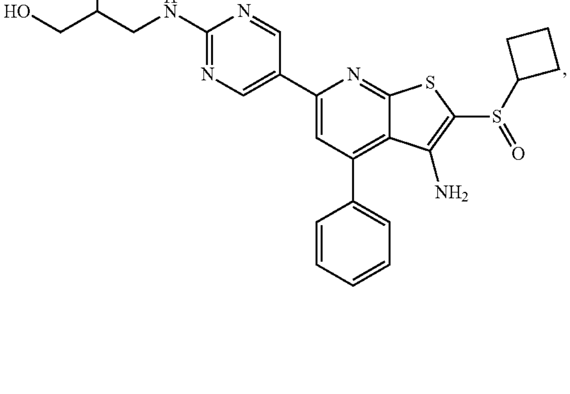
, -continued
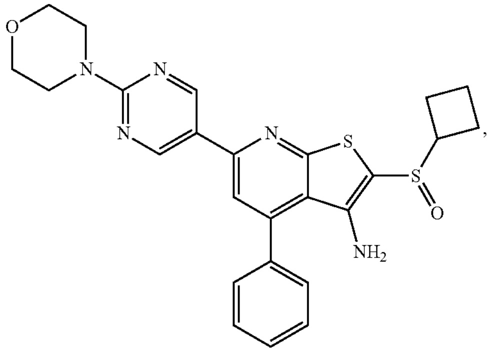
,
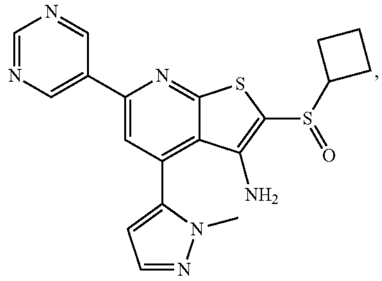
,
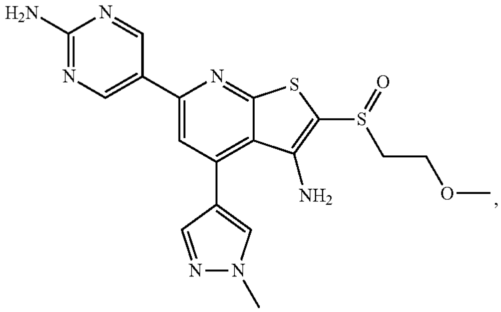
,
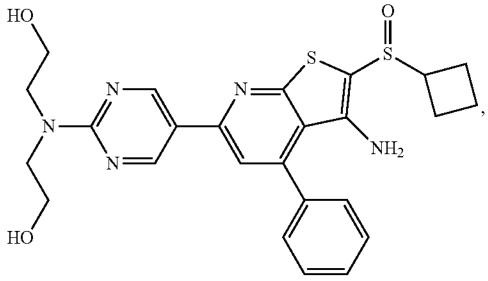
,
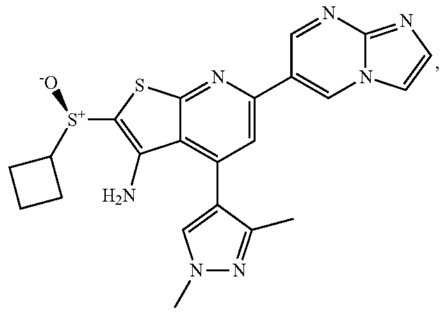
, -continued
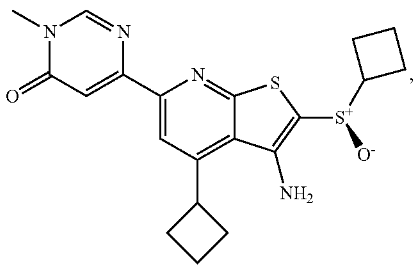
,
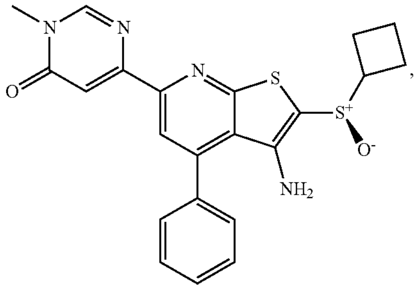
,
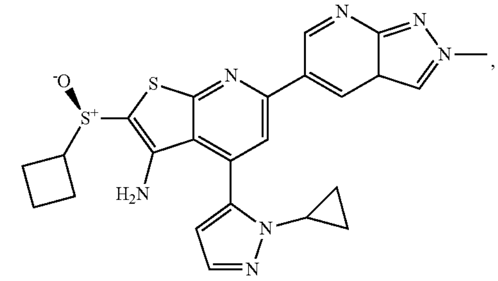
,
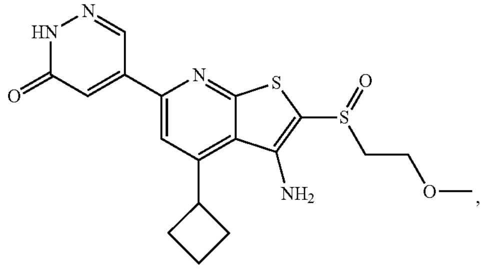
,
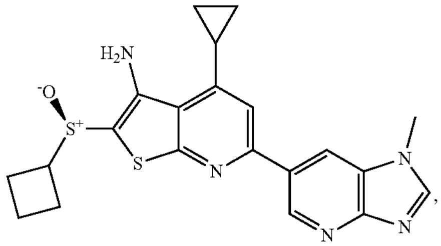
,
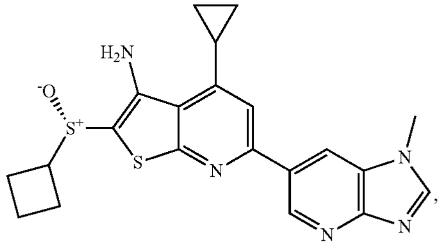
, -continued
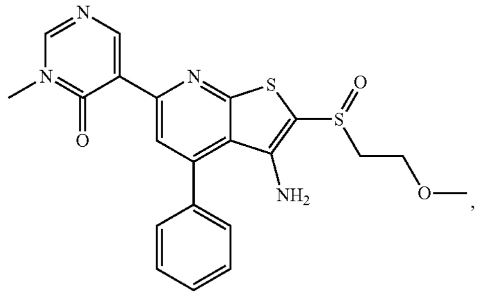
,
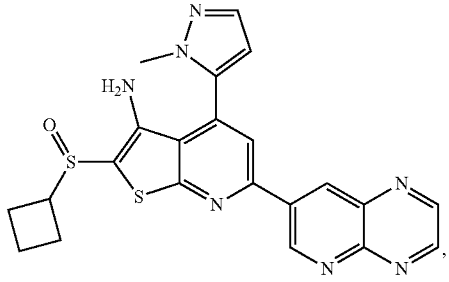
,
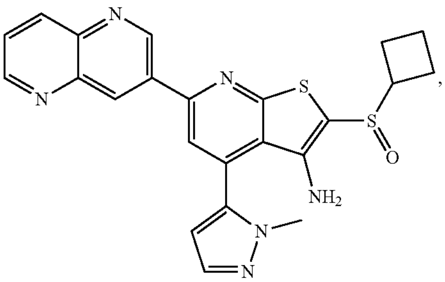
,
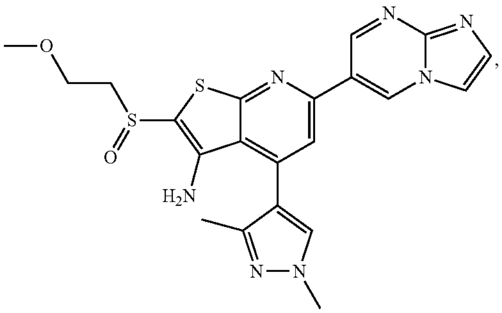
,
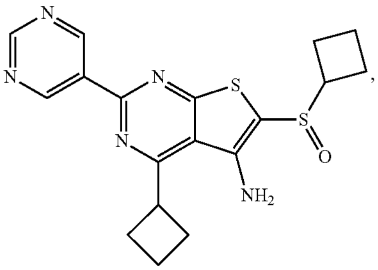
,
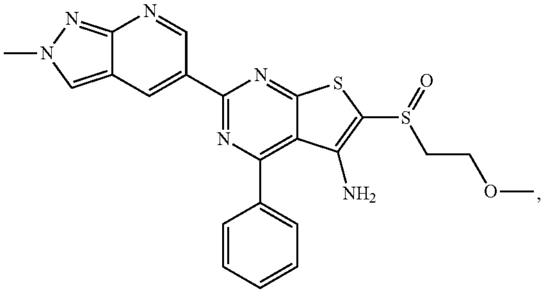
, -continued
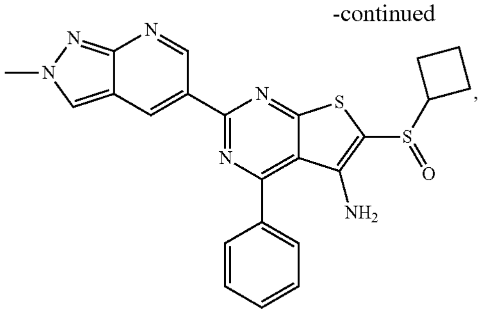
,
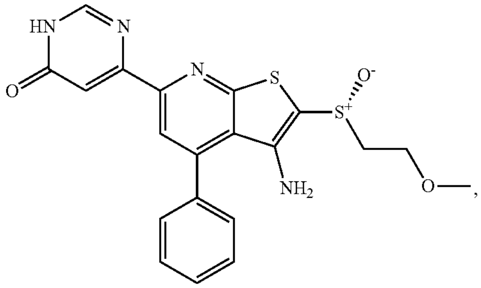
,
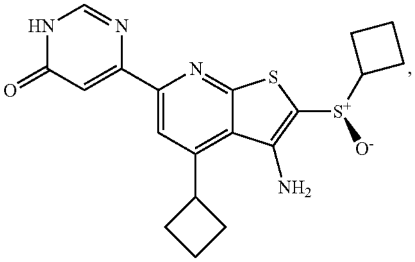
,
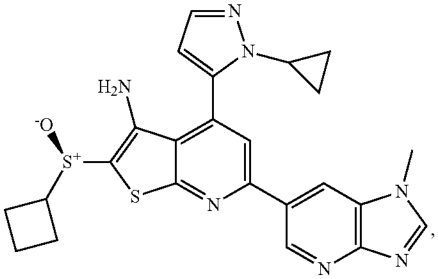
,
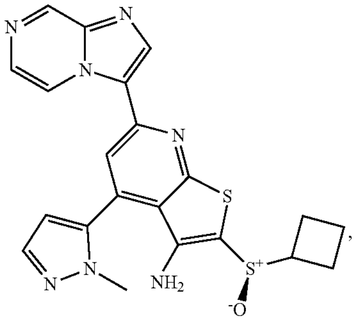
,
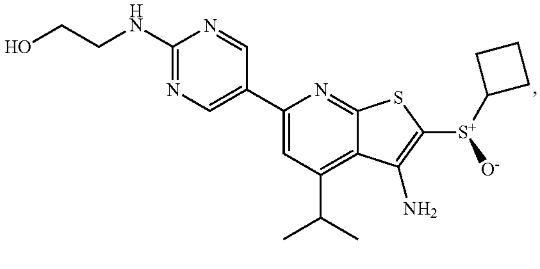
, or a pharmaceutically acceptable salt, tautomer, or solvate thereof.

In other embodiments, the 15-PGDH inhibitor can include compound having at least one of the formulas (IB) or (IIB), or a pharmaceutically acceptable salt, tautomer, or solvate thereof:

(IB)

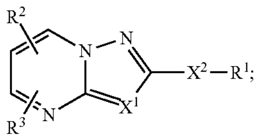

or (IIB)

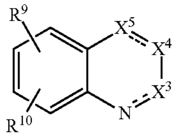

wherein $X^1$ is N or $CR^4$;

$X^2$ is S, S═O, S(═O)$_2$, or C═O;

$X^3$ is $CR^8$, the compound forming a polycyclic heteroaryl with 10 ring atoms, or absent, the compound forming a polycyclic heteroaryl with 9 ring atoms;

$X^4$ is N, NH, or $CR^7$;

$X^5$ is N, C═O, or $CR^{16}$, and $X^5$ is N if $X^4$ is $CR^7$, or $X^3$ is absent, $X^4$ is NH if $X^5$ is C═O, and $X^5$ is $CR^{16}$ if $X^4$ is N and $X^3$ is $CR^8$;

$R^1$, $R^2$, $R^3$, $R^4$, $R^9$, $R^{10}$, and $R^{16}$ are the same or different and are independently selected from the group consisting of hydrogen, substituted or unsubstituted $C_1$-$C_{24}$ alkyl, $C_2$-$C_{24}$ alkenyl, $C_2$-$C_{24}$ alkynyl, $C_3$-$C_{20}$ aryl, heterocycloalkenyl containing from 5-7 ring atoms, (wherein from 1-3 of the ring atoms is independently selected from N, NH, N($C_1$-$C_6$ alkyl), NC(O) ($C_1$-$C_6$ alkyl), O, and S), heteroaryl or heterocyclyl containing from 5-14 ring atoms, (wherein from 1-6 of the ring atoms is independently selected from N, NH, N($C_1$-$C_3$ alkyl), O, and S), $C_6$-$C_{24}$ alkaryl, $C_6$-$C_{24}$ aralkyl, halo, silyl, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO— alkyl) and $C_6$-$C_{20}$ arylcarbonyl (—CO-aryl)), acyloxy (—O-acyl), $C_2$-$C_{24}$ alkoxycarbonyl (—(CO)—O— alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO—), carbamoyl (—(CO)—$NH_2$), $C_1$-$C_{24}$ alkyl-carbamoyl (—(CO)—NH($C_1$-$C_{24}$ alkyl)), arylcarbamoyl (—(CO)—NH-aryl), thiocarbamoyl (—(CS)—$NH_2$), carbamido (—NH—(CO)—$NH_2$), cyano(—CN), isocyano (—$N^+C^-$), cyanato (—O—CN), isocyanato (—O—$N^+$═$C^-$), isothiocyanato (—S—CN), azido (—N═$N^+$═$N^-$), formyl (—(CO)—H), thioformyl (—(CS)—H), amino (—$NH_2$), $C_1$-$C_{24}$ alkyl amino, $C_5$-$C_{20}$ aryl amino, $C_2$-$C_{24}$ alkylamido (—NH—(CO)-alkyl), $C_6$-$C_{20}$ arylamido (—NH—(CO)-aryl), sulfanamido (—$SO_2N(R)_2$ where R is independently H, alkyl, aryl or heteroaryl), imino (—CR═NH where R is hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR═N(alkyl), where R=hydrogen, alkyl, aryl, alkaryl, aralkyl, etc.), arylimino (—CR═N(aryl), where R=hydrogen, alkyl, aryl, alkaryl, etc.), nitro (—$NO_2$), nitroso (—NO), sulfo (—$SO_2$—OH), sulfonato (—$SO_2$—O—), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—$SO_2$-alkyl), $C_5$-$C_{20}$ arylsulfonyl (—$SO_2$-aryl), sulfonamide (—$SO_2$—$NH_2$, —$SO_2NY_2$ (wherein Y is independently H, aryl or alkyl), phosphono (—$P(O)(OH)_2$), phosphonato (—P(O)(O—)$_2$), phosphinato (—P(O)(O—)), phospho (—$PO_2$), phosphino (—$PH_2$), polyalkyl ethers (—$[(CH_2)_nO]_m$), phosphates, phosphate esters [—OP(O)$(OR)_2$ where R═H, methyl or other alkyl], groups incorporating amino acids or other moieties expected to bear positive or negative charge at physiological pH, and combinations thereof;

$R^7$ and $R^8$ are same or different and are each independently selected from the group consisting of H, a substituted or unsubstituted aryl, a substituted or unsubstituted heteroaryl, a substituted or unsubstituted cycloalkyl, and a substituted or unsubstituted heterocyclyl, and at least one of $R^7$ or $R^8$ is not H.

In some embodiments, at least one of $R^2$ or $R^3$ is not H, and at least one of $R^9$ or $R^{10}$ is not H.

In some embodiments, the 15-PGDH inhibitor can include a compound having at least one of the following formulas:

(IBa)

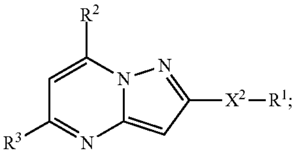

(IBb)

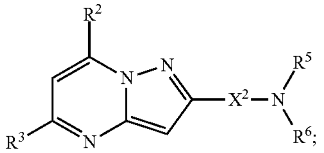

(IBc)

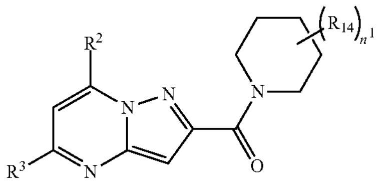

(IBd)

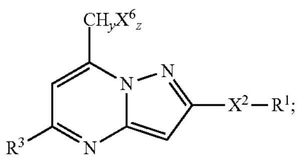

or (IBe)

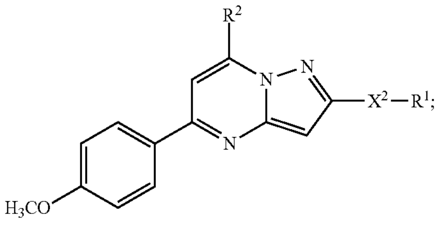

or a pharmaceutically acceptable salt, tautomer, or solvate thereof;

wherein $X^2$ is S, S═O, S(═O)$_2$, or C═O;

$X^6$ is $C_1$, Br, or F, and y+z=3;

$R^1$, $R^2$, $R^3$, $R^5$, $R^6$, and $R^{14}$ are the same or different and are independently selected from the group consisting of hydrogen, substituted or unsubstituted $C_1$-$C_{24}$ alkyl, $C_2$-$C_{24}$ alkenyl, $C_2$-$C_{24}$ alkynyl, $C_3$-$C_{20}$ aryl, heterocycloalkenyl containing from 5-7 ring atoms, (wherein from 1-3 of the ring atoms is independently selected from N, NH, N($C_1$-$C_6$ alkyl), NC(O) ($C_1$-$C_6$ alkyl), O, and S), heteroaryl or heterocyclyl containing from 5-14 ring atoms, (wherein from 1-6 of the ring atoms is independently selected from N, NH, N($C_1$-$C_3$ alkyl), O, and S), $C_6$-$C_{24}$ alkaryl, $C_6$-$C_{24}$ aralkyl, halo, silyl, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—$COO^-$), carbamoyl (—(CO)—$NH_2$), $C_1$-$C_{24}$ alkyl-carbamoyl (—(CO)—NH($C_1$-$C_{24}$ alkyl)), arylcarbamoyl (—(CO)—NH-aryl), thiocarbamoyl (—(CS)—$NH_2$), carbamido (—NH—(CO)—$NH_2$), cyano(—CN), isocyano (—$N^+C^-$), cyanato (—O—CN), isocyanato (—O—$N^+$═$C^-$), isothiocyanato (—S—CN), azido (—N═$N^+$═$N^-$), formyl (—(CO)—H), thioformyl (—(CS)—H), amino (—$NH_2$), $C_1$-$C_{24}$ alkyl amino, $C_5$-$C_{20}$ aryl amino, $C_2$-$C_{24}$ alkylamido (—NH—(CO)-alkyl), $C_6$-$C_{20}$ arylamido (—NH—(CO)-aryl), sulfanamido (—$SO_2N(R)_2$ where R is independently H, alkyl, aryl or heteroaryl), imino (—CR═NH where R is hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR═N(alkyl), where R=hydrogen, alkyl, aryl, alkaryl, aralkyl, etc.), arylimino (—CR═N (aryl), where R=hydrogen, alkyl, aryl, alkaryl, etc.), nitro (—$NO_2$), nitroso (—NO), sulfo (—$SO_2$—OH), sulfonato (—$SO_2$—O—), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—$SO_2$-alkyl), $C_5$-$C_{20}$ arylsulfonyl (—$SO_2$-aryl), sulfonamide (—$SO_2$—$NH_2$, —$SO_2NY_2$ (wherein Y is independently H, aryl or alkyl), phosphono (—P(O)$(OH)_2$), phosphonato (—P(O)$(O^-)_2$), phosphinato (—P(O)(O—)), phospho (—$PO_2$), phosphino (—$PH_2$), polyalkyl ethers (—$[(CH_2)_nO]_m$), phosphates, phosphate esters [—OP(O)$(OR)_2$ where R═H, methyl or other alkyl], groups incorporating amino acids or other moieties expected to bear positive or negative charge at physiological pH, and combinations thereof; wherein $R^5$ and $R^6$ may be linked to form a cyclic or polycyclic ring, wherein the ring is a substituted or unsubstituted aryl, a substituted or unsubstituted heteroaryl, a substituted or unsubstituted cycloalkyl, and a substituted or unsubstituted heterocyclyl, $n^1$ is 0-4, and each $R^{14}$ is the same or different.

In other embodiments, the 15-PGDH inhibitor can include a compound having at least one of the following formulas:

(IIBa)

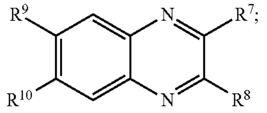

(IIBb)

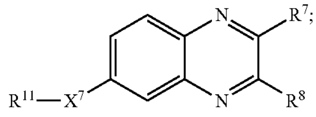

(IIBc)

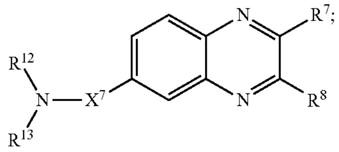

(IIBd)

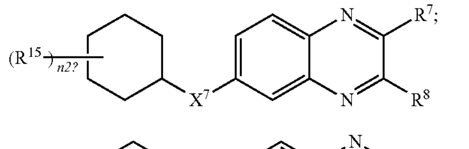

(IIBf)

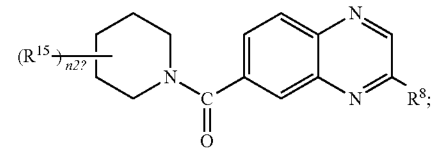

or a pharmaceutically acceptable salt, tautomer, or solvate thereof;

wherein $X^7$ is S, S═O, S(═O)$_2$, or C═O;

$R^7$ and $R^8$ are same or different and are each independently selected from the group consisting of H, a substituted or unsubstituted aryl, a substituted or unsubstituted heteroaryl, a substituted or unsubstituted cycloalkyl, and a substituted or unsubstituted heterocyclyl, and at least one of $R^7$ or $R^8$ is not H;

$R^9$, $R^{10}$, $R^{11}$, $R^{12}$, $R^{13}$, and $R^{15}$ are the same or different and are independently selected from the group consisting of hydrogen, substituted or unsubstituted $C_1$-$C_{24}$ alkyl, $C_2$-$C_{24}$ alkenyl, $C_2$-$C_{24}$ alkynyl, $C_3$-$C_{20}$ aryl, heterocycloalkenyl containing from 5-7 ring atoms, (wherein from 1-3 of the ring atoms is independently selected from N, NH, N($C_1$-$C_6$ alkyl), NC(O) ($C_1$-$C_6$ alkyl), O, and S), heteroaryl or heterocyclyl containing from 5-14 ring atoms, (wherein from 1-6 of the ring atoms is independently selected from N, NH, N($C_1$-$C_3$ alkyl), O, and S), $C_6$-$C_{24}$ alkaryl, $C_6$-$C_{24}$ aralkyl, halo, silyl, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO— alkyl) and $C_6$-$C_{20}$ arylcarbonyl (—CO-aryl)), acyloxy (—O-acyl), $C_2$-$C_{24}$ alkoxycarbonyl (—(CO)—O— alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO—), carbamoyl (—(CO)—$NH_2$), $C_1$-$C_{24}$ alkyl-carbamoyl (—(CO)—NH($C_1$-$C_{24}$ alkyl)), arylcarbamoyl (—(CO)—NH-aryl), thiocarbamoyl (—(CS)—$NH_2$), carbamido (—NH—(CO)—$NH_2$), cyano(—CN), isocyano (—$N^+C^-$), cyanato (—O—CN), isocyanato (—O—$N^+$═$C^-$), isothiocyanato (—S—CN), azido (—N═$N^+$═$N^-$), formyl (—(CO)—H), thioformyl (—(CS)—H), amino (—$NH_2$), $C_1$-$C_{24}$ alkyl amino, $C_5$-$C_{20}$ aryl amino, $C_2$-$C_{24}$ alkylamido (—NH—(CO)-alkyl), $C_6$-$C_{20}$ arylamido (—NH—(CO)-aryl), sulfanamido (—$SO_2N(R)_2$ where R is independently H, alkyl, aryl or heteroaryl), imino (—CR═NH where R is hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR═N(alkyl), where R=hydrogen, alkyl, aryl, alkaryl, aralkyl, etc.), arylimino (—CR═N (aryl), where R=hydrogen, alkyl, aryl, alkaryl, etc.), nitro (—$NO_2$), nitroso (—NO), sulfo (—$SO_2$—OH), sulfonato (—$SO_2$—O—), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—$SO_2$-alkyl), $C_5$-$C_{20}$ arylsulfonyl (—$SO_2$-aryl), sulfonamide (—$SO_2$—$NH_2$, —$SO_2NY_2$ (wherein Y is independently H, aryl or alkyl), phosphono (—$P(O)(OH)_2$), phosphonato (—$P(O)(O^-)_2$), phosphinato (—P(O)(O—)), phospho (—$PO_2$), phosphino (—$PH_2$), polyalkyl ethers (—$[(CH_2)_nO]_m$), phosphates, phosphate esters [—OP (O)$(OR)_2$ where R═H, methyl or other alkyl], groups incorporating amino acids or other moieties expected to bear positive or negative charge at physiological pH, and combinations thereof; wherein $R^{12}$ and $R^{13}$ may be linked to form a cyclic or polycyclic ring, wherein the ring is a substituted or unsubstituted aryl, a substituted or unsubstituted heteroaryl, a substituted or unsubstituted cycloalkyl, and a substituted or unsubstituted heterocyclyl, $n^2$ is 0-4, and each $R^{15}$ is the same or different.

Examples of 15-PGDH inhibitors having formulas (IB), (IBa), (IBb), (IBc), (IBd), (IBe), (IIB), (IIBa), (IIBb), (IIBc), (IIBd), (IBe), or (IIBf) can include the following compounds:

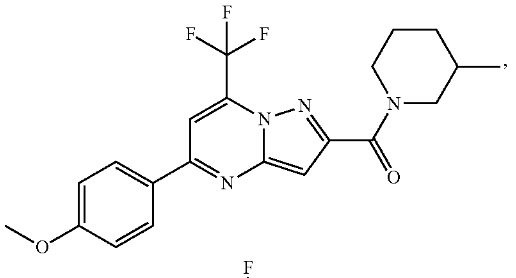

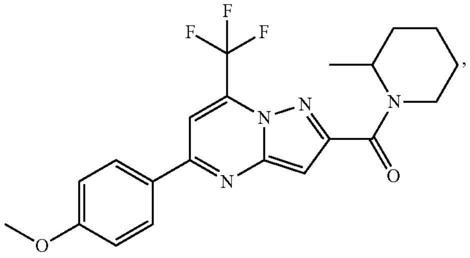

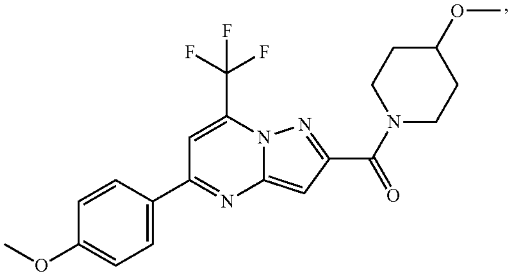

-continued

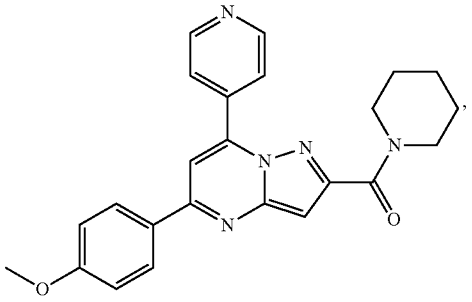

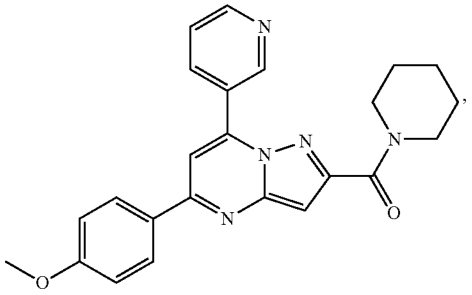

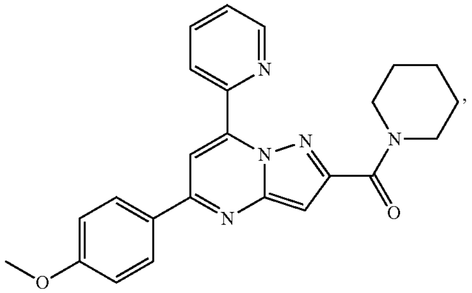

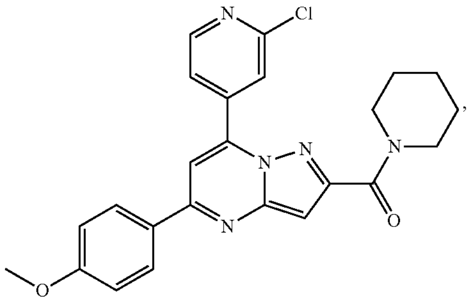

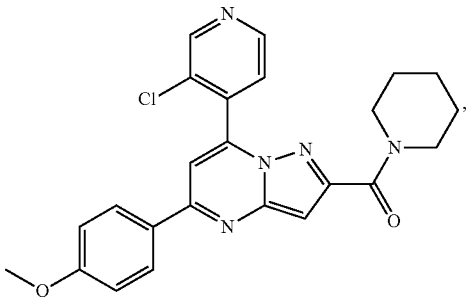

-continued
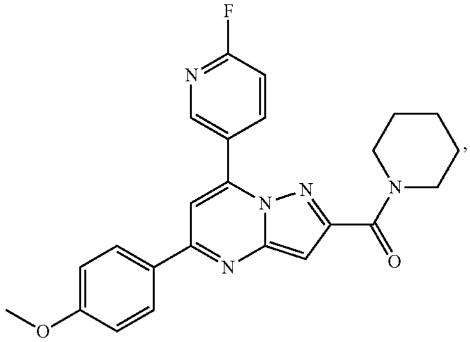
,
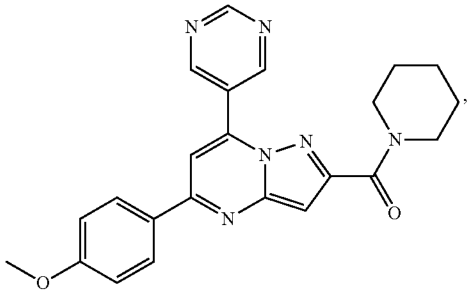
,
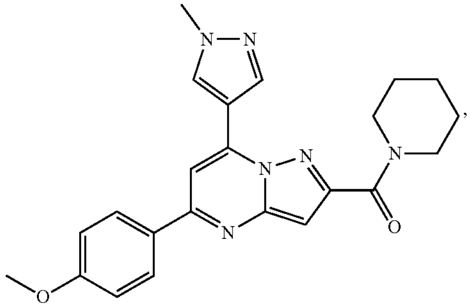
,
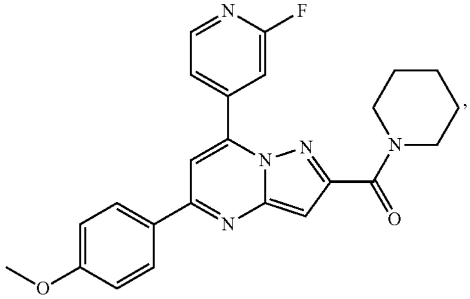
,
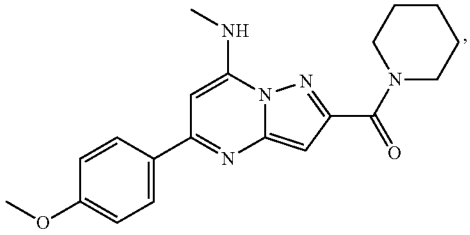
,
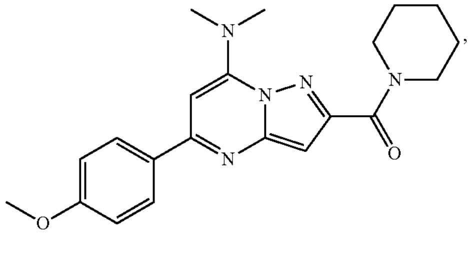
,
-continued
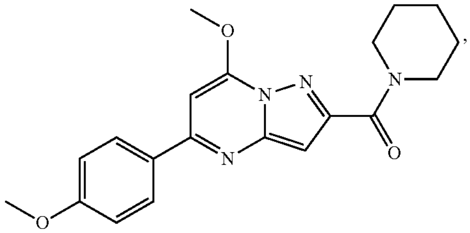
,
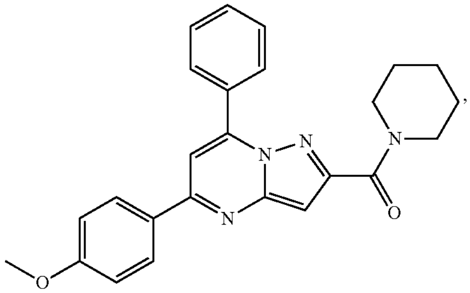
,
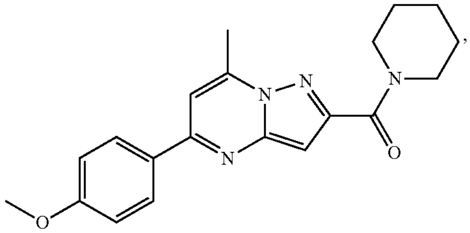
,
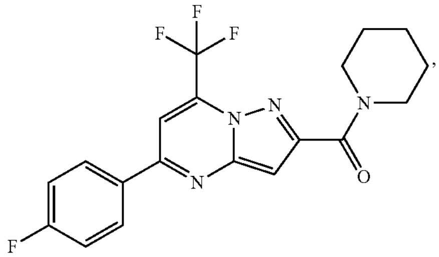
,
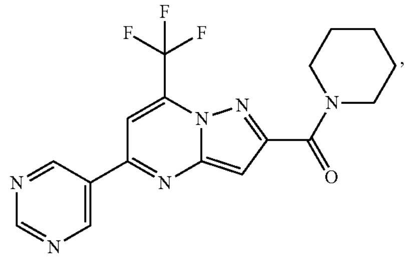
,
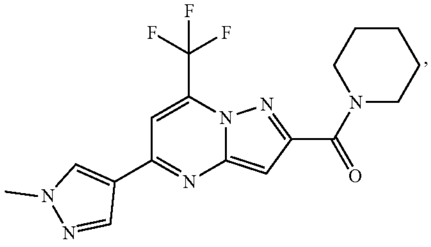
, -continued
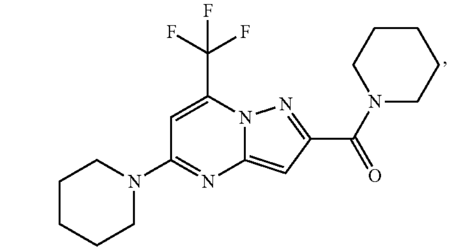
,
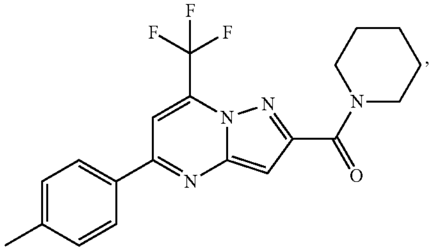
,
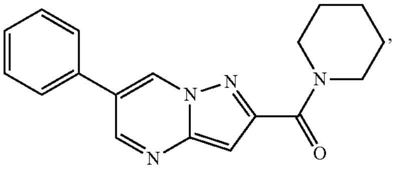
,
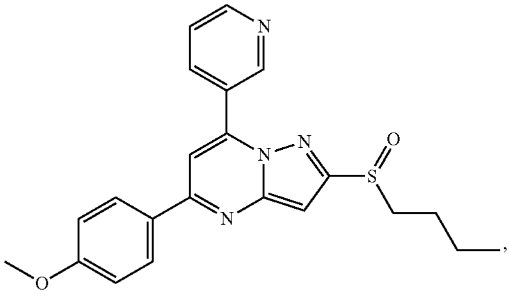
,
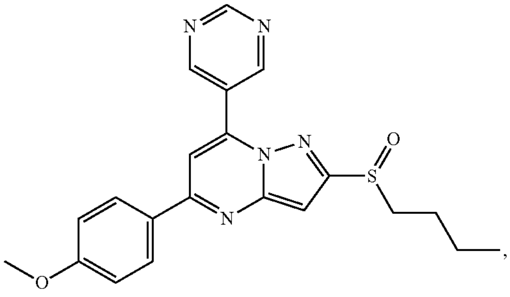
,
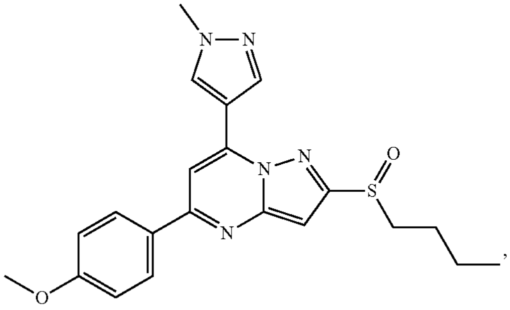
,
-continued
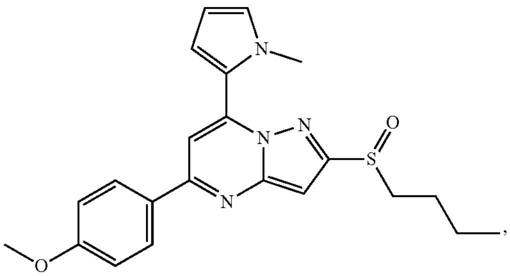
,
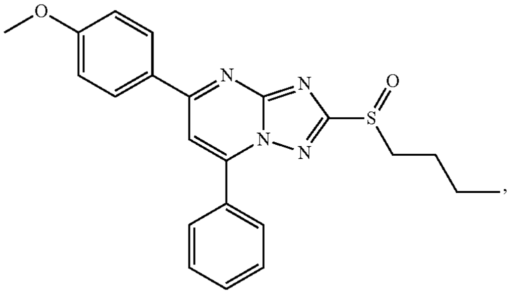
,
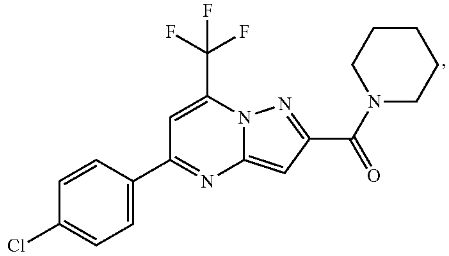
,
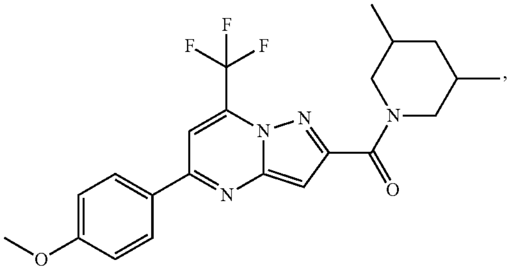
,
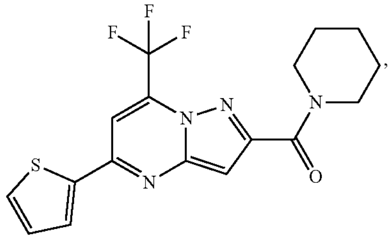
,
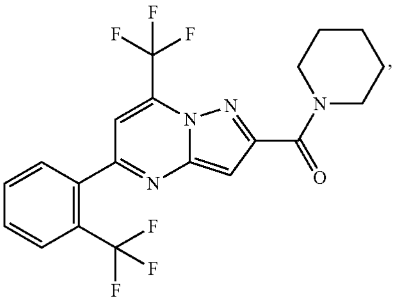
, -continued
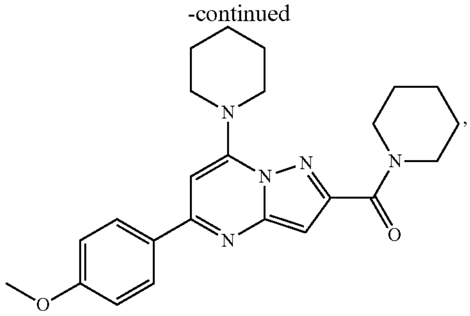
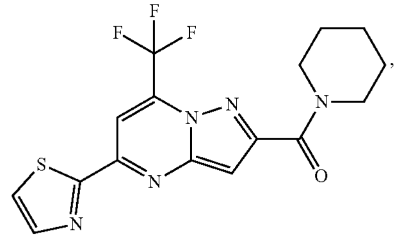
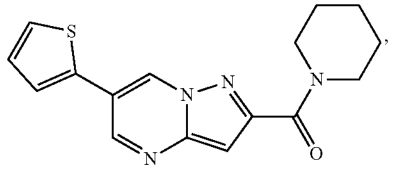
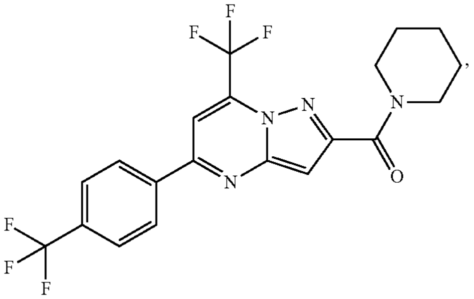
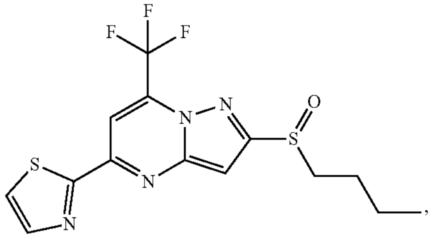
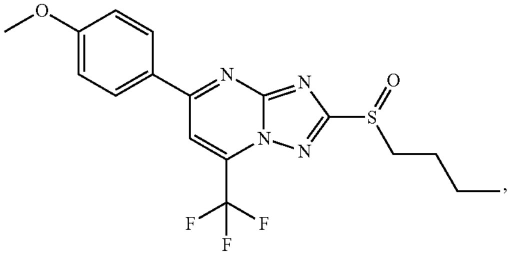
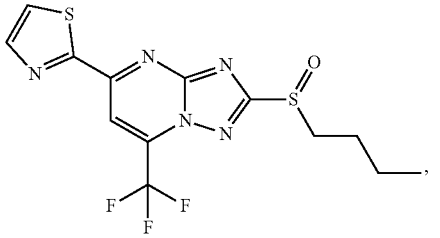
-continued
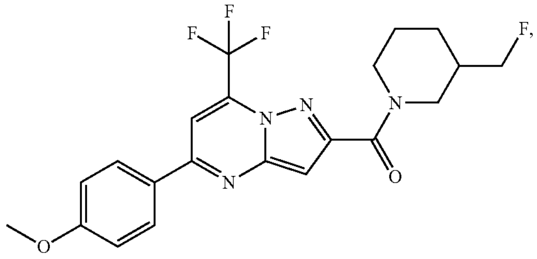
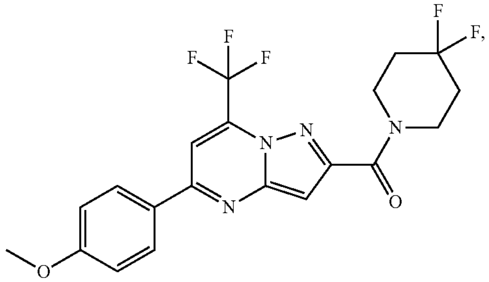
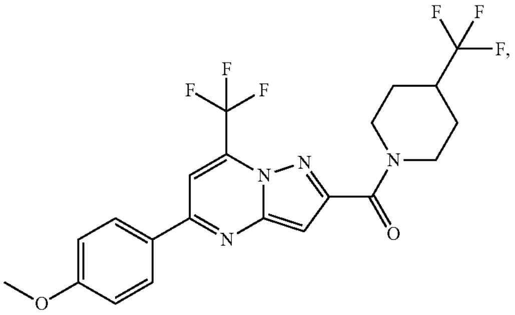
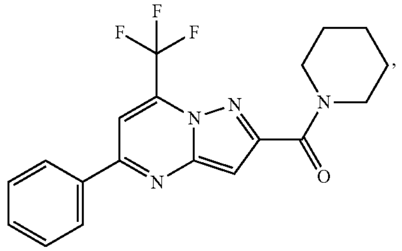
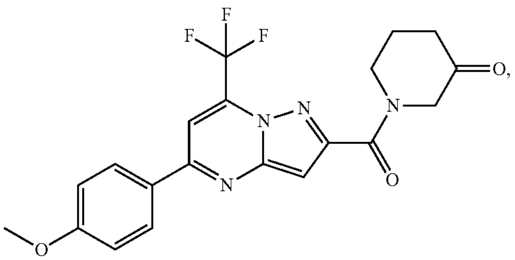
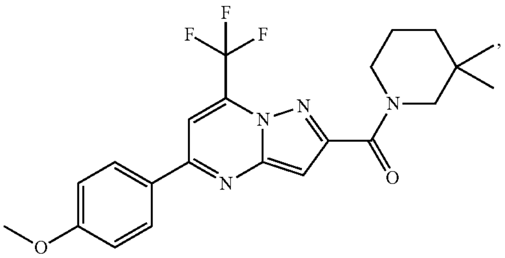

-continued
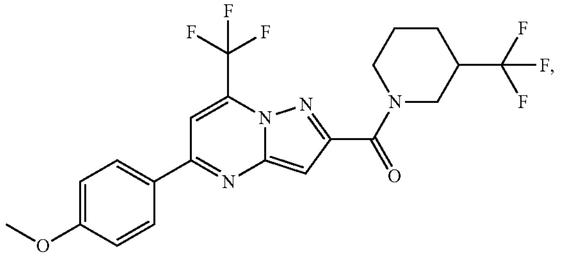
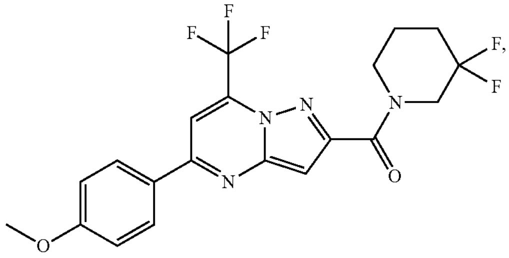
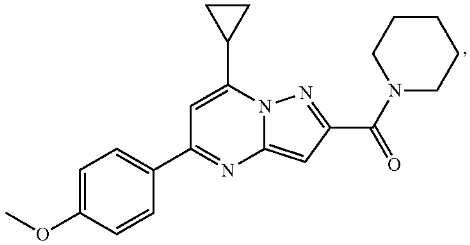
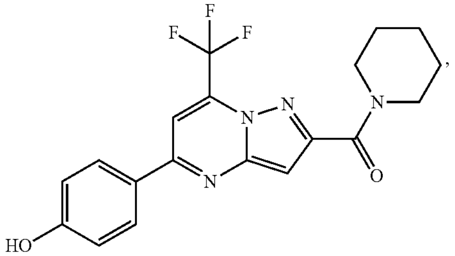
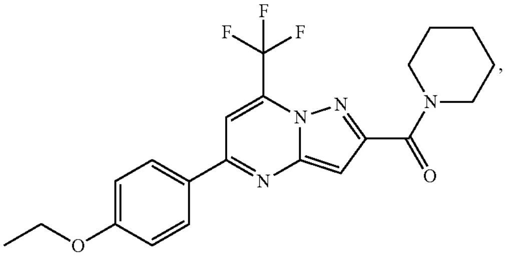
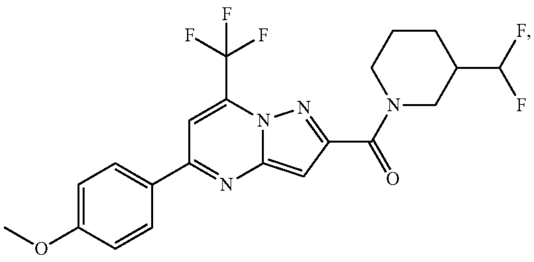
-continued
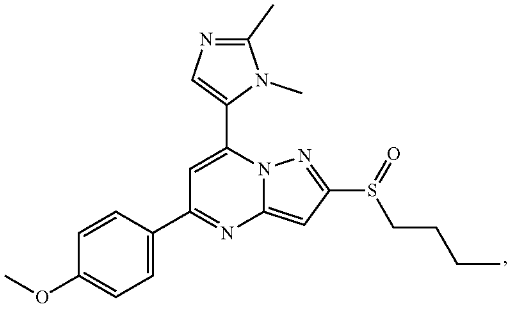
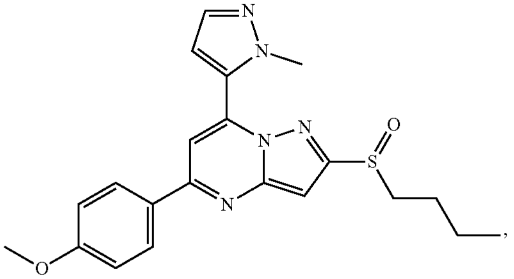
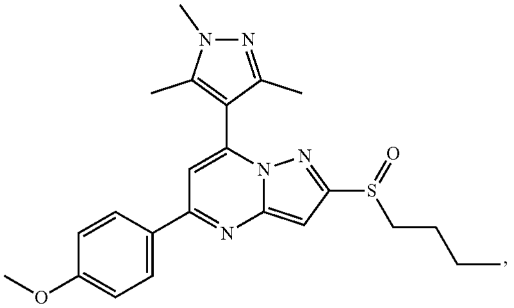
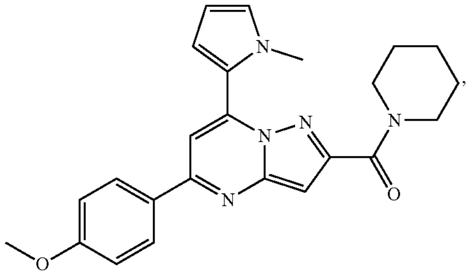
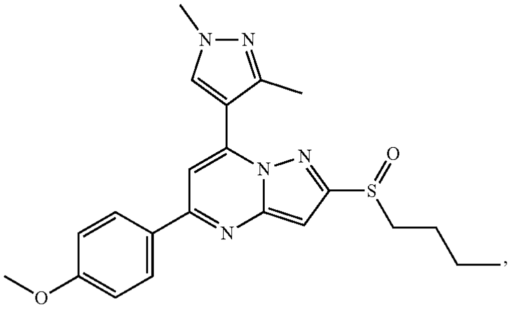
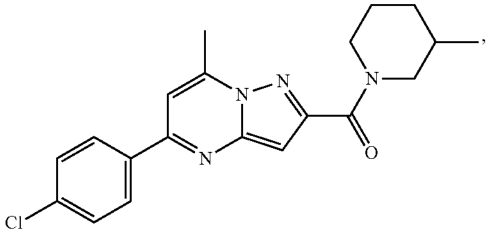

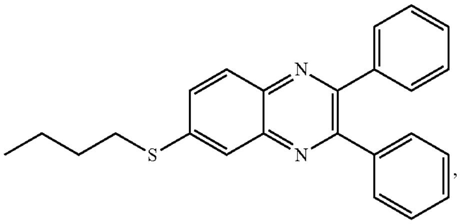
,
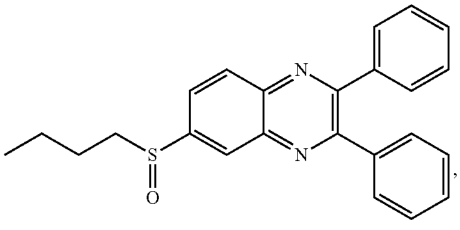
,
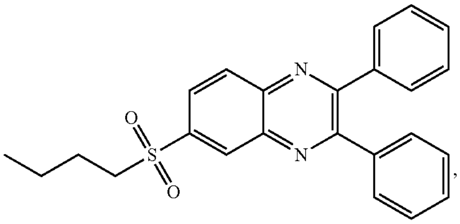
,
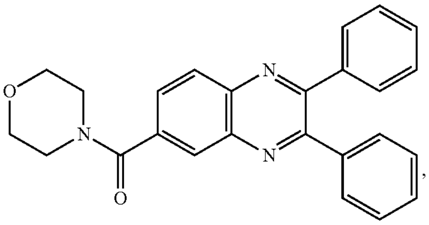
,
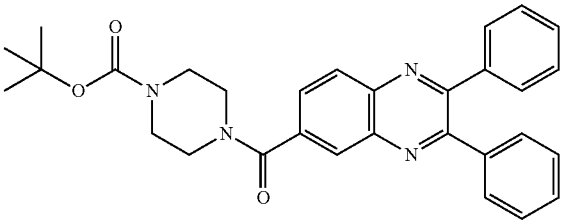
,
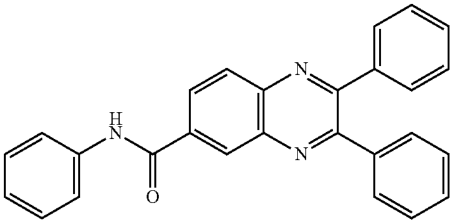
,
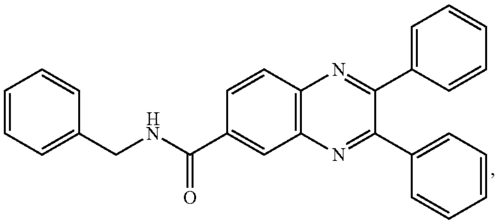
,
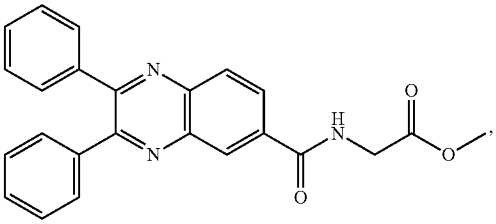
,
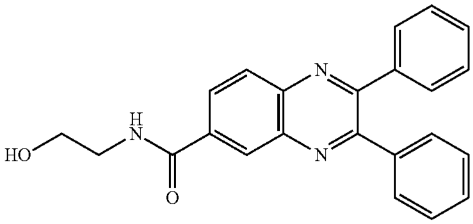
,
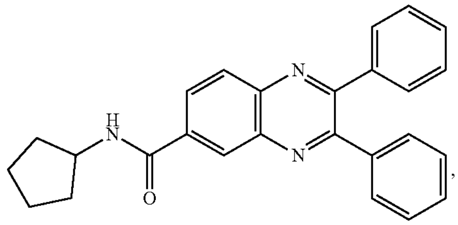
,
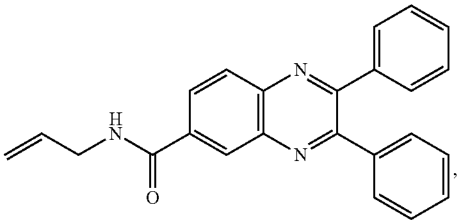
,
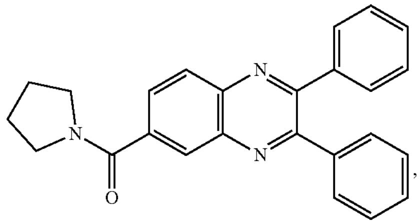
,
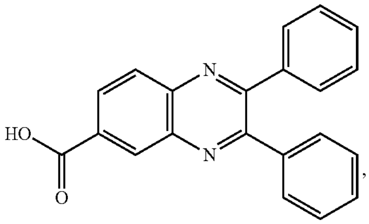
,
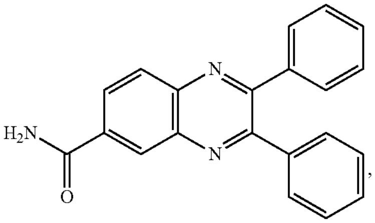
, -continued
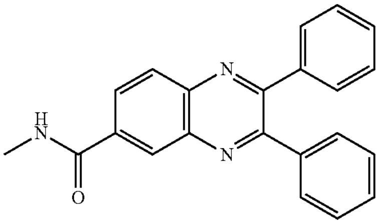
,
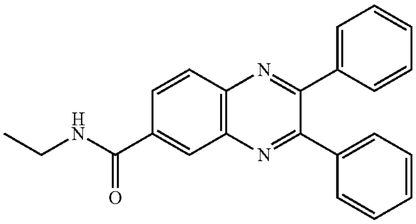
,
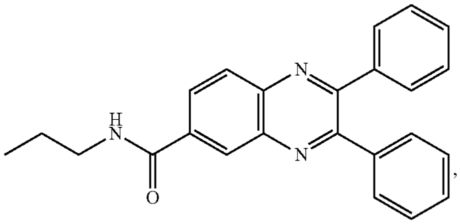
,
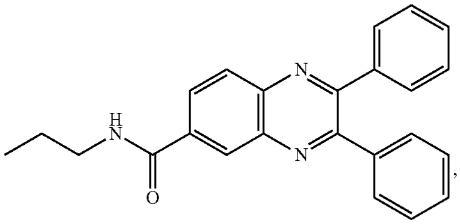
,
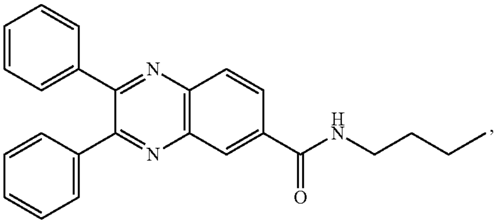
,
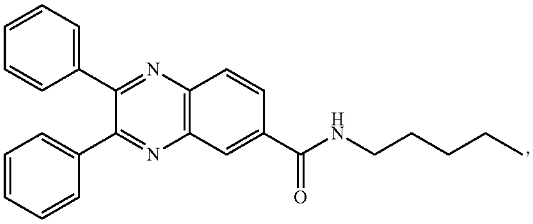
,
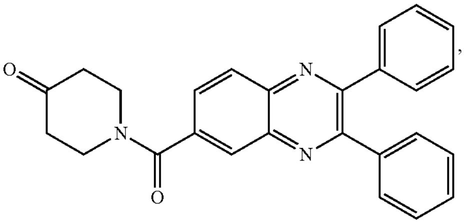
,
-continued
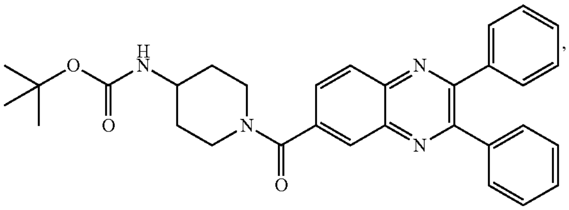
,
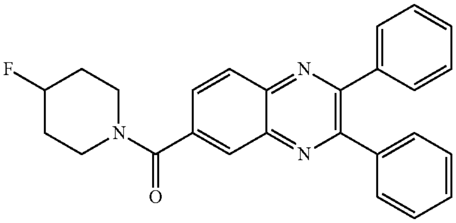
,
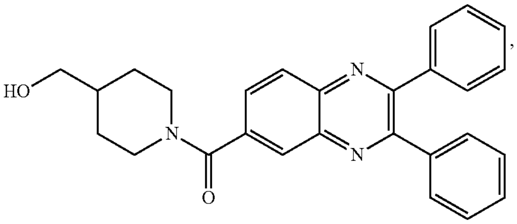
,
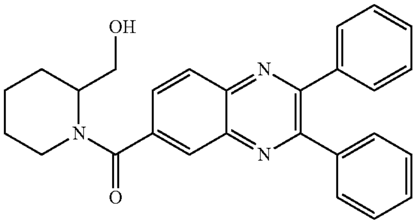
,
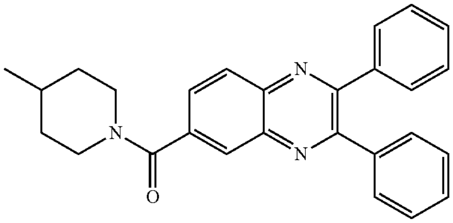
,
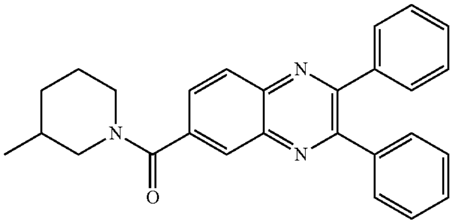
,
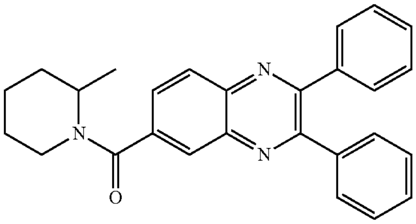
, -continued
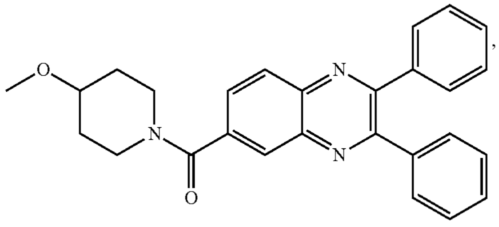
,
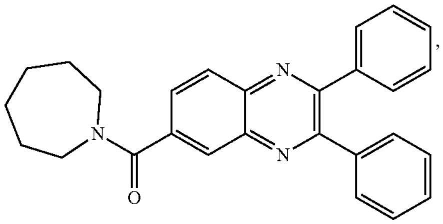
,
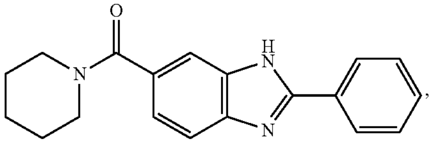
,
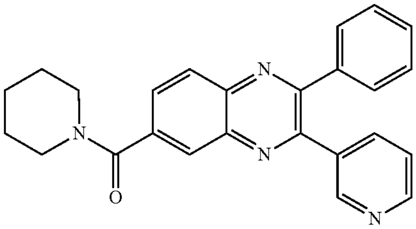
,
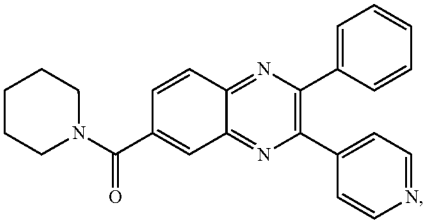
,
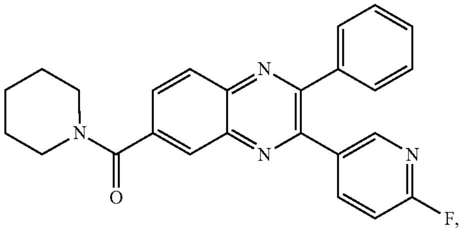
,
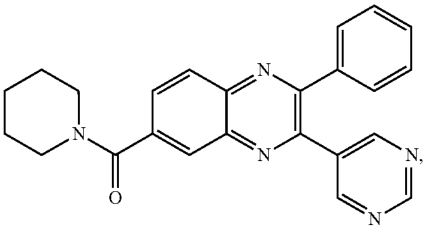
,
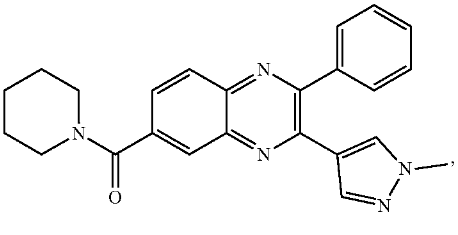
,
-continued
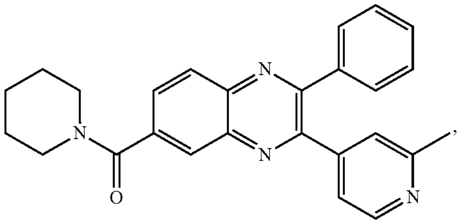
,
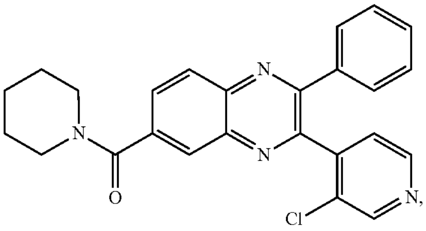
,
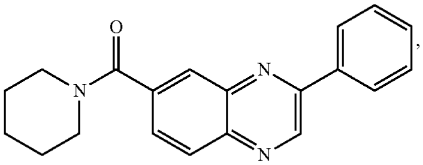
,
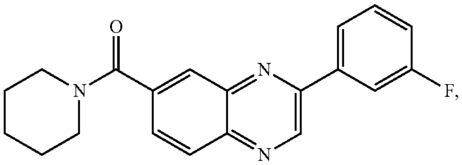
,
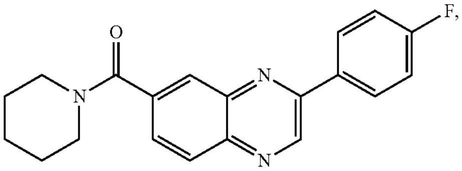
,
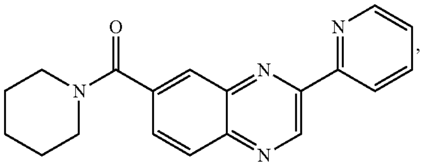
,
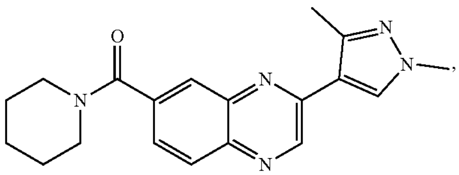
,
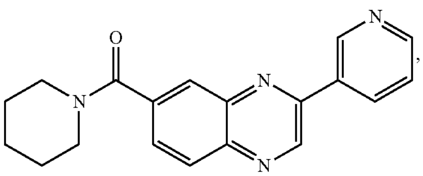
,
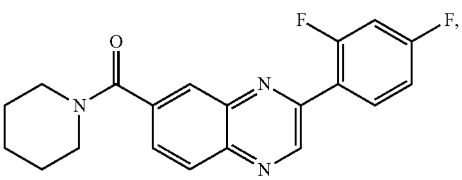
, -continued
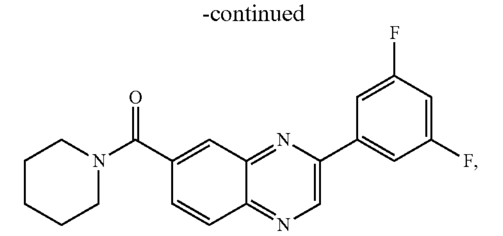
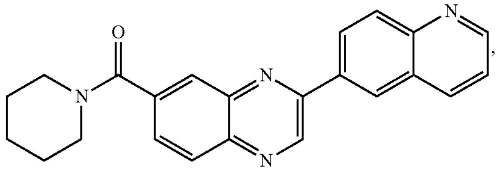
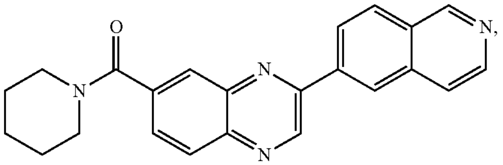
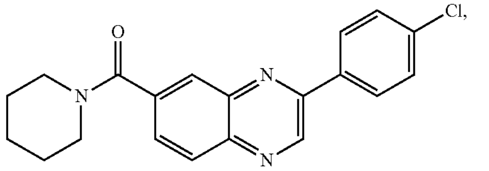
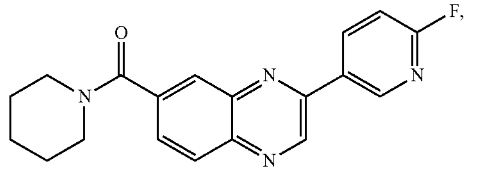
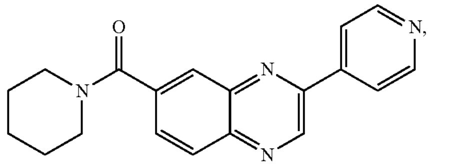
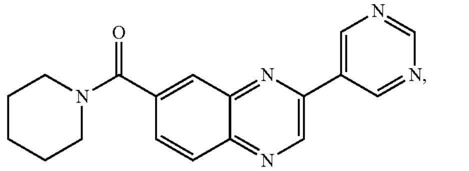
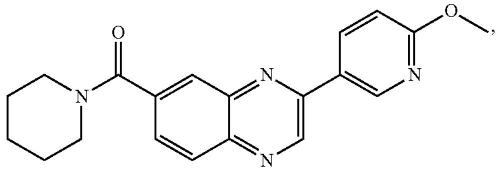
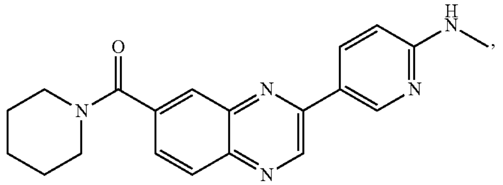
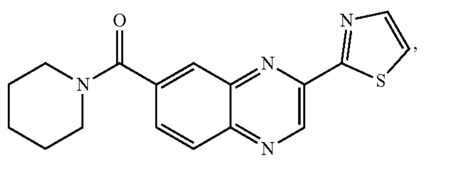
-continued
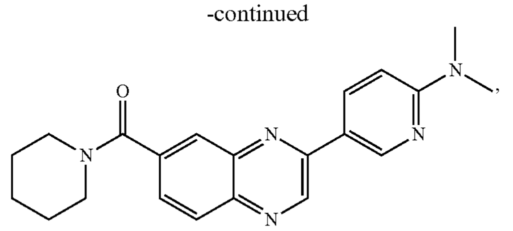
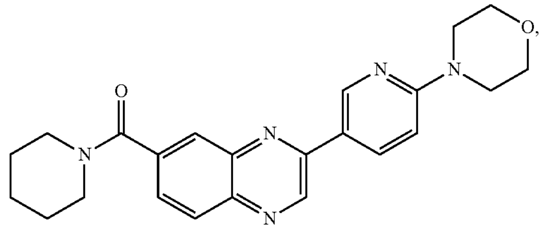
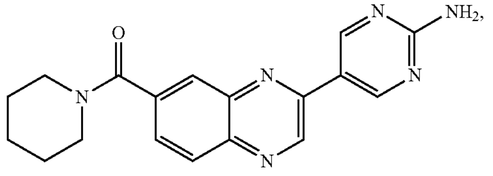
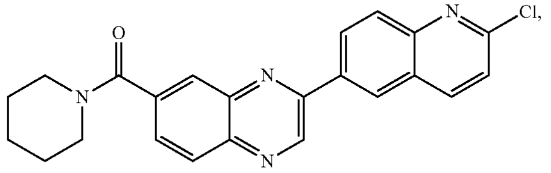
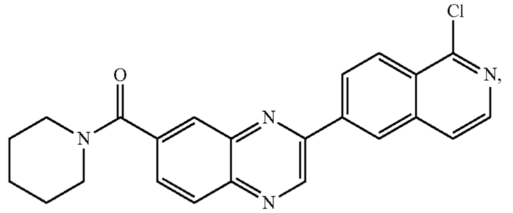
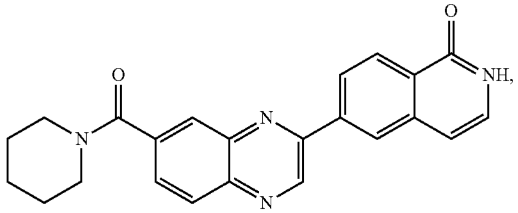
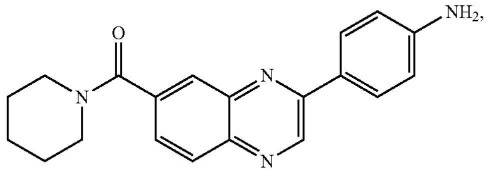
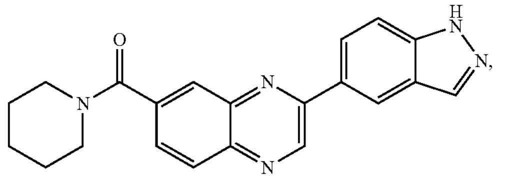
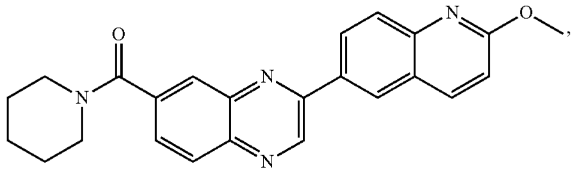

-continued
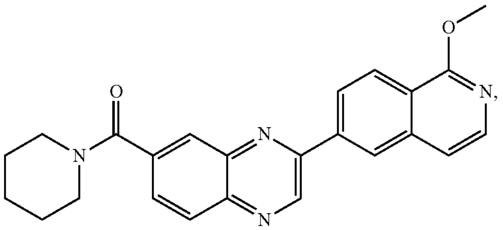
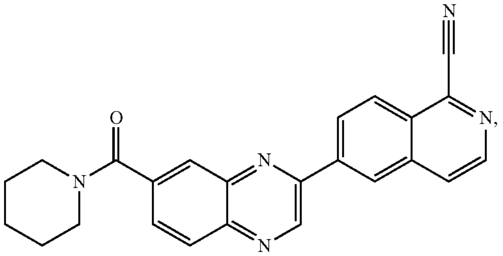
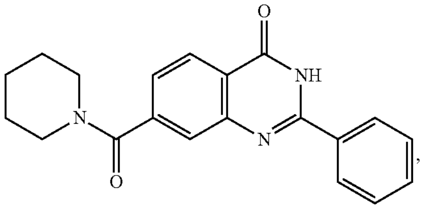
,
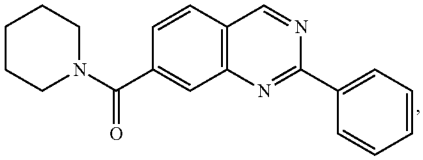
,
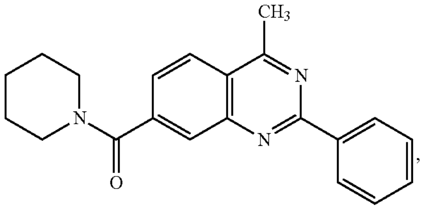
,
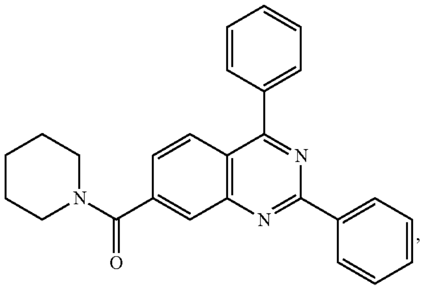
,
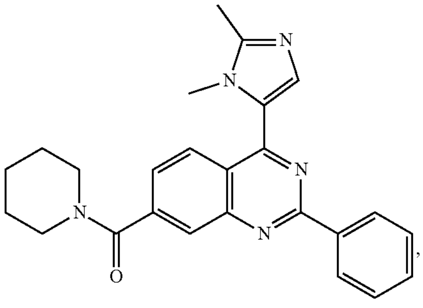
,
-continued
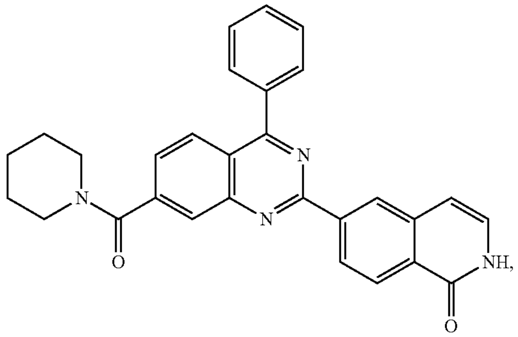
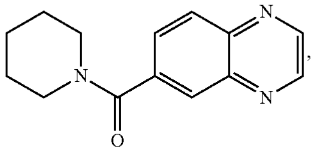
,
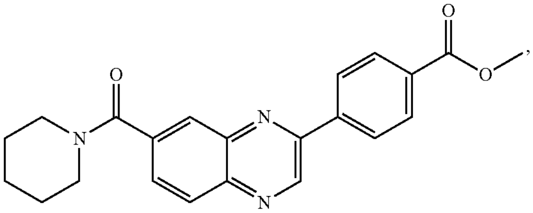
,
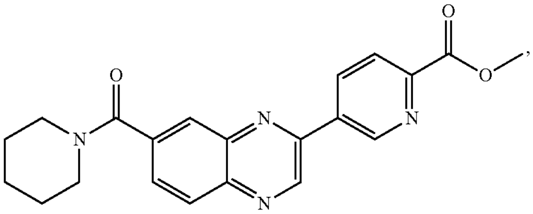
,
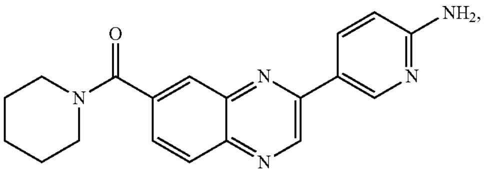
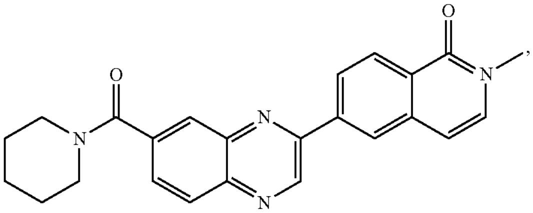
,
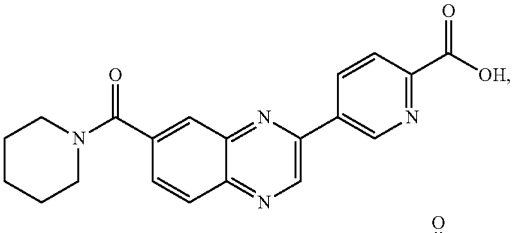
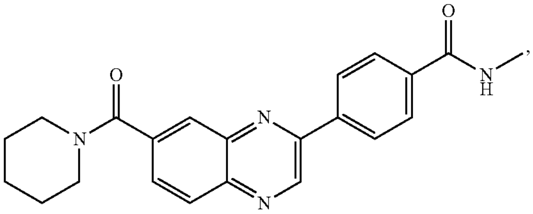
, -continued

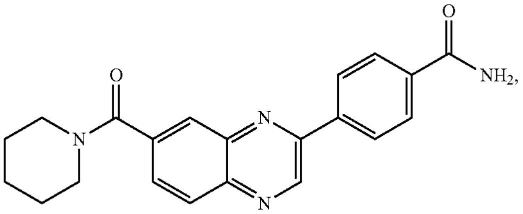

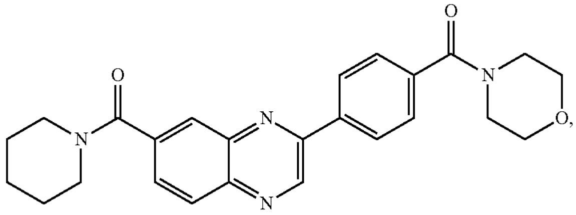

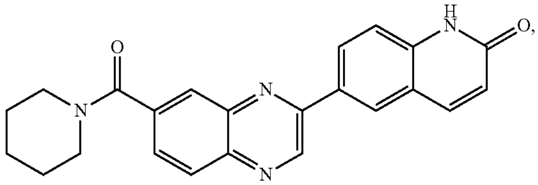

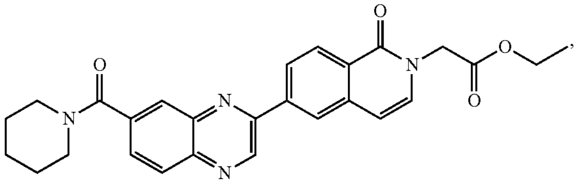

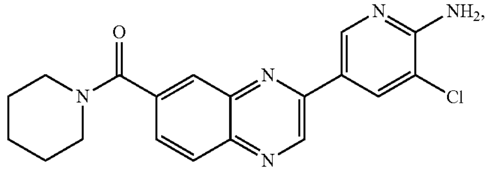

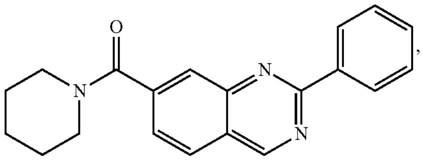

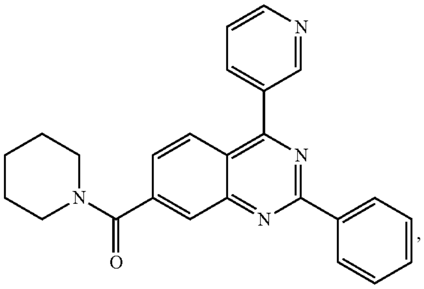

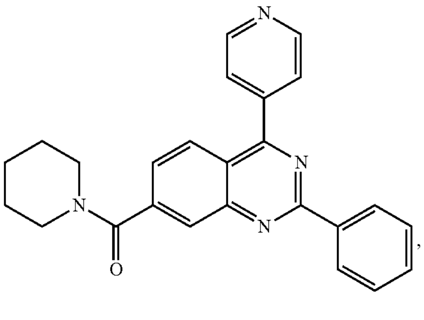

-continued

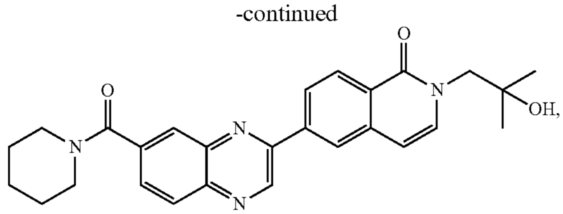

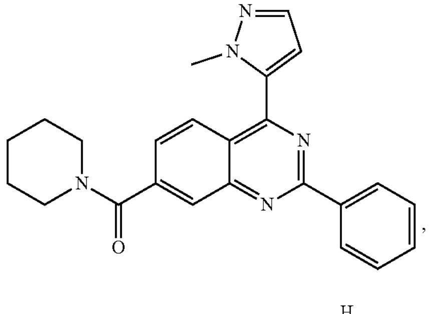

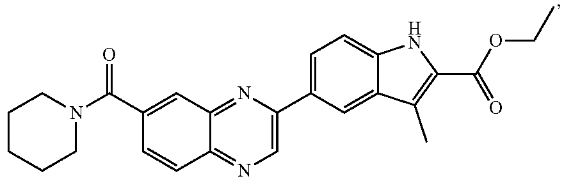

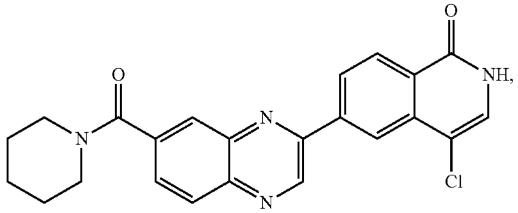

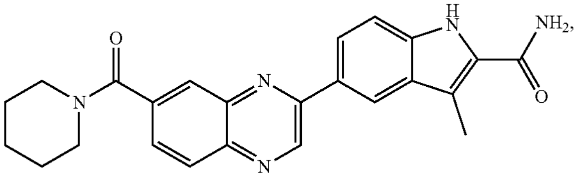

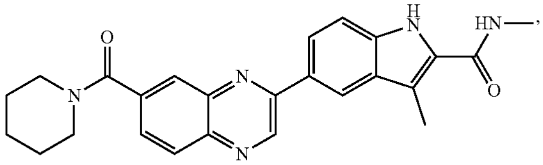

or

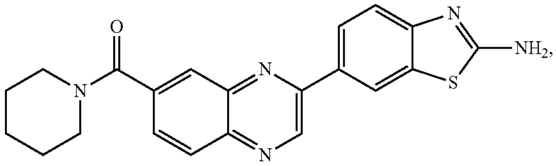

or a pharmaceutically acceptable salt, tautomer, or solvate thereof.

Still other example of 15-PGDH inhibitors include compounds described in WO2018/145080, which is incorporated by reference in its entirety.

In certain embodiments, the 15-PGDH inhibitor can be selected that can ia) at 2.5 μM concentration, stimulate a Vaco503 reporter cell line expressing a 15-PGDH luciferase fusion construct to a luciferase output level of greater than 70 (using a scale on which a value of 100 indicates a doubling of reporter output over baseline); iia) at 2.5 μM concentration stimulate a V9m reporter cell line expressing a 15-PGDH luciferase fusion construct to a luciferase output level of greater than 75; iiia) at 7.5 μM concentration stimulate a LS174T reporter cell line expressing a 15-PGDH luciferase fusion construct to a luciferase output level of greater than 70; and iva) at 7.5 μM concentration, does not activate a negative control V9m cell line expressing TK-renilla luciferase reporter to a level greater than 20; and va) inhibits the enzymatic activity of recombinant 15-PGDH protein at an $IC_{50}$ of less than 1 μM.

In other embodiments, the 15-PGDH inhibitor can ib) at 2.5 μM concentration, stimulate a Vaco503 reporter cell line expressing a 15-PGDH luciferase fusion construct to increase luciferase output; iib) at 2.5 μM concentration stimulate a V9m reporter cell line expressing a 15-PGDH luciferase fusion construct to increase luciferase output; iiib) at 7.5 μM concentration stimulate a LS174T reporter cell line expressing a 15-PGDH luciferase fusion construct to increase luciferase output; ivb) at 7.5 μM concentration, does not activate a negative control V9m cell line expressing TK-renilla luciferase reporter to a luciferase level greater than 20% above background; and vb) inhibits the enzymatic activity of recombinant 15-PGDH protein at an $IC_{50}$ of less than 1 μM.

In other embodiments, the 15-PGDH inhibitor can inhibit the enzymatic activity of recombinant 15-PGDH at an $IC_{50}$ of less than 1 μM, or preferably at an $IC_{50}$ of less than 250 nM, or more preferably at an $IC_{50}$ of less than 50 nM, or more preferably at an $IC_{50}$ of less than 10 nM, or more preferably at an $IC_{50}$ of less than 5 nM at a recombinant 15-PGDH concentration of about 5 nM to about 10 nM.

It will be appreciated that other 15-PGDH inhibitors can be used in the methods described herein. These other 15-PGDH inhibitors can include known 15-PGDH inhibitors including, for example, tetrazole compounds of formulas (I) and (II), 2-alkylideneaminooxyacetamide compounds of formula (I), heterocyclic compounds of formulas (VI) and (VII), and pyrazole compounds of formula (III) described in U.S. Patent Application Publication No. 2006/0034786 and U.S. Pat. No. 7,705,041; benzylidene-1,3-thiazolidine compounds of formula (I) described in U.S. Patent Application Publication No. 2007/0071699; phenylfurylmethylthiazolidine-2,4-dione and phenylthienylmethylthiazolidine-2,4-dione compounds described in U.S. Patent Application Publication No. 2007/0078175; thiazolidenedione derivatives described in U.S. Patent Application Publication No. 2011/0269954; phenylfuran, phenylthiophene, or phenylpyrrazole compounds described in U.S. Pat. No. 7,294,641, 5-(3,5-disubstituted phenylazo)-2-hydroxybenzene-acetic acids and salts and lactones described in U.S. Pat. No. 4,725,676, and azo compounds described in U.S. Pat. No. 4,889,846.

Still other examples of 15-PGDH inhibitors are described in the following publications: Seo S Y et al. Effect of 15-hydroxyprostaglandin dehydrogenase inhibitor on wound healing. Prostaglandins Leukot Essent Fatty Acids. 2015; 97:35-41. doi: 10.1016/j.plefa.2015.03.005. PubMed PMID: 25899574; Piao Y L et al. Wound healing effects of new 15-hydroxyprostaglandin dehydrogenase inhibitors. Prostaglandins Leukot Essent Fatty Acids. 2014; 91(6):325-32. doi: 10.1016/j.plefa.2014.09.011. PubMed PMID: 25458900; Choi D et al. Control of the intracellular levels of prostaglandin E(2) through inhibition of the 15-hydroxyprostaglandin dehydrogenase for wound healing. Bioorg Med Chem. 2013; 21(15):4477-84. doi: 10.1016/j.bmc.2013.05.049. PubMed PMID: 23791868; Wu Y et al. Synthesis and biological evaluation of novel thiazolidinedione analogues as 15-hydroxyprostaglandin dehydrogenase inhibitors. J Med Chem. 2011; 54(14):5260-4. Epub 2011/06/10. doi: 10.1021/jm200390u. PubMed PMID: 21650226; Duveau D Y et al. Structure-activity relationship studies and biological characterization of human NAD(+)-dependent 15-hydroxyprostaglandin dehydrogenase inhibitors. Bioorg Med Chem Lett. 2014; 24(2):630-5. doi: 10.1016/j.bmcl.2013.11.081. PubMed PMID: 24360556; PMCID: PMC3970110; Duveau D Y et al. Discovery of two small molecule inhibitors, ML387 and ML388, of human NAD+-dependent 15-hydroxyprostaglandin dehydrogenase. Probe Reports from the NIH Molecular Libraries Program. Bethesda (MD) 2010; Wu Y et al. Synthesis and SAR of thiazolidinedione derivatives as 15-PGDH inhibitors. Bioorg Med Chem. 2010; 18(4):1428-33. doi: 10.1016/j.bmc.2010.01.016. PubMed PMID: 20122835; Wu Y et al. Synthesis and biological evaluation of novel thiazolidinedione analogues as 15-hydroxyprostaglandin dehydrogenase inhibitors. J Med Chem. 2011; 54(14):5260-4. Epub 2011/06/10. doi: 10.1021/jm200390u. PubMed PMID: 21650226; Jadhav A et al. Potent and selective inhibitors of NAD+-dependent 15-hydroxyprostaglandin dehydrogenase (HPGD). Probe Reports from the NIH Molecular Libraries Program. Bethesda (MD) 2010; Niesen F H et al. High-affinity inhibitors of human NAD-dependent 15-hydroxyprostaglandin dehydrogenase: mechanisms of inhibition and structure-activity relationships. PLoS One. 2010; 5(11): e13719. Epub 2010/11/13. doi: 10.1371/journal-.pone.0013719. PubMed PMID: 21072165; PMCID: 2970562; Michelet, J. et al. Composition comprising at least one 15-PGDH inhibitor. US20080206320 A1, 2008; and Rozot, R et al. Care/makeup compositions comprising a 2-alkylideneaminooxyacetamide compound for stimulating the growth of the hair or eyelashes and/or slowing loss thereof. U.S. Pat. No. 7,396,525 B2, 2008.

The 15-PGDH inhibitors described herein can be used to treat, prevent, or reduce the symptoms or severity of the renal disorder, disease, and/or injury in a subject (e.g., a human subject) in need thereof. The 15-PGDH inhibitors are also useful in preventing the development of chronic kidney disease in a subject in need thereof. In certain embodiments, the 15-PGDH inhibitors are useful in preventing the development of chronic kidney disease in a subject in need thereof following an insult that can cause or causes acute kidney injury. In addition, the 15-PGDH inhibitors described herein can be used in methods for protecting a kidney from acute or chronic kidney injury in a subject in need thereof. Furthermore, the 15-PGDH inhibitors described herein can be used in methods for treating patients with renal insufficiency or renal failure, attributable at least in part to use of a drug or chemical.

Acute kidney injury is commonly divided into two major categories based on the type of insult. The first category is ischemic acute kidney injury (alternatively referred to as kidney hypoperfusion) and the second category is nephrotoxic acute kidney injury. The former results from impaired blood flow (kidney hypoperfusion) and oxygen delivery to the kidney; whereas, the latter results from a toxic insult to the kidney. Both of these categories of insults can lead to a secondary condition called acute tubular necrosis (ATN).

The most common causes of ischemic acute kidney injury are intravascular volume depletion, reduced cardiac output, systemic vasodilatation, and renal vasoconstriction. Intravascular volume depletion can be caused by hemorrhage (e.g., following surgery, postpartum, or trauma); gastrointestinal loss (e.g., from diarrhea, vomiting, nasogastric loss); renal losses (e.g., caused by diuretics, osmotic diuresis, diabetes insipidus); skin and mucous membrane losses (e.g., burns, hyperthermia); nephrotic syndrome; cirrhosis; or capillary leak. Reduced cardiac output can be due to cardiogenic shock, pericardial disease (e.g., restrictive, constrictive, tamponade), congestive heart failure, valvular heart disease, pulmonary disease (e.g., pulmonary hypertension, pulmonary embolism), or sepsis. Systemic vasodilation can be the result of cirrhosis, anaphylaxis, or sepsis. Finally, renal vasoconstriction can be caused by early sepsis, hepatorenal syndrome, acute hypercalcemia, drug-related (e.g., norepinephrine, vasopressin, nonsteroidal anti-inflammatory drugs, angiotensin-converting enzyme inhibitors, calcineurin inhibitors), or use of a radiocontrast agent. The 15-PGDH inhibitors described herein can be used to treat or reduce the symptoms or severity of acute kidney injury or any other kidney injury caused by any of the above mentioned causes of ischemic acute kidney injury. In addition, the 15-PGDH inhibitors thereof described herein can be used to prevent the development of acute kidney injury or any other kidney injury following exposure to the above-mentioned causes of ischemic acute kidney injury.

Nephrotoxic acute kidney injury is often associated with exposure to a nephrotoxin such as a nephrotoxic drug. Examples of nephrotoxic drugs include an antibiotic (e.g., aminoglycosides such as gentamicin), a chemotherapeutic agent (e.g., cis-platinum), a calcineurin inhibitor (e.g., tacrolimus, cyclosporine), cephalosporins such as cephaloridine, cyclosporin, pesticides (e.g., paraquat), environmental contaminants (e.g., trichloroethylene, dichloroacetylene), amphotericin B, puromcyin, aminonucleoside (PAN), a radiographic contrast agent (e.g., acetrizoate, diatrizoate, iodamide, ioglicate, iothalamate, ioxithalamate, metrizoate, metrizamide, iohexol, iopamidol, iopentol, iopromide, iodixanol, iobitridol, and ioversol), a nonsteroidal anti-inflammatory, an anti-retroviral, an immunosuppressant, an oncological drug, or an ACE inhibitor. A nephrotoxin can be, for example, a trauma injury, a crush injury, an illicit drug, analgesic abuse, a gunshot wound, or a heavy metal. The 15-PGDH inhibitors described herein can be used to treat or reduce the symptoms or severity of acute kidney injury or any other kidney injury caused by any of the above mentioned causes of nephrotoxic acute kidney injury. In addition, the 15-PGDH inhibitors described herein can be used to prevent the development of acute kidney injury or any other kidney injury following exposure to the above mentioned causes of nephrotoxic acute kidney injury.

In certain embodiments, the 15-PGDH inhibitors described herein can be used to prevent the development of ATN following exposure to an insult such as ischemia or nephrotoxins/nephrotoxic drugs. In certain embodiments, the 15-PGDH inhibitors described herein can be used to treat or reduce the symptoms or severity of ATN following ischemia or exposure to nephrotoxins/nephrotoxic drugs.

In certain embodiments, the 15-PGDH inhibitors described herein can be used to prevent a drop in glomerular filtration following ischemia or exposure to nephrotoxins/nephrotoxic drugs. In some embodiments, the 15-PGDH inhibitors can be used to prevent tubular epithelial injury and/or necrosis following ischemia or exposure to nephrotoxins/nephrotoxic drugs. In some embodiments, the 15-PGDH inhibitors can be used to decrease the microvascular permeability, improve vascular tone, and/or reduce inflammation of endothelial cells. In other embodiments, the 15-PGDH inhibitors described herein can be used to restore blood flow in the kidney following ischemia or exposure to nephrotoxins/nephrotoxic drugs. In further embodiments, the 15-PGDH inhibitors described herein can be used to prevent chronic renal failure.

The 15-PGDH inhibitors described herein can also be used to treat or prevent acute kidney injury resulting from surgery complicated by hypoperfusion. In certain specific embodiments, the surgery is one of cardiac surgery, major vascular surgery, major trauma, or surgery associated with treating a gunshot wound. In one embodiment, the cardiac surgery is coronary artery bypass grafting (CABG). In another embodiment, the cardiac surgery is valve surgery.

In some embodiments, the 15-PGDH inhibitors described herein can be used to treat or prevent acute kidney injury following organ transplantation such as kidney transplantation or heart transplantation.

In some embodiments, the 15-PGDH inhibitors described herein can be used to treat or prevent acute kidney injury following reduced effective arterial volume and kidney hypoperfusion.

In some embodiments, the 15-PGDH inhibitors described herein can be used to treat or prevent acute kidney injury in a subject who is taking medication (e.g., an anticholinergic) that interferes with normal emptying of the bladder. In certain embodiments, the 15-PGDH inhibitors described herein can be used to treat or prevent acute kidney injury in a subject who has an obstructed urinary catheter. In some embodiments, the 15-PGDH inhibitors described herein can be used to treat or prevent acute kidney injury in a subject who is taking a drug that causes crystalluria. In some embodiments, the 15-PGDH inhibitors described herein can be used to treat or prevent acute kidney injury in a subject who is taking a drug that causes or leads to myoglobinuria. In some embodiments, the 15-PGDH inhibitors described herein can be used to treat or prevent acute kidney injury in a subject who is taking a drug that causes or leads to cystitis.

In some embodiments, the 15-PGDH inhibitors described herein can be used to treat or prevent acute kidney injury in a subject who has benign prostatic hypertrophy or prostate cancer.

In some embodiments, the 15-PGDH inhibitors described herein can be used to treat or prevent acute kidney injury in a subject who has a kidney stone.

In some embodiments, the 15-PGDH inhibitors described herein can be used to treat or prevent acute kidney injury in a subject who has an abdominal malignancy (e.g., ovarian cancer, colorectal cancer).

In certain embodiments, the 15-PGDH inhibitors described herein can be used to treat or prevent acute kidney injury, wherein sepsis does not cause or result in the acute kidney injury.

Acute kidney injury typically occurs within hours to days following the original insult (e.g., ischemia or nephrotoxin insult). Thus, 15-PGDH inhibitors described herein can be administered before the insult, or within an hour to 30 days (e.g., 0.5 hours, 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 1 day, 2 days, 3 days, 4 days, 5 days, 6 days, 7 days, 8 days, 9 days, 10 days, 11 days, 12 days, 13 days, 15 days, 20 days, 25 days, 28 days, or 30 days) after the insult (e.g., a surgery or nephrotoxin insult described herein).

A subject can be determined to have, or have the risk of developing, acute kidney injury based on, e.g., the Risk Injury Failure Loss ESRD (RIFLE) criteria or the Acute Kidney Injury Network criteria (Bagshaw et al., Nephrol. Dial. Transplant., 23 (5):1569-1574 (2008); Lopes et al., Clin. Kidney J., 6(1):8-14 (2013)).

In certain embodiments, the methods of this disclosure involve determining measuring the levels of one or more of: serum, plasma or urine creatinine or blood urea nitrogen (BUN); measuring the levels of serum or urine neutrophil gelatinase-associated lipocalin (NGAL), serum or urine interleukin-18 (IL-18), serum or urine cystatin C, or urine KIM-1, compared to a healthy control subject, to assess whether the subject has, or has a risk of developing, acute kidney injury.

The efficacy of the 15-PGDH inhibitors can be assessed in various animal models. Animal models for acute kidney injury include those disclosed in e.g., Heyman et al., Contrin. Nephrol., 169:286-296 (2011); Heyman et al., Exp. Opin. Drug Disc., 4(6): 629-641 (2009); Morishita et al., Ren. Fail., 33(10):1013-1018 (2011); Wei Q et al., Am. J. Physiol. Renal Physiol., 303(11):F1487-94 (2012).

The efficacy of treatments may be measured by a number of available diagnostic tools, including physical examination, blood tests, measurements of blood systemic and capillary pressure, proteinuria (e.g., albuminuria), microscopic and macroscopic hematuria, assessing serum creatinine levels, assessment of the glomerular filtration rate, histological evaluation of renal biopsy, urinary albumin creatinine ratio, albumin excretion rate, creatinine clearance rate, 24-hour urinary protein secretion, and renal imaging (e.g., MRI, ultrasound).

In some embodiments, the amount of 15-PGDH inhibitor administered to the subject can be an amount effective to induce endogenous renal PGE2 levels of the subject.

In other embodiments, the amount of 15-PGDH inhibitor administered to the subject can be an amount effective to induce renal vasodilatation, enhance resistance to hypoxia, improve renal hemodynamics, decrease renal oxidative stress, reduce renal inflammation, and preserve renal function.

In other embodiments, the amount of 15-PGDH inhibitor administered to the subject is an amount effective to reduce malondialdehyde (MDA) and NGAL levels, attenuate medulla tubular damage, reduce medulla acute tubular necrosis (ATN) and apoptosis, reduces induction of high-mobility group box 1 (HMGB1) and proinflammatory cytokines, induce renal EP4 PGE2 receptors and A2A adenosine receptors in vascular smooth muscle cells that regulate renal arterioles, increase renal cAMP, AMP, and adenosine levels, and/or inhibit induction of creatinine and KIM-1.

In some embodiments, the pharmaceutical composition may be formulated into a parenteral or oral dosage form. The solid dosage form for oral administration may be manufactured by adding excipient, if necessary, together with binder, disintegrants, lubricants, coloring agents, and/or flavoring agents, to the 15-PGDH inhibitors and shaping the resulting mixture into the form of tablets, sugar-coated pills, granules, powder or capsules. The additives that can be added in the composition may be ordinary ones in the art. For example, examples of the excipient include lactose, sucrose, sodium chloride, glucose, starch, calcium carbonate, kaolin, microcrystalline cellulose, silicate and the like. Exemplary binders include water, ethanol, propanol, sweet syrup, sucrose solution, starch solution, gelatin solution, carboxymethylcellulose, hydroxypropyl cellulose, hydroxypropyl starch, methylcellulose, ethylcellulose, shellac, calcium phosphonate and polypyrrolidone. Examples of the disintegrant include dry starch, sodium arginate, agar powder, sodium bicarbonate, calcium carbonate, sodium lauryl sulfate, stearic monoglyceride and lactose. Further, purified talc, stearates, sodium borate, and polyethylene glycol may be used as a lubricant; and sucrose, bitter orange peel, citric acid, tartaric acid, may be used as a flavoring agent. In some embodiments, the pharmaceutical composition can be made into aerosol formulations (e.g., they can be nebulized) to be administered via inhalation.

The 15-PGDH inhibitors described herein may be combined with flavoring agents, buffers, stabilizing agents, and the like and incorporated into oral liquid dosage forms such as solutions, syrups or elixirs in accordance with conventional methods. One example of the buffers may be sodium citrate. Examples of the stabilizing agents include tragacanth, acacia and gelatin.

In some embodiments, the 15-PGDH inhibitors may be incorporated into an injection dosage form, for example, for a subcutaneous, intramuscular or intravenous route by adding thereto pH adjusters, buffers, stabilizing agents, relaxants, topical anesthetics. Examples of the pH adjusters and the buffers include sodium citrate, sodium acetate and sodium phosphate. Examples of the stabilizing agents include sodium pyrosulfite, EDTA, thioglycolic acid and thiolactic acid. The topical anesthetics may be procaine HCl, lidocaine HCl and the like. The relaxants may be sodium chloride, glucose and the like.

In other embodiments, the 15-PGDH inhibitors may be incorporated into suppositories in accordance with conventional methods by adding thereto pharmaceutically acceptable carriers that are known in the art, for example, polyethylene glycol, lanolin, cacao butter or fatty acid triglycerides, if necessary, together with surfactants such as Tween.

The pharmaceutical composition may be formulated into various dosage forms as discussed above and then administered through various routes including an oral, inhalational, transdermal, subcutaneous, intravenous or intramuscular route. The dosage can be a pharmaceutically or therapeutically effective amount.

Therapeutically effective dosage amounts of the 15-PGDH inhibitor may be present in varying amounts in various embodiments. For example, in some embodiments, a therapeutically effective amount of the 15-PGDH inhibitor may be an amount ranging from about 10-1000 mg (e.g., about 20 mg-1,000 mg, 30 mg-1,000 mg, 40 mg-1,000 mg, 50 mg-1,000 mg, 60 mg-1,000 mg, 70 mg-1,000 mg, 80 mg-1,000 mg, 90 mg-1,000 mg, about 10-900 mg, 10-800 mg, 10-700 mg, 10-600 mg, 10-500 mg, 100-1000 mg, 100-900 mg, 100-800 mg, 100-700 mg, 100-600 mg, 100-500 mg, 100-400 mg, 100-300 mg, 200-1000 mg, 200-900 mg, 200-800 mg, 200-700 mg, 200-600 mg, 200-500 mg, 200-400 mg, 300-1000 mg, 300-900 mg, 300-800 mg, 300-700 mg, 300-600 mg, 300-500 mg, 400 mg-1,000 mg, 500 mg-1,000 mg, 100 mg-900 mg, 200 mg-800 mg, 300 mg-700 mg, 400 mg-700 mg, and 500 mg-600 mg). In some embodiments, the 15-PGDH inhibitor is present in an amount of or greater than about 10 mg, 50 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg. In some embodiments, the 15-PGDH inhibitor is present in an amount of or less than about 1000 mg, 950 mg, 900 mg, 850 mg, 800 mg, 750 mg, 700 mg, 650 mg, 600 mg, 550 mg, 500 mg, 450 mg, 400 mg, 350 mg, 300 mg, 250 mg, 200 mg, 150 mg, or 100 mg.

In other embodiments, a therapeutically effective dosage amount may be, for example, about 0.001 mg/kg weight to 500 mg/kg weight, e.g., from about 0.001 mg/kg weight to 400 mg/kg weight, from about 0.001 mg/kg weight to 300 mg/kg weight, from about 0.001 mg/kg weight to 200 mg/kg weight, from about 0.001 mg/kg weight to 100 mg/kg weight, from about 0.001 mg/kg weight to 90 mg/kg weight, from about 0.001 mg/kg weight to 80 mg/kg weight, from about 0.001 mg/kg weight to 70 mg/kg weight, from about 0.001 mg/kg weight to 60 mg/kg weight, from about 0.001 mg/kg weight to 50 mg/kg weight, from about 0.001 mg/kg weight to 40 mg/kg weight, from about 0.001 mg/kg weight to 30 mg/kg weight, from about 0.001 mg/kg weight to 25 mg/kg weight, from about 0.001 mg/kg weight to 20 mg/kg weight, from about 0.001 mg/kg weight to 15 mg/kg weight, from about 0.001 mg/kg weight to 10 mg/kg weight.

In still other embodiments, a therapeutically effective dosage amount may be, for example, about 0.0001 mg/kg weight to 0.1 mg/kg weight, e.g. from about 0.0001 mg/kg weight to 0.09 mg/kg weight, from about 0.0001 mg/kg weight to 0.08 mg/kg weight, from about 0.0001 mg/kg weight to 0.07 mg/kg weight, from about 0.0001 mg/kg weight to 0.06 mg/kg weight, from about 0.0001 mg/kg weight to 0.05 mg/kg weight, from about 0.0001 mg/kg weight to about 0.04 mg/kg weight, from about 0.0001 mg/kg weight to 0.03 mg/kg weight, from about 0.0001 mg/kg weight to 0.02 mg/kg weight, from about 0.0001 mg/kg weight to 0.019 mg/kg weight, from about 0.0001 mg/kg weight to 0.018 mg/kg weight, from about 0.0001 mg/kg weight to 0.017 mg/kg weight, from about 0.0001 mg/kg weight to 0.016 mg/kg weight, from about 0.0001 mg/kg weight to 0.015 mg/kg weight, from about 0.0001 mg/kg weight to 0.014 mg/kg weight, from about 0.0001 mg/kg weight to 0.013 mg/kg weight, from about 0.0001 mg/kg weight to 0.012 mg/kg weight, from about 0.0001 mg/kg weight to 0.011 mg/kg weight, from about 0.0001 mg/kg weight to 0.01 mg/kg weight, from about 0.0001 mg/kg weight to 0.009 mg/kg weight, from about 0.0001 mg/kg weight to 0.008 mg/kg weight, from about 0.0001 mg/kg weight to 0.007 mg/kg weight, from about 0.0001 mg/kg weight to 0.006 mg/kg weight, from about 0.0001 mg/kg weight to 0.005 mg/kg weight, from about 0.0001 mg/kg weight to 0.004 mg/kg weight, from about 0.0001 mg/kg weight to 0.003 mg/kg weight, from about 0.0001 mg/kg weight to 0.002 mg/kg weight. In some embodiments, the therapeutically effective dose may be 0.0001 mg/kg weight, 0.0002 mg/kg weight, 0.0003 mg/kg weight, 0.0004 mg/kg weight, 0.0005 mg/kg weight, 0.0006 mg/kg weight, 0.0007 mg/kg weight, 0.0008 mg/kg weight, 0.0009 mg/kg weight, 0.001 mg/kg weight, 0.002 mg/kg weight, 0.003 mg/kg weight, 0.004 mg/kg weight, 0.005 mg/kg weight, 0.006 mg/kg weight, 0.007 mg/kg weight, 0.008 mg/kg weight, 0.009 mg/kg weight, 0.01 mg/kg weight, 0.02 mg/kg weight, 0.03 mg/kg weight, 0.04 mg/kg weight, 0.05 mg/kg weight, 0.06 mg/kg weight, 0.07 mg/kg weight, 0.08 mg/kg weight, 0.09 mg/kg weight, or 0.1 mg/kg weight. The effective dose for a particular individual can be varied (e.g., increased or decreased) over time, depending on the needs of the individual.

In some embodiments, a therapeutically effective dosage may be a dosage of 10 μg/kg/day, 50 μg/kg/day, 100 μg/kg/day, 250 μg/kg/day, 500 μg/kg/day, 1000 μg/kg/day or more. In various embodiments, the amount of the 15-PGDH inhibitor or pharmaceutical salt thereof is sufficient to provide a dosage to a patient of between 0.01 μg/kg and 10 μg/kg; 0.1 μg/kg and 5 μg/kg; 0.1 μg/kg and 1000 μg/kg; 0.1 μg/kg and 900 μg/kg; 0.1 μg/kg and 900 μg/kg; 0.1 μg/kg and 800 μg/kg; 0.1 μg/kg and 700 μg/kg; 0.1 μg/kg and 600 μg/kg; 0.1 μg/kg and 500 μg/kg; or 0.1 μg/kg and 400 μg/kg.

Various embodiments may include differing dosing regimen. In some embodiments, the 15-PGDH inhibitor can be administered via continuous infusion. In some embodiments, the continuous infusion is intravenous. In other embodiments, the continuous infusion is subcutaneous. The dosing regimen for a single subject need not be at a fixed interval, but can be varied over time, depending on the needs of the subject.

In one aspect, a pharmaceutical composition comprising an effective amount of the 15-PGDH inhibitor is administered at least twice. In another aspect, a pharmaceutical composition is administered at least five times. In yet another aspect, a pharmaceutical composition is administered at least 10 times. One of ordinary skill in the art can determine how often to administer the composition based on the particular disease or disorder being treated or how the subject has responded to prior treatments. One of ordinary skill in the art can also determine when to administer a treatment relative to the time that renal injury occurs, including before, after, or both.

In one embodiment, the subject is treated with the 15-PGDH inhibitor prior to the renal injury. In one aspect, the subject can be treated starting at least several days before the injury or as close to several minutes before the renal injury. For example, the 15-PGDH inhibitor therapy can begin at about 2 hours, 8 hours, 24 hours, or 26 hours prior to ischemic reperfusion injury. One of ordinary skill in the art will appreciate that the 15-PGDH inhibitor can be administered at varying times and not just at about 2, 8, 24, or 26 hours prior to the renal injury. In one aspect, the range of time for treating prior to the renal injury can be from about 1.0 minutes to about 72 hours. In another aspect, the range of time for treating prior to the renal injury can be from about 10 minutes to about 48 hours. In another aspect, the range of time for treating prior to the renal injury event can be from about 30 minutes to about 24 hours.

In one embodiment, the subject is treated with the 15-PGDH inhibitor after the renal injury event or both before and after as described above. In one aspect, the subject can be treated starting immediately after such as several minutes after the renal injury. For example, the 15-PGDH inhibitor therapy can begin at about 30 minutes, 2 hours, 8 hours, 24 hours, or 48 hours after the ischemic reperfusion injury. One of ordinary skill in the art will appreciate that the 15-PGDH inhibitor can be administered at varying times as well.

Example 1

In this Example, we examined SW033291, a potent small-molecule inhibitor of 15-PGDH, for effects in the kidney, demonstrating that SW033291 shows potent in vivo activity in increasing endogenous renal $PGE_2$, in mediating renal vasodilation, and in conferring renal protection against ischemic acute kidney injury (AKI).

Materials and Methods

Animals

Male C57/BL6 mice (10 wk) were purchased from Orient Bio. The care of and experimental procedures involving animals were approved by the Institutional Animal Care and Use Committee of Inje University (protocol no. 2016-010).

Induction of Renal IRI

Briefly, mice were anesthetized with isoflurane using a vaporizer, and bilateral renal arteries were clamped for 30 min (2, 49). After the ischemic time, clamps were released to induce blood reperfusion. SW033291 (5 mg/kg, Cayman, Ann Arbor, MI), indomethacin (5 mg/kg, Sigma-Aldrich), or vehicle [10% ethanol, 5% cremophor EL, and 85% D5W (5% dextrose in water)] were intraperitoneally administered three times at 1 h before, immediately after, and 12 h after AKI. Serum and kidney tissue were collected 24 h after renal IRI. These dose levels of SW033291 and indomethacin have been demonstrated as biologically effective in C57/BL6 mice in our prior published study. As an additional comparator, celecoxib (100 mg/kg, Pfizer), a selective COX-2 inhibitor, was also orally administered two times at 2 h before and 12 h after renal IRI. Additionally, an $EP_4$ receptor antagonist, ONO-AE3-208 (10 mg/kg, Cayman), was administered for three doses, either concurrently with SW033291 or individually on the same schedule.

Measurement of $PGE_2$ Levels and Renal Function

After reperfusion for 24 h, kidney tissues (~20 mg) were homogenized in cold PBS containing indomethacin (10 μg/mL) and then centrifuged for 10 min at 12,000 rpm. Protein concentrations of supernatant were determined by BCA assay (ThermoFisher Scientific, Rockford, IL). The $PGE_2$ level was measured using a $PGE_2$ ELISA kit (R&D Systems, Minneapolis, MN) in triplicate. $PGE_2$ levels were expressed as nanograms of $PGE_2$ per milligram of protein. Renal function was assessed by determining the serum levels of blood urea nitrogen (BUN; Abcam), serum creatinine (Agilent 6410 LC-MS/MS, Agilent, Santa Clara, CA), lipocalin-2 (R&D Systems), and kidney injury molecule-1 (KIM-1; R&D Systems) after reperfusion for 24 h. Measurement of serum creatinine was by HPLC. Serum creatinine was assessed using an Agilent 6410 LC-MS/MS system coupled with an Agilent 1200 series HPLC system (Agilent). The sample preparation for serum creatinine was that 50 μL of serum samples were mixed with 100 μL of acetonitrile that contained creatinine-d3 as an internal standard (5 μg/mL). The mixture was centrifuged at 13,000 rpm for 10 min after vigorous vortex, and 1 μL of supernatant was then injected into the LC-MS/MS system. The chromatography separation was performed on a Hypersil GOLD C18 column (150×2.1 mm, 3 m, Thermo Scientific) using a mobile phase of 0.1% formic acid solution and acetonitrile [70:30 (vol/vol)]. The flow rate was 0.2 mL/min. Electrospray ionization was performed in the positive ion mode. The capillary voltage was set at 4,000 V. Nitrogen as the nebulizing gas was set at 15 psi, and the drying gas temperature was set at 300° C., with a flow rate of 6 L/min. The multiple-reaction monitoring mode using specific precursor/production transition was used for quantification. Detection of ions was performed by monitoring m/z 114.1→44.1 for creatinine and 117.1→77.1 for creatinine-d3. The collision energies were 10 and 15 eV for creatinine and creatinine-d3, respectively. The peak areas for all analytes were integrated automatically using Agilent Mass Hunter Analysis software (version B.01.04).

Necrotic and Apoptotic Cell Death Assays

To evaluate necrosis, 5-μm-thick paraffin sections were stained with hematoxylin and eosin. Tubular injury of individual slides was scored semi-quantitatively according to a scoring system by a pathologist in a blinded manner. The scoring system was as follows: 0, no damage; 1, patchy isolated unicellular necrosis; 2, tubular necrosis <25%; 3, tubular necrosis 25-50%; and 4, tubular necrosis >50%. To analyze the frequency of apo ptosis, 5-μm-thick paraffin sections were subjected to a TUNEL assay (Millipore, Temecula, CA) according to the manufacturer's protocol. TUNEL-positive cells were counted in at least five separate fields (64 magnification) in the outer medulla, and the apoptosis index (in %, number of apoptosis cells/total number of cells) was calculated using GENASIS software.

Measurement of Proinflammatory Cytokine Levels

Inflammatory cytokine mRNA and protein levels were measured by real-time PCR and ELISA. Kidney tissue and serum were harvested after reperfusion for 24 h. Total RNA was extracted from frozen kidney tissue using TRIzol reagent (ThermoFisher Scientific) according to the manufacturer's protocol. RNA was converted to cDNA using oligo-dT primers. IL-17, TNF-α, and IL-1b mRNA levels were determined by real-time PCR. Serum IL-17 (R&D Systems), TNF-α (R&D Systems), and IL-10 (R&D Systems) were measured using commercial ELISA kits according to the manufacturer's instructions.

Assessment of Renal Vasodilation

The inner arteriolar area of the outer medulla was determined using α-smooth muscle actin (α-SMA)-stained sections. Kidneys were removed without perfusion under inhalational isoflurane anesthesia, divided into three pieces horizontally, immediately fixed in 10% formalin, and then embedded in paraffin. The inner area of α-SMA-positive vessels in the outer medulla was measured using ImageJ. The results are expressed as average areas of renal arteries in the outer medulla. As a surrogate for RBF, we used noninvasive laser Doppler flowmetry (periflux system 5000, Perimed) to measure flux, placing laser-Doppler probes at a fixed position on the kidney surface and recording renal cortical measurements. Renal-Doppler flux (RDF) was measured before (1 h after administration of vehicle, indomethacin, and SW033291), during, and 24 h after renal IRI. The relative increase represents the percent increase in RDF from baseline to peak for each test.

Measurement of cAMP, AMP, and Adenosine Levels

After reperfusion for 24 h, kidney tissues were harvested, homogenized in 10 volumes of 0.1 M HCl, and centrifuged for 10 min at 12,000 rpm. cAMP levels in kidney tissues and serum were measured using a cAMP Complete ELISA kit (Enzo Life Science, Farmingdale, NY). AMP and adenosine in kidney tissue were assessed by Agilent 6410 LC-MS/MS. Serum adenosine was measured using an assay kit (Abnova, Walnut, CA).

Assessment of $PGE_2$ and Adenosine Receptor $PGE_2$ receptors (EP1, $EP_2$, $EP_3$, and $EP_4$) and adenosine$A_{2A}$ receptor mRNA levels were deter-mined by real-time PCR. Their protein levels were determined by Western blot assay and immunofluorescence analysis.

Measurement of Reactive Oxygen Species Levels

Reactive oxygen species (ROS) levels were determined by measurement of malondialdehyde (MDA), the end product of lipid peroxidation in kidney lysates. Free MDA reacts with thiobarbituric acid (TBA) at 95° C. to generate an MDA-TBA adduct, which can be quantified colorimetrically at a wavelength of 532 nm. MDA levels were measured in kidney lysates using a lipid peroxidation (MDA) assay kit (Abcam, Cambridge, UK). Results were corrected for total protein level and are expressed as M MDA/g protein.

Statistical Analysis

Statistical analyses were performed with one-way ANOVA followed by a Bonferroni post hoc test when three or more experimental groups were compared. Data are presented as means±SE, using Student's t-test for two-group analysis. Values of $P<0.05$ were considered indicative of statistical significance.

Results

15-PGDH Inhibition Ameliorates Renal Dysfunction in Mice with Ischemic AKI

Figure 1B:
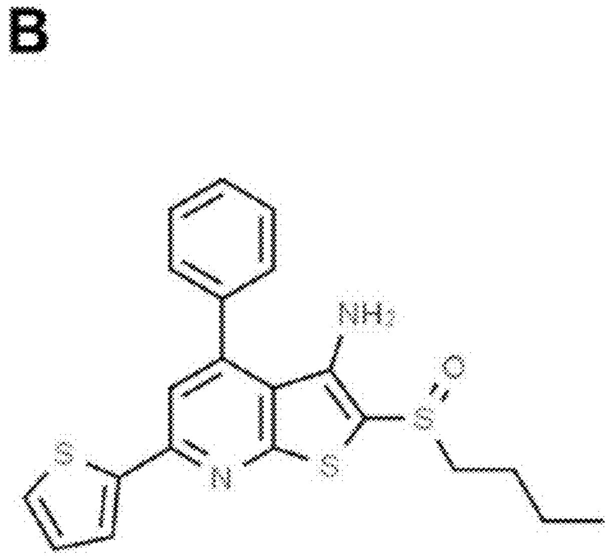
Figure 1C:
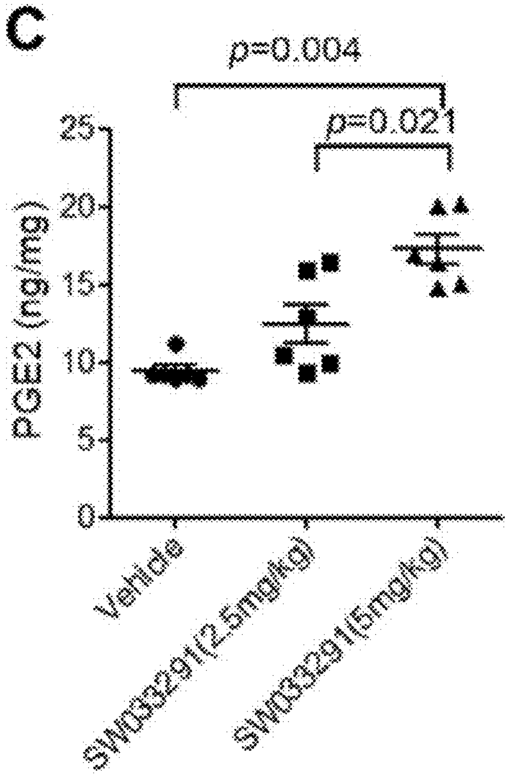
Figure 1D:
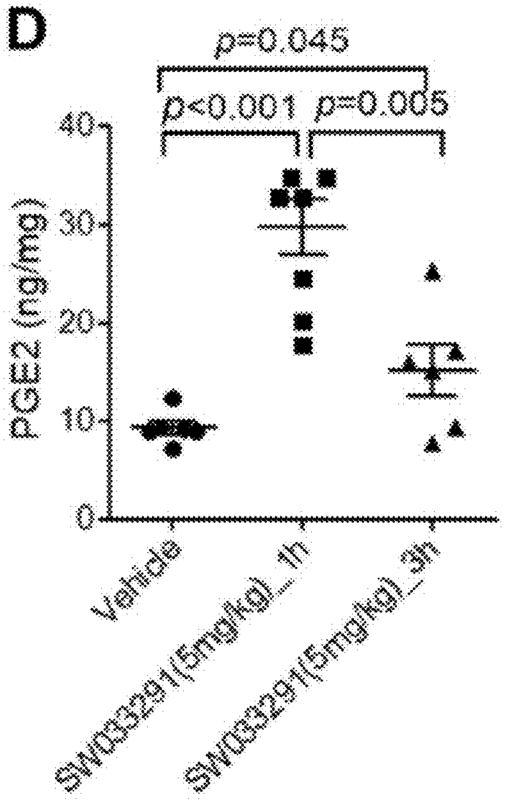
Figure 1E:
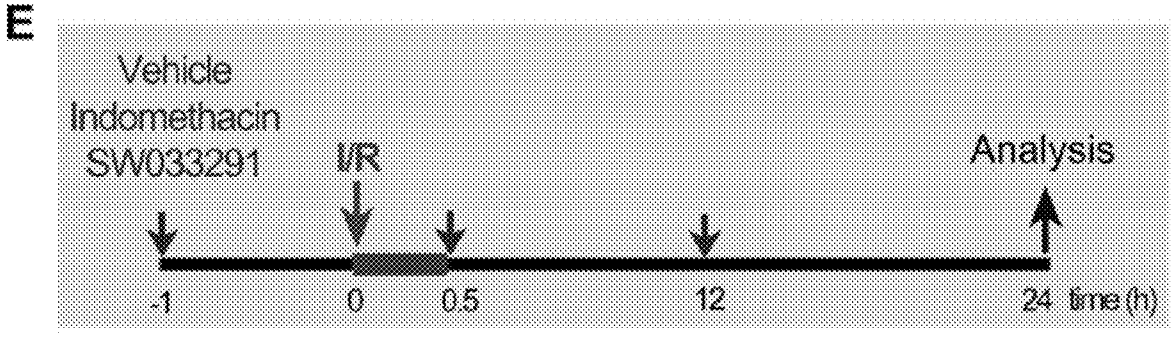

Endogenous $PGE_2$ levels are decreased by blocking $PGE_2$ synthesis with NSAIDs that inhibit COX-1 and/or COX-2 but are increased by blocking $PGE_2$ degradation by inhibiting 15-PGDH (FIG. 1A). SW033291 is a potent and specific chemical inhibitor of 15-PGDH with a subnanomolar $IC_{50}$ value (FIG. 1B). Treatment of mice with SW033291 induced a dose-dependent increase in renal $PGE_2$ at 3 h after intraperitoneal injection of 2.5 or 5 mg/kg SW033291 (FIG. 1C) and showed a peak at 1 h with 5 mg/kg SW033291 tripling endogenous renal $PGE_2$ (FIG. 1D). To interrogate effects of inhibition of 15-PGDH on protection from IRI, mice were subjected to 30 min of IRI and administered three doses of SW033291 (IRI-SW033291) versus vehicle (IRI-vehicle), versus indomethacin (IRI-indomethacin), or versus celecoxib (IRI-celecoxib). Treatments were administered beginning 1 h before, immediately after, and 12 h after renal IRI (FIG. 1E) (with the exception that the celecoxib dose was administered 2 h before and 12 h after renal IRI). IRI-vehicle mice exhibited significant ischemic AKI, as indicated by increases in BUN, creatinine, neutrophil gelatinase-associated lipocalin (NGAL), and KIM-1 (FIG. 1, F-I). However, IRI-SW033291 markedly protected the kidney from IRI, significantly reducing BUN, creatinine, NGAL, and KIM-1 compared with IRI-vehicle mice (FIG. 1, F-I). In contrast, inhibition of endogenous $PGE_2$ production with administration of either indomethacin or celecoxib significantly aggravated IRI, as reflected by the increase in BUN of the indomethacin-treated group (FIG. 1F) and the increase of BUN and creatinine in the celecoxib-treated group. In summary, inhibition of 15-PGDH increased endogenous renal $PGE_2$ levels and ameliorated renal dysfunction from ischemic AKI compared with renal dysfunction being worsened by inhibiting COX-1 and COX-2 with indomethacin or COX-2 alone with celecoxib.

Figure 2A:
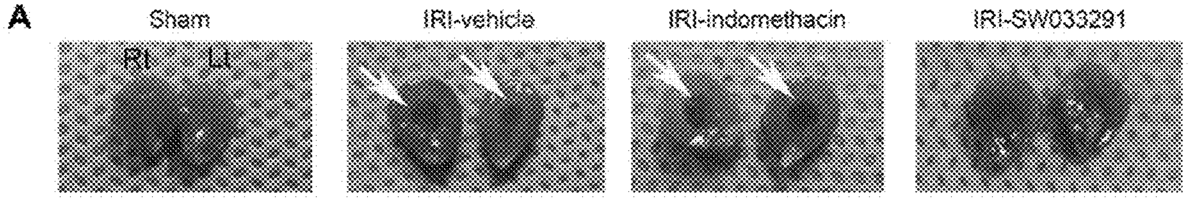
FIGS. 2(A-E) illustrate images and plots showing 15-hydoxyprostaglandin dehydrogenase inhibition ameliorates renal tubular cell death in mice with ischemic acute kidney injury. Before and after renal ischemia-reperfusion injury (IRI), mice were injected intraperitoneally three times with vehicle, SW033291 (5 mg/kg), or indomethacin (5 mg/kg). Assessments were performed at 24 h after renal IRI. A: representative gross appearance of the right (Rt) and left (Lt) kidneys of mice injected with vehicle (IRI-vehicle), indomethacin (IRI-indomethacin), or SW033291 (IRI-SW033291) before and after renal IRI. Vascular congestion in the renal medulla is indicated by white arrows. B: representative image of tubular injury in the outer zone of the renal medulla (hematoxylin and eosin staining). Scale bars in the enlarged images=50 μm; scale bars in insets=500 μm. C: statistical analysis of tubular injury scores (n=20 per group). D: representative images of apoptosis in the outer zone of the renal medulla (TUNEL staining). Scale bar in the enlarged images=25 μm; scale bars in insets=500 μm; E: statistical analysis of apoptosis (n=20 per group). Data are presented as means±SE. Analysis was performed using Student's t test.
Figure 2B:
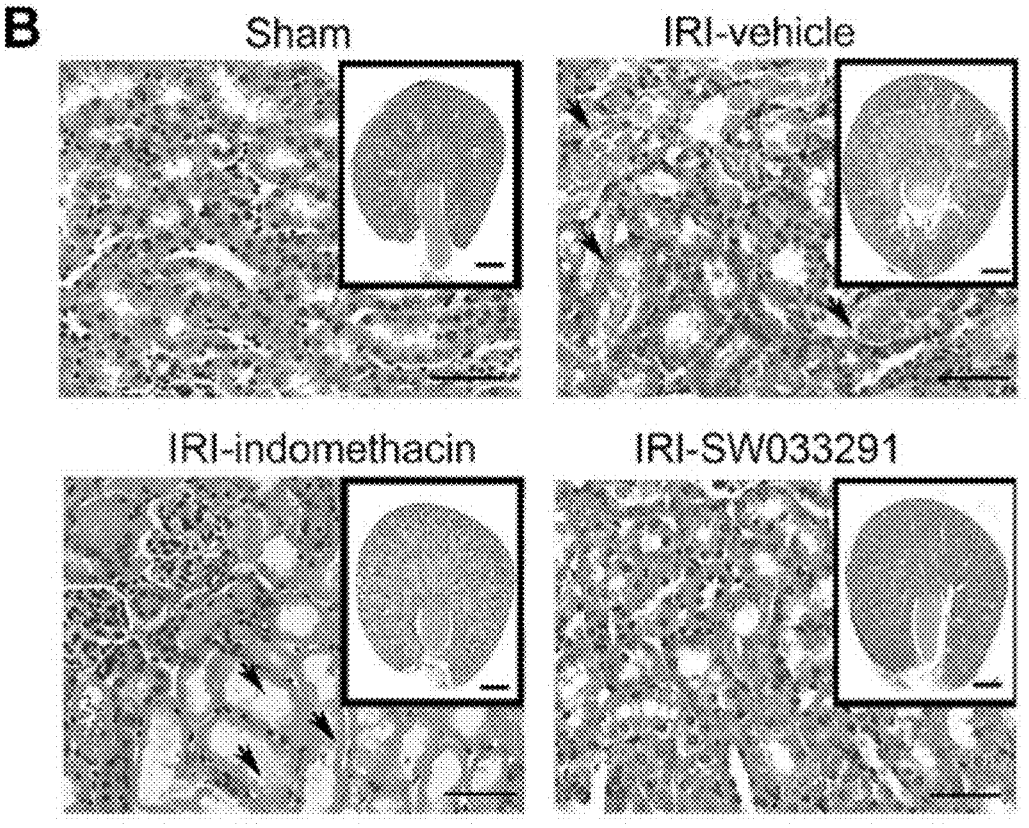
Figure 2C:
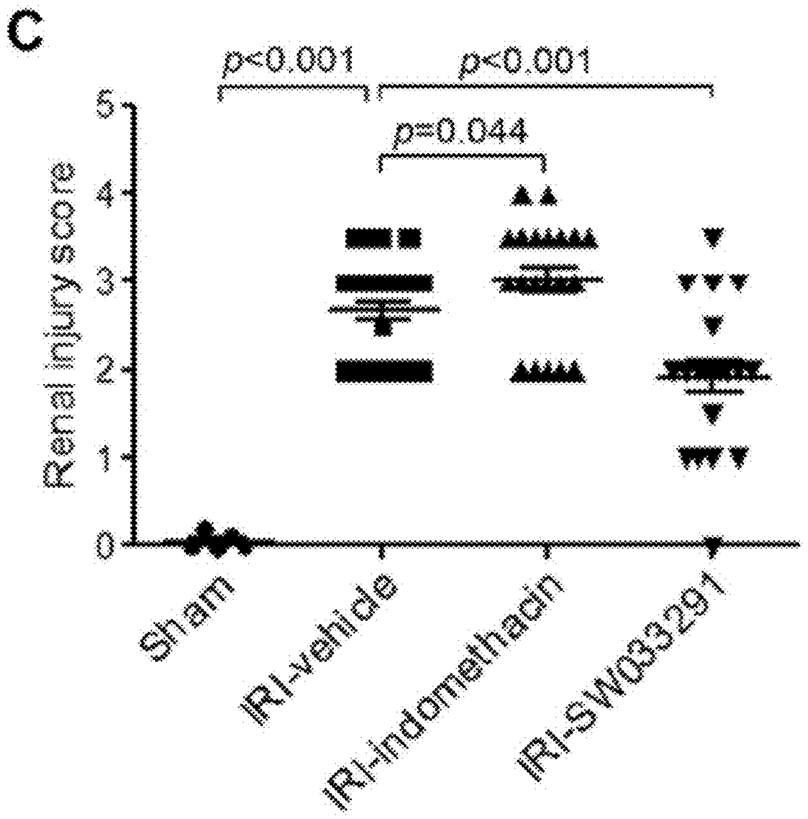
Figure 2D:
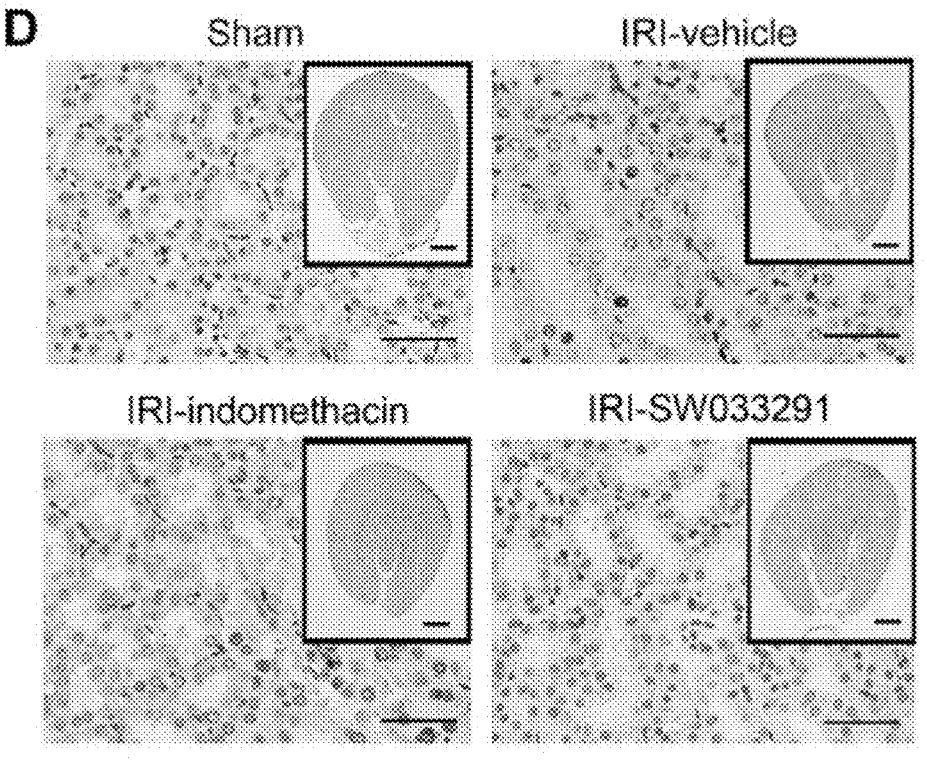
Figure 2E:
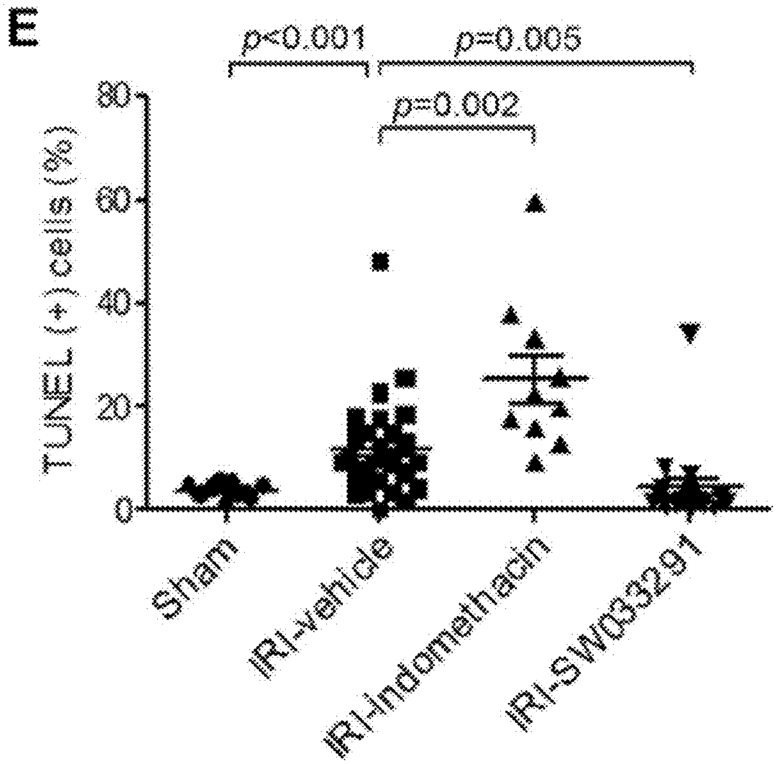

15-PGDH Inhibition Attenuates Renal Necrosis and Apoptosis in Mice with Ischemic AKI During renal IRI, tubular epithelial cells undergo injury, apoptosis, and acute tubular necrosis. Postischemic congestion that persists in the outer medulla further exacerbates renal injury by worsening hypoxia. By gross pathology, IRI-vehicle mice showed increased tissue congestion in the outer medulla versus sham mice. This congestion was ameliorated by treatment with SW033291 but was worsened by treatment with indomethacin (FIG. 2A). Histopathological assessment of IRI-vehicle revealed features of acute tubular damage with tubular dilatation, extensive tubular necrosis, and apoptosis (FIG. 2, B-E). In contrast, SW033291 treatment markedly alleviated renal injury, reducing the histological renal injury score and the count of TUNEL-positive apoptotic cells (FIGS. 2, C and E). Additionally, high-mobility group box 1 (HMGB1) promotes kidney damage after IRI and induces proinflammatory cytokines. Similarly, compared with IRI-vehicle mice, SW033291 treatment reduced HMGB1 levels (FIGS. 3, G and H) and blocked induction of IL-17, TNF-α, and IL-10 (protein only) (FIG. 3, A-F). In contrast to the effects of SW033291, treatment of IRI mice with indomethacin increased HMGB1 (FIGS. 3, G and H). In summary, prophylactic SW0333291 protects from AKI, reducing tubular damage in the outer medulla, ATN, apoptosis, HMGB1, and downstream inflammatory cytokines that promote kidney damage after IRI.

15-PGDH Inhibition Induces Renal Vasodilatation in the Outer Medulla Concomitant with Induction of a $PGE_2/EP_4$ Receptor and Adenosine/$A_{2A}$ Receptor Signaling Pathway To investigate the mechanism of the renal protective effect of the 15-PGDH inhibitor shown in FIGS. 1-3, we interrogated the effects of inhibition of 15-PGDH on renal hemodynamics using measurement of renal cortical Doppler flux as a surrogate to infer RBF. SW033291 increased inferred RBF above baseline within 1 h after the first injection, reflecting elevated RBF just before when AKI was initiated (FIGS. 4, A and B). These benefits persisted throughout the 24-h course of study. Thus, at 24 h following IRI, vehicle-treated mice demonstrated a nearly 40% decrease in RDF-inferred RBF (vs. sham mice) (FIGS. 4, A and B), whereas, in marked contrast, treatment of mice with SW033291 completely preserved RDF-inferred RBF at this time point (FIGS. 4, A and B). SW033291 increases in cortical RDF-inferred RBF at 24 h were paralleled by findings of significantly increased renal arteriolar area in the outer medulla of SW033291-treated mice at 24 h post-IRI (compared with both post-IRI-vehicle-treated mice and sham mice; FIGS. 4, C and D). Again, in contrast, both indomethacin or celecoxib administration reduced RDF (FIGS. 4, A and B). In summary, these findings suggest that SW033291 increased RBF via a PGE2-mediated vasodilatory mechanism.

Figure 4A:
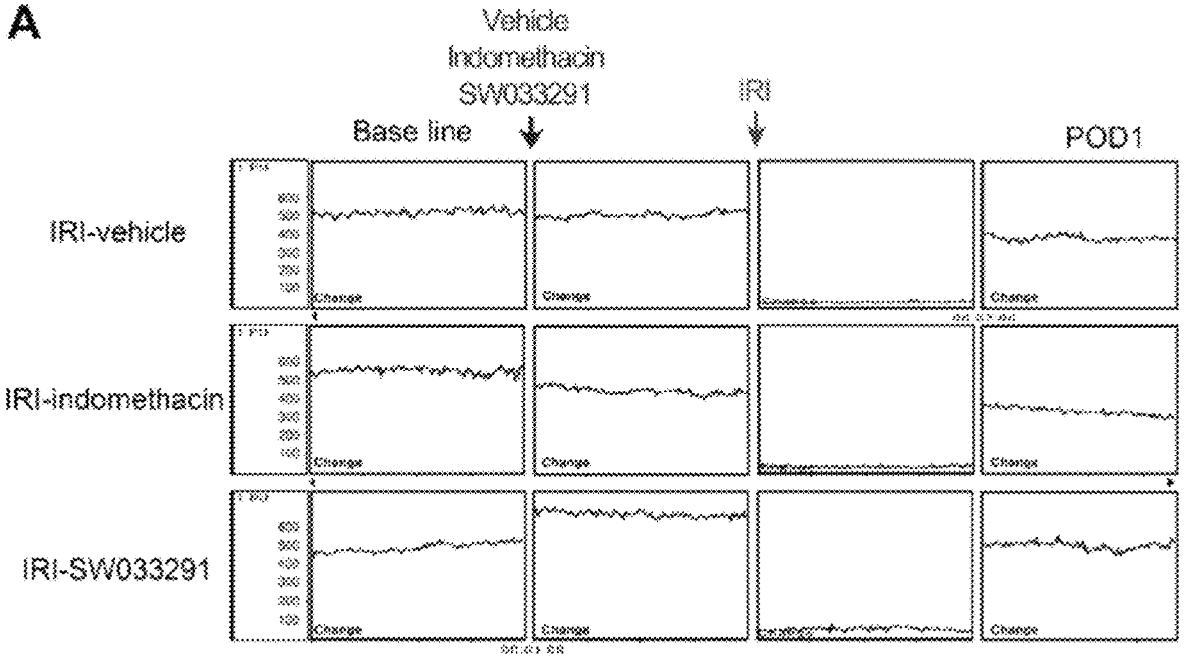
FIGS. 4(A-D) illustrate plots and images showing 15-hydoxyprostaglandin dehydrogenase inhibition induces renal vasodilation in the outer medulla of mice with ischemic acute kidney injury. To quantify vasodilation, the inner arteriolar area in the outer medulla was identified by α-smooth muscle actin staining. Assessments were performed at postoperative day 1 (POD1), 24 h after renal ischemia-reperfusion injury (IRI). A: representative images of the change in renal blood flow, as assessed by renal Doppler flux, with administration of vehicle, indomethacin, and SW033291. B: statistical analysis of renal blood flow in sham animals at time 0, in sham animals administered SW033291 (sham-SW033291) at 1 h post-administration of drug, and in cohorts subject to IRI and administered vehicle, indomethacin, and SW033291, which were then assayed at 24 h post-IRI. C: representative images of an arteriole in the outer zone of the renal medulla. Zoomed images are enlargements of the outlined areas. Scale bars in the enlarged images=50 μm; scale bars in insets=500 μm. D: statistical analysis of the inner arteriolar area of the outer medulla. Data are presented as means±SE. Analysis was performed using Student's t test.
Figure 4B:
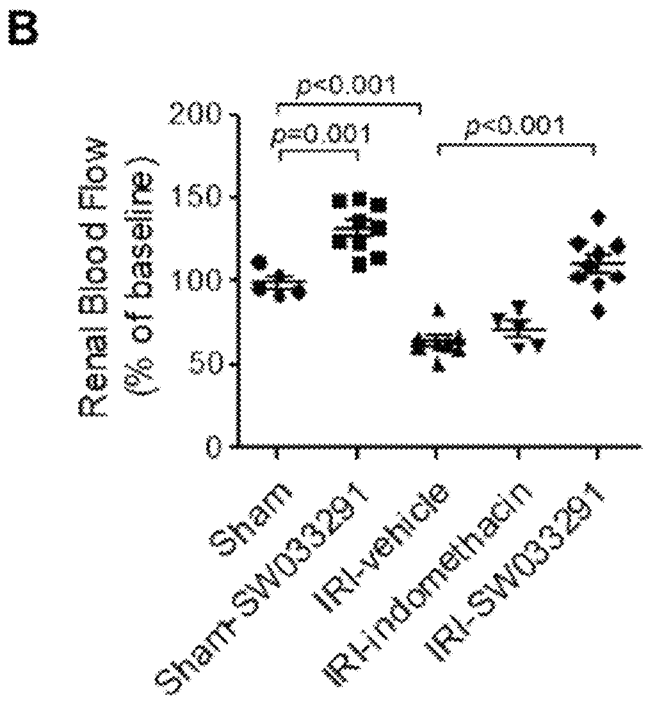
Figure 4C:
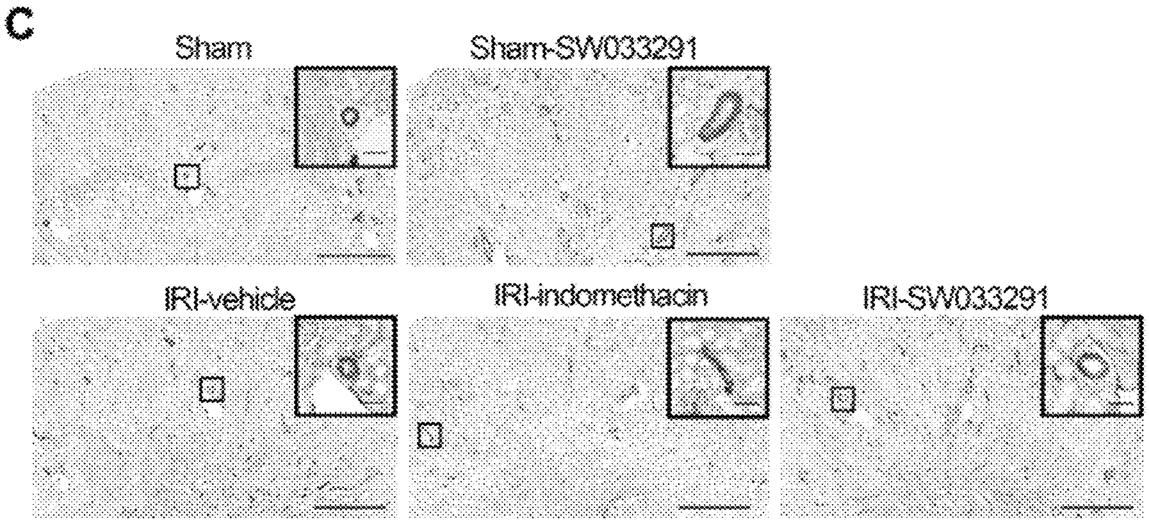
Figure 4D:
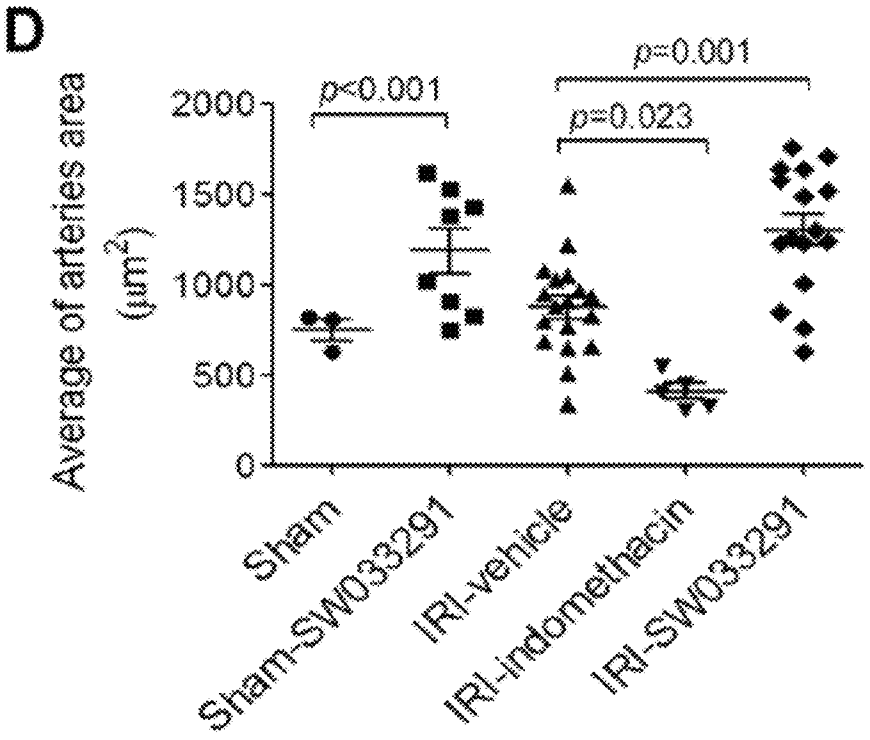
Figure 5A:
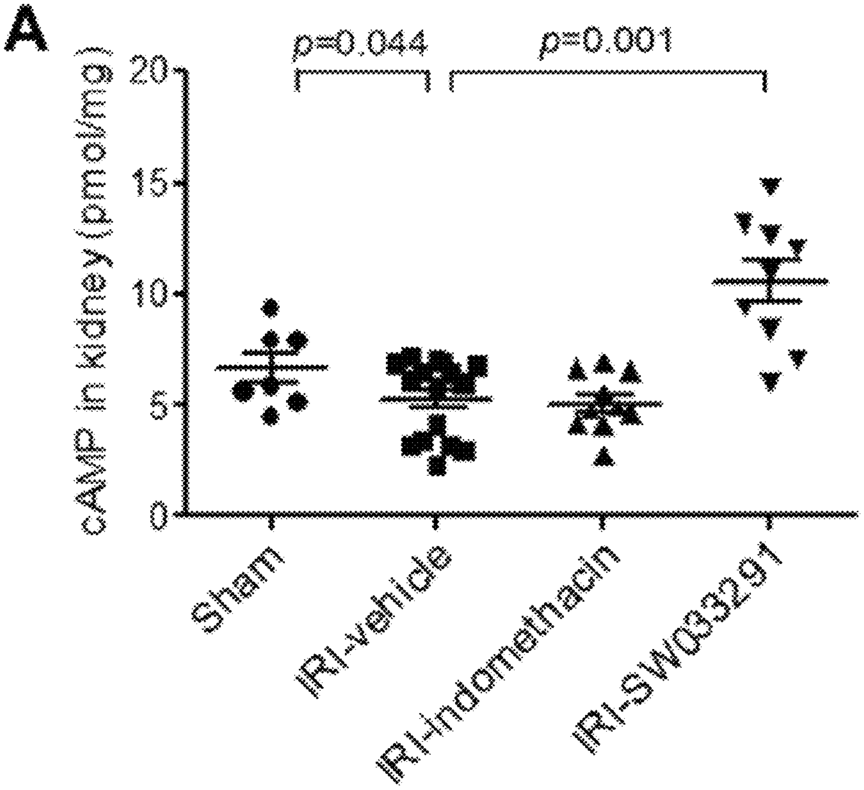
FIGS. 5(A-G) illustrate plots, a western blot, and images showing 15-hydoxyprostaglandin dehydrogenase inhibitor promoted adenosine production and upregulated the expression of adenosine $A_{2A}$ receptors in the renal arterioles in the outer medulla via the cAMP/AMP signaling pathway. Assessments were performed at 24 h after renal ischemia-reperfusion injury (IRI). A and B: statistical analysis of cAMP (A) and AMP levels (B) in kidney tissue. n=12-18 animals/group. C and D: statistical analysis of renal (C) and serum (D) adenosine levels. n=6-10 animals/group. E: Western blots for $A_{2A}$ receptor protein (45 kDa) in kidney tissue (representative of three experiments). F: statistical analysis of $A_{2A}$ receptor protein levels in kidney tissue (n=9 per group). G: representative confocal microscopy images of kidneys immunostained for $A_{2A}$ receptor and α-smooth muscle actin (α-SMA). $A_{2A}$ receptor-positive cells were observed in α-SMA-positive cells in the renal arteriolar outer medulla (yellow color). *α-SMA-positive renal arterioles in the outer medullar. Scale bars=25 μm. Data are presented as means±SE. Analysis was performed using Student's t test.
Figure 5B:
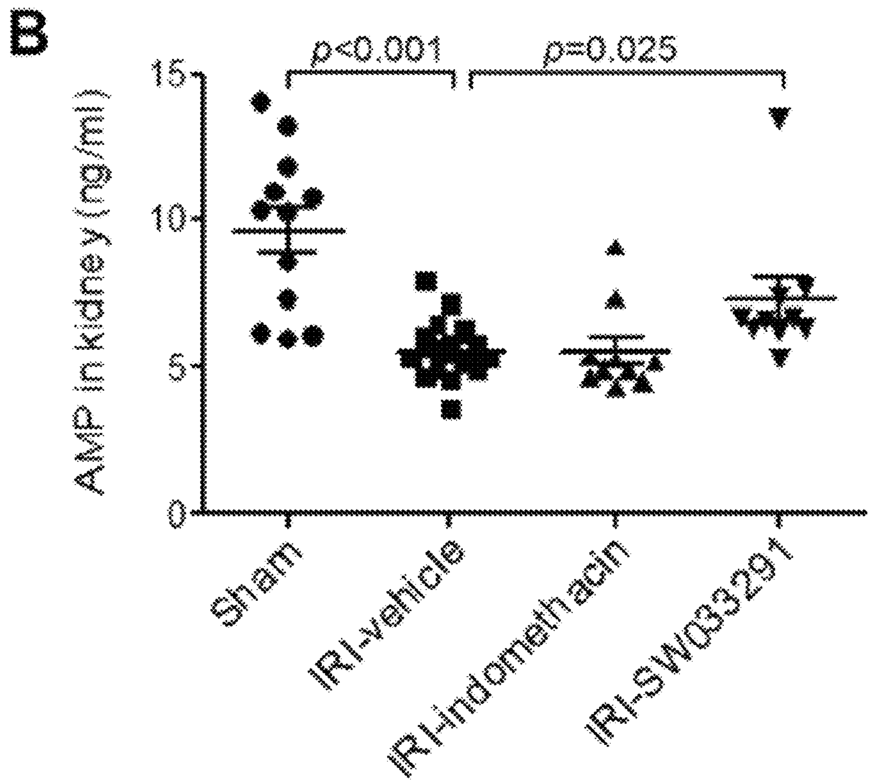
Figure 5C:
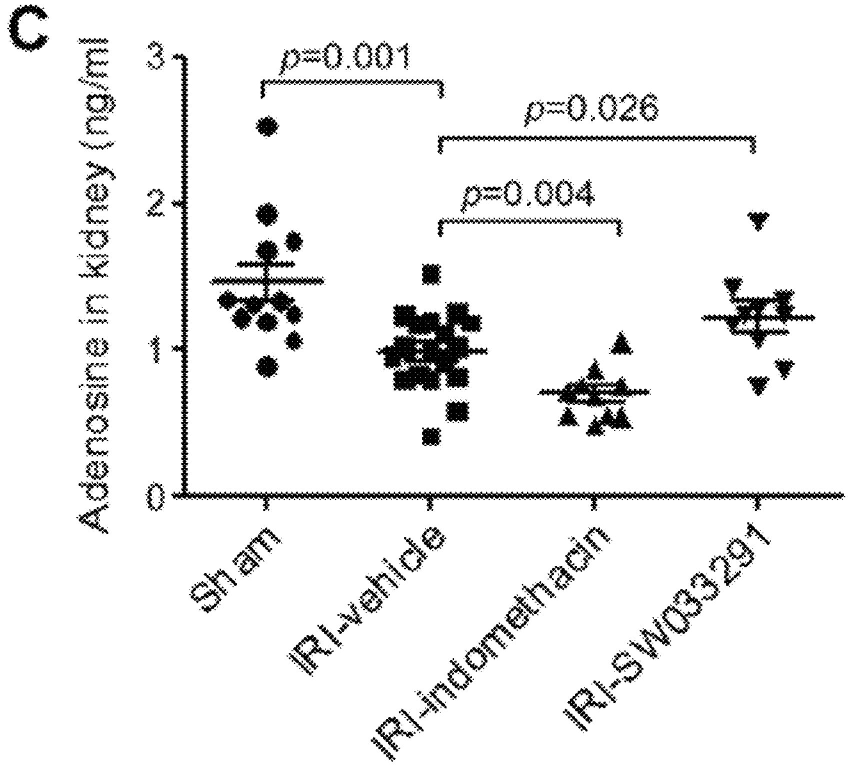
Figure 5D:
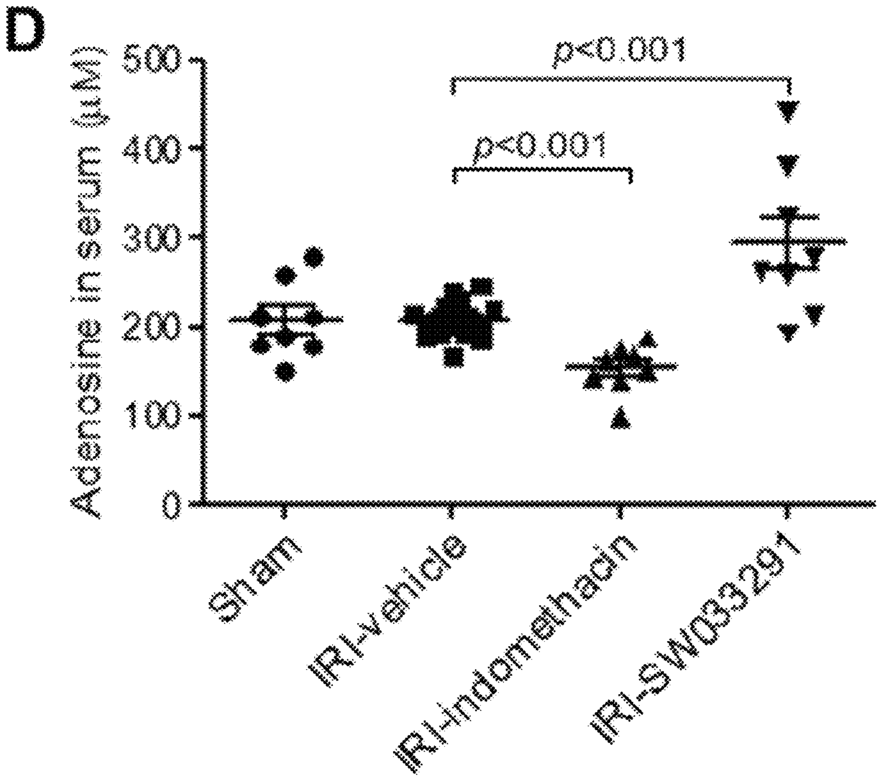
Figure 5E:
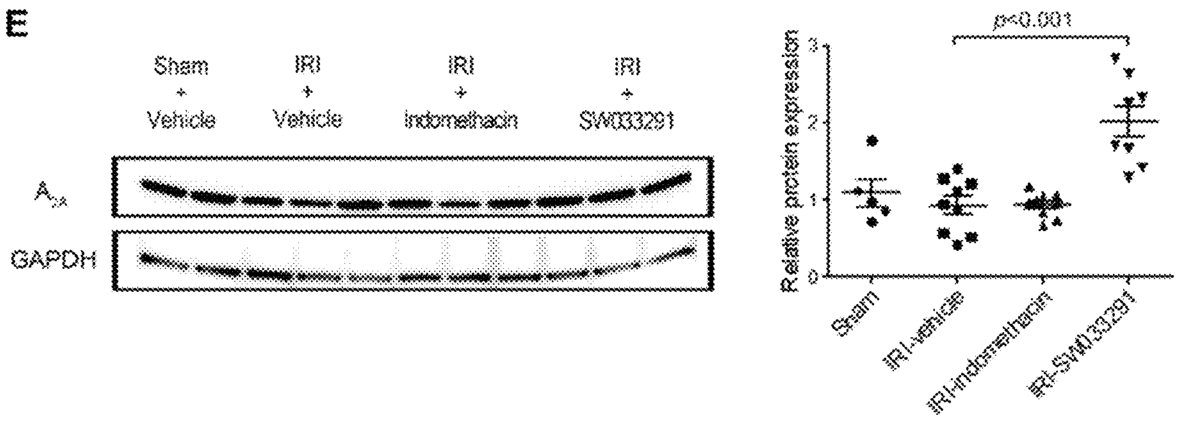
Figure 5F:
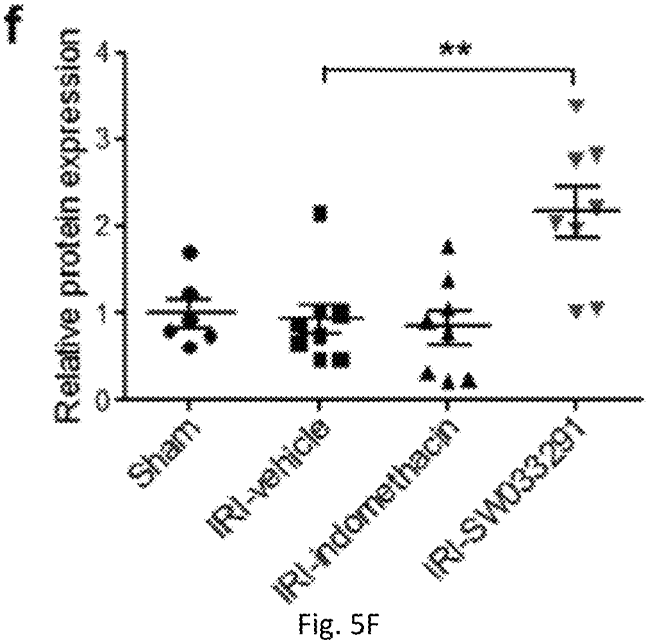
Figure 5G:
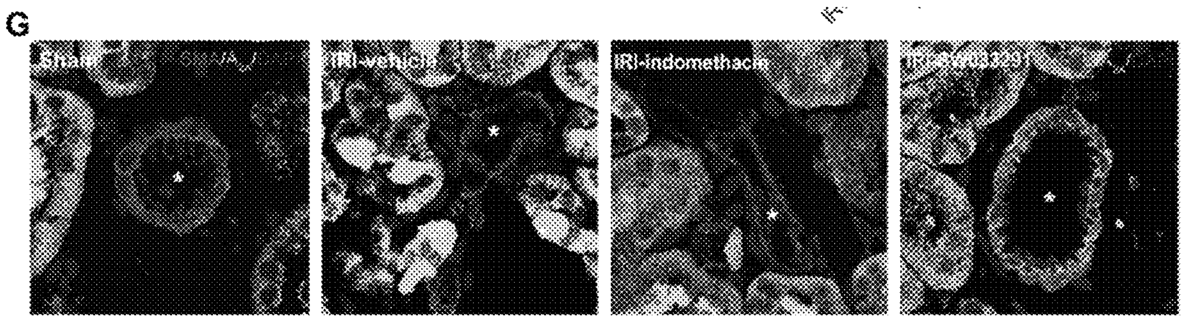

$PGE_2$ induces cAMP levels by signaling via $EP_2$ and $EP_4$ receptors, a pathway that is well characterized as inducing vasodilation in the renal afferent arteriole. Thus, we interpreted the coincident induction of $PGE_2$ and of increased RDF at 1 h after SW033291 as likely reflecting this established biology (FIGS. 1D and 4B). This biology further motivated us to examine cAMP as a potential downstream mechanism for the persistent SW033291-induced increase in RDF-inferred RBF at 24 h post-IRI. At 24 h post-IRI, both vehicle- and indomethacin-treated mice showed reduced renal cAMP versus sham mice (FIG. 5A). However, in parallel with RDF-inferred increased RBF, cAMP levels at 24 h were also elevated over sham mice in IRI-SWO33291-treated mice (FIG. 5A). Moreover, at 24 h post-IRI, SW033291-treated mice also showed increased levels of the cAMP breakdown product AMP (FIG. 5B). Furthermore, an additional vasodilatory molecule, adenosine, was also decreased in the kidney at 24 h after IRI, and, like cAMP, this decrease was also reversed in mice treated with SW033291 (FIG. 5C). Increased adenosine was, furthermore, detectable at 24 h post-IRI in serum SW033391-treated mice (FIG. 5D). Moreover, at 24 h, SW0332391 also induced the adenosine $A_{2A}$ receptor (compared with both sham and IRI mice) (FIGS. 5, E and F), with immunohistochemistry localizing the upregulated adenosine $A_{2A}$ receptors to the membrane of α-SMA-positive vascular smooth muscle cells that directly regulate constriction or dilation of renal arterioles (FIG. 5G).

Figure 6A:
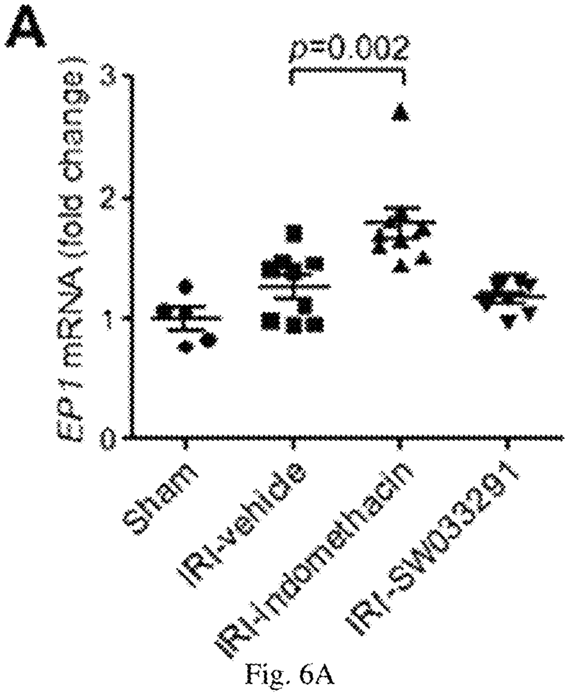
FIGS. 6(A-L) illustrate plots, a western blot, and images showing 15-hydoxyprostaglandin dehydrogenase inhibitor treatment promoted the expression of $EP_4$ receptors in the renal arteriolar outer medulla. Assessments were performed at 24 h after renal ischemia-reperfusion injury (IRI). A D: statistical analysis of $EP_1$ (A), $EP_2$ (B), $EP_3$ (C), and $EP_4$ (D) receptor mRNA levels in kidney tissue by real-time PCR. n=6-10 animals/group. E: Western blots for $EP_4$ receptor protein (73 kDa) in kidney tissue (representative of three experiments). F: statistical analysis of $EP_4$ receptor protein levels in kidney tissue (n=8 per group except sham, where n=6). G: representative confocal microscopy images for $EP_4$ receptors (green), α-smooth muscle actin (α-SMA; red), and DAPI (blue)-stained kidney sections. $EP_4$ receptor-positive cells were observed in α-SMA-positive cells in the renal arteriolar outer medulla (arrow). *α-SMA-positive renal arterioles in the outer medullar. Scale bars=25 μm. H-L: effects of the $EP_4$ inhibitor ONO-AE3-208 on SW033291 amelioration of IRI-induced renal injury. Data are presented as means±SE. Analysis was performed using Student's t test.
Figure 6B:
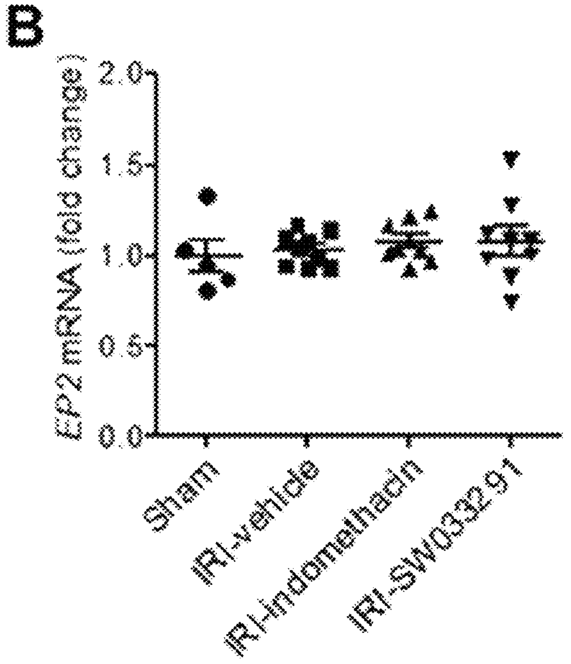
Figure 6C:
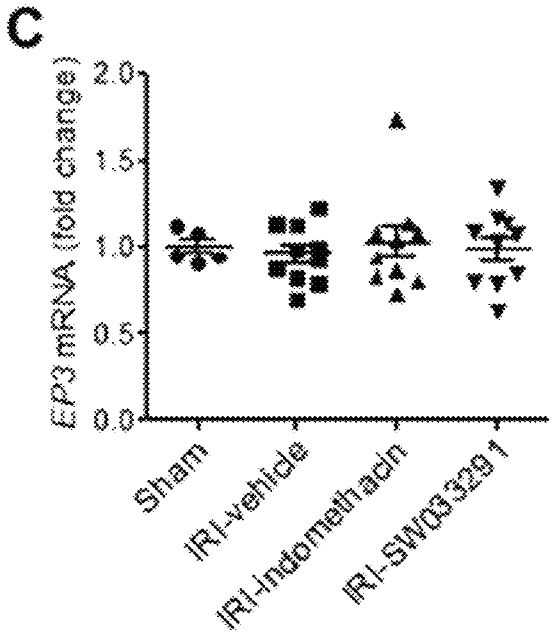
Figure 6D:
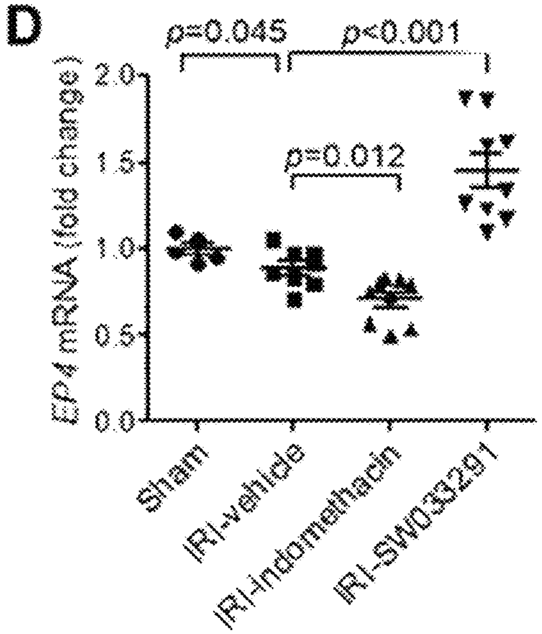
Figure 6E:
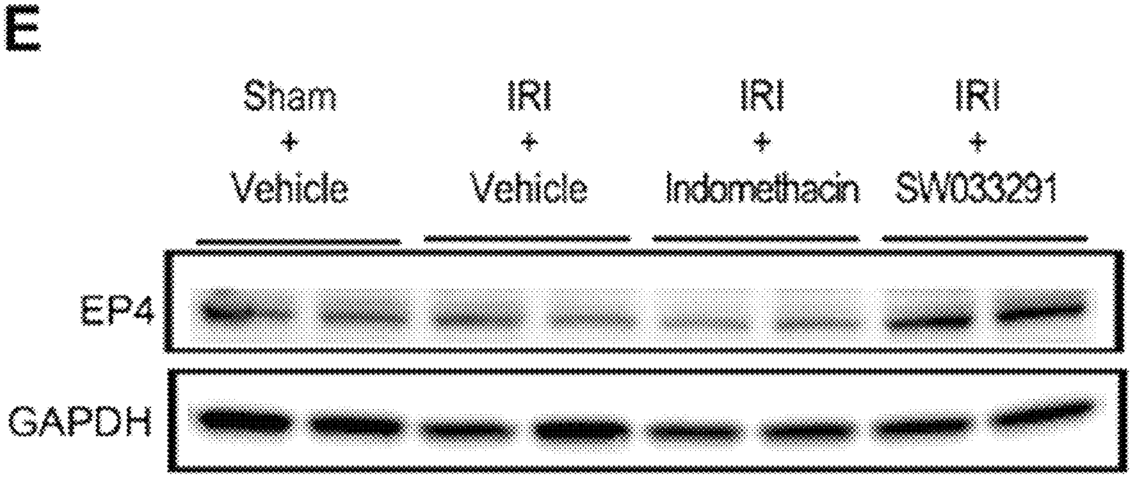
Figure 6F:
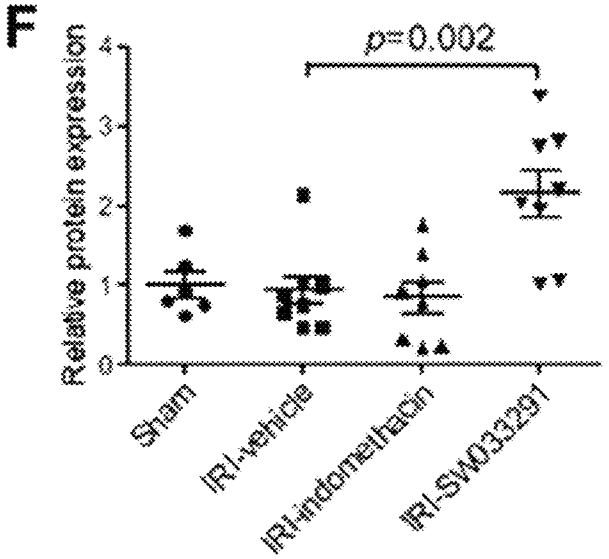
Figure 6G:
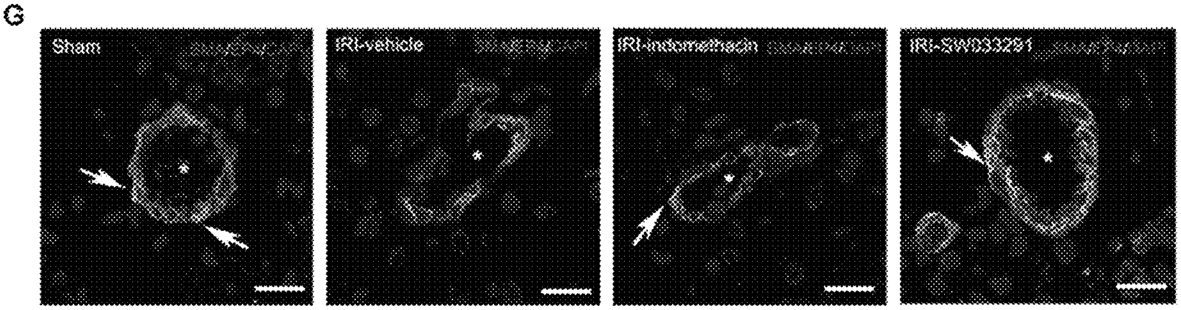
Figure 6H:
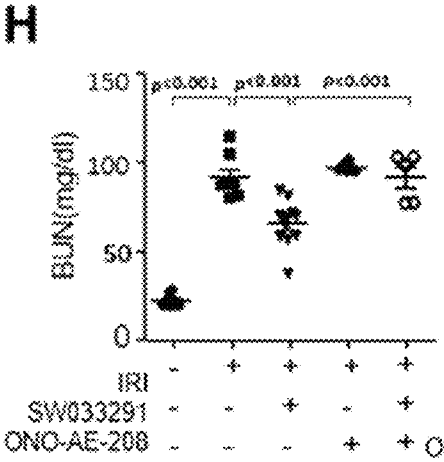
Figure 6I:
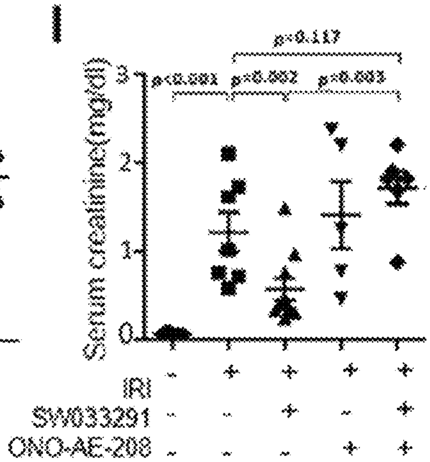
Figure 6J:
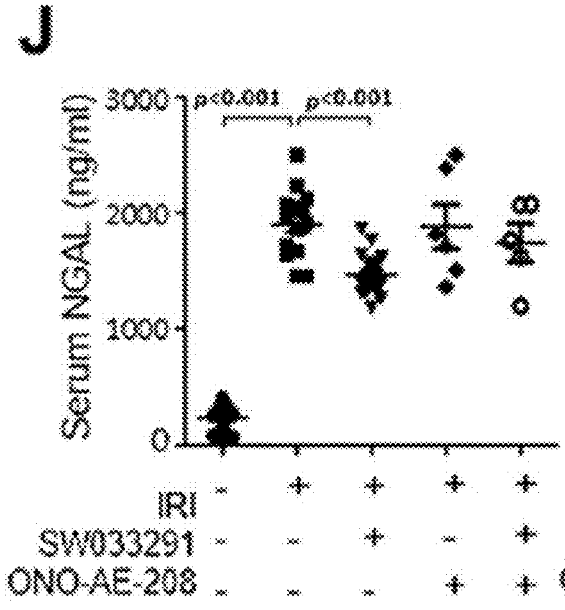
Figure 6K:
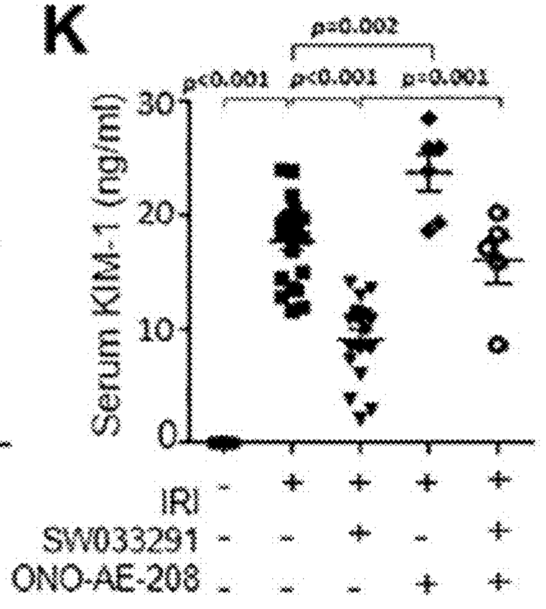
Figure 6L:
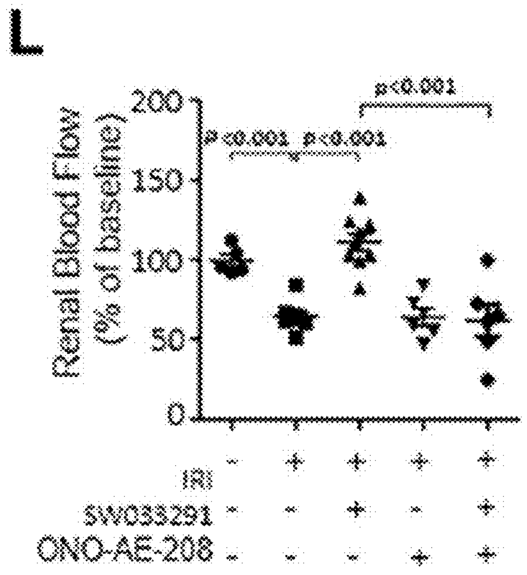

To inspect for upstream elements of the $PGE_2$ signaling pathway that might correlate with SW033291-induced signaling events at the 24-h post IRI time point, we looked for simultaneous effects of SW0332391 on the expression of $PGE_2$ receptors. Intriguingly, we found that at 24 h post-IRI, mice treated with SW033291 had significantly increased $EP_4$ receptor expression, at both mRNA and protein levels, with $EP_4$ receptor protein more than twice as high in SW033291—versus vehicle-treated mice (FIG. 6, D-F) (compared with both sham and vehicle-treated IRI mice). Indomethacin, in contrast, reduced $EP_4$ receptor mRNA levels (FIG. 6, D-F) and moreover increased $EP_1$ receptor mRNA levels, a receptor known to be involved in vasoconstriction (FIG. 6A). SW033291 and indomethacin had no effect on levels of $EP_2$ and $EP_3$ receptors (FIGS. 6, B and C). $EP_4$ receptors induced by SW033291 were localized to the membrane of α-SMA-positive vascular smooth muscle cells that directly regulate constriction or dilation of renal arterioles (FIG. 6G).

To interrogate the functional role of $EP_4$ receptors in media-ting SW033291 effects, we conducted experiments of IRI mice co-administered the three-dose schedule of SW033291 together with an $EP_4$ receptor antagonist, ONO-AE3-208. Co-administration of ONO-AE3-208 substantially blocked the beneficial effects of SW033291 on reversing IRI-induced increases of BUN, serum creatinine, and serum Kim-1 and on reversing IRI-induced decreases in RDF-inferred RBF (FIG. 6, H-L).

In overview, induction of renal vasodilation by 15-PGDH inhibition was well correlated with increased $PGE_2$ levels at 1 h post administration of drug, and, at 24 h, it was well correlated with induction of downstream mediators that included cAMP, AMP, adenosine, and adenosine $A_{2A}$ and $EP_4$ receptors, with induction of both $EP_4$ and $A_{2A}$ receptors targeted to vascular smooth muscle cells and with $EP_4$ function required for drug activity.

Pretreatment with a Single 15-PGDH Inhibitor Dose Mitigates Renal Dysfunction

Figure 7A:
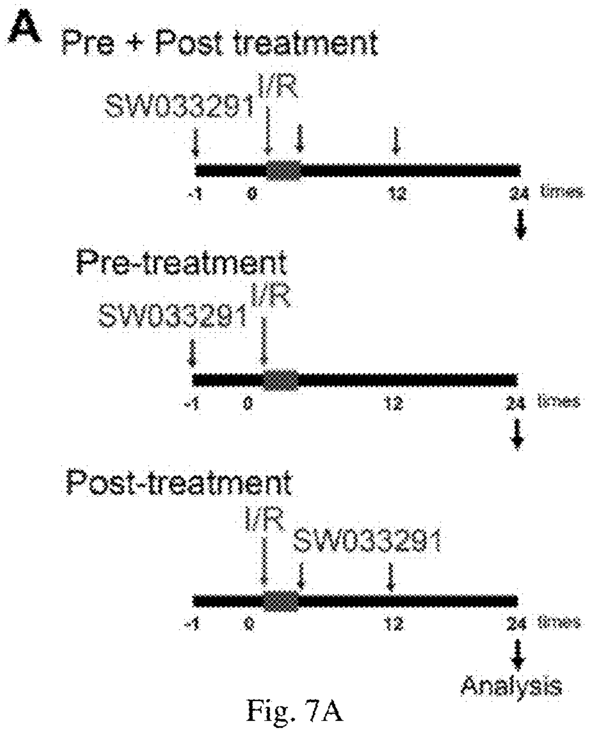
FIGS. 7(A-F) illustrate plots showing 15-hydoxyprostaglandin dehydrogenase inhibitor pretreatment mitigates renal dysfunction after renal ischemia-reperfusion injury (IRI). A: experimental setup for the three different injection protocols. Mice were injected with vehicle or SW033291 (5 mg/kg) according to three different injection protocols. Renal function was assessed at 24 h after renal IRI. B D: serum levels of blood urea nitrogen (BUN; B), creatinine (C), neutrophil gelatinase-associated lipocalin (NGAL; D), and kidney injury molecule-1 (KIM-1; E). n=9-11 animals/group. F: renal blood flow. Data are presented as means±SE. Analysis was performed with Student's t test.
Figure 7B:
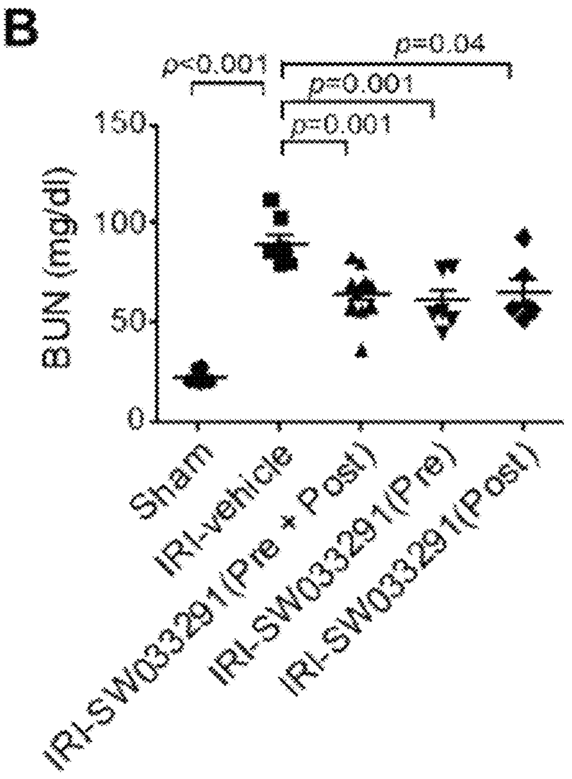
Figure 7C:
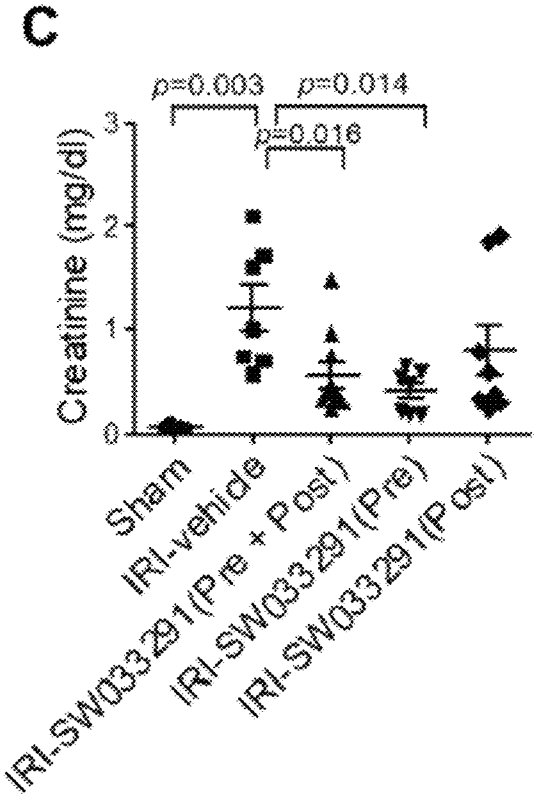
Figure 7D:
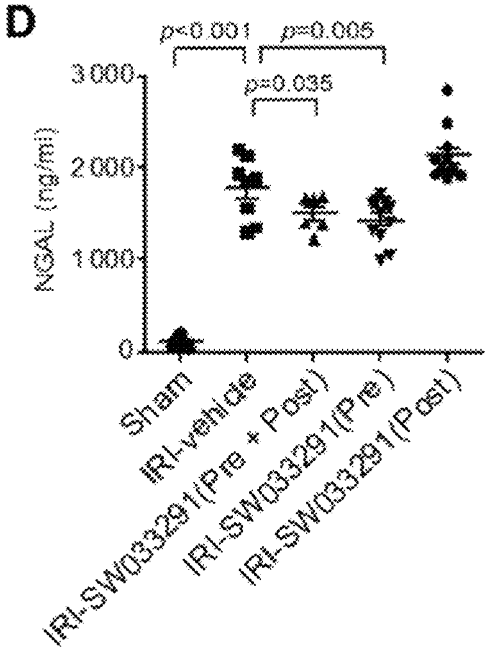
Figure 7E:
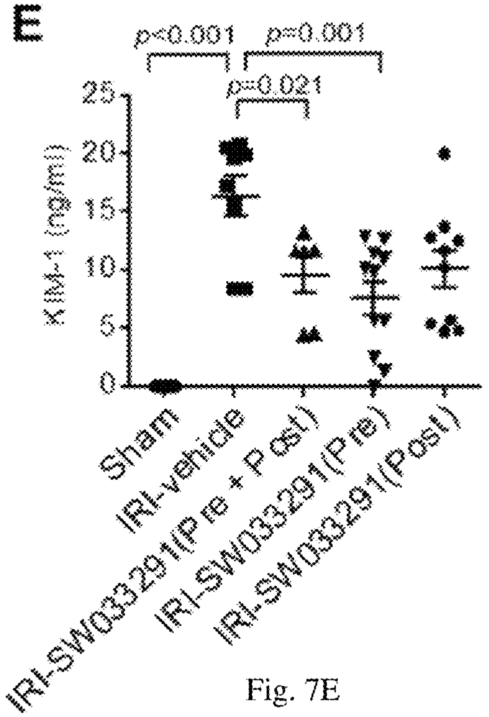
Figure 7F:
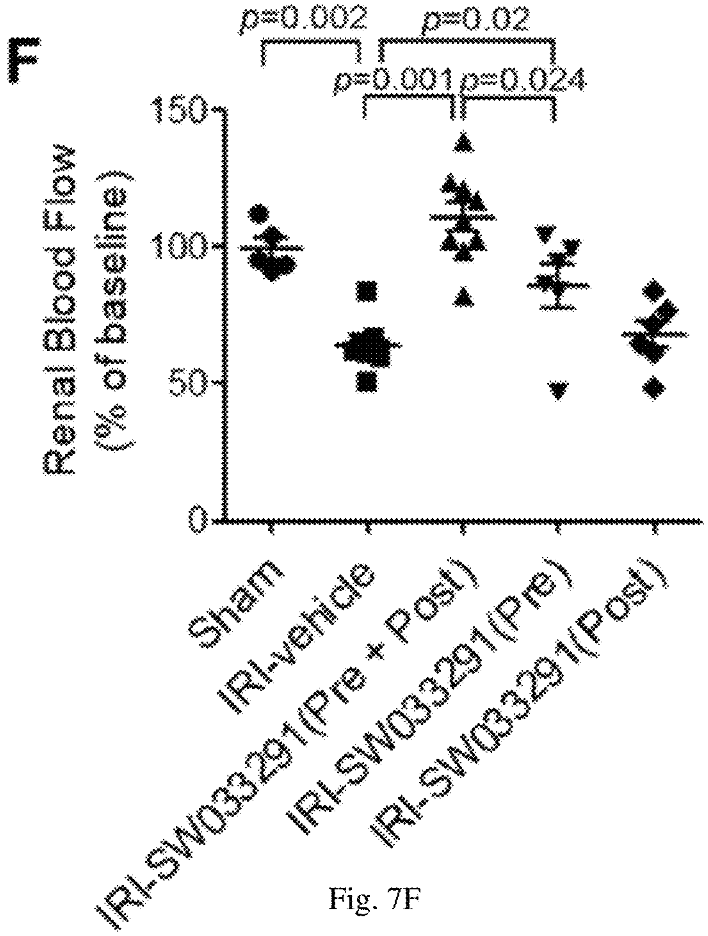

To interrogate the contributions of SW033291 administered just before versus just after AKI, we compared the effects of administration of a single dose of SW033291 given 1 h before IRI (Pre) versus two doses given immediately after IRI (Post) versus our standard three-dose regimen given 1 h before, immediately after, and 12 h after IRI (Pre+Post) (FIG. 7A). Surprisingly, IRI-SW033291 (Pre) was as effective in ameliorating AKI as IRI-SW033291 (Pre+Post) (FIG. 7, B-E), as assessed by BUN, creatinine, NGAL, and KIM-1, although IRI-SW033291 (Pre) provided somewhat less protection from reduction of RDF-inferred RBF versus IRI-SW033291 (Pre+Post) (FIG. 7F). IRI-SW033291 (Post) was insufficient to ameliorate AKI in the absence of concomitant pretreatment with drug. These findings suggest that a single dose of SW033291 administered before IRI can provide prophylaxis from inducing AKI.

Figure 8A:
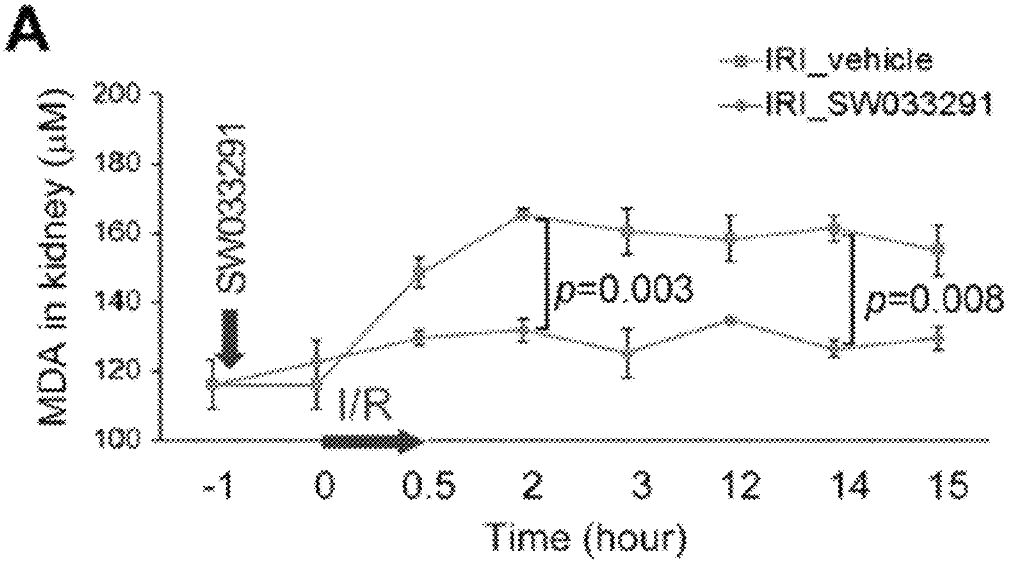
FIGS. 8(A-H) illustrate plots showing pretreatment with a single dose of 15-hydoxyprostaglandin dehydrogenase inhibitor attenuates the increase of $PGE_2$ level and renal damage after renal ischemia-reperfusion injury (IRI). Shown are expression changes of related factors in renal tissue or serum after ischemic acute kidney injury. A: malondialdehyde (MDA) levels in kidney tissue. B-D: neutrophil gelatinase-associated lipocalin (NGAL; B), kidney injury molecule-1 (KIM-1; C), and creatinine (D) levels in serum. E and F: renal $PGE_2$ levels (E) and serum $PGE_2$ levels (F). G and H: $EP_4$ receptor (G) and $A_{2A}$ receptor (H) mRNA levels in kidney tissue. n=4-8 animals/group. Data are presented as means±SE. Analysis was performed using Student's t test.
Figure 8B:
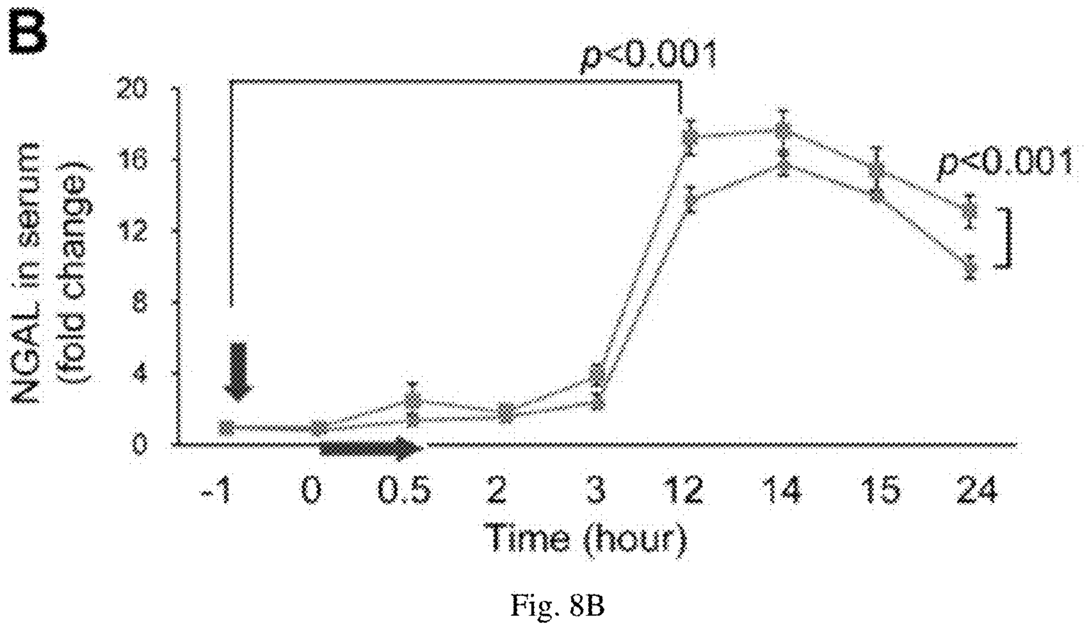
Figure 8C:
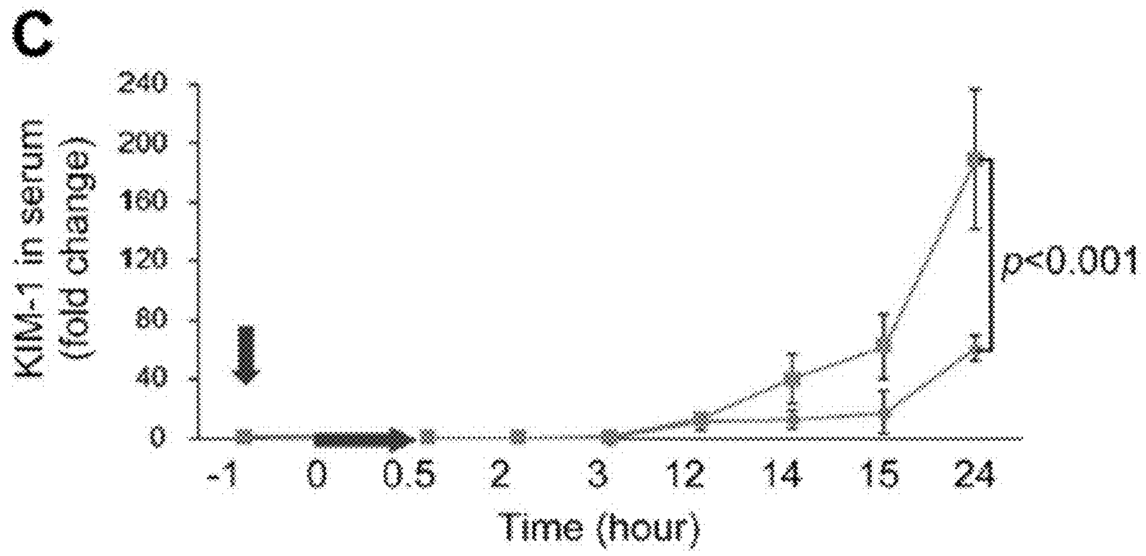
Figure 8D:
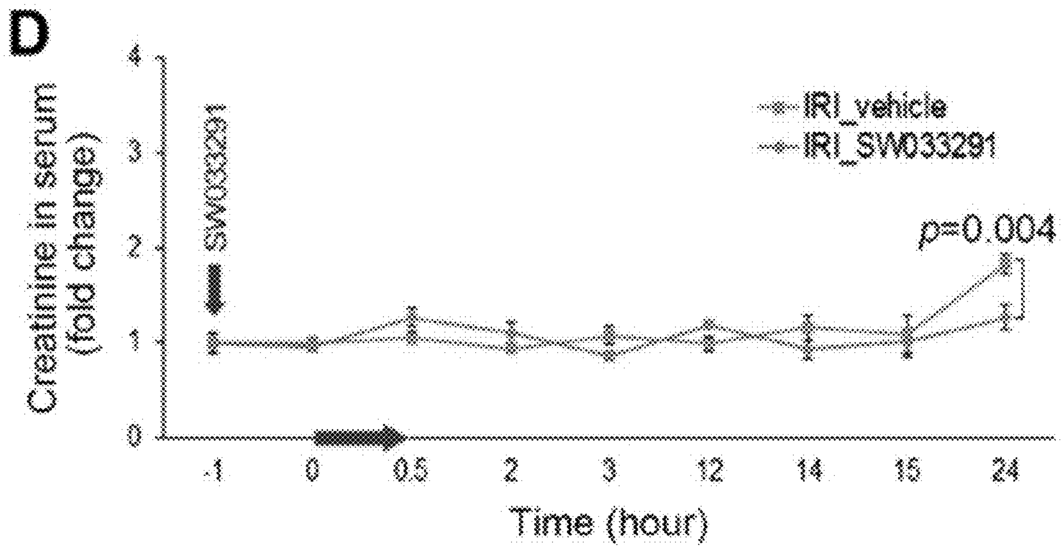
Figure 8E:
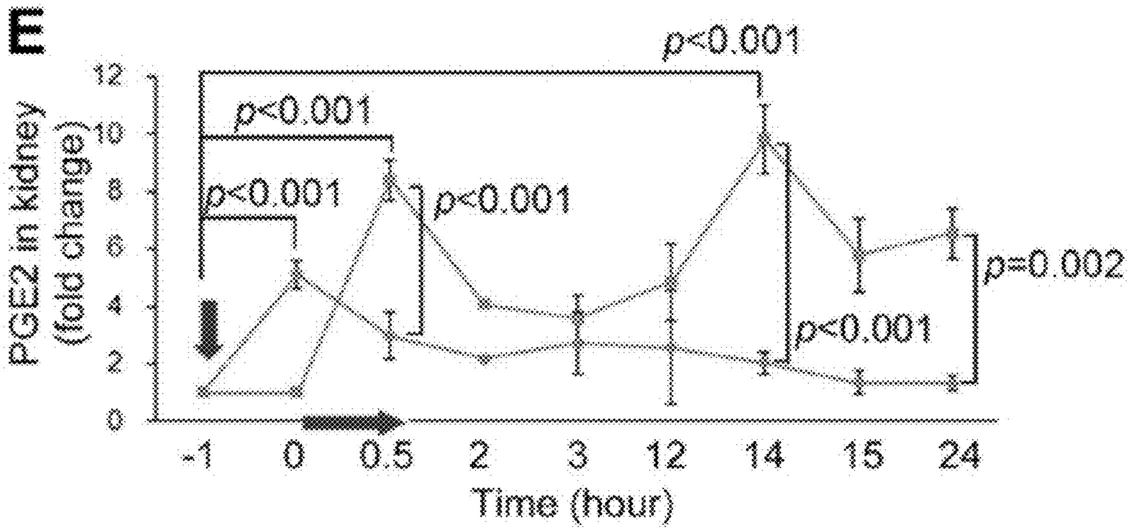
Figure 8F:
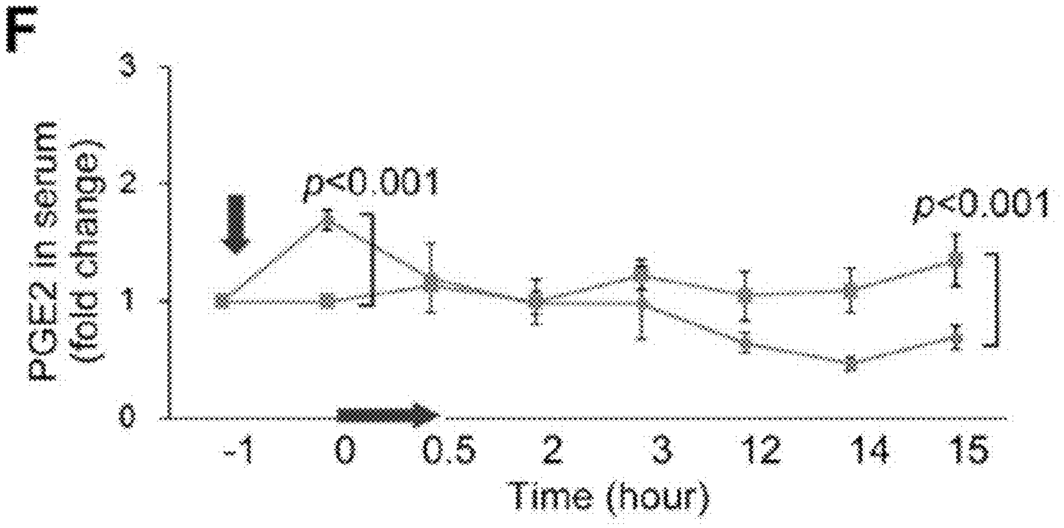
Figure 8G:
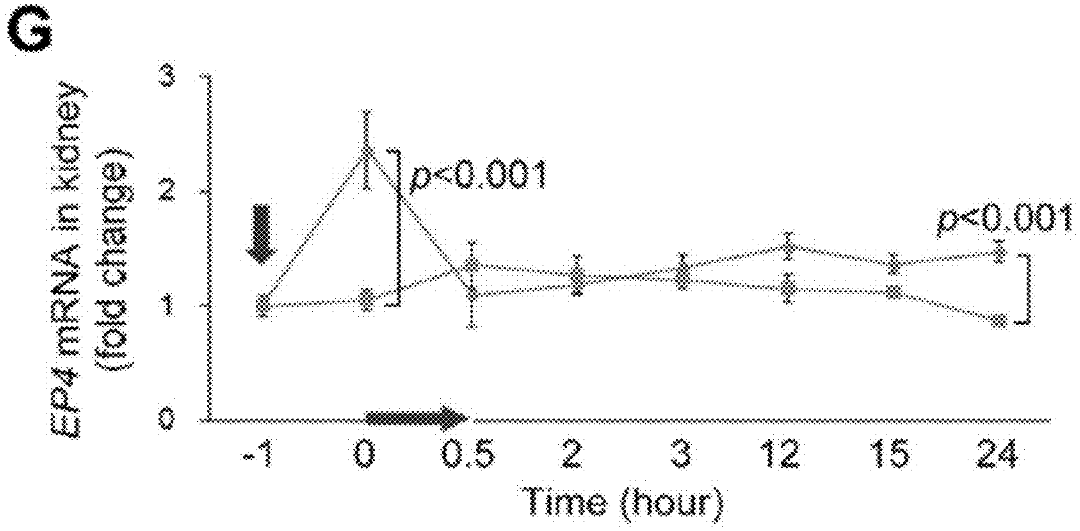
Figure 8H:
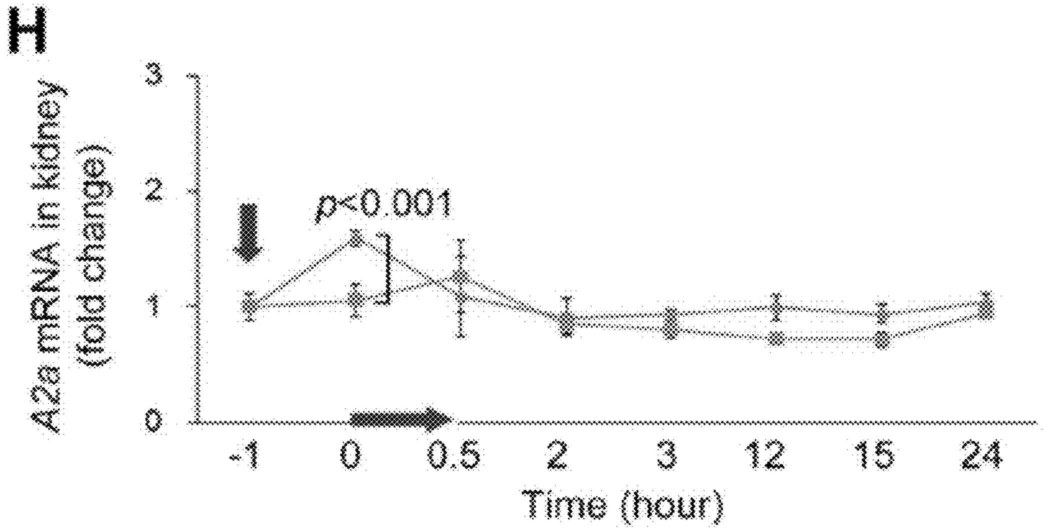

Pretreatment with a Single 15-PGDH Inhibitor Dose Attenuates AKI-Induced Oxidative Stress and Blocks Injury-Induced Increases in Renal $PGE_2$ MDA, a marker of oxidative stress, began to increase immediately after renal IRI of vehicle-treated mice and peaked at 2 h at 48% above baseline. A single pre-IRI dose of SW033291 blunted and reduced this increase to only 14% (FIG. 8A). IRI-SW033291 (Pre) mice also showed notable protection from the induction of NGAL, KIM-1, and creatinine (FIG. 8, B-D). In vehicle-treated mice, IRI induced two peaks of renal $PGE_2$, an immediate post-IRI peak plus a 14-h post-IRI peak (FIG. 8E). Intriguingly, a single pre-IRI dose of SW033291 induced an early $PGE_2$ peak just before IRI and was then sufficient to substantially block both of the later post-IRI peaks of $PGE_2$ (FIG. 8E). Moreover, the single pretreatment dose of SW033291 also significantly decreased both renal and serum $PGE_2$ levels at 24 h (FIGS. 8, E and F). Furthermore, pretreatment with SW033291 increased pre-IRI levels of both $EP_4$ and $A_{2A}$ receptors (FIGS. 8, G and H). In overview, induction of endogenous $PGE_2$ by administration of a prophylactic 15-PGDH inhibitor before IRI increases $EP_4$ and $A_{2A}$ receptors, induces vasodilatation, attenuates post-IRI oxidative stress, and, thereby, reduces multiple markers of renal injury.

In this example, we showed that pretreatment with a 15-PGDH inhibitor (SW033291) markedly protected the kidney from induction of the classic injury hallmarks of ischemic AKI. In particular, we demonstrated that administration of SW033291 improved renal hemodynamics (FIG. 4), decreased induction of oxidative stress (FIG. 8A), reduced induction of inflammation (FIG. 3), attenuated multiple markers of renal damage, and preserved renal function (FIGS. 1 and 2). These benefits were also associated with the prophylactic use of a single pre-IRI dose of SW033291, which showed notable protection from induction of NGAL, KIM-1, and creatinine (FIG. 7, C-E). The activity of SW033291 in preventing renal injury is likely to be an on-target effect due to modulation of $PGE_2$, as efficacy of SW033291 was blocked by inhibiting $EP_4$ signaling with ONO-AE3-208 and as treatment with indomethacin, a COX antagonist, and celecoxib, a COX-2 antagonist, acted opposite to SW033291 and further exacerbated renal injury (FIGS. 1, 2, and 6, H-L).

$PGE_2$ is known to regulate renal hemodynamics and inflammation, but its rapid degradation in vivo has been an obstacle to therapeutic applications. Our data demonstrate that pretreatment with a single dose of SW033291 can induce $PGE_2$ and reduce renal damage from ischemic AKI (FIG. 7). Specifically, inhibition of 15-PGDH and increasing endogenous $PGE_2$ before ischemic IRI provides a protective effect in the kidney via increasing renal vasodilation and RBF that would be expected to enhance oxygen delivery capacity and increase resistance to hypoxia. These results suggest that the renal protective effect of $PGE_2$, in part, relates to the timing of its increase. RBF is determined by the vasodilator-vasoconstriction balance, with $PGE_2$ and adenosine both acting as significant endogenous vasoactive mediators. $PGE_2$ exerts a vasodilatory effect in the kidney, and the use of NSAIDs in the early postoperative period is associated with renal dysfunction due to reduced RBF from suppression of synthesis of endogenous renal $PGE_2$.

Our findings are consistent with observations that in most blood vessels, the vasodilation effect of $PGE_2$ is mediated by the $EP_4$ receptor, which, via coupling to Gas, can directly activate adenylate cyclase and cAMP production. Our results are also consistent with the role of adenosine and its $A_{2A}$ receptor as important regulators of renal vasodilatation and mediators of protection from ischemic AKI. Induction of cAMP by SW033291 is, thus, likely the direct result of induction of renal $PGE_2$ and activation of $EP_4$ receptors.

Figure 9:
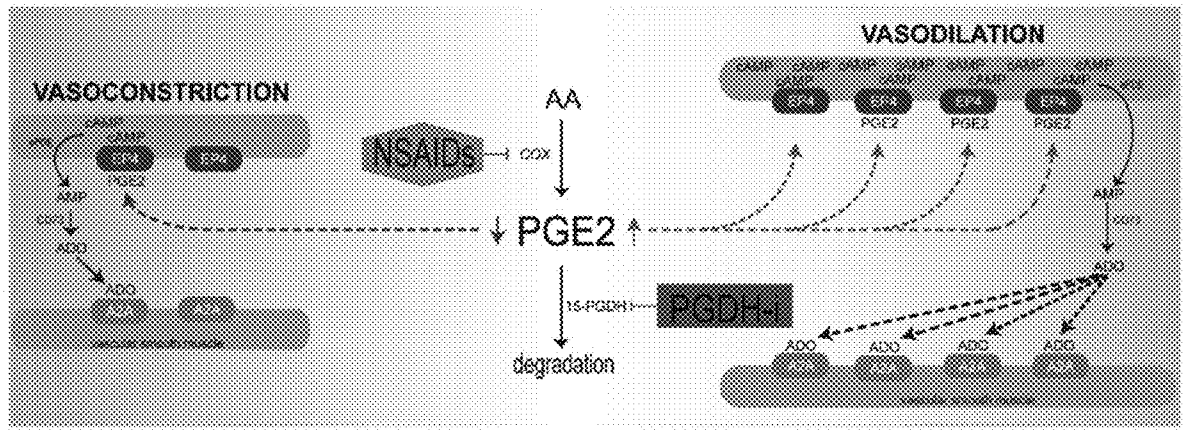
FIG. 9 illustrates a schematic mechanism of intrarenal vasodilation by the 15-hydoxyprostaglandin dehydrogenase (15-PGDH) inhibitor (PGDH-i) in ischemic acute kidney injury. 15-PGDH inhibitor pretreatment increases endogenous $PGE_2$ by inhibiting degradation of $PGE_2$ prior to an ischemic event in the kidney. Endogenous $PGE_2$ induces vasodilation through the activated $EP_4$ receptor. Activation of $EP_4$ receptors increases the intracellular cAMP level in vascular smooth muscle cells and the effect on vasodilation. Increased cAMP is converted to the adenosine (ADO) substrate AMP, which, in turn, increases the endovascular adenosine level. ADO activates $A_{2A}$ receptors to induce vasodilation. On the other hand, nonsteroidal anti-inflammatory drugs (NSAIDs), cyclooxygenase (cox) inhibitors, lead to vasoconstriction, in contrast to the hemodynamic effects of 15-PGDH inhibitors. AA, arachidonic acid; ePDE, extracellular phosphodiesterase; RBC, red blood cell.

Our results support the role of 15-PGDH inhibition in renal vasodilation due to PGE2-dependent increases in $PGE_2/EP_4$ and adenosine/$A_{2A}$ receptors plus the induction of cAMP/AMP (FIG. 9). Most significantly, our results demonstrate that enhancement of renal $PGE_2$ by 15-PGDH inhibition before IRI induces renal vasodilation, which we suggest enhances resistance to hypoxia and results in prophylaxis against ischemic AKI. Inhibition of 15-PGDH may provide a novel pharmacological approach for prophylaxis against ischemic AKI in various clinical settings, including renal transplantation, shock, and cardiovascular surgery.

Example 2

In this Example, we analyzed whether a 15-PGDH inhibitor in a contrast-induced acute kidney injury (CIAKI) mouse model has a protective effect against renal deterioration and histological damage by contrast media (CM), and against direct tubular cell toxicity by culturing renal tubular cells in vitro. In addition, we investigated the changes in intrarenal hemodynamic and renal blood flow (RBF) as a mechanism, and the role of receptors related to PGE2.

Materials and Methods

Mice and Reagents

Female C57/BL6 mice (age, 10 weeks; body weight, 20-25 g) were purchased from Orient Bio Inc. (Daejeon, Republic of Korea). Before the experiments, all mice were housed individually in standard cages and were allowed to acclimate under specific-pathogen-free conditions in the animal care facility of the College of Medicine of Inje University, Republic of Korea. The care of and experimental procedures involving the animals were approved by the Institutional Animal Care and Use Committee of Inje University (protocol no. 2018-019).

Induction of CIAKI

The two different radioactive iodine in terms of viscosity and osmolality were administered intravenously to 5 mice for each group. Ten grams of iodine per body weight (gI/kg) of each CM was injected by a 26-gauge syringe through the tail vein. The blood samples for the analysis of functional assessment of kidney injury such as Cr, NGAL, and KIM-1 were taken at 48 h after administration (FIGS. 10(A, B)).

Study Design of Each Group with Drug Administration

Female mice were injected with 10 gI/kg of Visipaque (iodixanol) via the tail vein. SW033291 (5 mg/kg; Cayman, Ann Arbor, MI, USA), PGE1 (20 mg/kg; Cayman), or PGE2 (5 mg/kg; Sigma-Aldrich, St. Louis, MO, USA) or a vehicle (10%, ethanol; 5%, cremophor EL; and 85%, dextrose 5% in water) were intraperitoneally administered 1 h before, immediately after, and 8, 16, and 24 h after the iodixanol injection (FIG. 11(C)). For inhibition of the EP4s, mice were treated with 0.2 mg/kg/day of ONO-AE3-208 by subcutaneous injection for 14 days. Serum and kidney tissue were collected 48 h after the iodixanol injection.

Measurement of PGE2 Levels

Aside from the CIAKI experiment design, we first confirmed whether SW033291 administration actually increases PGE2 levels in kidney tissue in normal mice. Kidney tissues were harvested 1 h after the SW033291 injection, rinsed in ice-cold phosphate-buffered saline (PBS) containing indomethacin (10 μg/mL), and snap-frozen in liquid nitrogen. Next, 20 mg kidney tissue was homogenized in 500 mL cold PBS containing indomethacin (10 μg/mL) using a tissue homogenizer. The suspension was sonicated in an ice-water bath for 1 min using cycles of 10 s of sonication with 10 s of cooling, and then they were centrifuged for 10 min at 12,000 rpm. The supernatant was collected for PGE-2 assay. Protein concentrations were determined by bicinchoninic acid assay (Cat. #23225, Thermo Scientific). The PGE2 level in the supernatant was measured using a PGE2 enzyme-linked immunosorbent assay kit (R&D Systems, Minneapolis, MN, USA) in triplicate. PGE-2 levels were expressed as ng of PGE2/mg protein.

Assessment of Renal Function

Renal function was assessed by determining the serum levels of creatinine (Arbor Assays, Ann Arbor, MI, USA), NGAL (R&D Systems), and KIM-1 (R&D Systems) at 48 h after the iodixanol injection.

Necrotic and Apoptotic Cell Death Assays

Kidneys were harvested at 48 h after the CM injection, fixed in 4% phosphate-buffered formalin, and embedded in paraffin. To evaluate necrosis, 5 mm thick paraffin sections were stained with hematoxylin and eosin. Tubular injury was scored semi-quantitatively according to a system by a pathologist who examined at least 20 separate fields (400× magnification) in the outer medulla, which is the zone most sensitive to ischemic injury. The scoring system was as follows: 0, no damage; 1, patchy isolated unicellular necrosis; 2, tubular necrosis <25%; 3, tubular necrosis 25-50%; and 4, tubular necrosis >50%. At least 20 consecutive high-power fields per section were scored by two operators blind to the details of the experiment. To analyze the frequency of apoptosis, 5 mm thick paraffin sections were subjected to terminal deoxynucleotidyl transferase-mediated dUTP nick-end labeling (TUNEL) assay (Millipore, Temecula, CA, USA) according to the manufacturer's protocol. Four 5 mm thick paraffin sections were incubated with the TUNEL reaction mixture at 37° C. for 1 h, followed by incubation with a horseradish peroxidase-conjugated detection antibody. The signals were visualized using diaminobenzidine (Sigma-Aldrich). After counterstaining with Mayer's hematoxylin, TUNEL-positive cells were counted in at least five separate fields (640× magnification) in the outer medulla, and the apoptosis index (%, number of apoptosis cells/total number of cells) was calculated using GENASIS software.

Human Renal Proximal Tubular Epithelial Cells Culture

Human renal proximal tubular epithelial cells (hRPTECs) were purchased from the American Type Culture Collection (#PCS-400-010TM, Manassas, VA, USA). These cells were grown in 75 $cm^2$ flasks in Renal Epithelial Cell Basal Medium (PCS-400-030TM, ATCCVR) supplemented with Renal Epithelial Cell Growth Kit (PCS-400-040TM, ATCCVR).

Cell Viability Assay 3-(4,5-Dimethyl thiazol-2-yl)-2,5-diphenyl tetrazolium bromide (MTT) assay was used to assess cell viability. The hRPTECs were cultivated in 96-well plates at a density of $10^5$ cells/mL and then incubated for 24 h. They were treated with SW033291 (1 μM), PGE1 (100 ng/mL), or PGE2 (100 nM) simultaneously with Visipaque (iodixanol, 50 mgI/mL) for 24 h. Then, 10 lM MTT (Sigma-Aldrich) was added to each well for an additional 4 h. The blue MTT formazan precipitate was dissolved in 100 mL dimethyl sulfoxide. The absorbance at 540 nm was measured with a multi-well plate reader. Cell viability was expressed as a percentage of the no-treatment cells, as the mean value±standard deviation of the six independent experiments.

Analyses of Apoptosis by Flow Cytometry

After the treatment described in the section above, the hRPTECs were pelleted by centrifugation at 1800 rpm for 10 min and incubated with annexin V fluorescein isothiocyanate and propidium iodide using an Apoptosis Detection Kit I (#556547, BD Biosciences, San Jose, CA, USA) according to the manufacture's instruction. Then quantification was conducted using a FACSC flow cytometer with Cell Quest software (BD Biosciences).

Assessment of Renal Vasodilation in the Outer Medulla 48 h after CM injection, kidney tissues were harvested, fixed in 4% phosphate-buffered formalin, and embedded in paraffin. To quantify vasodilation, the inner arteriole area of the outer medulla was determined using α-SMA-stained sections. They were incubated for 1 h with an α-SMA antibody. 3,30-diamino-benzidine (0.7 g/tablet; Sigma-Aldrich) was added, followed by washing three times with PBS for 1 min each. After counterstaining with Mayer's hematoxylin, the inner areas of α-SMA-positive vessels in the outer medulla (25× magnification) were measured using ImageJ software. The results were expressed as the average area of all of the renal arteries in each outer medulla section.

Renal Blood Flow (RBF) Assessment

Total RBF was assessed by measuring renal Doppler flux using noninvasive laser Doppler flowmetry (PeriFlux System 5000, Perimed AB, Sweden). Laser Doppler probes were placed on the kidney surface to measure the renal flux. The flux was measured 48 h after CM administration. The relative increase represented the percentage increase in renal blood flow from baseline to peak for each test. Statistical significance was set as $p<0.05$.

Measurement of Adenosine Monophosphate (AMP) and Adenosine Levels 48 h after CM administration, serum and kidney tissues were harvested. The adenosine levels in the serum and kidney tissues were measured using high-performance liquid chromatography.

Statistical Analyses

Results are presented as mean±standard error of the mean. Statistical analyses were performed with one-way analysis of variance followed by the Bonferroni post-test when three or more experimental groups were compared. Values of p<0.05 were considered indicative of statistical significance.

Results

CIAKI is Occurred in Mice with Intravenous Injection of visipaqueVR (Iodixanol)

While Xenetix and Visipaque have the same iodine concentration, Visipaque has a relatively lower osmolality and a higher viscosity than Xenetix (FIG. 10(A)). When compared with normal control, Xenetix showed a significant increase in Cr only; NGAL and KIM-1 did not show significant differences. On the other hand, Visipaque showed elevation in all three renal damage markers, Cr, NGAL and KIM-1, when compared with normal control (FIGS. 10(C-E)). Furthermore, Visipaque showed a significantly higher necrosis and apoptosis shown by Renal injury score and TUNEL assay than nor-mal control (FIG. 12). Therefore, it can be said that Visipaque, an isosmolar and high viscosity agent, successfully induced CIAKI in mouse, and thus we chose Visipaque as the contrast media for CIAKI mouse model.

15-PGDH Inhibitor Attenuates Renal Dysfunction in CIAKI Mouse Model

Figure 11A:
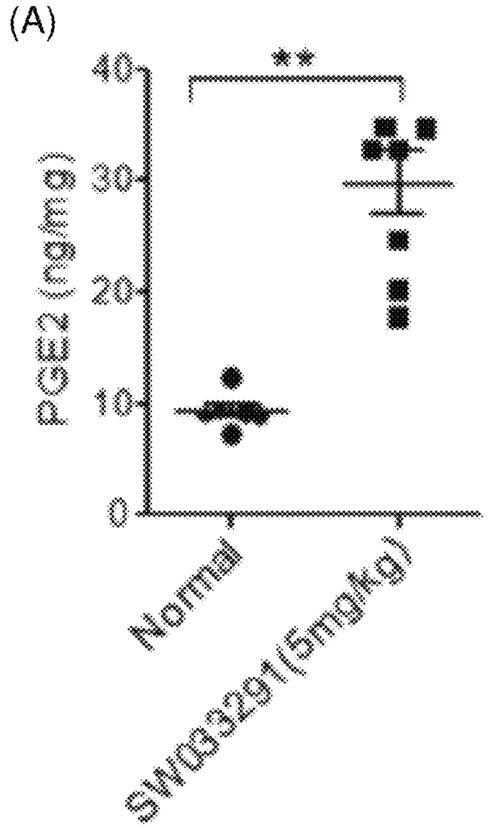
FIGS. 11(A-E) illustrate plots and a schematic showing 15-hydroxyprostaglandin dehydrogenase (15-PGDH) inhibition of contrast-induced acute kidney injury decreases the levels of renal injury biomarkers. (A) Prostaglandin $E_2$ (PGE2) levels in kidney tissue 1 h after intraperitoneal injection of 5 mg/kg SW033291 or a vehicle. (B) Experimental setup: mice received SW033291, PGE1, PGE2, or vehicle at 1 h before, immediately after, and 8, 16, and 24 h after administration of 10 gI/kg iodixanol. (C-E) Serum levels of creatinine, neutrophil gelatinase-associated lipocalin (NGAL), and kidney injury molecule-1 (KIM-1), respectively. Renal function was evaluated at 48 h after contrast medium (CM) injection. *p<0.05; p<0.01; *p<0.001.
Figure 11B:
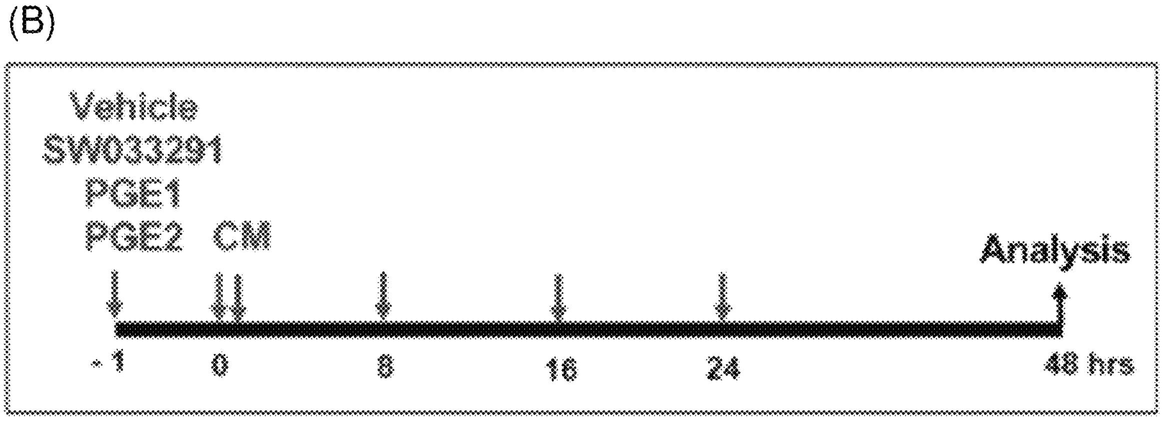

Renal PGE2 levels measured 1 h after administration of a 15-PGDH inhibitor (SW033291) increased by an average of three times compared to vehicle-administered, normal, control mice (9.29±0.67 ng/mg in normal vs. 29.71±2.79 ng/mg in SW033291, p<0.01; FIG. 11(A)). Compared to the control group, creatinine, neutrophil gelatinase-associated lipocalin (NGAL), and kidney injury molecule-1 (KIM-1) levels were significantly increased in CM-treated mice (CM þ vehicle; creatinine, 62±0.02 mg/dL [normal] vs. 1.94±0.24 mg/dL [iodixanol (10 gI/kg)], p<0.001; NGAL, 63.55±8.88 ng/mL [normal] vs. 299.71±38.64 ng/mL [iodixanol (10 gI/kg)], p<0.001; KIM-1, 0.03±0.001 ng/mL [normal] vs. 1.41±0.41 ng/mL [iodixanol (10 gI/kg)], p<0.001; FIG. 11(C-E)).

SW033291 treatment in CIAKI mice led to marked reductions in the levels of creatinine, NGAL, and KIM-1 (creatinine, 1.94±0.24 mg/dL [CM þ vehicle] vs. 1.10±0.11 mg/dL [CM þ SW033291], p<0.05; NGAL, 299.71±38.64 ng/mL [CM þ vehicle] vs. 140.41±25.52 ng/mL[CM þ SW033291], p<0.001; KIM-1, 1.41±0.41 ng/mL [CM þ vehicle] vs. 0.43±0.30 ng/mL [CM þ SW033291], p<0.05; FIG. 11(C-E)). In addition, in a group treated with PGE2, the reduction in renal injury biomarkers was similar to that of the SW033291 administration group. However, PGE1 decreased serum levels of creatinine in CIAKI mice, but not NGAL and KIM-1.

15-PGDH Inhibitor Ameliorates Renal Necrosis and Apoptosis in CIAKI

Figure 3A:
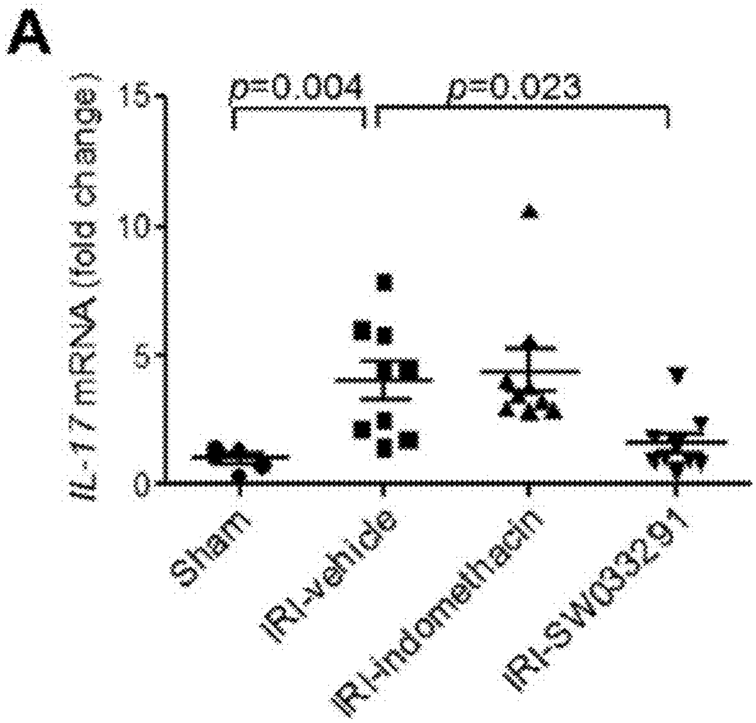
FIGS. 3(A-H) illustrate plots and a western blot showing 15-hydoxyprostaglandin dehydrogenase inhibitor pretreatment ameliorates the inflammatory response in mice with ischemic acute kidney injury. Before and after renal ischemia-reperfusion injury (IRI), mice were injected intraperitoneally three times with vehicle, SW033291 (5 mg/kg), or indomethacin (5 mg/kg). Assessments were performed at 24 h after renal IRI. A F: proinflammatory cytokine mRNA by real-time PCR (A-C) and protein levels by ELISA (D-F). A and D: IL-17; B and E: TNF-α; C and F: IL-13. G: Western blots of high-mobility group box 1 (HMGB1; 29 kDa) in kidney tissue (representative of three experiments). H: statistical analysis of HMGB1 levels in kidney tissue (n=9 per group). n=9 animals/group. Data are presented as means±SE. Analysis was performed using Student's t test.
Figure 3B:
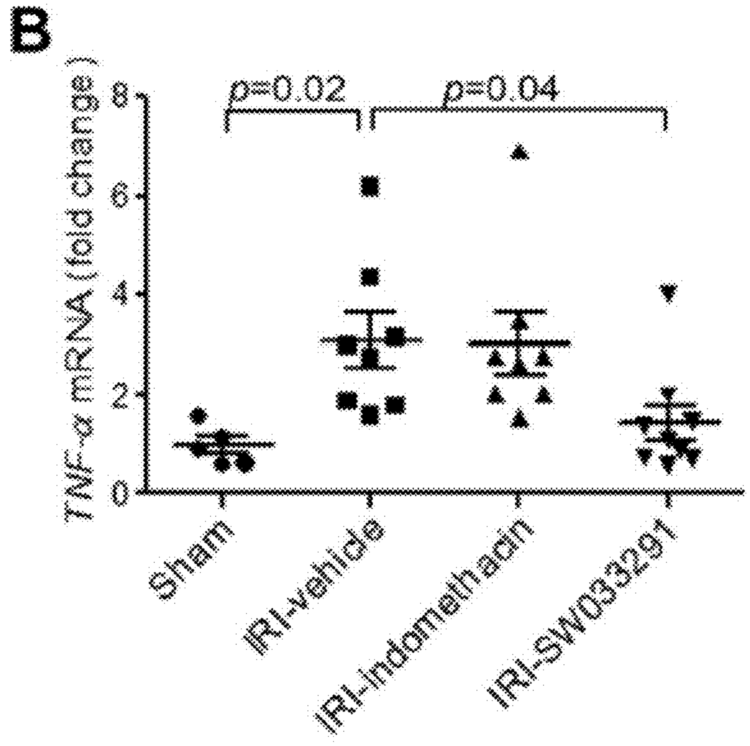
Figure 3C:
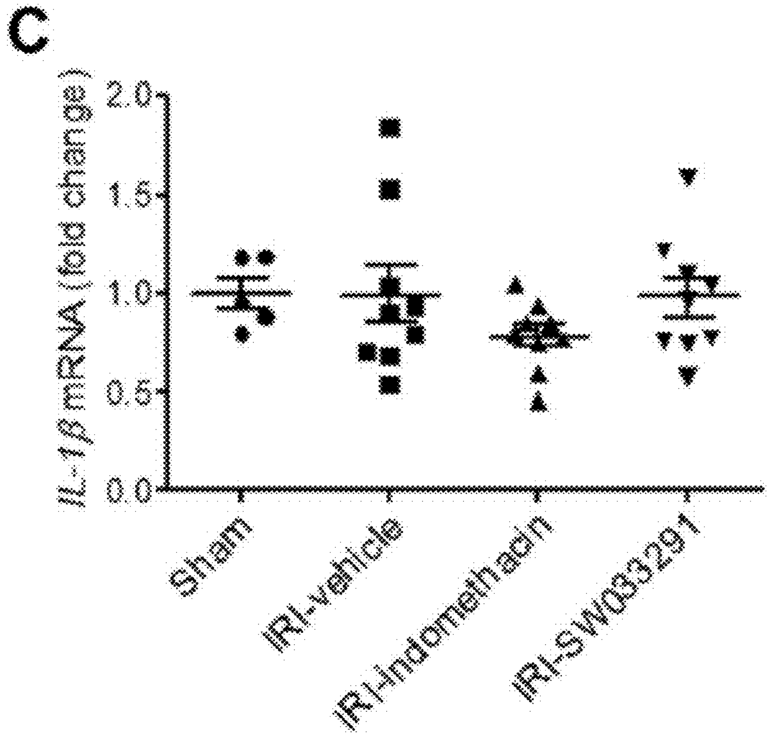
Figure 3D:
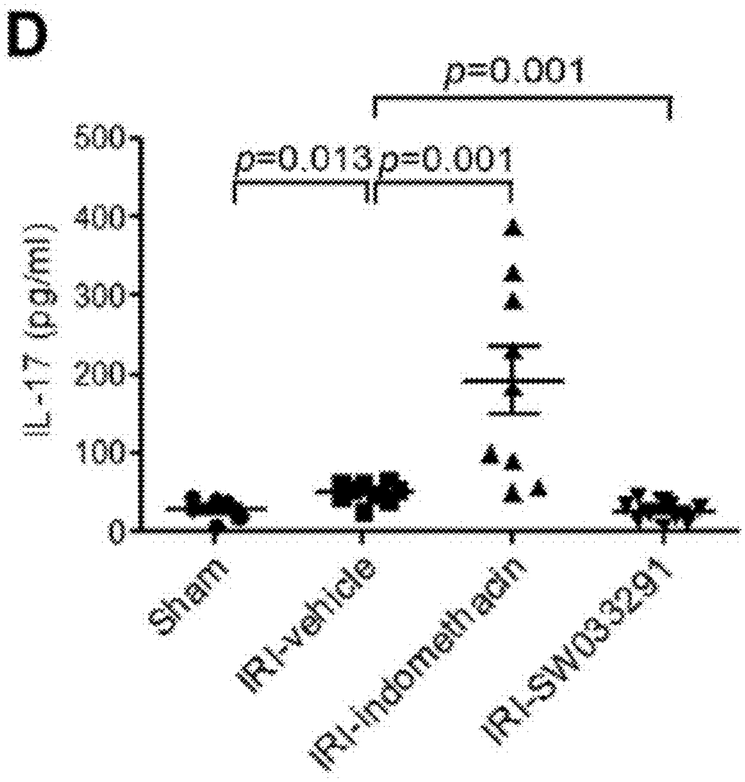
Figure 3E:
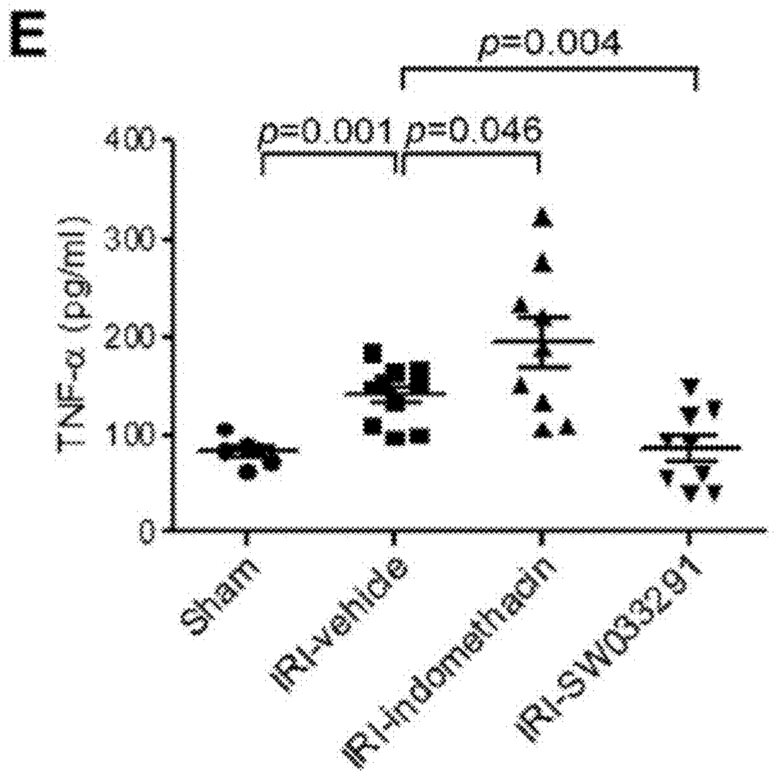
Figure 3F:
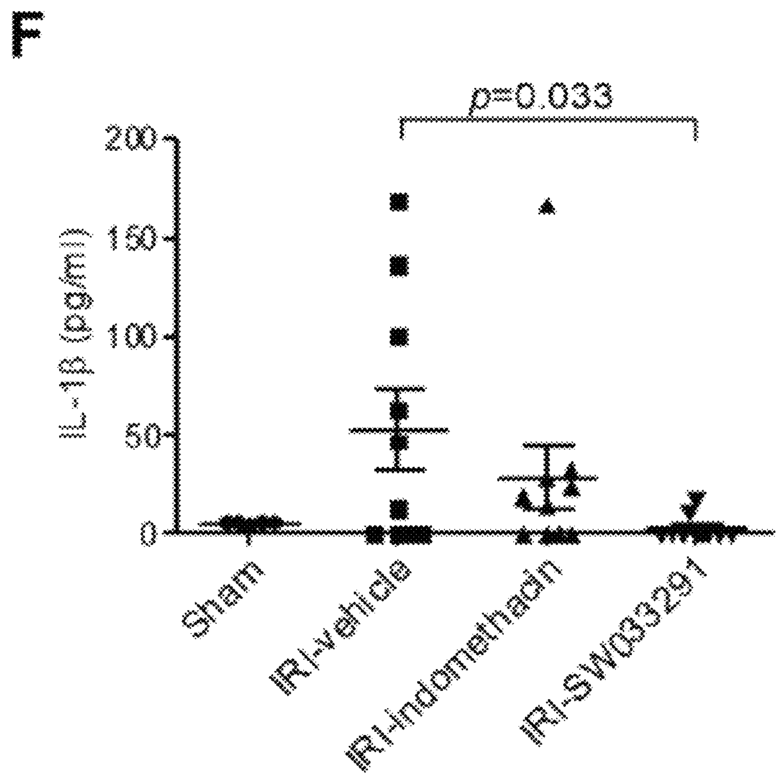
Figure 3G:
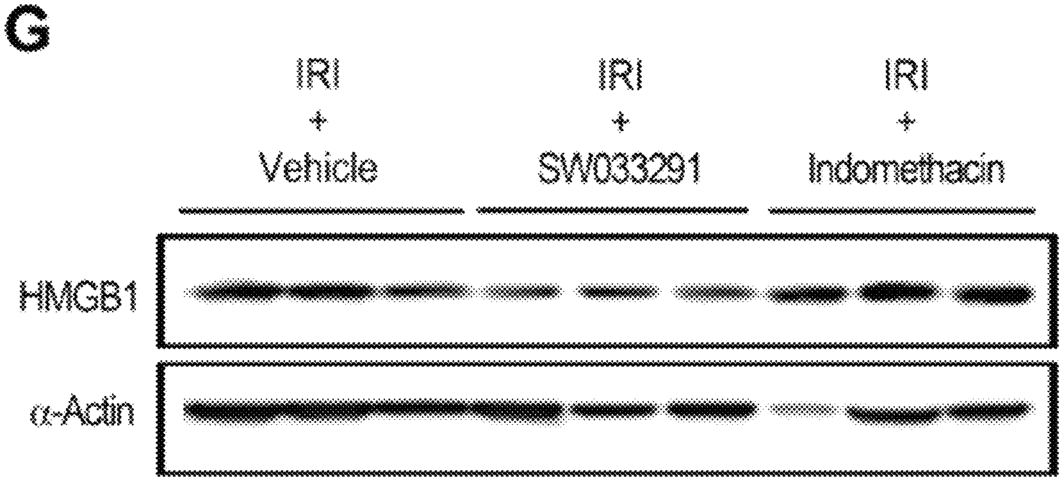
Figure 3H:
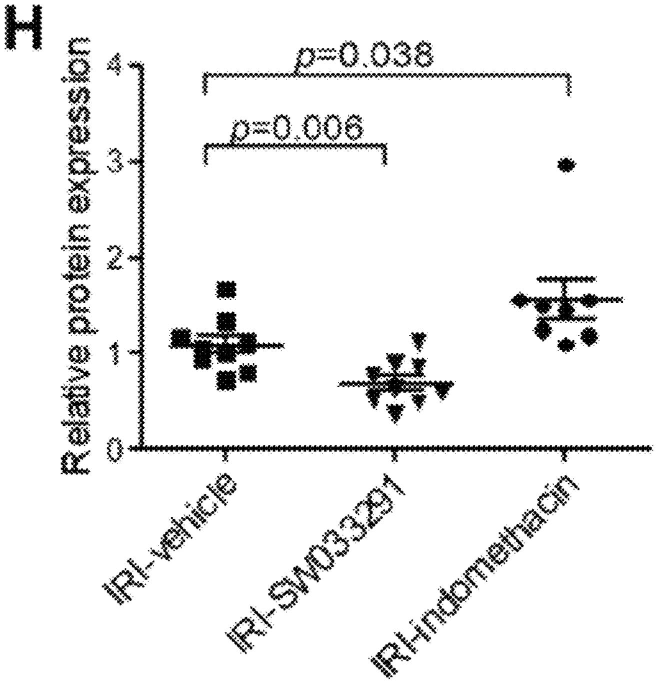
Figure 12A:
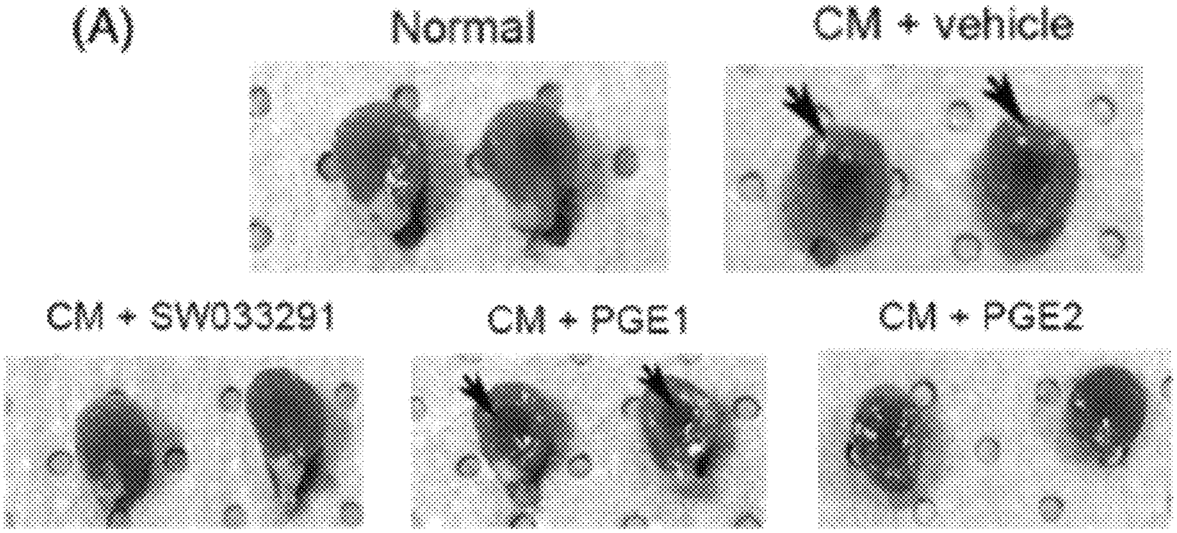
FIGS. 12(A-E) illustrate images and a plot showing 15-hydroxyprostaglandin dehydrogenase inhibition ameliorates renal tubular cell death in contrast-induced acute kidney injury mice. Before and after contrast medium (CM) administration, mice were injected intraperitoneally with a vehicle, SW033291 (15-PGDH inhibitor; 5 mg/kg), prostaglandin $E_1$ (PGE1; 20 mg/kg), or PGE2 (5 mg/kg). Assessments were performed at 48 h after intravenous CM injection. (A) Representative gross appearances of the left and right kidneys of normal mice, and of those after injection with CM vehicle, CM SW033291, CM PGE1, or CM PGE2. Renal congestion in the outer medullary region is indicated by a black arrow. (B) Representative images of tubular injury in the outer zone of the renal medulla (hematoxylin and eosin staining). Scale bars in small panels, 500 lm and those in enlarged images, 50 μm. (C) Statistical analyses of tubular injury scores (n=20 per group). (D) Representative images of apoptosis in the outer zone of the renal medulla (terminal deoxynucleotidyl transferase dUTP nick end labeling staining). Scale bars in small panels, 500 μm, those in enlarged images, 25 μm. (E) Statistical analyses of apoptosis (n=20 per group). *p<0.05; **p<0.001.
Figure 12B:
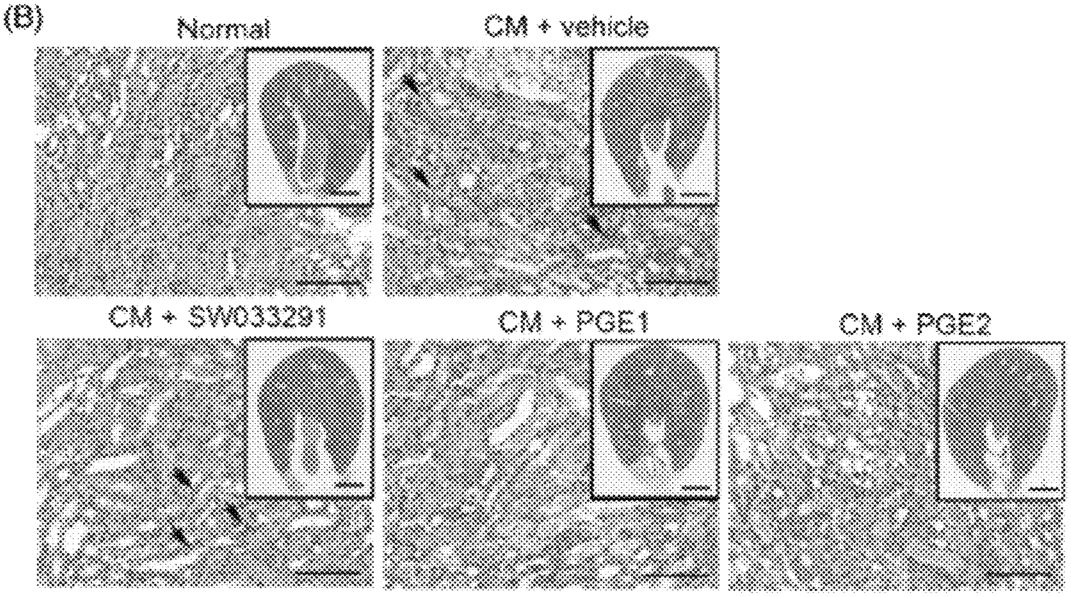
Figure 12C:
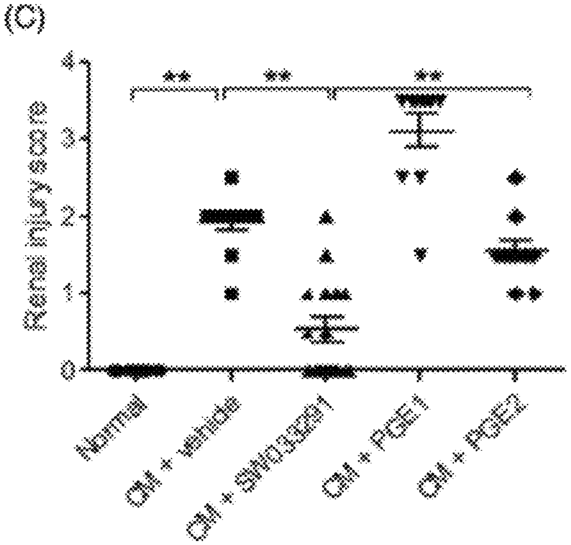
Figure 12D:
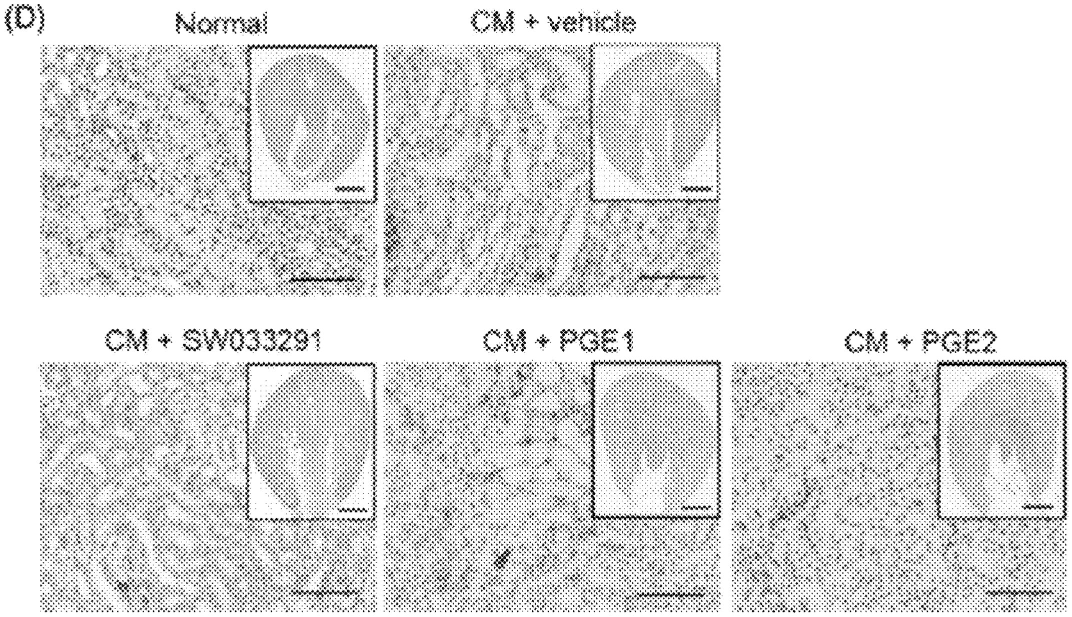
Figure 12E:
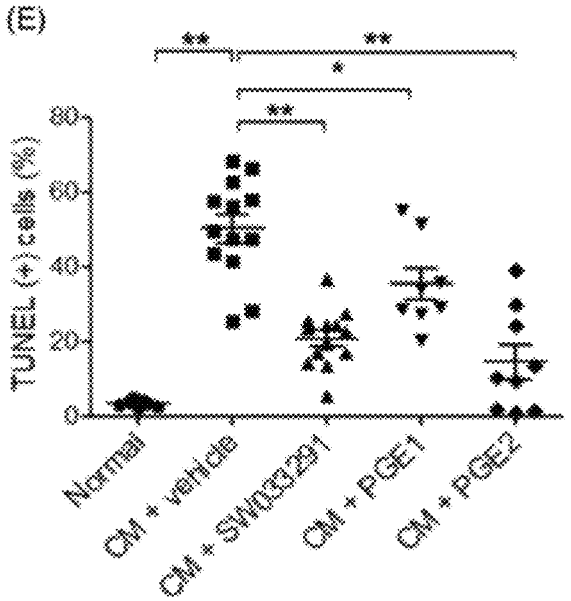

In the gross findings of the mice kidneys, two groups, those treated with CM þ vehicle and CM þ PGE1, showed prominent vascular congestion (red blood cells sludging and medullary hyperemia) in the outer medullary region compared to the normal group, whereas two other groups, those treated with CM þ SW033291 and CM þ PGE2, showed less-congested outer medullary areas (FIG. 12A). In the microscopic findings of the mouse kidneys, CM þ vehicle mice showed distinct tubular dilation, necrotic cells, and loss of brush border compared to normal renal tissue (FIG. 3B). The microscopic renal injury score of the SW033291 administration group was significantly lower than that of the CM þ vehicle mice (1.90±0.10 (CM þ vehicle) vs. 0.53±0.16 (CM þ SW033291), p<0.001; FIG. 12(B, C)). The CM þ PGE2 group also showed significantly lower renal injury scores than the CM þ vehicle group, but significantly higher than the SW033291 administration group (0.53±0.16 [CM þ SW033291] vs. 1.55±0.14 [CM þ PGE2], p<0.001). No reduction in renal injury score was observed in the PGE1 group (FIG. 12(B, C)). The frequency of apoptosis detected by terminal deoxy-nucleotidyl transferase dUTP nick end labeling (TUNEL) staining was higher in the CIAKI mice than normal ones, and administration of SW033291 reduced the proportion of TUNEL-positive cells caused by CM (46.77±4.77% [CM þ vehicle] vs. 24.01±2.90% [CM þ SW033291], p<0.001). The mice treated with PGE1 and PGE2 also showed significantly lower TUNEL-positive cell proportions compared to the CIAKI mice (FIGS. 12(D, E)).

Figure 13A:
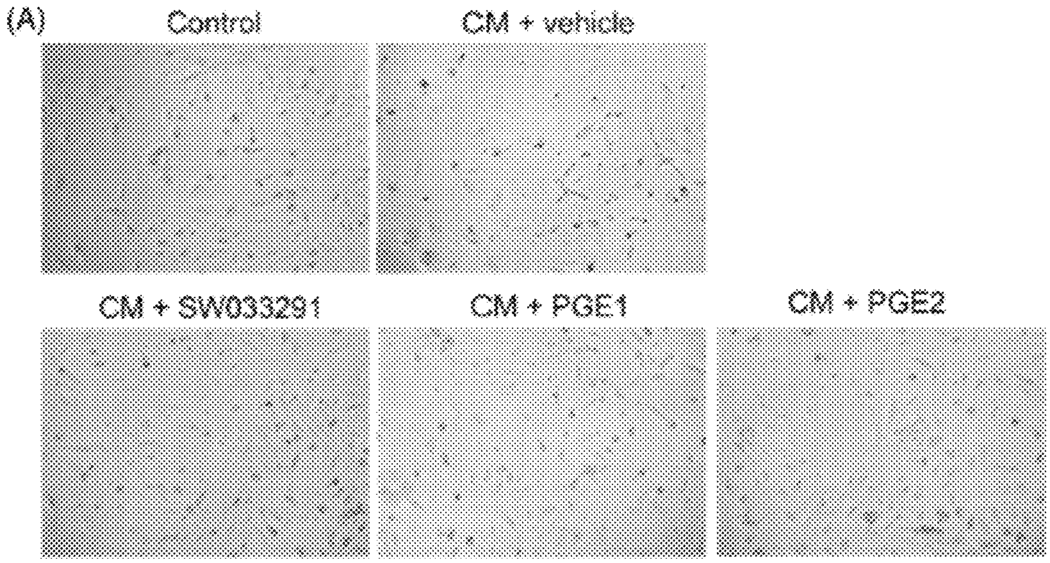
FIGS. 13(A-C) illustrate images and a graph showing 15-hydroxyprostaglandin dehydrogenase inhibitor effects on iodixanol-induced apoptosis in human renal proximal tubular epithelial cells (hRPTECs). hRPTECs were treated with SW033291 (15-PGDH inhibitor), prostaglandin $E_1$ (PGE1), or PGE2 simultaneously with Visipaque (iodixanol 50 mgI/mL). (A) Representative pictures of hRPTECs viability 24 h after Visipaque (iodixanol 50 mgI/mL) treatment. (B) Quantification of hRPTEC viability by MTT assay. (C) Quantification of hRPTECs apoptosis by flow cytometry; *p<0.05; **p<0.001. CM: contrast medium.
Figure 13B:
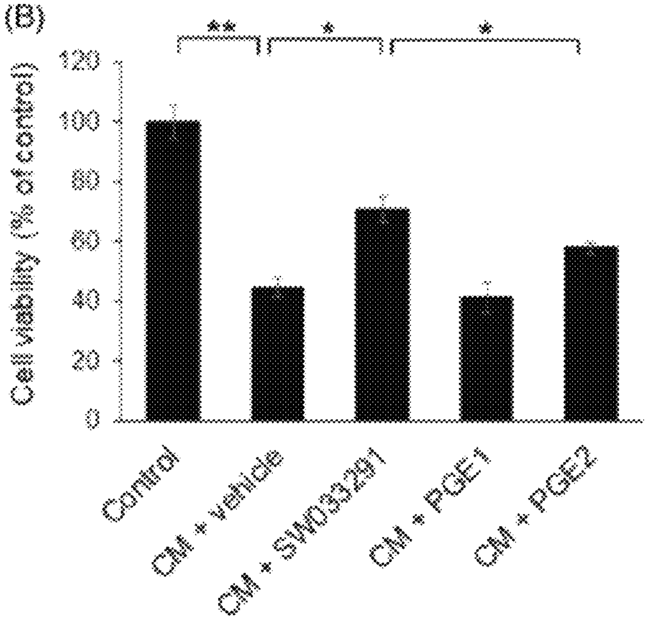
Figure 13C:
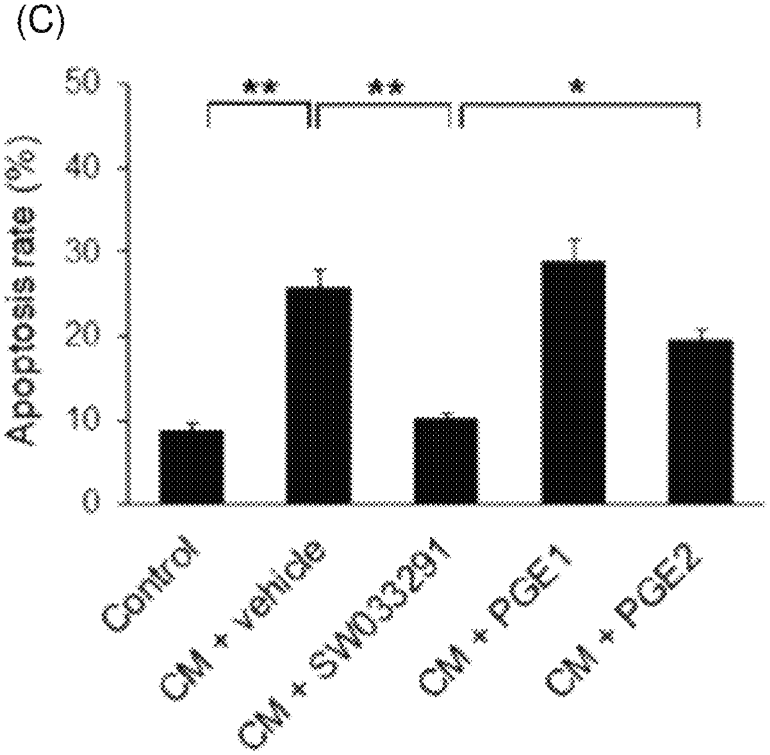
Figure 14A:
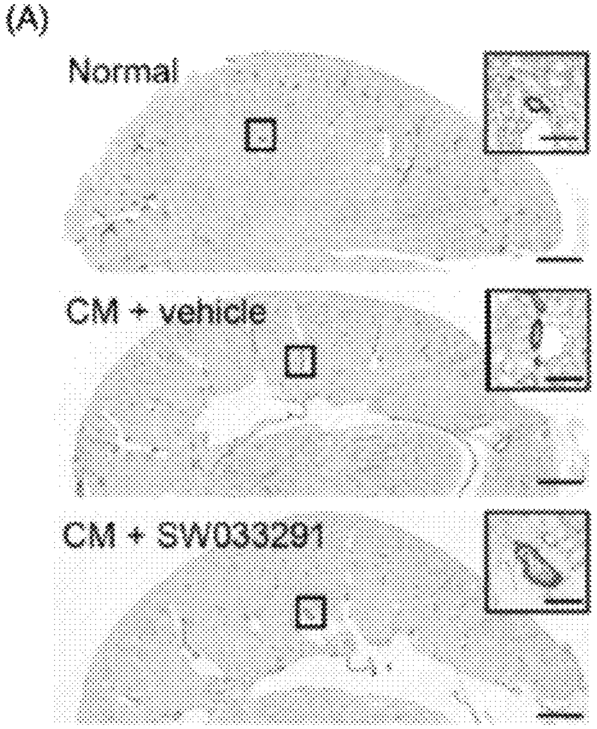
FIGS. 14(A-F) illustrate images and plots showing 15-hydroxyprostaglandin dehydrogenase inhibition induces renal vasodilation in the outer medulla via the adenosine monophosphate (AMP)-adenosine signaling pathway. (A) Representative images of arterioles in the outer zone of the renal medulla. Magnified images are enlargements of the outlined areas. (B) Statistical analyses of the inner arteriole area of the outer medulla. (C) Statistical analyses of renal blood flow following administration of a vehicle, SW033291 (inhibitor), prostaglandin $E_1$ (PGE1), or PGE2 in contrast-induced acute kidney injury mice. (D) Representative images of renal blood flux measurements of the study groups. (E, F) Statistical analyses of AMP and adenosine levels in kidney tissue. *p<0.05; p<0.01; *p<0.001. Scale bars, 500 μm; scale bar in the enlarged image, 50 μm CM: contrast medium.
Figure 14B:
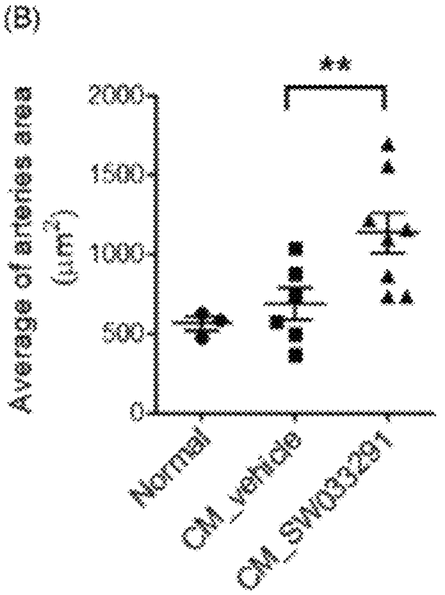
Figure 14C:
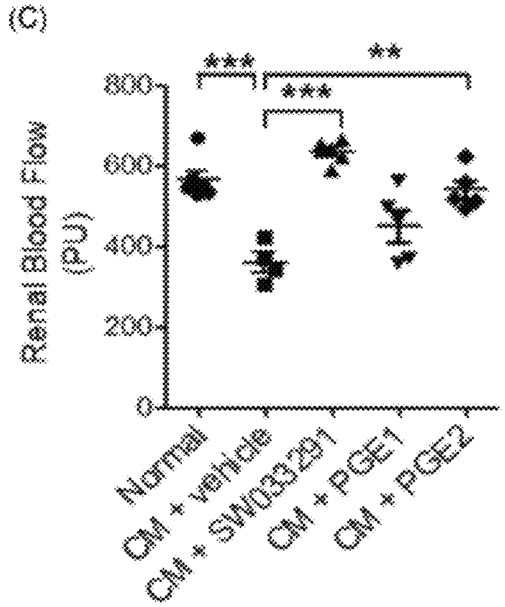
Figure 14D:
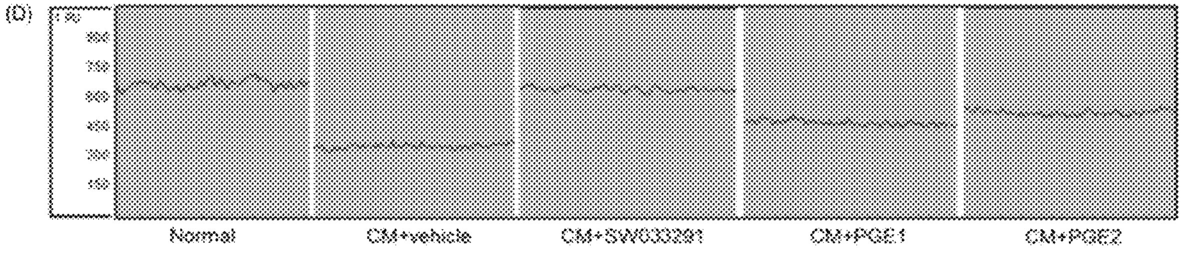
Figure 14E:
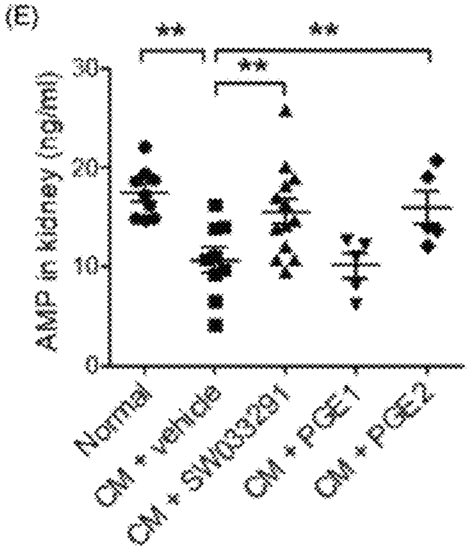
Figure 14F:
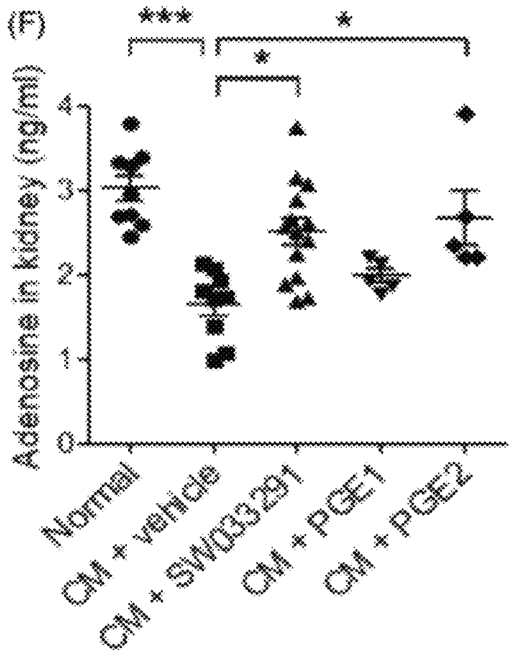

15-PGDH Inhibitor Protects Human Renal Proximal Tubular Epithelial Cells from Iodixanol-Induced Apoptosis We assessed the viability of hRPTECs using a MTT assay. This was significantly lower in the CM group than in the normal, control group. However, SW033291 treatment significantly increased cell viability compared to the CM þ vehicle group (44.77±3.01 [CM þ vehicle] vs. 70.87±1 [CM þ SW033291], p<0.05), but the PGE1 and PGE2 treatment groups did not show any difference in cell viability from the CM þ vehicle group (FIGS. 13(A, B)). The apoptosis rate of hRPTECs also increased more than 2.5 times in the CM group compared to the normal group, but when SW033291 was added, the apoptosis rate caused by CM significantly decreased (25.78±2.17% [CM þ vehicle] vs. 10.06±0.85% [CM þ SW033291], p<0.001). The PGE2 group tended to have a lower apoptotic rate than the CM þ vehicle group (25.78±2.17% [CM þ vehicle] vs. 19.43±1.38% [CM þ PGE2], p ¼ 0.069), but this was not statistically significant. However, comparing the SW033291 and PGE2 treatment groups, SW033291 had a significantly higher anti-apoptosis effect (10.06±0.85% [CM þ SW033291] vs. 19.43±1.38 [CM þ PGE2], p<0.05; FIG. 13C). There were no differences in apoptotic rate between the PGE1 treatment and CM þ vehicle groups.

15-PGDH Inhibitor Induces Renal Vasodilation Via the PGE2 Receptor 4-Adenosine Monophosphate-Adenosine Pathway in the Outer Medulla SW033291 treatment in CIAKI mice significantly increased the average renal arteriole area in the outer medulla compared to untreated CIAKI mice (683.63±111.11 $\mu m^2$ [CM þ vehicle] vs. 1132.97±159.86 $\mu m^2$ [CM þ SW033291], p<0.05; FIG. 14(A, B)). CIAKI mice exhibited a decrease in RBF, but SW033291 treatment significantly prevented the reduction of RBF by CM injection (360.0±24.86 [CM þ vehicle] vs. 635.2±11.10 [CM þ SW033291], p<0.001; FIGS. 14(C, D)). PGE2 treatment also significantly preserved RBF from the CM-induced reduction of RBF (360.0±24.86 [CM þ vehicle] vs. 541.4±22.65 [CM þ PGE2], p ¼ 0.001), but PGE1 did not. Levels of AMP and adenosine in renal tissue were all significantly decreased in CIAKI mice compared to the sham, but these changes were substantially reversed by SW033291-treated mice (AMP, 10.64±1.27 ng/mL [CM þ vehicle] vs. 15.60±1.26 ng/mL [CM þ SW033291], p<0.05; adenosine, 1.65±0.14 ng/mL [CM þ vehicle] vs. 2.65±0.15 ng/mL [CM þ SW033291], p<0.01; FIGS. 14(E, F)). Administering PGE2 also increased AMP and adenosine levels compared to CIAKI mice (FIGS. 14(E, F)).

Figure 15A:
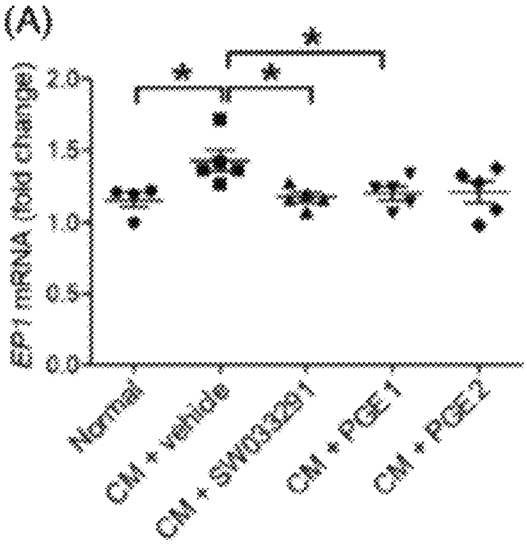
FIG. 15(A-H) illustrate plots showing 15-hydroxyprostaglandin dehydrogenase inhibition changes the level of prostaglandin $E_2$ (PGE2) receptor (EP) expression in kidney tissue. The protective effects of the 15-PGDH inhibitor, SW033291, can be blocked by an EP4 antagonist, ONO-AE3-208. (A-D) Statistical analyses of the EP expression level. (E-G) Serum levels of creatinine, neutrophil gelatinase-associated lipocalin (NGAL), and kidney injury molecule-1 (KIM-1) due to the absence or presence of ONO-AE3-208 in the contrast-induced acute kidney injury model. (H) Statistical analyses of renal blood flow. p<0.05; p<0.01; p<0.001; CM: contrast medium.
Figure 15B:
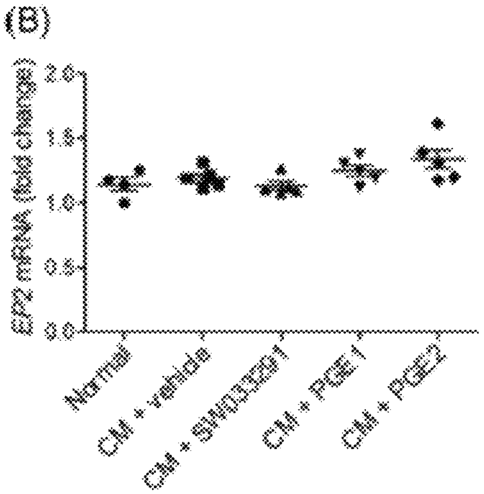

Next, we analyzed PGE2 receptor (EP) expression. EP1 increased in the CM þ vehicle group, but not in the SW033291, PGE1, or PGE2 groups (FIG. 15(A)). There were no differences in the expression level of EP2 between the groups (FIG. 15(B)). However, the SW033291 group showed significantly lower EP3 expression than the CM group (1.10±0.03-fold [CM þ vehicle] vs. 1.00±0.02-fold

Figure 15C:
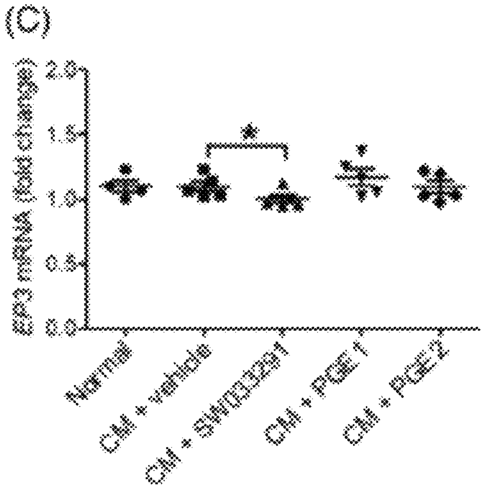
Figure 15D:
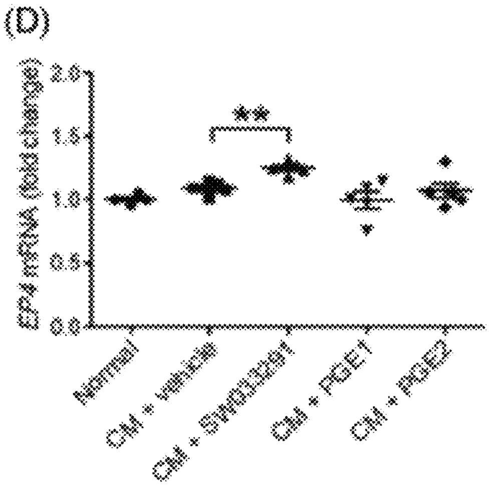
Figure 15E:
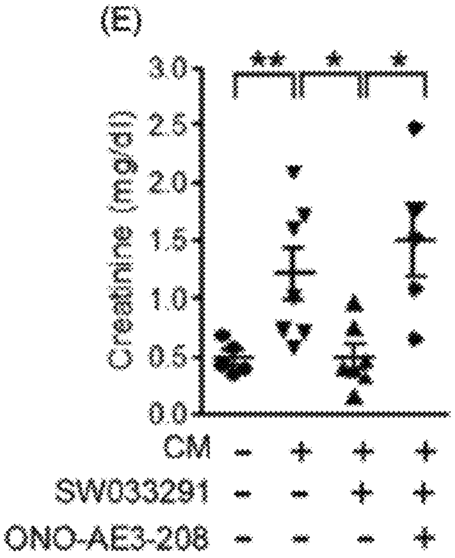
Figure 15F:
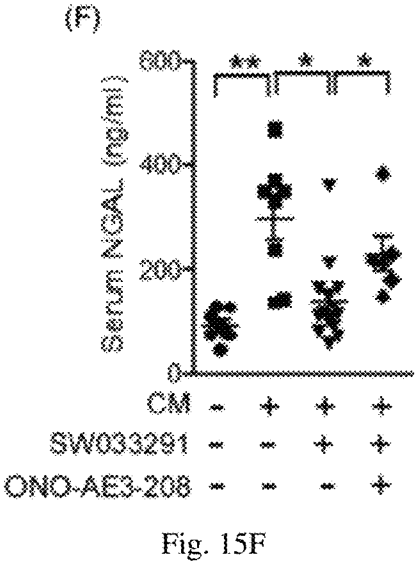
Figure 15G:
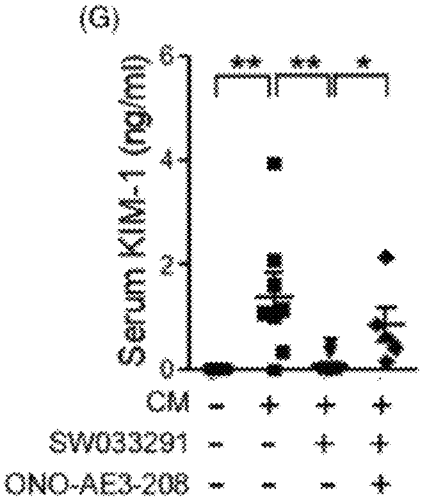
Figure 15H:
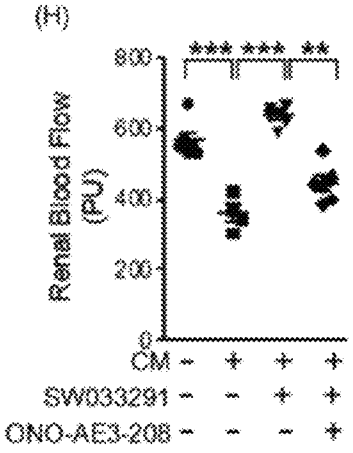

[CM þ SW033291], p<0.05; FIG. 15(C)). The EP4 expression level was significantly increased only in the SW033291 group (1.09±0.02-fold [CM þ vehicle] vs. 1.25±0.02-fold [CM þ SW033291], p<0.01; FIG. 15(D)). An EP4 antagonist, ONO-AE3-208, attenuated the renoprotective effects of SW033291, as indicated by increases in creatinine, NGAL, and KIM-1 (creatinine, 0.50±0.10 mg/dL [CM þ SW033291] vs. 1.51±0.31 mg/dL [CM þ ONO-AE3-208 þ SW033291], p<0.05; NGAL, 140.41±25.52 ng/mL [CM þ SW033291] vs. 229.85±27.12 ng/mL [CM þ ONO-AE3-208 þ SW033291], p<0.05; KIM-1, 0.09±0.05 ng/mL [CM þ SW033291] vs. 0.85±0.26 ng/mL [CM þ ONO-AE3-208 þ SW033291], p<0.05; FIG. 15(E-G)). Moreover, we assessed RBF, and ONO-AE3-208 blocked the increase in RBF by SW033291 treatment in CIAKI mice (FIG. 15(H)).

To establish a CIAKI animal model, we considered the conventional rat models using water depletion and furosemide to induce a severe dehydration, and then administering CM to achieve CIAKI; however, this method is rather complicated and time-consuming, and most importantly, far from clinical settings. We specifically chose mouse over rat to establish a CIAKI animal model, and using a number of different CM with varying osmolality and viscosity, we aimed to find the appropriate CM that induces CIAKI. Visipaque (iodixanol), a CM with high viscosity and iso-osmolality, showed a significant functional and histopathological renal damage. This example shows that CM with a high viscosity can induce CIAKI in mouse on its own, without dehydration or using other drugs. CM viscosity is a key element in the pathophysiology of CIAKI, and when CM is administrated in a dehydrated state, fluid viscosity increases exponentially and flow through medullary tubules and vessels decreases, which increases the duration of contact of CM to tubular cells, thereby increasing renal tubular toxicity.

Figure 11C:
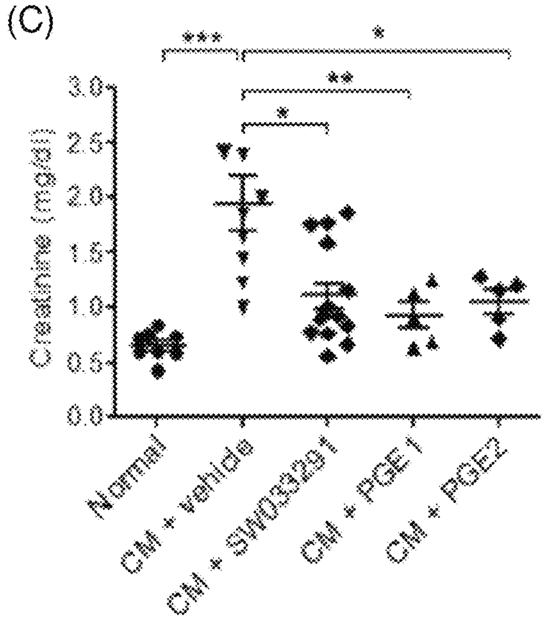
Figure 11D:
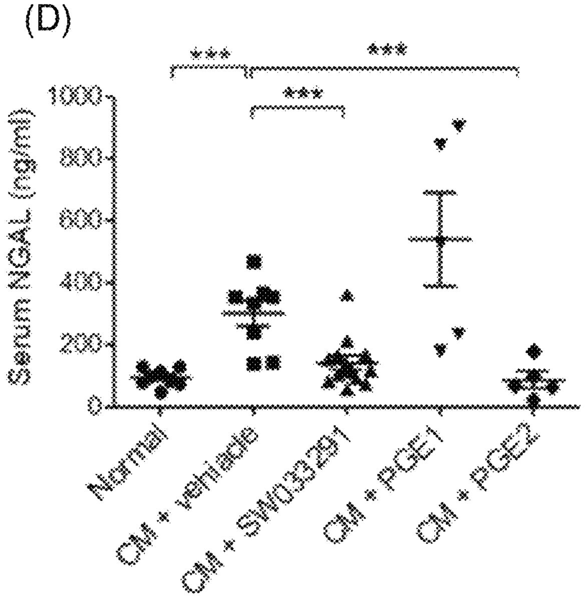
Figure 11E:
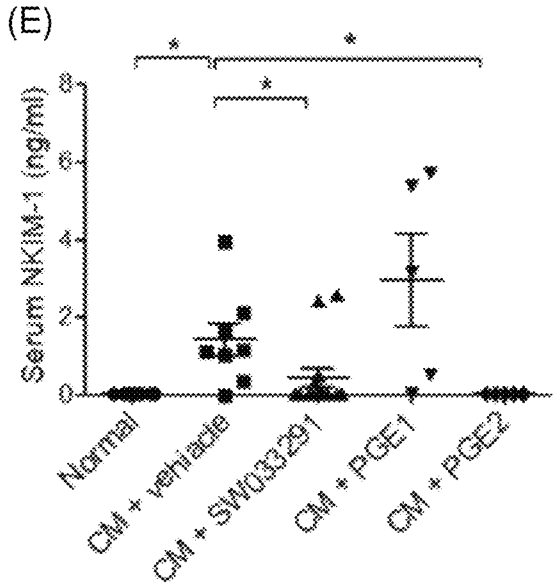

We analyzed whether functional and histological protection against CIAKI is possible by administering a 15-PGDH inhibitor, PGE1, or PGE2. Biomarker analyses were used to detect the functional changes of the kidneys; the 15-PGDH inhibitor, PGE1, and PGE2 all showed a similar effect by reducing serum creatinine levels in the CIAKI model (FIG. 11C). On the other hand, NGAL and KIM-1 showed varying results; with 15-PGDH inhibitor and PGE2, the concentration of the two markers decreased, whereas PGE1 did not decrease them (FIGS. 11(D, E)). Creatinine is a biomarker that reflects the kidney's ability to excrete waste, while NGAL and KIM-1 suggest that the kidney has under-gone a tubular injury. Therefore, we can assume that PGE1, PGE2, and the 15-PGDH inhibitor all have a protective effect in the excretory function against CM, but only PGE2 and the 15-PGDH inhibitor have a protective effect against tubular toxicity.

To assess the degree of histological renal injury, we used the renal injury score to evaluate necrosis, and TUNEL staining for apoptosis. The 15-PGDH inhibitor effectively inhibited both necrosis and apoptosis of renal tissues by CM, whereas PGE2 inhibited apoptosis but failed to successfully reduce necrosis. PGE1 decreased apoptosis but increased necrosis (FIG. 12). Interestingly, the 15-PGDH inhibitor showed a greater effect in reducing renal necrosis than PGE2. The estimated half-life of PGE2 is less than 15 s because PGE2 is rapidly degraded by 15-PGDH. Therefore, increasing the level and extending the half-life of intrinsic PGE2 induced by blocking 15-PGDH (FIGS. 11(A, B)) would be more effective for reducing the renal injury score than directly administering PGE2, which has a short half-life.

We performed cell culture experiments using hRPTECs to determine whether CM has a direct cellular toxicity to renal tubular cells and whether the 15-PGDH inhibitor, PGE1, and PGE2 have protective effects. CM showed a decrease in cellular viability and increase in apoptosis on the hRPTECs, as reported by other previous studies. However, such harmful effects of CM were significantly reversed by the administration of the 15-PGDH inhibitor (FIG. 13); PGE1 had no protective effect against cellular toxicity, and PGE2 showed only a minimal effect, much less than that of the 15-PGDH inhibitor. Therefore, the protective effect on the renal tubular cells against CM could be better achieved by inhibiting the 15-PGDH to block the catabolism of the endogenous PGE2, rather than administering exogenous PGE2.

CM is also known as a toxic agent that decreases renal blood flow and increases vasoconstriction in many studies. Our renal hemodynamic study also showed that CM has obviously decreased renal blood flow (FIG. 14). However, this deteriorating effect of CM on renal hemodynamics was definitely reversed by the administration of PGE2 or 15-PGDH inhibitor, but not by PGE1. Moreover, 15-PGDH inhibitor has increased renal vasodilation more than that of CM group, confirmed by measuring the size of arterioles. Furthermore, the analysis of vasoactive substances to increase the renal vasodilation showed that both adenosine, involved in renal blood vessel expansion, and its precursor, AMP, were increased in the 15-PGDH inhibitor or PGE2 administration group than CM group. Thus, we can suggest that the protective effects of PGE2 and 15-PGDH inhibitor from renal vasoconstriction of CM are induced by increasing adenosine and AMP, which cause renal vasodilation.

To investigate the mechanism behind the renal protective effect of 15-PGDH inhibitor, we examined the change in expression of PGE2 receptors. According to many studies regarding the contribution of prostaglandin EP receptors to renal microvascular reactivity, EP1 and EP3 mediate renal vasoconstrictor responses, whereas EP2 and EP4 mediate vasodilation. Our results are consistent with these observations that vasodilatory effect of 15-PGDH inhibitor is mediated by the decreased EP 3 expression and increased EP4 expression. Moreover, ONO-AE3-208, an EP4 antagonist, clearly offsets the renal protective effect of the 15-PGDH inhibitor. We can assume that the 15-PGDH inhibitor maximizes the protective action against renal damage by CM through the EP4.

In summary, administering the 15-PGDH inhibitor, SW033291, before and after CM in the CIAKI mouse model had a functional and histological protection against CIAKI. This was achieved by providing protection against both hemodynamic and tubular toxic effects, the two main mechanisms of CIAKI. The intrarenal vasodilation and increased renal blood flow induced by SW033291 were via the EP4s, which were strongly associated with the increase in AMP and adenosine levels. The protective effect of SW033291 on the tubular cell toxicity of CM was achieved by inhibiting tubular cell apoptosis. Therefore, we suggest that 15-PGDH inhibitor may be a novel prophylactic agent for CIAKI, and further studies are needed for clinical implications.

From the above description of the invention, those skilled in the art will perceive improvements, changes and modifications. Such improvements, changes and modifications within the skill of the art are intended to be covered by the appended claims. All references, publications, and patents cited in the present application are herein incorporated by reference in their entirety.

Having described the invention, we claim:

1. A method for preventing or treating contrast agent induced acute kidney injury (CIAKI) in a subject in need thereof, the method comprising:

administering to the subject a therapeutically effective amount of a 15-PGDH inhibitor.

2. The method of claim 1, wherein the amount of 15-PGDH inhibitor administered to the subject is an amount effective to induce endogenous renal PGE2 levels of the subject.

3. The method of claim 1, wherein the amount of 15-PGDH inhibitor administered to the subject is an amount effective to induce renal vasodilatation, enhance resistance to hypoxia, improve renal hemodynamics, decrease renal oxidative stress, reduce renal inflammation, and/or preserve renal function.

4. The method of claim 1, the amount of 15-PGDH inhibitor administered to the subject is an amount effective to reduce malondialdehyde (MDA) and NGAL levels, attenuate medulla tubular damage, reduce medulla acute tubular necrosis (ATN) and apoptosis, reduces induction of high-mobility group box 1 (HMGB1) and proinflammatory cytokines, induce renal EP4 PGE2 receptors and A2A adenosine receptors in vascular smooth muscle cells that regulate renal arterioles, increase renal CAMP, AMP, and adenosine levels, and/or inhibit induction of creatinine and KIM-1.

5. The method of claim 1, wherein the 15-PGDH inhibitor is administered before contrast agent administration.

6. The method of claim 1, wherein the 15-PGDH inhibitor is administered at a range of about 1 minute to about 72 hours before contrast agent administration.

7. The method of claim 6, wherein the 15-PGDH inhibitor is administered at a range of about 10 minutes to about 48 hours before contrast agent administration.

8. The method of claim 6, wherein the 15-PGDH inhibitor is administered at a range of about 30 minutes to about 36 hours before contrast agent administration.

9. The method of claim 6, wherein the 15-PGDH inhibitor is administered at time less than 2 hours before contrast agent administration.

10. The method of claim 1, wherein the 15-PGDH inhibitor has the following formula (V):

(V)

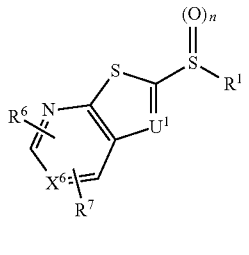

or a pharmaceutically acceptable salt, tatomer, or solvate thereof;

wherein n is 0-2

$X^6$ is independently is N or $CR^c$ $R^1$, $R^6$, $R^7$, and $R^c$ are the same or different each independently hydrogen or a substituted or unsubstituted group selected from $C_1$-$C_{24}$ alkyl, $C_2$-$C_{24}$ alkenyl, $C_2$-$C_{24}$ alkynyl, $C_3$-$C_{20}$ aryl, heteroaryl, heterocycloalkenyl containing from 5-6 ring atoms, $C_6$-$C_{24}$ alkaryl, $C_6$-$C_{24}$ aralkyl, halo, —Si($C_1$-$C_3$ alkyl)$_3$, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl, acyloxy, $C_2$-$C_{24}$ alkoxycarbonyl, $C_6$-$C_{20}$ aryloxycarbonyl, $C_2$-$C_{24}$ alkylcarbonato, $C_6$-$C_{20}$ arylcarbonato, carboxy, carboxylato, carbamoyl, $C_1$-$C_{24}$ alkyl-carbamoyl, arylcarbamoyl, thiocarbamoyl, carbamido, cyano, isocyano, cyanato, isocyanato, isothiocyanato, azido, formyl, thioformyl, amino, $C_1$-$C_{24}$ alkyl amino, $C_5$-$C_{20}$ aryl amino, $C_2$-$C_{24}$ alkylamido, $C_2$-$C_{24}$ alkylamido substituted with a hydroxyl, $C_6$-$C_{20}$ arylamido, imino, alkylimino, arylimino, nitro, nitroso, sulfo, sulfonato, $C_1$-$C_{24}$ alkylsulfanyl, arylsulfanyl, $C_1$-$C_{24}$ alkylsulfinyl, $C_5$-$C_{20}$ arylsulfinyl, $C_1$-$C_{24}$ alkylsulfonyl, $C_5$-$C_{20}$ arylsulfonyl, sulfonamide, phosphono, phosphonato, phosphinato, phospho, phosphino, polyalkylethers, phosphates, and phosphate esters, groups incorporating amino acids, and combinations thereof, and wherein $R^6$ and $R^7$ may be linked to form a cyclic or polycyclic ring, wherein the ring is a substituted or unsubstituted aryl, a substituted or unsubstituted heteroaryl, a substituted or unsubstituted cycloalkyl, and a substituted or unsubstituted heterocyclyl; and $U^1$ is N, C—$R^2$, or C—$NR^3R^4$, wherein $R^2$ is selected from the group consisting of a H, a lower alkyl group, O, $(CH_2)_{n1}OR'$ (wherein n1=1, 2, or 3), $CF_3$, $CH_2$—$CH_2X$, O—$CH_2$—$CH_2X$, $CH_2$—$CH_2$—$CH_2X$, O—$CH_2$—$CH_2X$, X, (wherein X=H, F, Cl, Br, or I), CN, (C=O)—R', (C=O)N(R')$_2$, O(CO)R', COOR' (wherein R' is H or a lower alkyl group), and wherein $R^1$ and $R^2$ may be linked to form a cyclic or polycyclic ring, wherein $R^3$ and $R^4$ are the same or different and are each selected from the group consisting of H, a lower alkyl group, O, $(CH_2)_{n1}OR'$ (wherein n1=1, 2, or 3), $CF_3$, $CH_2$—$CH_2X$, $CH_2$—$CH_2$—$CH_2X$, (wherein X=H, F, Cl, Br, or I), CN, (C=O)—R', (C=O)N(R')$_2$, COOR' (wherein R' is H or a lower alkyl group), and $R^3$ or $R^4$ may be absent.

11. The method of claim 1, wherein the contrast agent is an iodinated radio contrast agent.

12. The method of claim 11, wherein the contrast agent comprises at least one of acetrizoate, diatrizoate, iodamide, ioglicate, iothalamate, ioxithalamate, metrizoate, metrizamide, iohexol, iopamidol, iopentol, iopromide, or ioversol.

* * * * *